(12) United States Patent
Witek et al.

(10) Patent No.: US 11,041,166 B2
(45) Date of Patent: Jun. 22, 2021

(54) LATE BLIGHT RESISTANCE GENES AND METHODS OF USE

(71) Applicant: TWO BLADES FOUNDATION, Evanston, IL (US)

(72) Inventors: Kamil Witek, Norwich (GB); Hari S. Karki, Middleton, WI (US); Florian Gunter Jupe, Ellisville, MO (US); Jonathan D. G. Jones, Norwich (GB)

(73) Assignee: Two Blades Foundation, Evanston, IL (US)

( * ) Notice: Subject to any disclaimer, the term of this patent is extended or adjusted under 35 U.S.C. 154(b) by 0 days.

(21) Appl. No.: 16/469,080

(22) PCT Filed: Dec. 15, 2017

(86) PCT No.: PCT/US2017/066691
§ 371 (c)(1),
(2) Date: Jun. 12, 2019

(87) PCT Pub. No.: WO2018/112356
PCT Pub. Date: Jun. 21, 2018

(65) Prior Publication Data
US 2019/0359998 A1    Nov. 28, 2019

Related U.S. Application Data

(60) Provisional application No. 62/435,451, filed on Dec. 16, 2016.

(51) Int. Cl.
*C12N 15/82* (2006.01)
*C07K 14/415* (2006.01)

(52) U.S. Cl.
CPC ........ *C12N 15/8282* (2013.01); *C07K 14/415* (2013.01)

(58) Field of Classification Search
None
See application file for complete search history.

(56) References Cited

FOREIGN PATENT DOCUMENTS

| WO | 2009-013468 A2 | 1/2009 |
| WO | 2013-009935 A2 | 1/2013 |
| WO | 2016-182881 A1 | 11/2016 |

OTHER PUBLICATIONS

Uniprot M0ZPC5_SOLTU (2013, https://www.genome.jp/dbget-bin/www_bget?uniprot: M0ZPC5_SOLTU).*
McHale et al, 2006, Genome Biol., vol. 7, article 212.*
Witek et al, 2020, https://doi.org/10.1101/2020.05.15.095497.*
Guo et al, 2004, Proc. Natl. Acad. Sci. USA 101: 9205-9210; p. 9209.*
Kamil Witek, et al. "Accelerated Cloning of a potato late blight-resistance gene using RenSeq and SMRT Sequencing," Nature Biotechnology, vol. 34, No. 6, Apr. 25, 2016, pp. 656-660 (XP055285612).
International Search Report and Written Opinion dated Mar. 16, 2018 in PCT/US2017/066691.

* cited by examiner

*Primary Examiner* — Anne Kubelik
(74) *Attorney, Agent, or Firm* — Williams Mullen; David M. Saravitz

(57) ABSTRACT

Compositions and methods and for enhancing the resistance of plants to a plant disease caused by a *Phytophthora* species are provided. The compositions comprise nucleic acid molecules encoding resistance (R) gene products and variants thereof and plants, seeds, and plant cells comprising such nucleic acid molecules. The methods for enhancing the resistance of a plant to a plant disease caused by a *Phytophthora* species comprise introducing a nucleic acid molecule encoding an R gene product into a plant cell. Additionally provided are methods for using the plants in agriculture to limit plant disease.

14 Claims, 15 Drawing Sheets

Specification includes a Sequence Listing.

LATE BLIGHT RESISTANCE GENES AND METHODS OF USE

CROSS-REFERENCE TO RELATED APPLICATIONS

This application is the U.S. National Stage of International Application PCT/US2017/066691, filed Dec. 15, 2017, which designates the U.S. and was published by the International Bureau in English on Jun. 21, 2018, and which claims the benefit of U.S. Provisional Patent Application No. 62/435,451, filed Dec. 16, 2016, which is hereby incorporated herein in its entirety by reference.

REFERENCE TO A SEQUENCE LISTING SUBMITTED AS A TEXT FILE

The official copy of the sequence listing is submitted electronically via EFS-Web as an ASCII formatted sequence listing with a file named 070294-0127SEQLST.TXT, created on Dec. 11, 2017, and having a size of 440 kilobytes, and is filed concurrently with the specification. The sequence listing contained in this ASCII formatted document is part of the specification and is herein incorporated by reference in its entirety.

FIELD OF THE INVENTION

The present invention relates to the fields of gene isolation and plant improvement, particularly to enhancing the resistance of plants to plant disease through the use of disease resistance genes.

BACKGROUND OF THE INVENTION

Late blight, caused by oomycete pathogen *Phytophthora infestans*, is a devastating disease of cultivated potato (*Solanum tuberosum*) and tomato (*Solanum lycopersicum*), causing several billion dollars annual losses (Jones (2014) *Philos. Trans. R. Soc. Lond. B Biol. Sci.* 369:20130087-20130087). It was estimated that only in Europe late blight cost in potato production is over 1 billion euros including costs of control and damage caused by the pathogen (Haverkort (2008) *Potato Res.* 51:47-57).

Plant breeders have typically introduced one Rpi (i.e. Resistance to *Phytophthora infestans*) gene at a time from wild relatives into cultivated potato. However, this process is laborious and slow, and so far has resulted in an Rpi gene that is overcome by new *P. infestans* races in less time than it took to breed the new potato variety that contains it (Jones et al. 2014). A transgenic approach allows introduction of several genes at the same time ('gene stacking'), providing more durable resistance. Several major genes conferring resistance against late blight has been reported, however due to quick *P. infestans* evolution, there is still need to clone additional Rpi genes.

Cloned Rpi genes and their functional alleles include, for example: Rpi-blb1/RB from *Solanum demissum* (van der Vossen et al. (2003) *Plant J.* 36:867-882; Song et al. (2003) *PNAS* 100:9128-9133) and its homologues Rpi-sto1 and Rpi-pta1 from *S. stoloniferum* and *S. papita*, respectively (Vleeshouwers et al. (2008) *PLOS ONE* 3:e2875); Rpi-blb2 from *S. demissum* (van der Vossen E A et al. (2005) *Plant J.* 44:208-222); Rpi-blb3 and its homologues Rpi-abpt and R2-like from *S. bulbocastanum* and R2 from *S. demissum* (Lokossou et al. (2009) *MPMI* 22:630-641) and additional homologues Rpi-edn1.1. Rpi-edn1.2. Rpi-snk1.1. Rpi-snk1.2 and Rpi-hjt1.1-Rpi-hjt1.3 from *S. edinense, S. schenckii* and *S. hjertingii*, respectively, described by Champouret ((2010) "Functional genomics of *Phytophthora infestans* effectors and *Solanum* resistance genes," Ph.D. Thesis, Wageningen Univ., Wageningen); Rpi-bt1 from *S. demissum* (Oosumi et al. (2009) *Amer. J. Potato Res.* 86:456-465); R1 from *S. demissum* (Ballvora et al. (2002) *Plant J.* 30:361-71); R3a and R3b from *S. demissum* (Huang et al. (2005) *Plant J.* 42:261-271; Li et al. (2011) MPMI 24:1132-1142; respectively); Rpi-vnt1.1, Rpi-vnt1.2. Rpi-vnt1.3 from *S. venturii* (Foster et al. (2009) MPMI22:589-600; Pel et al. (2009) MPMI 22:601-615; WO2009013468); Rpi-mcq1 from *S. mochiquense* (WO2009013468); Rpi-chc from *S. chacoense* (WO 2011/034433) and Ph-3 from *S. pimpinellifolium* (Zhang et al. (2014) *Theor. Appl. Genet.* 127:1353-1364).

*Solanum nigrum* and closely related species are generally regarded as non-hosts for infection by *P. infestans*. They are not infected under laboratory conditions, and infections are very rarely observed in the field (Lebecka (2009) *Eur. J. Plant Pathol.* 124:345-348). However, there is one report of *S. nigrum* susceptibility to *P. infestans* infection, and of Mendelian segregation for resistance when a susceptible line is crossed to a resistant line, and the F1 selfed to produce F2 progeny (Lebecka (2008) *Eur. J. Plant Pathol.* 120:233-240; Lebecka (2009) *Eur. J. Plant Pathol.* 124:345-348). This resistance under strong pathogen pressure suggests that resistance genes present in *S. nigrum* might have unique efficacy and recognition specificities, making them valuable to clone and characterize. *S. nigrum* is a hexaploid plant of complex polyploid origin, making classical map-based cloning laborious and time consuming.

Recently, the cloning of a new Rpi gene, Rpi-amr3i, from a Mexican accession of *Solanum americanum* was reported (Witek et al. (2016) *Nat. Biotechnol.* 34: 656). *S. americanum* is an herbaceous flowering plant growing worldwide that has been reported to be a putative diploid ancestor of *S. nigrum* (Poczai and Hyvonen (2010) *Mol. Biol. Rep.* 38:1171-1185). Due to the rapid evolution of *P. infestans* races that can overcome the existing Rpi genes, additional new Rpi genes will be needed soon to combat late blight disease in potatoes and tomatoes. Because the cloning of new Rpi genes from diploid *Solanaceous* species like *S. americanum* is expected to be less time consuming than cloning Rpi genes from a *Solanaceous* species with a complex polyploid genome like *S. nigrum*, the use of diploid *Solanaceous* species as a source of Rpi genes may allow researchers to clone new Rpi genes more quickly to provide plant breeders with new sources of resistance against late blight caused by *P. infestans*.

BRIEF SUMMARY OF THE INVENTION

The present invention provides nucleic acid molecules for resistance (R) genes that are capable of conferring to a plant, particularly a solanaceous plant, resistance to at least one race of a *Phytophthora* species (sp.) that is known to cause a plant disease in the plant. In one embodiment, the present invention provides nucleic acid molecules comprising an R gene, which is referred to herein as Rpi-amr1e, and its variants including, for example, alleles of Rpi-amr1e, homologs of Rpi-amr1e, and other naturally and non-naturally occurring variants of Rpi-amr1e. In another embodiment, the present invention provides nucleic acid molecules comprising an R gene, which is referred to herein as Rpi-amr6b, and its variants including, for example, alleles of Rpi-amr6b, homologs of Rpt-amr6b, and other naturally and non-naturally occurring variants of Rpi-amr6b. In yet another embodiment, the present invention provides nucleic acid molecules comprising an R gene, which is referred to herein as Rpi-amr7d, and its variants including, for example, alleles of Rpi-amr7d, and homologs of Rpi-amr7d, and other naturally and non-naturally occurring variants of Rpi-amr7d. In a further embodiment, the present invention provides nucleic acid molecules comprising an R gene, which is referred to herein as Rpi-amr8c, and its variants including, for example, alleles of Rpi-amr8c, homologs of Rpi-amr8c, and other naturally and non-naturally occurring variants of Rpi-amr8c.

The present invention additionally provides plants, plant cells, and seeds comprising in their genomes one or more heterologous polynucleotides of the invention. The heterologous polynucleotides comprise a nucleotide sequence encoding a resistance (R) protein of the present invention. Such R proteins are encoded by the R genes of the present invention, particularly Rpi-amr1e, Rpi-amr6b, Rpi-amr7d, and Rpi-amr8c, and alleles, homologs, and other naturally and non-naturally occurring variants of such R genes. In a preferred embodiment, the plants and seeds are transgenic solanaceous plants and seeds that have been transformed with one or more heterologous polynucleotides of the invention. Preferably, such solanaceous plants comprise enhanced resistance to at least one race of a *Phytophthora* sp. that is known to cause a plant disease in a solanaceous plant, when compared to the resistance of a control plant that does not comprise the heterologous polynucleotide. Solanaceous plants of the invention include, but are not limited to, domesticated solanaceous plants including, for example, domesticated varieties of potato and tomato.

The present invention provides methods for enhancing the resistance of a plant, particularly a solanaceous plant, to a plant disease caused by at least one race of at least one *Phytophthora* sp. Such methods comprise introducing into at least one plant cell a heterologous polynucleotide comprising a nucleotide sequence of an R gene of the present invention. Preferably, the heterologous polynucleotide or part thereof is stably incorporated into the genome of the plant cell. The methods can optionally further comprise regenerating the plant cell into a plant that comprises in its genome the heterologous polynucleotide. Preferably, such a plant comprises enhanced resistance to a plant disease caused by at least one race of a *Phytophthora* sp., relative to a control plant not comprising the heterologous polynucleotide. More preferably, such a plant comprises enhanced resistance to plant disease(s) caused by at least two, three, four, five, or more races of a *Phytophthora* sp., relative to a control plant not comprising the heterologous polynucleotide.

The present invention additionally provides methods for identifying a solanaceous plant that displays newly conferred or enhanced resistance to a plant disease caused by at least one race of a *Phytophthora* sp. The methods comprise detecting in the solanaceous plant the presence of Rpi-amr1e, Rpi-amr6b, Rpi-amr7d, and/or Rpi-amr8c, and/or alleles, homologs, and other naturally and non-naturally occurring variants of such R genes.

Methods of using the plants of the present invention in agricultural crop production to limit plant disease caused by at least one race of a *Phytophthora* sp. are also provided. The methods comprise planting a plant (e.g. a seedling), a tuber, or a seed of the present invention, wherein the plant, tuber, or seed comprises at least one R gene nucleotide sequence of the present invention. The methods further comprise growing a plant under conditions favorable for the growth and development of the plant, and optionally harvesting at least one fruit, tuber, leaf, or seed from the plant.

Additionally provided are plants, plant parts, seeds, plant cells, other host cells, expression cassettes, and vectors comprising one or more of the nucleic acid molecules of the present invention.

Transgenic tetraploid potato 'Maris Piper' which expresses Rpi-amr1e under the native regulatory elements is resistant to *P. infestans* isolate 88069. The transgenic lines 1, 2, 3 4A, 6, 10, 12, 14A, 14B show no symptoms or display HR at the spot of inoculation. In contrast, the control, wild type '*Maris* Piper' potato plants and transgenic line 15 show typical symptoms of late blight disease with sporulation. Each leaflet was inoculated with a 3-4 droplets containing 1000-2000 zoospores; photographs were taken 10 days post inoculation.

FIG. 5 is a photographic illustration showing that the Rpi-amr1e alleles from additional resistant *S. americanum* accessions confer resistance against *P. infestans* in a transient complementation assay in *N. benthamiana* leaves. Third leaves of *N. benthamiana* plants were infiltrated with the vector pICSLUS0001 overexpressing Rpi-amr1e alleles from resistant lines SP1032, SP1123. SP2272, SP2307 and SP3408 (top to bottom, two leaves on left), or GFP (negative control, leave on right), and 24 hours later inoculated with the *P. infestans* strain 88069. No *P. infestans* growth was observed for all tested Rpi-amr1e alleles, while *P. infestans* growth was unaltered at infiltration sites of GFP control. Photographs were taken 10 days post inoculation.

FIG. 6 is a photographic illustration of leaves of stable transgenic *N. benthamiana* plants, carrying Rpi-amr1e_0.1032 or Rpi-amr1e_0.2307 under the control of the native regulatory elements demonstrating resistance to *P. infestans* race 88069. Transgenic *N. benthamiana* plants which expresses Rpi-amr1e_1032 (top) or Rpi-amr1e_2307 (bottom) under the native regulatory elements is resistant to *P. infestans* isolate 88069. The transgenic lines (left) show no symptoms at the spot of inoculation. In contrast, the control wild type (WT, right) *N. benthamiana* show typical symptoms of late blight disease with sporulation. Each leaflet was inoculated with a 3-4 droplets containing 1000-2000 zoospores; photographs were taken 14 days post inoculation.

FIG. 7 is a photographic illustration of the transient expression of Rpi-amr6b, Rpi-amr1e and Rpi-amr6b-s in *N. benthamiana* following infection with a *P. infestans* isolate. Four-week-old leaves of *N. benthamiana* were infiltrated with the binary vector pICSLUS0004 35S overexpressing the late blight resistance gene Rpi-amr3 (positive control), and binary vector pICSLUS0002 expressing either candidate Rpi-amr6b or negative control Rpi-amr6b-s from susceptible parent with their own native promoter and terminator. Leaves were inoculated with *P. infestans* isolate 88069 24 hours after infiltration. *P. infestans* grew well on the on the negative control susceptible allele of Rpi-amr6b; however, it failed to grow or displayed restricted growth on the leaves infiltrated with Rpi-amr3 (positive control) and candidate Rpi-amr6b.

FIG. 8 is a photographic illustration of leaves of stable transgenic potato plants, cultivar *Maris* Piper, carrying Rpi-amr6b under the control of the native regulatory elements demonstrating resistance to *P. infestans* isolate 88069. Transgenic tetraploid potato '*Maris* Piper' which expresses Rpi-amr6b under the native regulatory elements is resistant to *P. infestans* isolate 88069 (left). The transgenic lines show no symptoms or display HR at the spot of inoculation. In contrast, the control wild type *Maris* Piper plants show typical symptoms of late blight disease with sporulation (right leaf). Each leaflet was inoculated with a 3-4 droplets containing 500-1000 zoospores; photographs were taken 10 days post inoculation.

FIG. 9 is a photographic illustration of the transient expression of Rpi-amr7d, Rpi-amr1e and Rpi-amr6b-s in *N. benthamiana* following infection by a *P. infestans* isolate. Four-week-old leaves of *N. benthamiana* were infiltrated with the binary vector pICSLUS0004 35S overexpressing the late blight resistance gene Rpi-amr3 (positive control), and binary vector pICSLUS0002 expressing either candidate Rpi-amr67d or negative control Rpi-amr6b-s from susceptible parent with their own native promoter and terminator. Leaves were inoculated with *P. infestans* isolate 88069 24 hours after infiltration. *P. infestans* grew well on the on the negative control susceptible allele of Rpi-amr6b; however, it failed to grow or displayed restricted growth on the leaves infiltrated with Rpi-amr3 (positive control) and candidate Rpi-amr7d.

FIG. 10 is a photographic illustration of leaves of stable transgenic potato plants, cultivar *Maris* Piper, carrying Rpi-amr7d under the control of the native regulatory elements demonstrating resistance to *P. infestans* race 88069. Transgenic tetraploid potato '*Maris* Piper' which expresses Rpi-amr7d under the native regulatory elements is resistant to *P. infestans* isolate 88069. The transgenic line (left) show no symptoms or display HR at the spot of inoculation. In contrast, the control, wild type (WT, right) '*Maris* Piper' show typical symptoms of late blight disease with sporulation. Each leaflet was inoculated with a 3-4 droplets containing 1000-2000 zoospores; photographs were taken 10 days post inoculation.

FIG. 11 is a photographic illustration of the transient expression of Rpi-amr8c, Rpi-amr1e and Rpi-amr6b-s in *N. benthamiana* leaves following inoculation by a *P. infestans* isolate. Four-week-old leaves of *N. benthamiana* were infiltrated with the binary vector pICSLUS0004 35S overexpressing the late blight resistance gene Rpi-amr3 (positive control), and binary vector pICSLUS0002 expressing either candidate Rpi-amr8c or negative control Rpi-amr6b-s from susceptible parent with their own native promoter and terminator. Leaves were inoculated with *P. infestans* isolate 88069 24 hours after infiltration. *P. infestans* grew well on the on the negative control susceptible allele of Rpi-amr6b, however it failed or restricted to grow on the leaves infiltrated with Rpi-amr3 (positive control) and candidate Rpi-amr8c.

FIG. 12 is a photographic illustration of leaves of stable transgenic potato plants, cultivar *Maris* Piper, carrying Rpi-amr8c under the control of the native regulatory elements demonstrating resistance to *P. infestans* race 88069. Transgenic tetraploid potato '*Maris* Piper' which expresses Rpi-amr8c under the native regulatory elements is resistant to *P. infestans* isolate 88069. The transgenic line (left) show no symptoms or display HR at the spot of inoculation. In contrast, the control wild type (WT, right) *Maris* Piper show typical symptoms of late blight disease with sporulation. Each leaflet was inoculated with a 3-4 droplets containing 1000-2000 zoospores; photographs were taken 10 days post inoculation.

FIG. 13 is a photographic illustration of the transient expression of Rpi-amr9d, Rpi-amr1e and Rpi-amr6b-s in *N. benthamiana* following infection by a *P. infestans* isolate. Four-week-old leaves of *N. benthamiana* were infiltrated with the binary vector pICSLUS0004 35S overexpressing the late blight resistance gene Rpi-amr3 (positive control), and binary vector pICSLUS0002 expressing either candidate Rpi-amr9d or negative control Rpi-amr6b-s from susceptible parent with their own native promoter and terminator. Leaves were inoculated with *P. infestans* strains 88069 24 hours after infiltration. *P. infestans* grew well on the on the negative control susceptible allele of Rpi-amr6b, however it failed or restricted to grow on the leaves infiltrated with Rpi-amr3 (positive control) and candidate Rpi-amr9d.

Figure 14:
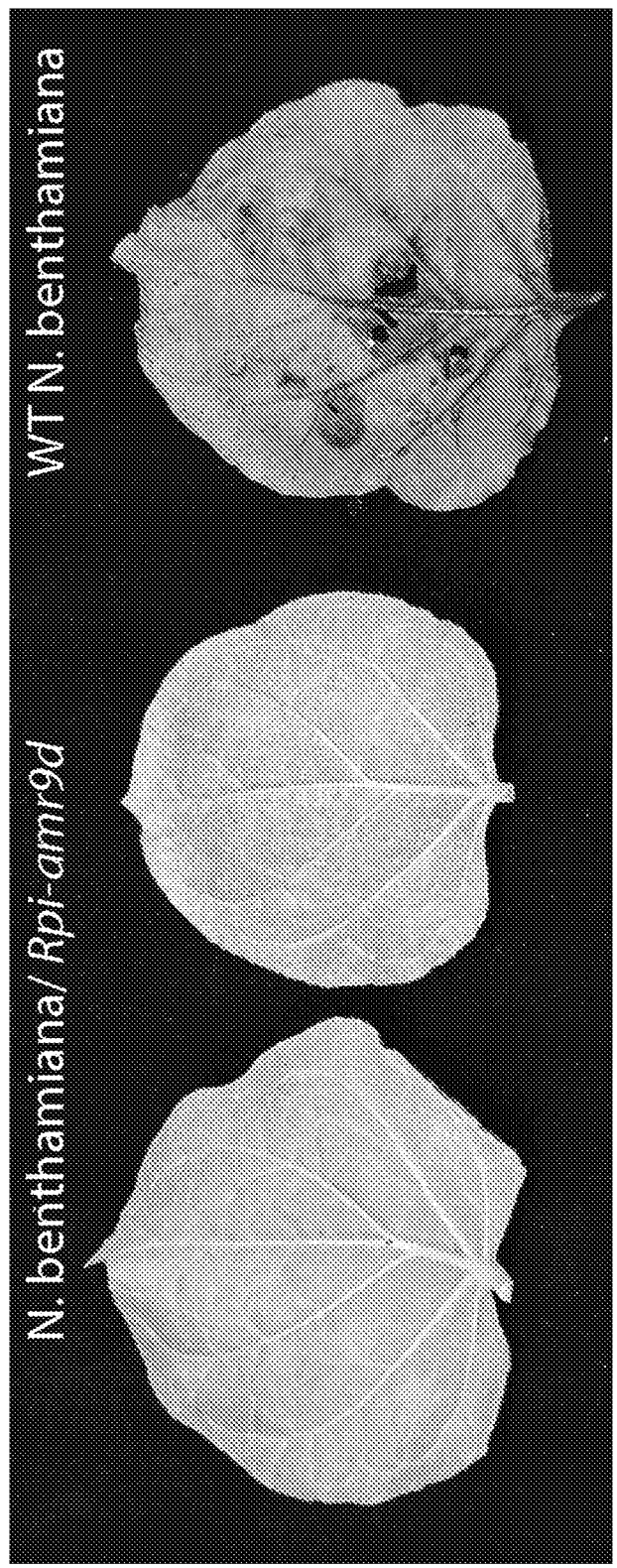
Figure 15:
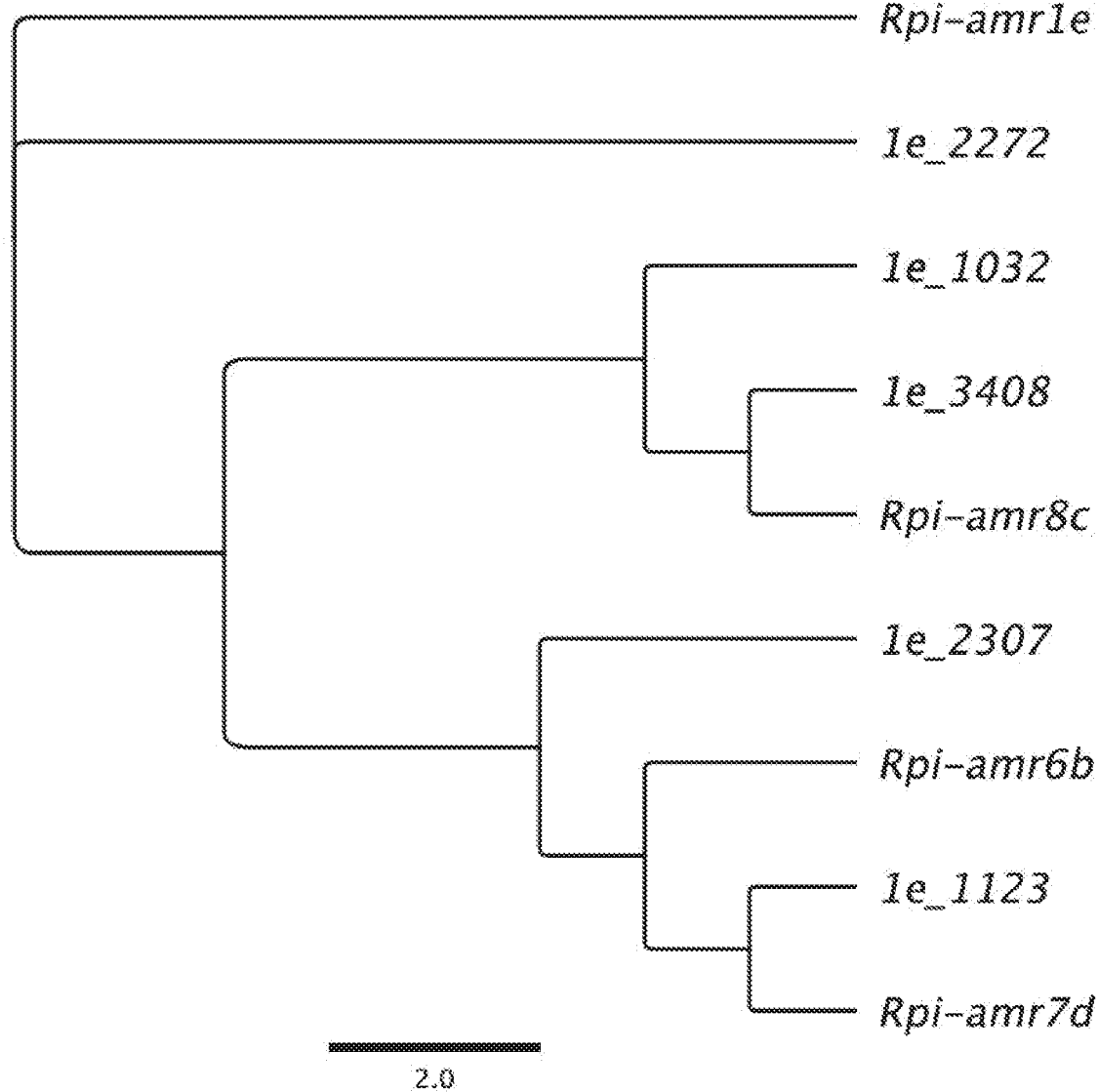

FIG. 14 is a photographic illustration of leaves of stable transgenic *N. benthamiana* plants, carrying Rpi-amr9d under the control of the native regulatory elements demonstrating resistance to *P. infestans* race 88069. Transgenic *N. benthamiana* plants which expresses Rpi-amr9d under the native regulatory elements are resistant to *P. infestans* isolate 88069. The transgenic line (left) show no symptoms at the spot of inoculation. In contrast, the control wild type (WT, right) *N. benthamiana* show typical symptoms of late blight disease with sporulation. Each leaflet was inoculated with a 3-4 droplets containing 1000-2000 zoospores; photographs were taken 14 days post inoculation.

FIG. 15 is a phylogenetic tree of all functional Rpi-amr1e alleles and homologs (i.e. Rpi-amr6b, Rpi-amr7d, and Rpi-amr8c) showing that Rpi-amr1e and Rpi-amr1e_SP2272 are the most distant genes from the other functional alleles and homologs while the remaining genes form two distinct classes.

SEQUENCE LISTING

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e. from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e. from left to right in each line) to the carboxy terminus.

SEQ ID NO: 1 sets forth a nucleotide sequence of the R gene, Rpi-amr1e, *Solanum americanum*.

SEQ ID NO: 2 sets forth the amino acid sequence of Rpi-amr1e, the R protein encoded by Rpi-amr1e.

SEQ ID NO: 3 sets forth the nucleotide sequence of the coding region of the Rpi-amr1e cDNA. If desired, a stop codon (e.g. TAA, TAG, TGA) can be operably linked to the 3' end of nucleic acid molecule comprising SEQ ID NO: 3. The native stop codon of this cDNA is TGA.

SEQ ID NO: 4 sets forth a nucleotide sequence of the Rpi-amr1e allele from *S. americanum* accession A14750130.

SEQ ID NO: 5 sets forth the amino acid sequence of the R protein encoded by the Rpi-amr1e allele from *S. americanum* accession A14750130.

SEQ ID NO: 6 sets forth the nucleotide sequence of the coding region of the cDNA of the Rpi-amr1e allele from *S. americanum* accession A14750130. If desired, a stop codon (e.g. TAA, TAG. TGA) can be operably linked to the 3' end of nucleic acid molecule comprising SEQ ID NO: 6. The native stop codon of this cDNA is TGA.

SEQ ID NO: 7 sets forth a nucleotide sequence of the Rpi-amr1e allele from *S. americanum* accession Veg422.

SEQ ID NO: 8 sets forth the amino acid sequence of the R protein encoded by the Rpi-amr1e allele from *S. americanum* accession Veg422.

SEQ ID NO: 9 sets forth the nucleotide sequence of the coding region of the cDNA of the Rpi-amr1e allele from *S. americanum* accession Veg422. If desired, a stop codon (e.g. TAA, TAG, TGA) can be operably linked to the 3' end of nucleic acid molecule comprising SEQ ID NO: 9. The native stop codon of this cDNA is TGA.

SEQ ID NO: 10 sets forth a nucleotide sequence of the Rpi-amr1e allele from *S. americanum* accession Wang2058.

SEQ ID NO: 11 sets forth the amino acid sequence of the R protein encoded by the Rpi-amr1e allele from *S. americanum* accession Wang2058.

SEQ ID NO: 12 sets forth the nucleotide sequence of the coding region of the cDNA of the Rpi-amr1e allele from *S. americanum* accession Wang2058. If desired, a stop codon (e.g. TAA, TAG, TGA) can be operably linked to the 3' end of nucleic acid molecule comprising SEQ ID NO: 12. The native stop codon of this cDNA is TGA.

SEQ ID NO: 13 sets forth a nucleotide sequence of the Rpi-amr1e allele from *S. americanum* accession sn27.

SEQ ID NO: 14 sets forth the amino acid sequence of the R protein encoded by the Rpi-amr1e allele from *S. americanum* accession sn27.

SEQ ID NO: 15 sets forth the nucleotide sequence of the coding region of the cDNA of the Rpi-amr1e allele from *S. americanum* accession sn27. If desired, a stop codon (e.g. TAA, TAG, TGA) can be operably linked to the 3' end of nucleic acid molecule comprising SEQ ID NO: 15. The native stop codon of this cDNA is TGA.

SEQ ID NO: 16 sets forth a nucleotide sequence of the Rpi-amr1e allele from *S. americanum* accession SOLA425.

SEQ ID NO: 17 sets forth the amino acid sequence of the R protein encoded by the Rpi-amr1e allele from *S. americanum* accession SOLA425.

SEQ ID NO: 18 sets forth the nucleotide sequence of the coding region of the cDNA of the Rpi-amr1e allele from *S. americanum* accession SOLA425. If desired, a stop codon (e.g. TAA, TAG. TGA) can be operably linked to the 3' end of nucleic acid molecule comprising SEQ ID NO: 18. The native stop codon of this cDNA is TAA.

SEQ ID NO: 19 sets forth a nucleotide sequence of the Rpi-amr1e allele from *S. americanum* accession A14750006.

SEQ ID NO: 20 sets forth the amino acid sequence of the R protein encoded by the Rpi-amr1e allele from *S. americanum* accession A14750006.

SEQ ID NO: 21 sets forth the nucleotide sequence of the coding region of the cDNA of the Rpi-amr1e allele from *S. americanum* accession A14750006. If desired, a stop codon (e.g. TAA, TAG, TGA) can be operably linked to the 3' end of nucleic acid molecule comprising SEQ ID NO: 21. The native stop codon of this cDNA is TGA.

SEQ ID NO: 22 sets forth a nucleotide sequence of the R gene, Rpi-amr1e. The promoter regions spans nucleotides 1-1633 and the terminator region spans nucleotides 6443-7349.

SEQ ID NO: 23 sets forth the nucleotide sequence of the coding region of the cDNA of splice variant 1 of Rpi-amr1e (SEQ ID NO: 22). If desired, a stop codon (e.g. TAA, TAG, TGA) can be operably linked to the 3' end of nucleic acid molecule comprising SEQ ID NO: 23. The native stop codon of this cDNA is TAA.

SEQ ID NO: 24 sets forth the amino acid sequence of the R protein encoded by the splice variant 1 cDNA set forth in SEQ ID NO: 23.

SEQ ID NO: 25 sets forth the nucleotide sequence of the coding region of the cDNA of splice variant 2 of Rpi-amr1e (SEQ ID NO: 22). If desired, a stop codon (e.g. TAA, TAG, TGA) can be operably linked to the 3' end of nucleic acid molecule comprising SEQ ID NO: 25. The native stop codon of this cDNA is TAA.

SEQ ID NO: 26 sets forth the nucleotide sequence of the coding region of the cDNA of splice variant 3 of Rpi-amr1e (SEQ ID NO: 22). If desired, a stop codon (e.g. TAA, TAG, TGA) can be operably linked to the 3' end of nucleic acid molecule comprising SEQ ID NO: 26. The native stop codon of this cDNA is TAA.

SEQ ID NO: 27 sets forth the nucleotide sequence of the coding region of the cDNA of splice variant 4 of Rpi-amr1e (SEQ ID NO: 22). If desired, a stop codon (e.g. TAA, TAG, TGA) can be operably linked to the 3' end of nucleic acid molecule comprising SEQ ID NO: 27. The native stop codon of this cDNA is TGA.

SEQ ID NO: 28 sets forth the amino acid sequence of the R protein encoded by the splice variant 2 cDNA set forth in SEQ ID NO: 25.

SEQ ID NO: 29 sets forth the amino acid sequence of the R protein encoded by the splice variant 3 cDNA set forth in SEQ ID NO: 26.

SEQ ID NO: 30 sets forth the amino acid sequence of the R protein encoded by the splice variant 4 cDNA set forth in SEQ ID NO: 27.

SEQ ID NO: 31 sets forth a nucleotide sequence of SP1032 allele of the R gene, Rpi-amr1e. The promoter regions spans nucleotides 1-1823 and the terminator region spans nucleotides 6944-7913.

SEQ ID NO: 32 sets forth a nucleotide sequence of SP1123 allele of the R gene. Rpi-amr1e. The promoter regions spans nucleotides 49-1577 and the terminator region spans nucleotides 6705-7662.

SEQ ID NO: 33 sets forth a nucleotide sequence of SP2272 allele of the R gene, Rpi-amr1e. The promoter regions spans nucleotides 641-1745 and the terminator region spans nucleotides 6802-7770.

SEQ ID NO: 34 sets forth a nucleotide sequence of SP2307 allele of the R gene, Rpi-amr1e. The promoter regions spans nucleotides 1-1991 and the terminator region spans nucleotides 9253-9596.

SEQ ID NO: 35 sets forth a nucleotide sequence of SP3408 allele of the R gene, Rpi-amr1e. The promoter regions spans nucleotides 1-1405 and the terminator region spans nucleotides 7567-8398.

SEQ ID NO: 36 sets forth the nucleotide sequence of the coding region of a cDNA of the SP1032 allele of Rpi-amr1e. If desired, a stop codon (e.g. TAA, TAG, TGA) can be operably linked to the 3' end of nucleic acid molecule comprising SEQ ID NO: 36. The native stop codon of this cDNA is TAA.

SEQ ID NO: 37 sets forth the nucleotide sequence of the coding region of a cDNA of the SP1123 allele of Rpi-amr1e. If desired, a stop codon (e.g. TAA, TAG, TGA) can be operably linked to the 3' end of nucleic acid molecule comprising SEQ ID NO: 37. The native stop codon of this cDNA is TAA.

SEQ ID NO: 38 sets forth the nucleotide sequence of the coding region of a cDNA of the SP2272 allele of Rpi-amr1e. If desired, a stop codon (e.g. TAA, TAG, TGA) can be operably linked to the 3' end of nucleic acid molecule comprising SEQ ID NO: 38. The native stop codon of this cDNA is TAA.

SEQ ID NO: 39 sets forth the nucleotide sequence of the coding region of a cDNA of the SP2307 allele of Rpi-amr1e. If desired, a stop codon (e.g. TAA, TAG, TGA) can be operably linked to the 3' end of nucleic acid molecule comprising SEQ ID NO: 39. The native stop codon of this cDNA is TAA.

SEQ ID NO: 40 sets forth the nucleotide sequence of the coding region of a cDNA of the SP3408 allele of Rpi-amr1e. If desired, a stop codon (e.g. TAA, TAG, TGA) can be operably linked to the 3' end of nucleic acid molecule comprising SEQ ID NO: 40. The native stop codon of this cDNA is TAA.

SEQ ID NO: 41 sets forth the amino acid sequence of the R protein encoded by the SP1032 cDNA sequence set forth in SEQ ID NO: 36.

SEQ ID NO: 42 sets forth the amino acid sequence of the R protein encoded by the SP1123 cDNA sequence set forth in SEQ ID NO: 37.

SEQ ID NO: 43 sets forth the amino acid sequence of the R protein encoded by the SP2272 cDNA sequence set forth in SEQ ID NO: 38.

SEQ ID NO: 44 sets forth the amino acid sequence of the R protein encoded by the SP2307 cDNA sequence set forth in SEQ ID NO: 39.

SEQ ID NO: 45 sets forth the amino acid sequence of the R protein encoded by the SP3408 cDNA sequence set forth in SEQ ID NO: 40.

SEQ ID NO: 46 sets forth a nucleotide sequence of the R gene, Rpi-amr6b, from *Solanum nigrescens* accession A14750423. The promoter regions spans nucleotides 1-2030 and the terminator region spans nucleotides 7162-8005.

SEQ ID NO: 47 sets forth the amino acid sequence of the R protein encoded by the splice variant 1 of Rpi-amr6b (SEQ ID NO: 46). A cDNA of splice variant 1 is set forth in SEQ ID NO: 49.

SEQ ID NO: 48 sets forth the amino acid sequence of the R protein encoded by the splice variant 2 of Rpi-amr6b (SEQ ID NO: 46). A cDNA of splice variant 2 is set forth in SEQ ID NO: 50.

SEQ ID NO: 49 sets forth the nucleotide sequence of the coding region of the cDNA of splice variant 1 of Rpi-amr6b (SEQ ID NO: 46). If desired, a stop codon (e.g. TAA. TAG, TGA) can be operably linked to the 3' end of nucleic acid molecule comprising SEQ ID NO: 49. The native stop codon of this cDNA is TAA.

SEQ ID NO: 50 sets forth the nucleotide sequence of the coding region of the cDNA of splice variant 1 of Rpi-amr6b (SEQ ID NO: 46). If desired, a stop codon (e.g. TAA, TAG, TGA) can be operably linked to the 3' end of nucleic acid molecule comprising SEQ ID NO: 50. The native stop codon of this cDNA is TAA.

SEQ ID NO: 51 sets forth a nucleotide sequence of the R gene, Rpi-amr7d, from *S. americanum* accession A54750014. The promoter regions spans nucleotides 1-1960 and the terminator region spans nucleotides 7032-7842.

SEQ ID NO: 52 sets forth the amino acid sequence of the R protein encoded by the splice variant 1 of Rpi-amr7d (SEQ ID NO: 51). A cDNA of splice variant 1 is set forth in SEQ ID NO: 54.

SEQ ID NO: 53 sets forth the amino acid sequence of the R protein encoded by the splice variant 2 of Rpi-amr7d (SEQ ID NO: 51). A cDNA of splice variant 2 is set forth in SEQ ID NO: 55.

SEQ ID NO: 54 sets forth the nucleotide sequence of the coding region of the cDNA of splice variant 1 of Rpi-amr7d (SEQ ID NO: 51). If desired, a stop codon (e.g. TAA, TAG, TGA) can be operably linked to the 3' end of nucleic acid molecule comprising SEQ ID NO: 54. The native stop codon of this cDNA is TAA.

SEQ ID NO: 55 sets forth the nucleotide sequence of the coding region of the cDNA of splice variant 2 of Rpi-amr7d (SEQ ID NO: 51). If desired, a stop codon (e.g. TAA, TAG, TGA) can be operably linked to the 3' end of nucleic acid molecule comprising SEQ ID NO: 55. The native stop codon of this cDNA is TAA.

SEQ ID NO: 56 sets forth a nucleotide sequence of the R gene, Rpi-amr8c, from *S. americanum* accession SOLA 226. The promoter regions spans nucleotides 1-1953 and the terminator region spans nucleotides 7078-7456.

SEQ ID NO: 57 sets forth the amino acid sequence of the R protein encoded by the splice variant 1 of Rpi-amr8c (SEQ ID NO: 56). A cDNA of splice variant 1 is set forth in SEQ ID NO: 60.

SEQ ID NO: 58 sets forth the amino acid sequence of the R protein encoded by the splice variant 2 of Rpi-amr8c (SEQ ID NO: 56). A cDNA of splice variant 2 is set forth in SEQ ID NO: 59.

SEQ ID NO: 59 sets forth the nucleotide sequence of the coding region of the cDNA of splice variant 2 of Rpi-amr8c (SEQ ID NO: 56). If desired, a stop codon (e.g. TAA, TAG, TGA) can be operably linked to the 3' end of nucleic acid molecule comprising SEQ ID NO: 59. The native stop codon of this cDNA is TAA.

SEQ ID NO: 60 sets forth the nucleotide sequence of the coding region of the cDNA of splice variant 1 of Rpi-amr8c (SEQ ID NO: 56). If desired, a stop codon (e.g. TAA, TAG, TGA) can be operably linked to the 3' end of nucleic acid molecule comprising SEQ ID NO: 60. The native stop codon of this cDNA is TAA.

SEQ ID NO: 61 sets forth a nucleotide sequence of the R gene, Rpi-amr9d, from *S. americanum* accession SOLA425. The promoter regions spans nucleotides 1-1991 and the terminator region spans nucleotides 9269-9596.

SEQ ID NO: 62 sets forth the amino acid sequence of the R protein encoded by the splice variant 1 of Rpi-amr9d (SEQ ID NO: 61). A cDNA of splice variant 1 is set forth in SEQ ID NO: 60.

SEQ ID NO: 63 sets forth the amino acid sequence of the R protein encoded by the splice variant 2 of Rpi-amr9d (SEQ ID NO: 61). A cDNA of splice variant 2 is set forth in SEQ ID NO: 60.

SEQ ID NO: 64 sets forth the nucleotide sequence of the coding region of the cDNA of splice variant 2 of Rpi-amr9d (SEQ ID NO: 61). If desired, a stop codon (e.g. TAA, TAG, TGA) can be operably linked to the 3' end of nucleic acid molecule comprising SEQ ID NO: 64. The native stop codon of this cDNA is TAA.

SEQ ID NO: 65 sets forth the nucleotide sequence of the coding region of the cDNA of splice variant 1 of Rpi-amr9d (SEQ ID NO: 61). If desired, a stop codon (e.g. TAA, TAG, TGA) can be operably linked to the 3' end of nucleic acid molecule comprising SEQ ID NO: 65. The native stop codon of this cDNA is TAA.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention relates to the isolation of plant resistance (R) genes, particularly R genes that confer upon a solanaceous plant resistance to late blight disease caused by one or more multiple races of *Phytophthora infestans*. As disclosed hereinbelow, an R gene, referred to herein as Rpi-amr1e, was isolated from *Solanum americanum* accession 954750184, a diploid, non-tuber-bearing relative of potato, using a map-based cloning approach with fine mapping on 1793 F2 plants and sequencing of co-segregating BAC clones. Additional Rpi-amr1e alleles from Veg422, A14750130, Wang 2058, sn27, A14750006 and SOLA425 *S. americanum* accessions were isolated using a method involving R gene sequence capture (RenSeq) with long-read sequencing that has been previously described (Eid et al. (2008) *Science* 323:133-138; Sharon et al. (2013) *Nat. Biotechnol.* 31:1009-14; both of which are herein incorporated by reference). The isolation of additional Rpi-amr1e alleles from *S. americanum* accessions 954750174, A14750130, and 954750172 is disclosed hereinbelow in Example 8. Also disclosed hereinbelow in Examples 9-16 is the isolation of three additional R genes that are homologs of Rpi-amr1e: Rpi-amr6b from *Solanum nigrescens* accession A14750423; Rpi-amr7d from *S. americanum* accession A54750014; and Rpi-amr8c from *S. americanum* accession SOLA 226.

The present invention provides nucleic acid molecules comprising the nucleotide sequences of R genes, particularly the nucleotide sequences of Rpi-amr1e, Rpi-amr6b, Rpi-amr7d, and Rpi-amr8c and alleles, homologs, orthologs, and other naturally occurring variants of such R genes and synthetic or artificial (i.e. non-naturally occurring) variants thereof. As used herein, such nucleic acid molecules are referred to herein as "Rpi-amr nucleic acid molecules" or "Rpi-amr genes", unless stated otherwise or apparent from the context of use. Likewise, the nucleotide sequences of Rpi-amr1e, Rpi-amr6b. Rpi-amr7d, and Rpi-amr8c and alleles, homologs, orthologs, and other naturally occurring variants of such R genes and synthetic or artificial (i.e. non-naturally occurring) variants thereof are referred to herein as "Rpi-amr nucleotide sequences" unless stated otherwise or apparent from the context of use.

The Rpi-amr nucleotide sequences of the present invention are nucleotide sequences of R genes, which are also referred to herein as R gene nucleotide sequences. Preferably, such nucleotide sequences of R genes encode R proteins. Rpi-amr nucleotide sequences of the invention include, but not limited to, the nucleotide sequences of wild-type Rpi-amr1e, Rpi-amr6b. Rpi-amr7d, and Rpi-amr8c genes comprising a native promoter and the 3' adjacent region comprising the coding region, cDNA sequences, and nucleotide sequences comprising only the coding region. Examples of such Rpi-amr nucleotide sequences include the nucleotide sequences set forth in SEQ ID NOS: 1, 3, 4, 6, 7, 9, 10, 12, 13, 15, 16, 18, 19, 21, 22, 23, 25, 26, 27, 31, 32, 33, 34, 35, 36, 37, 38, 39, 40, 46, 49, 50, 51, 54, 55, 56, 59, 60, 61, 64, and 65 and variants thereof. In embodiments in which the native Rpi-amr gene promoter is not used to drive the expression of the nucleotide sequence encoding the R protein, a heterologous promoter can be operably linked a nucleotide sequence encoding an R protein of the invention to drive the expression of nucleotide sequence encoding an R protein in a plant.

Preferably, the R proteins encoded by the Rpi-amr nucleotide sequences of the invention are functional R proteins, or part(s), or domain(s) thereof, which are capable of conferring on a plant, particularly a solanaceous plant, comprising the R protein enhanced resistance to a plant disease caused by at least one race of at least one *Phytophthora* sp. In certain preferred embodiments, the R proteins of the present invention are capable of conferring on a plant broad-spectrum resistance to at least one race, but preferably multiple races, of *P. infestans* and include, for example, Rpi-amr1e (SEQ ID NO: 2), the R protein encoded by Rpi-amr1e (SEQ ID NO: 1) and the R proteins (SEQ ID NOS: 5, 8, 11, 14, 17, 20, 41, 42, 43, 44, and 45) encoded by the alleles of Rpi-amr1e (SEQ ID NOS: 4, 7, 10, 13, 16, 19, 31, 32, 33, 34, and 35, respectively). Such R proteins of the present invention include, but are not limited to, the R proteins comprising the amino acid sequences set forth in SEQ ID NOS: 2, 5, 8, 11, 14, 17, 20, 24, 28, 29, 30, 41, 42, 43, 44, 45, 47, 48, 52, 53, 57, 58, 62, and 63 and/or are encoded by the Rpi-amr nucleotide sequences set forth in SEQ ID NOS: 1, 3, 4, 6, 7, 9, 10, 12, 13, 15, 16, 18, 19, 21, 22, 23, 25, 26, 27, 31, 32, 33, 34, 35, 36, 37, 38, 39, 40, 46, 49, 50, 51, 54, 55, 56, 59, 60, 61, 64, and 65.

Likewise, preferred Rpi-amr genes, Rpi-amr nucleic acid molecules, and Rpi-amr1e alleles of the present invention are capable of conferring on a plant, particularly a solanaceous plant, comprising the Rpi-amr gene, the Rpi-amr nucleic acid molecule, or Rpi-amr1e allele, enhanced resistance to a plant disease caused by at least one race of at least one *Phytophthora* sp. In certain preferred embodiments, the Rpi-amr genes. Rpi-amr nucleic acid molecules and Rpi-amr1e alleles of the present invention are capable of conferring on a plant broad-spectrum resistance to at least one race, but preferably multiple races, of *P. infestans*. Such Rpi-amr genes. Rpi-amr nucleic acid molecules and Rpi-amr1e alleles include, but are not limited to, Rpi-amr genes, Rpi-amr nucleic acid molecules, and Rpi-amr1e alleles comprising a nucleotide sequence selected from the group consisting of: a nucleotide sequences set forth in SEQ ID NO: 1, 3, 4, 6, 7, 9, 10, 12, 13, 15, 16, 18, 19, 21, 22, 23, 25, 26, 27, 31, 32, 33, 34, 35, 36, 37, 38, 39, 40, 46, 49, 50, 51, 54, 55, 56, 59, 60, 61, 64, or 65; and a nucleotide sequence encoding an amino acid sequence set forth in SEQ ID NO: 2, 5, 8, 11, 14, 17, 20, 24, 28, 29, 30, 41, 42, 43, 44, 45, 47, 48, 52, 53, 57, 58, 62, or 63.

The present invention further provides plants comprising a heterologous polynucleotide which comprises an R gene nucleotide sequence of the present invention. Preferably, such an R gene nucleotide sequence encodes a full-length R protein of the present invention, or at least a functional part(s) or domain(s) thereof. In some embodiments, such a heterologous polynucleotide of the present invention is stably incorporated into the genome of the plant, and in other embodiments, the plant is transformed by a transient transformation method and the heterologous polynucleotide is not stably incorporated into the genome of the plant.

In other embodiments, a plant comprising a heterologous polynucleotide which comprises an R gene nucleotide sequence of the present invention is produced using a method of the present invention that involves genome editing to modify the nucleotide sequence of a native or non-native gene in the genome of the plant. The native or non-native gene comprises a nucleotide sequence that is different from (i.e. not identical to) an R gene nucleotide sequence of the present invention, and after modification by methods disclosed in further detail hereinbelow, the modified native or non-native gene comprises an R gene nucleotide sequence of the present invention. Generally, such methods comprise the use of a plant comprising in its genome a native or non-native gene wherein the native or non-native gene comprises a nucleotide sequence that is homologous to an R gene nucleotide sequence of the present invention and further comprises introducing into the plant a nucleic acid molecule comprising at least part of an R gene nucleotide sequence of the present invention. Preferably, a nucleotide sequence of native or non-native gene comprises about 70%, 75% 80%, 85%, 90%, 95%, 96%, 97%, 98%, 99% or greater nucleotide sequence identity to at least one R gene nucleotide sequence of the present invention. Such a native or non-native gene can be, for example an R gene, particularly an Rpi-amr gene, or a non-functional homolog of such an R gene that is not, or is not known to be, capable of conferring to a plant, resistance to a plant disease. It is recognized that a plant produced by genome engineering as disclosed herein is a stably transformed plant when the native or non-native gene that is modified is stably incorporated in the genome of the plant.

Methods for both the stable and transient transformation of plants and genome editing are disclosed elsewhere herein or otherwise known in the art. In a preferred embodiment of the invention, the plants are stably transformed potato or tomato plants comprising a heterologous polynucleotide of the present invention stably incorporated into their respective genomes and further comprising enhanced resistance to late blight disease caused by at least one race of *P. infestans*. In a more preferred embodiment of the invention, the plants are stably transformed potato or tomato plants comprising a heterologous polynucleotide of the present invention stably incorporated into their respective genomes and further comprising enhanced resistance to late blight disease caused by at least two, three, four, five, six or more races of *P. infestans*.

In certain embodiments, a plant of the invention comprises a heterologous polynucleotide which comprises a nucleotide sequence encoding an R protein of the present invention and a heterologous promoter that is operably linked for expression of the nucleotide sequence encoding an R protein. The choice of heterologous promoter can depend on a number of factors such as, for example, the desired timing, localization, and pattern of expression as well as responsiveness to particular biotic or abiotic stimulus. Promoters of interest include, but are not limited to, pathogen-inducible, constitutive, tissue-preferred, wound-inducible, and chemical-regulated promoters.

In certain embodiments of the invention, the plant of the invention, particularly a solanaceous plant, can comprise one, two, three, four, five, six, or more nucleotide sequences encoding an R protein. Typically, but not necessarily, the two or more R proteins will be different from each other. For the present invention, an R protein is different from another R protein when the two R proteins have non-identical amino acid sequences. In certain embodiments of the invention, each of the different R proteins for resistance to a plant disease caused by a *Phytophthora* sp. has one or more differences in resistance characteristics such as, for example, resistance against a different race and/or group of races of the same *Phytophthora* sp. or even a different *Phytophthora* sp. It is recognized that by combining two, three, four, five, six, or more nucleotide sequences with each nucleotide sequence encoding a different R protein for resistance to a different race of a *Phytophthora* sp. or *Phytophthora* species (spp.), a solanaceous plant can be produced that comprises broad spectrum resistance against multiple races of a single *Phytophthora* sp. or even multiple *Phytophthora* spp. Such a solanaceous plant, particularly a potato or tomato plant, finds use in agriculture in regions where multiple races of a *Phytophthora* sp., such as, for example, multiple races of *P. infestans*, are prevalent.

Examples of R genes that can be combined in single potato plant with one or more Rpi-amr nucleotide sequences of the present invention include, but are not limited to, the following cloned Rpi genes: Rpi-amr3i (Accession No. KT373889; SEQ ID NO: 1 of WO 2016/182881) Rpi-blb1 (also known as "RB"; Accession Nos. FB764493.1 and AY336128.1). Rpi-sto1 (Accession No. EU884421), Rpi-pta1 (Accession No. EU884422). Rpi-blb2 (Accession No. DQ122125), Rpi-blb3 (Accession No. FJ536326), Rpi-abpt (Accession No. FJ536324), R2-like (Accession No. FJ536323). R2 (Accession No. FJ536325), Rpi-edn1.1 (Accession No. GU563963). Rpi-edn1.2. Rpi-snk1.1, Rpi-snk1.2, Rpi-hjt1.1-Rpi-hjt1.3 (Accession No. GU563971-3), Rpi-bt1 (Accession No. FJ188415), R1 (Accession No. AF447489). R3a (Accession No. AY849382), R3b (Accession No. JF900492), Rpi-vnt1.1 (Accession No. FJ423044), Rpi-vnt1.2 (Accession No. FJ423045), Rpi-vnt1.3 (Accession No. FJ423046), Rpi-mcq1 (Accession No. GN043561), Rpi-chc, Ph-3 (Accession No. KJ563933), and R8 (Accession No. KU530153). The nucleotide sequences corresponding to the accession numbers of the genes listed above or of any genes or proteins disclosed elsewhere herein can be obtained from publicly accessible, online nucleotide and amino acid sequence databases such as, for example, the GenBank and EMBL databases (available on the World Wide Web at ncbi.nlm.nih.gov/genbank and ebi.ac.uk, respectively).

A plant of the invention comprising multiple R genes can be produced, for example, by transforming a plant that already comprises one or more other R gene nucleotide sequences with a heterologous polynucleotide comprising at least one Rpi-amr nucleotide sequence of the present invention including, for example, one or more of an Rpi-amr1e nucleotide sequence, an Rpi-amr6b nucleotide sequence, an Rpi-amr7d nucleotide sequence, and an Rpi-amr8c nucleotide sequence. Such a plant that already comprises one or more other R gene nucleotide sequences can comprise R genes that are native to the genome or the plant, that were introduced into the plant via sexual reproduction, or that were introduced by transforming the plant or a progenitor thereof with an R gene nucleotide sequence. Alternatively, the one or more other R gene nucleotide sequences can be introduced into a plant of the invention, which already comprises a heterologous polynucleotide of the invention, by, for example, transformation or sexual reproduction.

In other embodiments, two or more different R gene sequences can be introduced into a plant by stably transforming the plant with a heterologous polynucleotide or vector comprising two or more R gene nucleotide sequences. It is recognized that such an approach can be preferred for plant breeding as it is expected that the two or more R gene nucleotide sequences will be tightly linked and thus, segregate a single locus. Alternatively, a heterologous polynucleotide of the present invention can be incorporated into the genome of a plant in the immediate vicinity of another R gene nucleotide sequence using homologous recombination-based genome modification methods that are described elsewhere herein or otherwise known in the art.

The present invention further provides methods for enhancing the resistance of a plant to a plant disease caused by at least one race of at least one *Phytophthora* sp. The methods comprise modifying at least one plant cell to comprise a heterologous polynucleotide, and optionally regenerating a plant from the modified plant comprising the heterologous polynucleotide. In a first aspect, the methods for enhancing the resistance of a plant to a plant disease caused by at least one race of at least one *Phytophthora* sp. comprise introducing a heterologous polynucleotide of the invention into at least one plant cell, particular a plant cell from a solanaceous plant. In certain embodiments, the heterologous polynucleotide is stably incorporated into the genome of the plant cell.

In a second aspect, the methods for enhancing the resistance of a plant to a plant disease caused by at least one race of at least one *Phytophthora* sp. involve the use of a genome-editing method to modify the nucleotide sequences of a native or non-native gene in the genome of the plant cell to comprise a heterologous polynucleotide of the present invention. The methods comprise introducing a nucleic acid molecule into the plant cell, wherein the nucleic acid molecule comprises a nucleotide sequence comprising at least a part of the Rpi-amr nucleotide sequence of the present invention and wherein at least a part of the nucleotide sequence of the native or non-native gene is replaced with at least a part of the nucleotide sequence of the nucleic acid molecule. Thus, the methods of the invention involve gene replacement to produce a heterologous polynucleotide of the present invention in the genome of a plant cell.

If desired, the methods of the first and/or second aspect can further comprise regenerating the plant cell into a plant comprising in its genome the heterologous polynucleotide. Preferably, such a regenerated plant comprises enhanced resistance to a plant disease caused by at least one race of at least one *Phytophthora* sp., relative to the resistance of a control plant to the plant disease.

The methods of the present invention for enhancing the resistance of a plant to a plant disease caused by at least one race of at least one *Phytophthora* sp. can further comprise producing a plant comprising two, three, four, five, six, or more nucleotide sequences encoding an R protein, preferably each nucleotide sequence encoding a different R protein. Such a plant comprising multiple R gene nucleotide sequences comprises one or more additional R gene nucleotide sequences of the present invention and/or any other nucleotide sequence encoding an R protein known in the art. It is recognized that the methods of the first and/or second aspect can be used to produce such a plant comprising multiple nucleotide sequences encoding an R protein. Moreover, it is recognized that a heterologous polynucleotide of the present invention can comprise, for example, one or more Rpi-amr nucleotide sequences of the present invention or at least one Rpi-amr nucleotide sequences of the present invention and one or more nucleotide sequences encoding an R protein that is known in the art.

The plants disclosed herein find use in methods for limiting plant disease caused by at least one race of at least one *Phytophthora* sp. in agricultural crop production, particularly in regions where such a plant disease is prevalent and is known to negatively impact, or at least has the potential to negatively impact, agricultural yield. The methods of the invention comprise planting a plant (e.g. a seedling), tuber, or seed of the present invention, wherein the plant, tuber, or seed comprises at least one R gene nucleotide sequence of the present invention. The methods further comprise growing the plant that is derived from the seedling, tuber, or seed under conditions favorable for the growth and development of the plant, and optionally harvesting at least one fruit, tuber, leaf, or seed from the plant.

The present invention additionally provides methods for identifying a solanaceous plant that displays newly conferred or enhanced resistance to a plant disease caused by at least one race of a *Phytophthora* sp. The methods find use in breeding solanaceous plants for resistance to plant diseases caused by *Phytophthora* spp. such as, for example, late blight disease. Such resistant plants find use in the agricultural production of fruits, tubers, leaves, and/or seeds for human or livestock consumption or other use. The methods comprise detecting in a solanaceous plant, or in at least one part or cell thereof, the presence of an Rpi-amr nucleotide sequence of the present invention. In some embodiments of the invention, detecting the presence of the Rpi-amr nucleotide sequence comprises detecting the entire Rpi-amr nucleotide sequence in genomic DNA isolated from a solanaceous plant. In preferred embodiments, however, detecting the presence of an Rpi-amr nucleotide sequence comprises detecting the presence of at least one marker within the Rpi-amr nucleotide sequence. In other embodiments of the invention, detecting the presence of an Rpi-amr nucleotide sequence comprises detecting the presence of the R protein encoded by the Rpi-amr nucleotide sequence using, for example, immunological detection methods involving antibodies specific to the R protein.

In the methods for identifying a solanaceous plant that displays newly conferred or enhanced resistance to a plant disease caused by at least one race of a *Phytophthora* sp., detecting the presence of the Rpi-amr nucleotide sequence in the solanaceous plant can involve one or more of the following molecular biology techniques that are disclosed elsewhere herein or otherwise known in the art including, but not limited to, isolating genomic DNA and/or RNA from the plant, amplifying nucleic acid molecules comprising the Rpi-amr nucleotide sequence and/or marker therein by PCR amplification, sequencing nucleic acid molecules comprising the Rpi-amr nucleotide sequence and/or marker, identifying the Rpi-amr nucleotide sequence, the marker, or a transcript of the Rpi-amr nucleotide sequence by nucleic acid hybridization, and conducting an immunological assay for the detection of the R protein encoded by the Rpi-amr nucleotide sequence. It is recognized that oligonucleotide probes and PCR primers can be designed to identity the Rpi-amr nucleotide sequences of the present invention and that such probes and PCR primers can be utilized in methods disclosed elsewhere herein or otherwise known in the art to rapidly identify in a population of plants one or more plants comprising the presence of an Rpi-amr nucleotide sequence of the present invention.

Depending on the desired outcome, the heterologous polynucleotides of the invention can be stably incorporated into the genome of the plant cell or not stably incorporated into genome of the plant cell. If, for example, the desired outcome is to produce a stably transformed plant with enhanced resistance to a plant disease caused by at least one race of a *Phytophthora* sp., then the heterologous polynucleotide can be, for example, fused into a plant transformation vector suitable for the stable incorporation of the heterologous polynucleotide into the genome of the plant cell. Typically, the stably transformed plant cell will be regenerated into a transformed plant that comprises in its genome the heterologous polynucleotide. Such a stably transformed plant is capable of transmitting the heterologous polynucleotide to progeny plants in subsequent generations via sexual and/or asexual reproduction. Plant transformation vectors, methods for stably transforming plants with an introduced heterologous polynucleotide and methods for plant regeneration from transformed plant cells and tissues are generally known in the art for both monocotyledonous and dicotyledonous plants or described elsewhere herein.

In other embodiments of the invention in which it is not desired to stably incorporate the heterologous polynucleotide in the genome of the plant, transient transformation methods can be utilized to introduce the heterologous polynucleotide into one or more plant cells of a plant. Such transient transformation methods include, for example, viral-based methods which involve the use of viral particles or at least viral nucleic acids. Generally, such viral-based methods involve constructing a modified viral nucleic acid comprising a heterologous polynucleotide of the invention operably linked to the viral nucleic acid and then contacting the plant either with a modified virus comprising the modified viral nucleic acid or with the viral nucleic acid or with the modified viral nucleic acid itself. The modified virus and/or modified viral nucleic acids can be applied to the plant or part thereof, for example, in accordance with conventional methods used in agriculture, for example, by spraying, irrigation, dusting, or the like. The modified virus and/or modified viral nucleic acids can be applied in the form of directly sprayable solutions, powders, suspensions or dispersions, emulsions, oil dispersions, pastes, dustable products, materials for spreading, or granules, by means of spraying, atomizing, dusting, spreading or pouring. It is recognized that it may be desirable to prepare formulations comprising the modified virus and/or modified viral nucleic acids before applying to the plant or part or parts thereof. Methods for making pesticidal formulations are generally known in the art or described elsewhere herein.

The present invention provides nucleic acid molecules comprising Rpi-amr nucleotide sequences. Preferably, such nucleic acid molecules are capable of conferring upon a host plant, particularly a solanaceous host plant enhanced resistance to a plant disease caused by at least one race of a *Phytophthora* sp. Thus, such nucleic acid molecules find use in limiting a plant disease caused by at least one race of a *Phytophthora* sp. in agricultural production. The nucleic acid molecules of the present invention include, but are not limited to, nucleic acid molecules comprising at least one Rpi-amr nucleotide sequence disclosed herein but also additional orthologs and other variants of the Rpi-amr nucleotide sequences that are capable of conferring to a plant resistance to a plant disease caused by at least one race of a *Phytophthora* sp. Methods are known in the art or otherwise disclosed herein for determining resistance of a plant a plant disease caused by at least one race of a *Phytophthora* sp., including, for example, the detached leaf assay (DLA) utilizing detached *Nicotiana benthamiana* leaves that is described elsewhere herein.

The present invention further provides plants and cells thereof, particularly solanaceous plants and cells thereof, comprising Rpi-amr1e, Rpi-amr6b, Rpi-amr7d, and/or Rpi-amr8c, and/or alleles, homologs, and other naturally and non-naturally occurring variants of such R genes, and that are produced by methods that do not involve the introduction of recombinant DNA into the plant or a cell thereof. Such methods can comprise, for example, interspecific hybridizations involving two or more different plant species. In preferred embodiments, the plants are solanaceous plants.

In certain embodiments, the solanaceous plant is any solanaceous plant except a *Solanum americanum* plant or a *Solanum nigrescens* plant. In certain other embodiments, the solanaceous plant is any solanaceous plant neither a *S. americanum* plant nor a *S. nigrescens* plant. In other embodiments, the solanaceous plant is any solanaceous plant except a *S. americanum* plant comprising Rpi-amr1e having the nucleotide sequence set forth in SEQ ID NO: 1 and/or 22, and/or one or more of alleles of Rpi-amr1e having the nucleotide sequences set forth in SEQ ID NOS: 4, 7, 10, 13, 16, 19, 31, 32, 33, 34, and 35 wherein Rpi-amr1e and/or one or more of alleles of Rpi-amr1e are the endogenous or native genes in their natural location(s) in the genome.

While it is believed that Rpi-amr nucleotide sequences set forth in SEQ ID NOS: 4, 7, 10, 13, 16, 19, 31, 32, 33, 34, and 35 are the nucleotide sequences of alleles of Rpi-amr1e (SEQ ID NO: 1) of *S. americanum*, it is recognized that the present invention does not depend on such Rpi-amr nucleotide sequences corresponding to alleles that are present at the Rpi-amr1e locus of *S. americanum* and/or other solanaceous plant(s). Such Rpi-amr nucleotide sequences, and Rpi-amr nucleic acid molecules and Rpi-amr genes comprising such Rpi-amr nucleotide sequences, find use in the methods and compositions of the present invention as disclosed herein irrespective of whether any such Rpi-amr nucleotide sequence corresponds to an allele of Rpi-amr1e of *S. americanum* and/or other solanaceous plant.

In yet other embodiments, the solanaceous plant is any solanaceous plant except a *S. americanum* plant comprising Rpi-amr7d having the nucleotide sequence set forth in SEQ ID NO: 51, wherein Rpi-amr7d is the endogenous or native gene in its natural location(s) in the genome. In still other embodiments, the solanaceous plant is any solanaceous plant except a *S. americanum* plant comprising Rpi-amr8c having the nucleotide sequence set forth in SEQ ID NO: 56, wherein the Rpi-amr8c is the endogenous or native genes in their natural location(s) in the genome. In further embodiments, the solanaceous plant is any solanaceous plant except a *S. nigrescens* plant comprising Rpi-amr6b having the nucleotide sequence set forth in SEQ ID NO: 46.

Additionally provided are methods for introducing at least one Rpi-amr gene of present invention into a plant, particularly a solanaceous plant, lacking in its genome the at least one Rpi-amr gene. The Rpi-amr genes of the present invention include, for example, Rpi-amr1e, Rpi-amr6b, Rpi-amr7d, and Rpi-amr8c, and alleles, homologs, and other naturally and non-naturally occurring variants of such R genes, and/or R genes comprising a nucleotide sequence set forth in SEQ ID NO: 1, 3, 4, 6, 7, 9, 10, 12, 13, 15, 16, 18, 19, 21, 22, 23, 25, 26, 27, 31, 32, 33, 34, 35, 36, 37, 38, 39, 40, 46, 49, 50, 51, 54, 55, 56, 59, 60, 61, 64, or 65 and/or encoding R protein comprising an amino acid sequence set forth in SEQ ID NO: 2, 5, 8, 11, 14, 17, 20, 24, 28, 29, 30, 41, 42, 43, 44, 45, 47, 48, 52, 53, 57, 58, 62, or 63. The methods comprise crossing (i.e. cross-pollinating) a first plant comprising in its genome at least one copy of an Rpi-amr gene of present invention with a second solanaceous plant lacking in its genome the Rpi-amr gene. The first and second plants can be the same species or can be different solanaceous species, although in preferred embodiments the first and second plants are solanaceous plants. For example, the first plant can be *Solanum americanum* and the solanaceous plant can be *Solanum tuberosum* or *Solanum lycopersicum*. Such a crossing of a first species of a plant to a second species of a plant is known as an interspecific hybridization and can be used to introgress a gene or genes of interest (e.g. Rpi-amr1e) from one species into a related species lacking the gene or genes of interest and typically involves multiple generations of backcrossing of the progeny with the related species and selection at each generation of progeny comprising the gene or genes of interest. Such interspecific hybridization, introgression, and backcrossing methods are well known in the art and can be used in the methods of the present invention. See "Principals of Cultivar Development." Fehr, 1993. Macmillan Publishing Company, New York; and "Fundamentals of Plant Genetics and Breeding," Welsh, 1981, John Wiley & Sons, Inc., New York.

In methods of the present invention for introducing at least one Rpi-amr gene of present invention into a plant lacking in its genome the at least one Rpi-amr gene, either the first plant or the second plant can be the pollen donor plant. For example, if the first plant is the pollen donor plant, then the second plant is the pollen-recipient plant. Likewise, if the second plant is the pollen donor plant, then the first plant is the pollen-recipient plant. Following the crossing, the pollen-recipient plant is grown under conditions favorable for the growth and development of the plant and for a sufficient period of time for seed to mature or to achieve an otherwise desirable growth stage for use in a subsequent in vitro germination procedure such as, for example, embryo rescue that is described below. The seed can then be harvested and those seed comprising the Rpi-amr gene(s) identified by any method known in the art including, for example, the methods for identifying a solanaceous plant that displays newly conferred or enhanced resistance to a plant disease caused by at least one race of a *Phytophthora* sp. that are described elsewhere herein. In certain embodiments, the first plant is a *Solanum americanum* plant comprising the Rpi-amr gene(s) and the second plant is *Solanum americanum* plant lacking the Rpi-amr gene(s). In preferred embodiments, the first plant is a *Solanum americanum* plant comprising the Rpi-amr gene(s) or other solanaceous plant species comprising in its genome the Rpi-amr gene(s) and the second plant is a solanaceous plant species other than *Solanum americanum*. Preferred solanaceous plants are potato, tomato, eggplant, pepper, tobacco, and *petunia*.

It is recognized, however, that in certain embodiments of the invention involving interspecific hybridizations, it may be advantageous to harvest the seed resulting from such interspecific hybridizations at an immature growth stage and then to germinate the immature seeds in culture (i.e. in vitro), whereby the seeds are allowed germinate in culture using methods known in art as "embryo rescue" methods. See Reed (2005) "Embryo Rescue," in *Plant Development and Biotechnology*, Trigiano and Gray, eds. (PDF). CRC Press, Boca Raton, pp. 235-239; and Sharma et al. (1996) *Euphytica* 89: 325-337. It is further recognized that "embryo rescue methods are typically used when mature seeds produced by an interspecific cross display little or no germination, whereby few or no interspecific hybrid plants are produced.

The methods of the present invention find use in producing plants with enhanced resistance to a plant disease caused by at least one race of at least one *Phytophthora* sp. Typically, the methods of the present invention will enhance or increase the resistance of the subject plant to the plant disease by at least 25%, 50%, 75%, 100%, 150%, 200%, 250%, 500% or more when compared to the resistance of a control plant to the same race or races of *Phytophthora* sp. Unless stated otherwise or apparent from the context of a use, a control plant for the present invention is a plant that does not comprise the heterologous polynucleotide and/or Rpi-amr1e nucleotide sequence of the present invention. Preferably, the control plant is essentially identical (e.g. same species, subspecies, and variety) to the plant comprising the heterologous polynucleotide of the present invention except the control does not comprise the heterologous polynucleotide or Rpi-amr nucleotide sequence. In some embodiments, the control will comprise a heterologous polynucleotide but not comprise the one or more Rpi-amr nucleotide sequences that are in a heterologous polynucleotide of the present invention.

Additionally, the present invention provides transformed plants, seeds, and plant cells produced by the methods of present invention and/or comprising a heterologous polynucleotide of the present invention. Also provided are progeny plants and seeds thereof comprising a heterologous polynucleotide of the present invention. The present invention also provides fruits, seeds, tubers, leaves, stems, roots, and other plant parts produced by the transformed plants and/or progeny plants of the invention as well as food products and other agricultural products comprising, or produced or derived from, the plants or any part or parts thereof including, but not limited to, fruits, tubers, leaves, stems, roots, and seed. Other agricultural products include, for example, smoking products produced from tobacco leaves (e.g. cigarettes, cigars, and pipe and chewing tobacco) and food and industrial starch products produced from potato tubers. It is recognized that such food products can be consumed or used by humans and other animals including, but not limited to, pets (e.g. dogs and cats), livestock (e.g. pigs, cows, chickens, turkeys, and ducks), and animals produced in freshwater and marine aquaculture systems (e.g. fish, shrimp, prawns, crayfish, and lobsters).

Non-limiting examples of the compositions and methods of the present invention are as follows:

1. A nucleic acid molecule comprising a nucleotide sequence selected from the group consisting of:
   (a) the nucleotide sequence set forth in SEQ ID NO: 1, 4, 7, 10, 13, 16, 19, 22, 31, 32, 33, 34, 35, 46, 51, 56, or 61;
   (b) a nucleotide sequence encoding the amino acid sequence set forth in SEQ ID NO: 2, 5, 8, 11, 14, 17, 20, 24, 28, 29, 30, 41, 42, 43, 44, 45, 47, 48, 52, 53, 57, 58, 62, or 63, and optionally, wherein the nucleotide sequence is not naturally occurring;
   (c) the nucleotide sequence set forth in SEQ ID NO: 3, 6, 9, 12, 15, 18, 21, 23, 25, 26, 27, 36, 37, 38, 39, 40, 49, 50, 54, 55, 59, 60, 64, or 65;
   (d) a nucleotide sequence having at least 90% sequence identity to at least one of the nucleotide sequences set forth in SEQ ID NOS: 1, 3, 4, 6, 7, 9, 10, 12, 13, 15, 16, 18, 19, 21, 22, 23, 25, 26, 27, 31, 32, 33, 34, 35, 36, 37, 38, 39, 40, 46, 49, 50, 51, 54, 55, 56, 59, 60, 61, 64, and 65, wherein the nucleic acid molecule is capable of conferring resistance to a plant disease caused by at least one race of at least one Phytophthora sp. to a plant comprising the nucleic acid molecule and optionally, wherein the nucleotide sequence is not naturally occurring; and
   (e) a nucleic acid molecule comprising a nucleotide sequence encoding an amino acid sequence having at least 90% sequence identity to at least one of the amino acid sequences set forth in SEQ ID NO: 2, 5, 8, 11, 14, 17, 20, 24, 28, 29, 30, 41, 42, 43, 44, 45, 47, 48, 52, 53, 57, 58, 62, and 63, wherein the nucleic acid molecule is capable of conferring resistance to a plant disease caused by at least one race of at least one Phytophthora sp. to a plant comprising the nucleic acid molecule and optionally, wherein the nucleotide sequence is not naturally occurring.

2. The nucleic acid molecule of embodiment 1, wherein the nucleic acid molecule is an isolated nucleic acid molecule.

3. An expression cassette comprising the nucleic acid molecule of embodiment 1 or 2 and an operably linked heterologous promoter.

4. A vector comprising the nucleic acid molecule of embodiment 1 or 2 or the expression cassette of embodiment 3.

5. A vector of embodiment 4, further comprising an additional R gene.

6. A host cell transformed with the nucleic acid molecule of embodiment 1 or 2, the expression cassette of embodiment 3, or the vector of embodiment 4 or 5.

7. The host cell of embodiment 6, wherein the host cell is a plant cell, a bacterium, a fungal cell, or an animal cell.

8. The host cell of embodiment 6 or 7, wherein the host cell is a solanaceous plant cell.

9. A plant or plant cell comprising the nucleic acid molecule of embodiment 1 or 2, the expression cassette of embodiment 3, or the vector of embodiment 4 or 5.

10. The plant or plant cell of embodiment 9, wherein the plant is a solanaceous plant and the plant cell is a solanaceous plant cell.

11. The plant of embodiment 10, wherein the solanaceous plant is not Solanum americanum and/or Solanum nigrescens, or wherein the solanaceous plant is selected from the group consisting of potato, tomato, eggplant, pepper, tobacco, and petunia.

12. A plant comprising stably incorporated in its genome a heterologous polynucleotide comprising a nucleotide sequence selected from the group consisting of:
   (a) the nucleotide sequence set forth in SEQ ID NO: 1, 4, 7, 10, 13, 16, 19, 22, 31, 32, 33, 34, 35, 46, 51, 56, or 61;
   (b) a nucleotide sequence encoding the amino acid sequence set forth in SEQ ID NO: 2, 5, 8, 11, 14, 17, 20, 24, 28, 29, 30, 41, 42, 43, 44, 45, 47, 48, 52, 53, 57, 58, 62, or 63;
   (c) the nucleotide sequence set forth in SEQ ID NO: 3, 6, 9, 12, 15, 18, 21, 23, 25, 26, 27, 36, 37, 38, 39, 40, 49, 50, 54, 55, 59, 60, 64, or 65;
   (d) a nucleotide sequence having at least 90% sequence identity to at least one of the nucleotide sequences set forth in SEQ ID NOS: 1, 3, 4, 6, 7, 9, 10, 12, 13, 15, 16, 18, 19, 21, 22, 23, 25, 26, 27, 31, 32, 33, 34, 35, 36, 37, 38, 39, 40, 46, 49, 50, 51, 54, 55, 56, 59, 60, 61, 64, and 65, wherein the nucleic acid molecule is capable of conferring resistance to a plant disease caused by at least one race of at least one Phytophthora sp. to a plant comprising the nucleic acid molecule; and
   (e) a nucleic acid molecule comprising a nucleotide sequence encoding an amino acid sequence having at least 90% sequence identity to at least one of the amino acid sequences set forth in SEQ ID NO: 2, 5, 8, 11, 14, 17, 20, 24, 28, 29, 30, 41, 42, 43, 44, 45, 47, 48, 52, 53, 57, 58, 62, and 63, wherein the nucleic acid molecule is capable of conferring resistance to a plant disease caused by at least one race of at least one Phytophthora sp. to a plant comprising the nucleic acid molecule.

13. The plant of embodiment 12, wherein the heterologous polynucleotide comprises the nucleotide sequence of any one of (b)-(e) and further comprises a promoter operably linked for the expression of the nucleotide sequence in a plant.

14. The plant of embodiment 13, wherein the promoter is selected from the group consisting of pathogen-inducible, constitutive, tissue-preferred, wound-inducible, and chemical-regulated promoters.

15. The plant of embodiment any one of embodiments 12-14, wherein the plant is a solanaceous plant.

16. The plant of embodiment any one of embodiments 12-15, wherein the solanaceous plant is selected from the group consisting of potato, tomato, eggplant, pepper, tobacco, and petunia.

17. The plant of any one of embodiments 12-16, wherein plant comprises enhanced resistance to a plant disease caused by at least one race of at least one Phytophthora sp., relative to a control plant.

18. The plant of embodiment 17, wherein the plant comprises enhanced resistance to late blight caused by at least one race of *Phytophthora infestans*, relative to a control plant.

19. The plant of any one of embodiments 12-18, wherein the plant is a potato or tomato plant.

20. A method for enhancing the resistance of a plant to a plant disease caused by at least one race of at least one *Phytophthora* sp., the method comprising modifying at least one plant cell to comprise a heterologous polynucleotide, the heterologous polynucleotide comprising a nucleotide sequence selected from the group consisting of:

(a) the nucleotide sequence set forth in SEQ ID NO: 1, 4, 7, 10, 13, 16, 19, 22, 31, 32, 33, 34, 35, 46, 51, 56, or 61;

(b) a nucleotide sequence encoding the amino acid sequence set forth in SEQ ID NO: 2, 5, 8, 11, 14, 17, 20, 24, 28, 29, 30, 41, 42, 43, 44, 45, 47, 48, 52, 53, 57, 58, 62, or 63;

(c) the nucleotide sequence set forth in SEQ ID NO: 3, 6, 9, 12, 15, 18, 21, 23, 25, 26, 27, 36, 37, 38, 39, 40, 49, 50, 54, 55, 59, 60, 64, or 65;

(d) a nucleotide sequence having at least 90% sequence identity to at least one of the nucleotide sequences set forth in SEQ ID NOS: 1, 3, 4, 6, 7, 9, 10, 12, 13, 15, 16, 18, 19, 21, 22, 23, 25, 26, 27, 31, 32, 33, 34, 35, 36, 37, 38, 39, 40, 46, 49, 50, 51, 54, 55, 56, 59, 60, 61, 64, and 65, wherein the nucleic acid molecule is capable of conferring resistance to a plant disease caused by at least one race of at least one *Phytophthora* sp. to a plant comprising the nucleic acid molecule; and (e) a nucleic acid molecule comprising a nucleotide sequence encoding an amino acid sequence having at least 90% sequence identity to at least one of the amino acid sequences set forth in SEQ ID NO: 2, 5, 8, 11, 14, 17, 20, 24, 28, 29, 30, 41, 42, 43, 44, 45, 47, 48, 52, 53, 57, 58, 62, and 63, wherein the nucleic acid molecule is capable of conferring resistance to a plant disease caused by at least one race of at least one *Phytophthora* sp. to a plant comprising the nucleic acid molecule.

21. The method of embodiment 20, wherein the heterologous polynucleotide is stably incorporated into the genome of the plant cell.

22. The method of embodiment 20 or 21, wherein the plant cell is regenerated into a plant comprising in its genome the heterologous polynucleotide.

23. The method of any one of embodiments 20-22, wherein modifying at least one plant cell to comprise a heterologous polynucleotide comprises introducing the heterologous polynucleotide into at least one plant cell.

24. The method of any one of embodiments 20-23, wherein the heterologous polynucleotide comprises the nucleotide sequence of any one of (b)-(e) and further comprises a promoter operably linked for the expression of the nucleotide sequence in a plant.

25. The method of embodiment 24, wherein the promoter is selected from the group consisting of pathogen-inducible, constitutive, tissue-preferred, wound-inducible, and chemical-regulated promoters.

26. The method of any one of embodiments 20-22, wherein modifying at least one plant cell to comprise a heterologous polynucleotide comprises using genome editing to modify the nucleotide sequences of a native or non-native gene in the genome of the plant cell to comprise the nucleotide sequence of any one of (a)-(e).

27. The method of embodiment 26, wherein the modifying further comprise introducing a nucleic acid molecule into the plant cell, wherein the nucleic acid molecule comprises a nucleotide sequence comprising at least a part of the nucleotide sequence of any one of (a)-(e).

28. The method of embodiment 27, wherein at least a portion of the at least a part of the nucleotide sequence of the native or non-native gene is replaced with at least a part of the nucleotide sequence of the nucleic acid molecule.

29. The method of any one of embodiments 22-28, wherein the plant comprising the heterologous polynucleotide comprises enhanced resistance to a plant disease caused by at least one race of at least one *Phytophthora* sp., relative to a control plant.

30. The method of any one of embodiments 22-29, wherein the plant comprising the heterologous polynucleotide comprises enhanced resistance to late blight caused by at least two races of *Phytophthora infestans*, relative to a control plant.

31. The method of any one of embodiments 20-30, wherein the plant is a potato or a tomato plant.

32. A plant produced by the method of any one of embodiments 20-31.

33. A fruit, tuber, leaf, or seed of the plant of any one of embodiments 9-19 and 32, wherein the fruit, tuber, leaf or seed comprises the heterologous polynucleotide.

34. A method of limiting a plant disease caused by at least one race of at least one *Phytophthora* sp. in agricultural crop production, the method comprising planting a seedling, tuber, or seed of the plant of any one of embodiments 9-19 and 32 and growing the seedling, tuber, or seed under conditions favorable for the growth and development of a plant resulting therefrom, wherein the seedling, tuber, or seed comprises the nucleic acid molecule, expression cassette, vector, or heterologous polynucleotide.

35. The method of embodiment 34, further comprising harvesting at least one fruit, tuber, leaf and/or seed from the plant.

36. A method for identifying a solanaceous plant that displays newly conferred or enhanced resistance to a plant disease caused by at least one race of at least one *Phytophthora* sp., the method comprising detecting in the plant, or in at least one part or cell thereof, the presence of an Rpi-amr nucleotide sequence.

37. The method of embodiment 36, wherein the plant disease is late blight caused by at least one race of *Phytophthora infestans*.

38. The method of embodiment 36 or 37, wherein the solanaceous plant is a potato or tomato plant.

39. The method of any one of embodiments 36-38, wherein the presence of the Rpi-amr nucleotide sequence is detected by detecting at least one marker within the Rpi-amr nucleotide sequence.

40. The method of any one of embodiments 36-39, wherein the Rpi-amr nucleotide sequence comprises or consists of the nucleotide sequence set forth in SEQ ID NOS: 11, 3, 4, 6, 7, 9, 10, 12, 13, 15, 16, 18, 19, 21, 22, 23, 25, 26, 27, 31, 32, 33, 34, 35, 36, 37, 38, 39, 40, 46, 49, 50, 51, 54, 55, 56, 59, 60, 61, 64, and 65.

41. The method of any one of embodiments 36-39, wherein detecting the presence of the Rpi-amr nucleotide sequence comprises a member selected from the group consisting of PCR amplification, nucleic acid sequencing, nucleic acid hybridization, and an immunological assay for the detection of the R protein encoded by the Rpi-amr nucleotide sequence.

42. A solanaceous plant identified by the method of any one of embodiments 36-41.

43. The solanaceous plant of embodiment 42, wherein the solanaceous plant is not *Solanum americanum* and/or *Solanum nigrescens*.

44. A fruit, tuber, leaf, or seed of the solanaceous plant of embodiment 42 or 43.

45. A plant or plant cell comprising: (i) at least one of an Rpi-amr1e, an allele of Rpi-amr1e, Rpi-amr7d, and Rpi-amr8c, wherein the plant is not a *Solanum americanum* plant and the plant cell is not a *Solanum americanum* plant cell or (ii) Rpi-amr6b, wherein the plant is not a *Solanum nigrescens* plant and the plant cell is not a *Solanum nigrescens* plant cell.

46. The plant or plant cell of embodiment 45, wherein the plant is a solanaceous plant and the plant cell is a solanaceous plant cell.

47. A method for introducing at least one Rpi-amr gene into a plant, the method comprising:
    (a) crossing a first plant comprising in its genome at least one copy of at least one Rpi-amr gene with a second plant lacking in its genome the at least one Rpi-amr gene, whereby at least one progeny plant is produced; and
    (b) selecting at least one progeny plant comprising in its genome the at least one Rpi-amr gene.

48. The method of embodiment 47, wherein the first plant is *Solanum americanum* plant and the second plant is not a *Solanum americanum* plant or wherein the first plant is *Solanum nigrescens* plant and the second plant is not a *Solanum nigrescens* plant.

49. The method of embodiment 47 or 48, wherein the second plant is a *Solanum tuberosum* plant or a *Solanum lycopersicum* plant.

50. The method of any one of embodiments 47-49, wherein at least one Rpi-amr gene comprises a nucleotide sequence selected from the group consisting of:
    (a) the nucleotide sequence set forth in SEQ ID NO: 1, 4, 7, 10, 13, 16, 19, 22, 31, 32, 33, 34, 35, 46, 51, 56, or 61:
    (b) a nucleotide sequence encoding the amino acid sequence set forth in SEQ ID NO: 2, 5, 8, 11, 14, 17, 20, 24, 28, 29, 30, 41, 42, 43, 44, 45, 47, 48, 52, 53, 57, 58, 62, or 63;
    (c) the nucleotide sequence set forth in SEQ ID NO: 3, 6, 9, 12, 15, 18, 21, 23, 25, 26, 27, 36, 37, 38, 39, 40, 49, 50, 54, 55, 59, 60, 64, or 65;
    (d) a nucleotide sequence having at least 90% sequence identity to at least one of the nucleotide sequences set forth in SEQ ID NOS: 1, 3, 4, 6, 7, 9, 10, 12, 13, 15, 16, 18, 19, 21, 22, 23, 25, 26, 27, 31, 32, 33, 34, 35, 36, 37, 38, 39, 40, 46, 49, 50, 51, 54, 55, 56, 59, 60, 61, 64, and 65, wherein the nucleic acid molecule is capable of conferring resistance to a plant disease caused by at least one race of at least one *Phytophthora* sp. to a plant comprising the nucleic acid molecule; and
    (e) a nucleic acid molecule comprising a nucleotide sequence encoding an amino acid sequence having at least 90% sequence identity to at least one of the amino acid sequences set forth in SEQ ID NO: 2, 5, 8, 11, 14, 17, 20, 24, 28, 29, 30, 41, 42, 43, 44, 45, 47, 48, 52, 53, 57, 58, 62, and 63, wherein the nucleic acid molecule is capable of conferring resistance to a plant disease caused by at least one race of at least one *Phytophthora* sp. to a plant comprising the nucleic acid molecule.

51. The method of any one of embodiments 47-50, wherein selecting at least one progeny plant comprises detecting in the progeny plant, or in at least one part or cell thereof, the presence of an Rpi-amr nucleotide sequence using the method according to any one of embodiments 36-41.

52. The method of any one of embodiments 47-51, further comprising (i) backcrossing at least one selected progeny plant of (b) to a solanaceous plant that is of the same species and genotype as second solanaceous plant or of the same species as the second solanaceous plant and lacking in its genome the at least one Rpi-amr gene, whereby at least one progeny plant is produced from the backcrossing; and (ii) selecting at least one progeny plant comprising in its genome the at least one Rpi-amr gene that is produced from the backcrossing of (i).

53. A progeny plant according to any one of embodiments 47-52.

54. The progeny plant of embodiment 53, wherein the solanaceous plant is not *Solanum americanum* and/or *Solanum nigrescens*.

55. A fruit, tuber, leaf, or seed of the solanaceous plant of embodiment 53 or 54.

56. Use of the plant, fruit, tuber, leaf or seed of any one of embodiments 9-19, 32, 33, 42-46, and 53-55 in agriculture.

57. A human or animal food product comprising, or produced using, the plant, fruit, tuber, leaf and/or seed of any one of embodiments 9-19, 32, 33, 42-46, and 53-54.

58. A polypeptide comprising an amino acid sequence selected from the group consisting of:
    (a) the amino acid sequence set forth in SEQ ID NO: 2, 5, 8, 11, 14, 17, 20, 24, 28, 29, 30, 41, 42, 43, 44, 45, 47, 48, 52, 53, 57, 58, 62, or 63:
    (b) the amino acid sequence encoded by the nucleotide sequence set forth in SEQ ID NO: 1, 3, 4, 6, 7, 9, 10, 12, 13, 15, 16, 18, 19, 21, 22, 23, 25, 26, 27, 31, 32, 33, 34, 35, 36, 37, 38, 39, 40, 46, 49, 50, 51, 54, 55, 56, 59, 60, 61, 64, or 65; and
    (c) an amino acid sequence having at least 90% sequence identity to at least one of the amino acid sequences set forth in SEQ ID NOS: 2, 5, 8, 11, 14, 17, 20, 24, 28, 29, 30, 41, 42, 43, 44, 45, 47, 48, 52, 53, 57, 58, 62, and 63, wherein a polypeptide comprising the amino acid sequence is capable of conferring resistance to a plant disease caused by at least one race of at least one *Phytophthora* sp. to a plant comprising the polypeptide.

Additional embodiments of the methods and compositions of the present invention are described elsewhere herein.

Unless expressly stated or apparent from the context of usage, the methods and compositions of the present invention can be used with any plant species including, for example, monocotyledonous plants, dicotyledonous plants, and conifers. Examples of plant species of interest include, but are not limited to, corn (*Zea mays*), *Brassica* sp. (e.g. *B. napus, B. rapa, B. juncea*), particularly those *Brassica* species useful as sources of seed oil, alfalfa (*Medicago sativa*), rice (*Oryza sativa*), rye (*Secale cereale*), triticale (×Triticosecale or *Triticum*×*Secale*) sorghum (*Sorghum bicolor, Sorghum vulgare*), teff (*Eragrostis tef*), millet (e.g. pearl millet (*Pennisetum glaucum*), proso millet (*Panicum miliaceum*), foxtail millet (*Setaria italica*), finger millet (*Eleusine coracana*)), switchgrass (*Panicum virgatum*), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), strawberry (e.g. *Fragaria*× *ananassa, Fragaria vesca, Fragaria moschata, Fragaria virginiana, Fragaria chiloensis*), sweet potato (*Ipomoea batatus*), yam (*Dioscorea* spp., *D. rotundata, D. cayenensis, D. alata, D. polystachwya, D. bulbifera, D. esculenta, D. dumetorum, D. trifida*), cassava (*Manihot esculenta*), coffee (*Coffea* spp.), coconut (*Cocos nucifera*), oil palm (e.g. *Elaeis guineensis, Elaeis oleifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), date (*Phoenix dactylifera*), cultivated forms of *Beta vulgaris* (sugar beets, garden beets, chard or spinach beet, mangelwurzel or fodder beet), sugarcane (*Saccharum* spp.), oat (*Avena sativa*), barley (*Hordeum vulgare*), cannabis (*Cannabis sativa, C. indica. C. ruderalis*), poplar (*Populus* spp.), eucalyptus (*Eucalyptus* spp.), *Arabidopsis thaliana. Arabidopsis rhizogenes, Nicotiana benthamiana, Brachypodium distachyon* vegetables, ornamentals, and conifers and other trees. In specific embodiments, plants of the present invention are crop plants (e.g. potato, tobacco, tomato, maize, sorghum, wheat, millet, rice, barley, oats, sugarcane, alfalfa, soybean, peanut, sunflower, cotton, safflower, *Brassica* spp., lettuce, strawberry, apple, citrus, etc.).

Vegetables include tomatoes (*Lycopersicon esculentum*), eggplant (also known as "aubergine" or "brinjal") (*Solanum melongena*), pepper (*Capsicum annuum*), lettuce (e.g. *Lactuca sativa*), green beans (*Phaseolus vulgaris*), lima beans (*Phaseolus limensis*), peas (*Lathyrus* spp.), chickpeas (*Cicer arietinum*), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Fruit trees and related plants include, for example, apples, pears, peaches, plums, oranges, grapefruits, limes, pomelos, palms, and bananas. Nut trees and related plants include, for example, almonds, cashews, walnuts, pistachios, macadamia nuts, filberts, hazelnuts, and pecans.

In specific embodiments, the plants of the present invention are crop plants such as, for example, maize (corn), soybean, wheat, rice, cotton, alfalfa, sunflower, canola (*Brassica* spp., particularly *Brassica napus, Brassica rapa, Brassica juncea*), rapeseed (*Brassica napus*), sorghum, millet, barley, triticale, safflower, peanut, sugarcane, tobacco, potato, tomato, and pepper.

Preferred plants of the invention are solanaceous plants. As used herein, the term "solanaceous plant" refers to a plant that is a member of the Solanaceae family. Such solanaceous plants include, for example, domesticated and non-domesticated members of Solanaceae family. *Solanaceous* plants of the present invention include, but are not limited to, potato (*Solanum tuberosum*), eggplant (*Solanum melongena*), petunia (*Petunia* spp., e.g. *Petunia×hybrida* or *Petunia hybrida*), tomatillo (*Physalis philadelphica*), Cape gooseberry (*Physalis peruviana*), *Physalis* sp., woody nightshade (*Solanum dulcamara*), garden huckleberry (*Solanum scabrum*), gboma eggplant (*Solanum macrocarpon*), pepper (*Capsicum* spp; e.g. *Capsicum annuum, C. baccaltum, C. chinense, C. frutescens, C. pubescens*, and the like), tomato (*Solanum lycopersicum* or *Lycopersicon esculentum*), tobacco (*Nicotiana* spp., e.g. *N. tabacum. N. benthamiana*), *Solanum americanum, Solanum nigrescens Solanum demissum, Solanum stolonferum, Solanum papita, Solanum bulbocastanum, Solanum edinense, Solanum schenckii, Solanum hjertingii, Solanum venturi, Solanum mochiquense, Solanum chacoense*, and *Solanum pimpinellifolium*. In preferred embodiments of the methods and compositions of the present invention, the solanaceous plants are solanaceous plants grown in agriculture including, but not limited to, potato, tomato, tomatillo, Cape gooseberry, eggplant, pepper, tobacco, and *petunia* In more preferred embodiments, the solanaceous plants are potato and tomato. In even more preferred embodiments, the preferred plant is potato. In certain other embodiments of the methods and compositions disclosed herein, the preferred solanaceous plants are all solanaceous plants except for *Solanum americanum* and/or *Solanum nigrescens*. In yet other embodiments of the methods and compositions disclosed herein, the preferred plants are all plants except for *Solanum americanum* and/or *Solanum nigrescens*.

The term "solanaceous plant" is intended to encompass solanaceous plants at any stage of maturity or development, as well as any cells, tissues or organs (plant parts) taken or derived from any such plant unless otherwise clearly indicated by context. *Solanaceous* plant parts include, but are not limited to, fruits, stems, tubers, roots, flowers, ovules, stamens, leaves, embryos, meristematic regions, callus tissue, anther cultures, gametophytes, sporophytes, pollen, microspores, protoplasts, and the like. As used herein, the term "tuber" is intended to mean a whole tuber or any part thereof such as, for example, a slice or a portion of potato tuber comprising one or more buds (i.e. "eyes") suitable for planting in a field to produce a potato plant. The present invention also includes seeds produced by the solanaceous plants of the present invention.

The composition and methods of the present invention find us in producing plants with enhanced resistance to at least one race of at least one *Phytophthora* sp. In preferred embodiments of the invention, the *Phytophthora* sp. is *Phytophthora infestans*. In other embodiments, the *Phytophthora* sp. is a *Phytophthora* sp. that is capable of causing a plant disease on at least one plant. For the present invention, *Phytophthora* spp. include, but are not limited to, *Phytophthora infestans, Phytophthora parasitica. Phytophthora ramorum, Phytophthora ipomoeae, Phytophthora mirabilis, Phytophthora capsici, Phytophthora porri, Phytophthora sojae, Phytophthora palmivora*, and *Phytophthora phaseoli*.

In one embodiment of the invention, the nucleotide sequences encoding R proteins have at least about 75%, 80%, 85%, 90%, 91%, 92%, 93%, 94%, 95%, 96%, 97%, 98%, 99% or more sequence identity to the entire nucleotide sequence set forth in at least one of SEQ ID NOS: 1, 4, 7, 10, 13, 16, 19, 22, 31, 32, 33, 34, 35, 46, 51, 56, and 61 or to a fragment thereof. In another embodiment of the invention, the nucleotide sequences encoding R proteins have at least about 75%, 80%, 85%, 90%, 91%, 92%, 93%, 94%, 95%, 96%, 97%, 98%, 99% or more sequence identity to the entire nucleotide sequence set forth in at least one of SEQ ID NOS: 3, 6, 9, 12, 15, 18, 21, 23, 25, 26, 27, 36, 37, 38, 39, 40, 49, 50, 54, 55, 59, 60, 64, and 65 or to a fragment thereof.

The present invention encompasses isolated or substantially purified polynucleotide (also referred to herein as "nucleic acid molecule", "nucleic acid" and the like) or protein (also referred to herein as "polypeptide") compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized.

Optimally, an "isolated" polynucleotide is free of sequences (optimally protein encoding sequences) that naturally flank the polynucleotide (i.e. sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed polynucleotides and proteins encoded thereby are also encompassed by the present invention. By "fragment" is intended a portion of the polynucleotide or a portion of the amino acid sequence and hence protein encoded thereby. Fragments of polynucleotides comprising coding sequences may encode protein fragments that retain biological activity of the full-length or native protein. Alternatively, fragments of a polynucleotide that are useful as hybridization probes generally do not encode proteins that retain biological activity or do not retain promoter activity. Thus, fragments of a nucleotide sequence may range from at least about 20 nucleotides, about 50 nucleotides, about 100 nucleotides, and up to the full-length polynucleotide of the invention.

In certain embodiments of the invention, the fragments and variants of the disclosed polynucleotides and proteins encoded thereby are those that are capable of conferring to a plant resistance to a plant disease caused by at least one race of at least one Phytophthora sp. Preferably, a polynucleotide comprising a fragment of a native R polynucleotide of the present invention is capable of conferring resistance to a plant disease caused by at least one race of at least one Phytophthora sp. to a plant comprising the polynucleotide. Likewise, a protein or polypeptide comprising a native R protein of the present invention is preferably capable of conferring resistance to a plant disease caused by at least one race of at least one Phytophthora sp. to a plant comprising the protein or polypeptide.

Polynucleotides that are fragments of a native R polynucleotide comprise at least 16, 20, 50, 75, 100, 125, 150, 175, 200, 250, 300, 350, 400, 450, 500, 600, 700, 800, 900, 1000, 1500, 2000, 3000, 4000, 5000, 6000, 7000, 8000, or 9000 contiguous nucleotides, or up to the number of nucleotides present in a full-length R polynucleotide disclosed herein.

"Variants" is intended to mean substantially similar sequences. For polynucleotides, a variant comprises a polynucleotide having deletions (i.e. truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the R proteins of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode an R protein of the invention. Generally, variants of a particular polynucleotide of the invention will have at least about 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein. In certain embodiments of the invention, variants of a particular polynucleotide of the invention will have at least about 75%, 80%, 85%, 90%, 91%, 92%, 93%, 94%, 95%, 96%, 97%, 98%, 99% or more sequence identity to at least one nucleotide sequence selected from the group consisting of SEQ ID NOS: 1, 3, 4, 6, 7, 9, 10, 12, 13, 15, 16, 18, 19, 21, 22, 23, 25, 26, 27, 31, 32, 33, 34, 35, 36, 37, 38, 39, 40, 46, 49, 50, 51, 54, 55, 56, 59, 60, 61, 64, and 65, and optionally comprise a non-naturally occurring nucleotide sequence that differs from the nucleotide sequence set forth in SEQ ID NO: 1, 3, 4, 6, 7, 9, 10, 12, 13, 15, 16, 18, 19, 21, 22, 23, 25, 26, 27, 31, 32, 33, 34, 35, 36, 37, 38, 39, 40, 46, 49, 50, 51, 54, 55, 56, 59, 60, 61, 64, and/or 65 by at least one nucleotide modification selected from the group consisting of the substitution of at least one nucleotide, the addition of at least one nucleotide, and the deletion of at least one nucleotide. It is understood that the addition of at least one nucleotide can be the addition of one or more nucleotides within a nucleotide sequence of the present invention (e.g. SEQ ID NO: 1, 3, 4, 6, 7, 9, 10, 12, 13, 15, 16, 18, 19, 21, 22, 23, 25, 26, 27, 31, 32, 33, 34, 35, 36, 37, 38, 39, 40, 46, 49, 50, 51, 54, 55, 56, 59, 60, 61, 64, or 65), the addition of one or more nucleotides to the 5' end of a nucleotide sequence of the present invention, and/or the addition of one or more nucleotides to the 3' end of a nucleotide sequence of the present invention.

Variants of a particular polynucleotide of the invention (i.e. the reference polynucleotide) can also be evaluated by comparison of the percent sequence identity between the polypeptide encoded by a variant polynucleotide and the polypeptide encoded by the reference polynucleotide. Thus, for example, a polynucleotide that encodes a polypeptide with a given percent sequence identity to at least one polypeptide having the amino acid sequence selected from the group consisting of SEQ ID NOS: 2, 5, 8, 11, 14, 17, 20, 24, 28, 29, 30, 41, 42, 43, 44, 45, 47, 48, 52, 53, 57, 58, 62, and 63 is disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 60%, 65%, 70%, 75%, 80%, 85%, 90%, 91%, 92%, 93%, 94%, 95%, 96%, 97%, 98%, 99% or more sequence identity. In certain embodiments of the invention, variants of a particular polypeptide of the invention will have at least about 60%, 65%, 70%, 750/6, 80%, 85%, 90%, 91%, 92%, 93%, 94%, 95%, 96%, 97%, 98%, 99% or more sequence identity to at least one of the amino acid sequences set forth in SEQ ID NOS: 2, 5, 8, 11, 14, 17, 20, 24, 28, 29, 30, 41, 42, 43, 44, 45, 47, 48, 52, 53, 57, 58, 62, or 63, and optionally comprises a non-naturally occurring amino acid sequence that differs from at least one amino acid sequence selected from the group consisting of SEQ ID NOS: 2, 5, 8, 11, 14, 17, 20, 24, 28, 29, 30, 41, 42, 43, 44, 45, 47, 48, 52, 53, 57, 58, 62, and 63 by at least one amino acid modification selected from the group consisting of the substitution of at least one amino acid, the addition of at least one amino acid, and the deletion of at least one amino acid. It is understood that the addition of at least one amino acid can be the addition of one or more amino acids within an amino acid sequence of the present invention (e.g. SEQ ID NO: 2, 5, 8, 11, 14, 17, 20, 24, 28, 29, 30, 41, 42, 43, 44, 45, 47, 48, 52, 53, 57, 58, 62, or 63), the addition of one or more amino acids to the N-terminal end of an amino acid sequence of the present invention, and/or the addition of one or more amino acids to the C-terminal end of an amino acid sequence of the present invention.

"Variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Such variants may result from, for example, genetic polymorphism or from human manipulation. Biologically active variants of an R protein will have at least about 75%, 80%, 85%, 90%, 91%, 92%, 93%, 94%°, 95%, 96%, 97%, 98%, 99% or more sequence identity to the amino acid sequence for the native protein (e.g. the amino acid sequence set forth in SEQ ID NO: 2, 5, 8, 11, 14, 17, 20, 24, 28, 29, 30, 41, 42, 43, 44, 45, 47, 48, 52, 53, 57, 58, 62, or 63) as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymollette.* 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington. D.C.), herein incorporated by reference. Conservative substitutions, such as exchanging one amino acid with another having similar properties, may be optimal.

Thus, the genes and polynucleotides of the invention include both the naturally occurring sequences as well as mutant and other variant forms. Likewise, the proteins of the invention encompass naturally occurring proteins as well as variations and modified forms thereof. More preferably, such variants confer to a plant or part thereof comprising the variant enhanced resistance a plant disease caused by at least one race of at least one *Phytophthora* sp. In some embodiments, the mutations that will be made in the DNA encoding the variant will not place the sequence out of reading frame. Optimally, the mutations will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assays that are disclosed herein below.

Variant polynucleotides and proteins also encompass sequences and proteins derived from a mutagenic and recombinogenic procedure such as DNA shuffling. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that encode R proteins having at least 60% amino acid sequence identity to a full-length amino acid sequence of at least one of the R proteins disclosed herein or otherwise known in the art, or to variants or fragments thereof, are encompassed by the present invention.

In one embodiment, the orthologs of the present invention have coding sequences comprising at least 80%, 85%, 90%, 91%, 92%, 93%, 94%, 95%, 96%, 97%, 98%, 99%, or greater nucleotide sequence identity to at least one nucleotide sequence selected from the group consisting of the nucleotide sequences set forth in SEQ ID NOS: 1, 3, 4, 6, 7, 9, 10, 12, 13, 15, 16, 18, 19, 21, 22, 23, 25, 26, 27, 31, 32, 33, 34, 35, 36, 37, 38, 39, 40, 46, 49, 50, 51, 54, 55, 56, 59, 60, 61, 64, and 65 and/or encode proteins comprising least 80%, 85%, 90%, 91%, 92%, 93%, 94%, 95%, 96%, 97%, 98%, 99%, or greater amino acid sequence identity to at least one amino acid sequence selected from the group consisting of the amino acid sequences set forth in SEQ ID NOS: 2, 5, 8, 11, 14, 17, 20, 24, 28, 29, 30, 41, 42, 43, 44, 45, 47, 48, 52, 53, 57, 58, 62, and 63.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, New York). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e. genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the polynucleotides of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, New York).

For example, an entire polynucleotide disclosed herein, or one or more portions thereof, may be used as a probe capable of specifically hybridizing to corresponding polynucleotide and messenger RNAs. To achieve specific hybridization under a variety of conditions, such probes include sequences that are unique among the sequence of the gene or cDNA of interest sequences and are optimally at least about 10 nucleotides in length, and most optimally at least about 20 nucleotides in length. Such probes may be used to amplify corresponding polynucleotides for the particular gene of interest from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, New York). An extensive guide to the hybridization of nucleic acids is found in Tijssen (1993) *Laboratory Techniques in Biochemistry and Molecular Biology Hybridization with Nucleic Acid Probes*, Part 1, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

It is recognized that the R protein coding sequences of the present invention encompass polynucleotide molecules comprising a nucleotide sequence that is sufficiently identical to the nucleotide sequence of any one or more of SEQ ID NOS: 1 and 3. The term "sufficiently identical" is used herein to refer to a first amino acid or nucleotide sequence that contains a sufficient or minimum number of identical or equivalent (e.g. with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, or 65% identity, preferably 75% identity, more preferably 85%, 90%, 95%, 96%, 97%, 98% or 99% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e. percent identity=number of identical positions/total number of positions (e.g. overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to the polynucleotide molecules of the invention. BLAST protein searches can be performed with the XBLAST program, score=50, wordlength=3, to obtain amino acid sequences homologous to protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g. XBLAST and NBLAST) can be used. BLAST, Gapped BLAST, and PSI-Blast, XBLAST and NBLAST are available on the World Wide Web at ncbi.nlm.nih.gov. Another preferred, non-limiting example of a mathematical algorithm utilized for the comparison of sequences is the algorithm of Myers and Miller (1988) *CABIOS* 4: 11-17. Such an algorithm is incorporated into the ALIGN program (version 2.0), which is part of the GCG sequence alignment software package. When utilizing the ALIGN program for comparing amino acid sequences, a PAM 120 weight residue table, a gap length penalty of 12, and a gap penalty of 4 can be used. Alignment may also be performed manually by inspection.

Unless otherwise stated, sequence identity/similarity values provided herein refer to the value obtained using the full-length sequences of the invention and using multiple alignment by mean of the algorithm Clustal W (Nucleic Acid Research, 22(22):4673-4680, 1994) using the program AlignX included in the software package Vector NTI Suite Version 7 (InforMax, Inc., Bethesda, Md., USA) using the default parameters; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by CLUSTALW (Version 1.83) using default parameters (available at the European Bioinformatics Institute website on the World Wide Web at ebi.ac.uk/Tools/clustalw/index).

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The heterologous polynucleotides or polynucleotide constructs comprising R protein coding regions can be provided in expression cassettes for expression in the plant or other organism or non-human host cell of interest. The cassette will include 5' and 3' regulatory sequences operably linked to the R protein coding region. "Operably linked" is intended to mean a functional linkage between two or more elements. For example, an operable linkage between a polynucleotide or gene of interest and a regulatory sequence (i.e. a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the R protein coding region to be under the transcriptional regulation of the regulatory regions. The expression cassette may additionally contain selectable marker genes.

The expression cassette will include in the 5'-3' direction of transcription, a transcriptional and translational initiation region (i.e. a promoter), a R protein coding region of the invention, and a transcriptional and translational termination region (i.e. termination region) functional in plants or other organism or non-human host cell. The regulatory regions (i.e. promoters, transcriptional regulatory regions, and translational termination regions) and/or the R protein coding region or of the invention may be native/analogous to the host cell or to each other. Alternatively, the regulatory regions and/or the R protein coding region of the invention may be heterologous to the host cell or to each other.

As used herein, "heterologous" in reference to a nucleic acid molecule, polynucleotide, nucleotide sequence, or polynucleotide construct is a nucleic acid molecule, polynucleotide, nucleotide sequence, or polynucleotide construct that originates from a foreign species, or, if from the same species, is modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

As used herein, a "native gene" is intended to mean a gene that is a naturally-occurring gene in its natural or native position in the genome of a plant. Such a native gene has not been genetically engineered or otherwise modified in nucleotide sequence and/or position in the genome the plant through human intervention, nor has such a native gene been introduced into the genome of the plant via artificial methods such as, for example, plant transformation.

As used herein, a "non-native gene" is intended to mean a gene that has been introduced into a plant by artificial means and/or comprises a nucleotide sequence that is not naturally occurring in the plant. Non-native genes include, for example, a gene (e.g. an R gene) that is introduced into the plant by a plant transformation method. Additionally, when a native gene in the genome of a plant is modified, for example by a genome-editing method, to comprise a nucleotide sequence that is different (i.e. non-identical) from the nucleotide sequence of native gene, the modified gene is a non-native gene.

The present invention provides host cells comprising at least of the nucleic acid molecules, expression cassettes, and vectors of the present invention. In preferred embodiments of the invention, a host cells is plant cell. In other embodiments, a host cell is selected from the group consisting of a bacterium, a fungal cell, and an animal cell. In certain embodiments, a host cell is non-human animal cell. However, in some other embodiments, the host cell is an in-vitro cultured human cell.

While it may be optimal to express the R protein using heterologous promoters, the native promoter of the corresponding R gene may be used.

The termination region may be native with the transcriptional initiation region, may be native with the operably linked R protein coding region of interest, may be native with the plant host, or may be derived from another source (i.e. foreign or heterologous to the promoter, the R protein of interest, and/or the plant host), or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) (ell 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); poty virus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625);

tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions, may be involved.

A number of promoters can be used in the practice of the invention. The promoters can be selected based on the desired outcome. The nucleic acids can be combined with constitutive, tissue-preferred, or other promoters for expression in plants. Such constitutive promoters include, for example, the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced expression of the R protein coding sequences within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) *Plant J.* 12(2):255-265; Kawamata et al. (1997) *Plant Cell Physiol.* 38(7):792-803; Hansen et al. (1997)*Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6): 1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Generally, it will be beneficial to express the gene from an inducible promoter, particularly from a pathogen-inducible promoter. Such promoters include those from pathogenesis-related proteins (PR proteins), which are induced following infection by a pathogen; e.g. PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988)*Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Additionally, as pathogens find entry into plants through wounds or insect damage, a wound-inducible promoter may be used in the heterologous polynucleotides of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225: 1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004). *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992)*Mol. Microbiol.* 6:2419-2422; Barkley et al. (1980) in *The Operon*, pp. 177-220; Hu et al. (1987) *Cell* 48:555-566;

Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not intended to be limiting. Any selectable marker gene can be used in the present invention.

Numerous plant transformation vectors and methods for transforming plants are available. See, for example, An, G. et al. (1986) *Plant Pysiol.*, 81:301-305; Fry, J., et al. (1987) *Plant Cell Rep.* 6:321-325; Block. M. (1988) *Theor. Appl Genet.* 76:767-774; Hinchee, et al. (1990) *Stadler. Genet. Symp.* 203212.203-212; Cousins, et al. (1991) *Aust. J. Plant Physiol.* 18:481-494; Chee, P. P. and Slightom, J. L. (1992) *Gene.* 118:255-260; Christou, et al. (1992) *Trends. Biotechnol.* 10:239-246; D'Halluin, et al. (1992) *Bio/Technol.* 10:309-314; Dhir, et al. (1992) *Plant Physiol.* 99:81-88; Casas et al. (1993) *Proc. Nat. Acad Sci. USA* 90:11212-11216; Christou, P. (1993) *In Vitro Cell. Dev. Biol.-Plant;* 29P:119-124; Davies, et al. (1993) *Plant Cell Rep.* 12:180-183; Dong, J. A. and Mchughen, A. (1993) *Plant Sci.* 91:139-148; Franklin. C. I. and Trieu, T. N. (1993) *Plant. Physiol.* 102:167; Golovkin, et al. (1993) *Plant Sci.* 90:41-52; *Guo Chin Sci. Bull.* 38:2072-2078; Asano, et al. (1994) *Plant Cell Rep.* 13; Ayeres N. M. and Park, W. D. (1994) *Crit. Rev. Plant. Sci.* 13:219-239; Barcelo, et al. (1994) *Plant. J.* 5:583-592; Becker, et al. (1994) *Plant. J.* 5:299-307; Borkowska et al. (1994) *Acta. Physiol Plant.* 16:225-230; Christou, P. (1994) *Agro. Food. Ind. Hi Tech.* 5: 17-27; Eapen et al. (1994) *Plant Cell Rep.* 13:582-586; Hartman, et al. (1994) *Bio-Technology* 12: 919923; Ritala, et al. (1994) *Plant. Mol. Biol.* 24:317-325; and Wan, Y. C. and Lemaux, P. G. (1994) *Plant Physiol.* 104:3748.

The methods of the invention involve introducing a heterologous polynucleotide or polynucleotide construct into a plant. By "introducing" is intended presenting to the plant the heterologous polynucleotide or polynucleotide construct in such a manner that the construct gains access to the interior of a cell of the plant. The methods of the invention do not depend on a particular method for introducing a heterologous polynucleotide or polynucleotide construct to a plant, only that the heterologous polynucleotide or polynucleotide construct gains access to the interior of at least one cell of the plant. Methods for introducing heterologous polynucleotides or polynucleotide constructs into plants are known in the art including, but not limited to, stable transformation methods, transient transformation methods, and virus-mediated methods.

By "stable transformation" is intended that the heterologous polynucleotide or polynucleotide construct introduced into a plant integrates into the genome of the plant and is capable of being inherited by progeny thereof. By "transient transformation" is intended that a heterologous polynucleotide or polynucleotide construct introduced into a plant does not integrate into the genome of the plant. It is recognized that stable and transient transformation methods comprise introducing one or more nucleic acid molecules (e.g. DNA), particularly one or more recombinant nucleic acid molecules (e.g. recombinant DNA) into a plant, plant cell, or other host cell or organism.

For the transformation of plants and plant cells, the nucleotide sequences of the invention are inserted using standard techniques into any vector known in the art that is suitable for expression of the nucleotide sequences in a plant or plant cell. The selection of the vector depends on the preferred transformation technique and the target plant species to be transformed.

Methodologies for constructing plant expression cassettes and introducing foreign nucleic acids into plants are generally known in the art and have been previously described. For example, foreign DNA can be introduced into plants, using tumor-inducing (Ti) plasmid vectors. Other methods utilized for foreign DNA delivery involve the use of PEG mediated protoplast transformation, electroporation, microinjection whiskers, and biolistics or microprojectile bombardment for direct DNA uptake. Such methods are known in the art. (U.S. Pat. No. 5,405,765 to Vasil et al.; Bilang et al. (1991) *Gene* 100: 247-250; Scheid et al., (1991) *Mol. Gen. Genet.*, 228: 104-112; Guerche et al., (1987) *Plant Science* 52: 111-116; Neuhause et al., (1987) *Theor. Appl Genet.* 75: 30-36; Klein et al., (1987) *Nature* 327: 70-73; Howell et al., (1980) *Science* 208:1265; Horsch et al., (1985) *Science* 227: 1229-1231; DeBlock et al., (1989) *Plant Physiology* 91: 694-701; *Methods for Plant Molecular Biology* (Weissbach and Weissbach, eds.) Academic Press, Inc. (1988) and *Methods in Plant Molecular Biology* (Schuler and Zielinski, eds.) Academic Press, Inc. (1989). The method of transformation depends upon the plant cell to be transformed, stability of vectors used, expression level of gene products and other parameters.

Other suitable methods of introducing nucleotide sequences into plant cells and subsequent insertion into the plant genome include microinjection as Crossway et al. (1986) *Biotechniques* 4:320-334, electroporation as described by Riggs et al. (1986) *Proc. Natl. Acad. Sci. USA* 83:5602-5606, *Agrobacterium*-mediated transformation as described by Townsend et al., U.S. Pat. No. 5,563,055, Zhao et al., U.S. Pat. No. 5,981,840, direct gene transfer as described by Paszkowski et al. (1984) *EMBO J.* 3:2717-2722, and ballistic particle acceleration as described in, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lecl transformation (WO 00/28058). Also see, Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563

(maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (*London*) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (*Longman*, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The polynucleotides of the invention may be introduced into plants by contacting plants with a virus or viral nucleic acids. Generally, such methods involve incorporating a heterologous polynucleotide or polynucleotide construct of the invention within a viral DNA or RNA molecule. Further, it is recognized that promoters of the invention also encompass promoters utilized for transcription by viral RNA polymerases. Methods for introducing polynucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

If desired, the modified viruses or modified viral nucleic acids can be prepared in formulations. Such formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48. Perry's Chemical Engineer's Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al. Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, antifreezing agents, for seed treatment formulation also optionally colorants and/or binders and/or gelling agents.

In specific embodiments, the polynucleotides, polynucleotide constructs, and expression cassettes of the invention can be provided to a plant using a variety of transient transformation methods known in the art. Such methods include, for example, microinjection or particle bombardment. See, for example, Crossway et al. (1986)*Mol Gen. Genet.* 202:179-185; Nomura et al. (1986) *Plant Sci.* 44:53-58; Hepler et al. (1994) *PNAS Sci.* 91: 2176-2180 and Hush et al. (1994) *J. Cell Science* 107:775-784, all of which are herein incorporated by reference. Alternatively, the polynucleotide can be transiently transformed into the plant using techniques known in the art. Such techniques include viral vector system and *Agrobacterium tumefaciens*-mediated transient expression as described elsewhere herein.

The cells that have been transformed may be grown into plants in accordance with conventional ways. See, for example. McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a heterologous polynucleotide or polynucleotide construct of the invention, for example, an expression cassette of the invention, stably incorporated into their genome.

Any methods known in the art for modifying DNA in the genome of a plant can be used to modify genomic nucleotide sequences in planta, for example, to create or insert a resistance gene or even to replace or modify an endogenous resistance gene or allele thereof. Such methods include, but are not limited to, genome-editing (or gene-editing) techniques, such as, for example, methods involving targeted mutagenesis, homologous recombination, and mutation breeding. Targeted mutagenesis or similar techniques are disclosed in U.S. Pat. Nos. 5,565,350; 5,731,181; 5,756,325; 5,760,012; 5,795,972, 5,871,984, and 8,106,259; all of which are herein incorporated in their entirety by reference. Methods for gene modification or gene replacement comprising homologous recombination can involve inducing double breaks in DNA using zinc-finger nucleases (ZFN), TAL (transcription activator-like) effector nucleases (TALEN), Clustered Regularly Interspaced Short Palindromic Repeats/CRISPR-associated nuclease (CRISPR/Cas nuclease), or homing endonucleases that have been engineered endonucleases to make double-strand breaks at specific recognition sequences in the genome of a plant, other organism, or host cell. See, for example, Durai et al., (2005) *Nucleic Acids Res* 33:5978-90; Mani et al. (2005) *Biochem Biophys Res Comm* 335:447-57; U.S. Pat. Nos. 7,163,824, 7,001,768, and 6,453,242; Arnould et al. (2006) *J Mol Biol* 355:443-58; Ashworth et al., (2006) *Nature* 441:656-9; Doyon et al. (2006) *J Am Chem Soc* 128:2477-84; Rosen et al., (2006) *Nucleic Acids Res* 34:4791-800; and Smith et al., (2006) *Nucleic Acids Res* 34:e149; U.S. Pat. App. Pub. No. 2009/0133152; and U.S. Pat. App. Pub. No. 2007/0117128; all of which are herein incorporated in their entirety by reference.

Unless stated otherwise or apparent from the context of a use, the term "gene replacement" is intended to mean the replacement of any portion of a first polynucleotide molecule or nucleic acid molecule (e.g. a chromosome) that involves homologous recombination with a second polynucleotide molecule or nucleic acid molecule using a genome-editing technique as disclosed elsewhere herein, whereby at least a part of the nucleotide sequence of the first polynucleotide molecule or nucleic acid molecule is replaced with the second polynucleotide molecule or nucleic acid molecule. It is recognized that such gene replacement can result in additions, deletions, and/or modifications in the nucleotide sequence of the first polynucleotide molecule or nucleic acid molecule and can involve the replacement of an entire gene or genes, the replacement of any part or parts of one gene, or the replacement of non-gene sequences in the first polynucleotide molecule or nucleic acid molecule.

TAL effector nucleases (TALENs) can be used to make double-strand breaks at specific recognition sequences in the genome of a plant for gene modification or gene replacement through homologous recombination. TAL effector nucleases are a class of sequence-specific nucleases that can be used to make double-strand breaks at specific target sequences in the genome of a plant or other organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) *PNAS* 10.1073/pnas. 1013133107; Scholze & Boch (2010) *Virulence* 1:428-432; Christian et al. *Genetics* (2010) 186: 757-761; Li el al. (2010) *Nuc. Acids Res.* (2010) doi: 10.1093/nar/gkq704; and Miller et al. (2011) *Nature Biotechnology* 29:143-148; all of which are herein incorporated by reference.

The CRISPR/Cas nuclease system can also be used to make double-strand breaks at specific recognition sequences in the genome of a plant for gene modification or gene replacement through homologous recombination. The CRISPR/Cas nuclease is an RNA-guided (simple guide RNA, sgRNA in short) DNA endonuclease system performing sequence-specific double-stranded breaks in a DNA segment homologous to the designed RNA. It is possible to design the specificity of the sequence (Cho S. W. et al., Nat. Biotechnol. 31:230-232, 2013; Cong L. et al., Science 339:819-823, 2013; Mali P. et al., Science 339:823-826, 2013; Feng Z. et al., Cell Research: 1-4, 2013).

In addition, a ZFN can be used to make double-strand breaks at specific recognition sequences in the genome of a plant for gene modification or gene replacement through homologous recombination. The Zinc Finger Nuclease (ZFN) is a fusion protein comprising the part of the FokI restriction endonuclease protein responsible for DNA cleavage and a zinc finger protein which recognizes specific, designed genomic sequences and cleaves the double-stranded DNA at those sequences, thereby producing free DNA ends (Urnov F. D. et al., Nat Rev Genet. 11:636-46, 2010; Carroll D., Genetics. 188:773-82, 2011).

Breaking DNA using site specific nucleases, such as, for example, those described herein above, can increase the rate of homologous recombination in the region of the breakage. Thus, coupling of such effectors as described above with nucleases enables the generation of targeted changes in genomes which include additions, deletions and other modifications.

The nucleic acid molecules, expression cassettes, vectors, and heterologous polynucleotides of the present invention may be used for transformation and/or genome editing of any plant species, including, but not limited to, monocots and dicots.

As used herein, the term "plant" includes seeds, plant cells, plant protoplasts, plant cell tissue cultures from which plants can be regenerated, plant calli, plant clumps, and plant cells that are intact in plants or parts of plants such as embryos, pollen, ovules, seeds, tubers, propagules, leaves, flowers, branches, fruits, roots, root tips, anthers, and the like. Progeny, variants, and mutants of the regenerated plants are also included within the scope of the invention, provided that these parts comprise the introduced polynucleotides. As used herein, "progeny" and "progeny plant" comprise any subsequent generation of a plant whether resulting from sexual reproduction and/or asexual propagation, unless it is expressly stated otherwise or is apparent from the context of usage.

As used herein, the terms "transgenic plant" and "transformed plant" are equivalent terms that refer to a "plant" as described above, wherein the plant comprises a heterologous nucleic acid molecule, heterologous polynucleotide, or heterologous polynucleotide construct that is introduced into a plant by, for example, any of the stable and transient transformation methods disclosed elsewhere herein or otherwise known in the art. Such transgenic plants and transformed plants also refer, for example, the plant into which the heterologous nucleic acid molecule, heterologous polynucleotide, or heterologous polynucleotide construct was first introduced and also any of its progeny plants that comprise the heterologous nucleic acid molecule, heterologous polynucleotide, or heterologous polynucleotide construct.

In certain embodiments of the invention, the methods involve the planting of seedlings and/or tubers and then growing such seedlings and tubers so as to produce plants derived therefrom and optionally harvesting from the plants a plant part or parts. As used herein, a "seedling" refers to a less than fully mature plant that is typically grown in greenhouse or other controlled- or semi-controlled (e.g. a cold frame) environmental conditions before planting or replanting outdoors or in a greenhouse for the production a harvestable plant part, such as, for example, a tomato fruit, a potato tuber or a tobacco leaf. As used herein, a "tuber" refers to an entire tuber or part or parts thereof, unless stated otherwise or apparent from the context of use. A preferred tuber of the present invention is a potato tuber.

In the methods of the invention involving planting a tuber, a part of tuber preferably comprises a sufficient portion of the tuber whereby the part is capable of growing into a plant under favorable conditions for the growth and development of a plant derived from the tuber. It is recognized that such favorable conditions for the growth and development of crop plants, particularly solanaceous crop plants, are generally known in the art.

In some embodiments of the present invention, a plant cell is transformed with a heterologous polynucleotide encoding an R protein of the present invention. The term "expression" as used herein refers to the biosynthesis of a gene product, including the transcription and/or translation of said gene product. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide. Examples of heterologous polynucleotides and nucleic acid molecules that encode R proteins are described elsewhere herein.

The use of the terms "DNA" or "RNA" herein is not intended to limit the present invention to polynucleotide molecules comprising DNA or RNA. Those of ordinary skill in the art will recognize that the methods and compositions of the invention encompass polynucleotide molecules comprised of deoxyribonucleotides (i.e. DNA), ribonucleotides (i.e. RNA) or combinations of ribonucleotides and deoxyribonucleotides. Such deoxyribonucleotides and ribonucleotides include both naturally occurring molecules and synthetic analogues including, but not limited to, nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). The polynucleotide molecules of the invention also encompass all forms of polynucleotide molecules including, but not limited to, single-stranded forms, double-stranded forms, hairpins, stem-and-loop structures, and the like. Furthermore, it is understood by those of ordinary skill in the art that the nucleotide sequences disclosed herein also encompasses the complement of that exemplified nucleotide sequence.

The invention is drawn to compositions and methods for enhancing the resistance of a plant to plant disease, particularly to compositions and methods for enhancing the resistance of a plant to a plant disease caused by at least one race of at least one Phytophthora sp. By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened.

The following examples are offered by way of illustration and not by way of limitation.

EXAMPLES

Example 1: Population Development for Testing the Genetic Basis of Solanum americanum Resistance to Phytophthora infestans Recently, the cloning of Rpi-amr3i from a Mexican accession of Solanum americanum has been reported (Witek et al. (2016) Nat. Biotechnol. 34: 656; see also WO 2016/182881; both of which are herein incorporated by reference). In an attempt to identify additional S *americanum* genes for resistance to *Phytophthora infestans*, we investigated a set of *S. americanum* (2n) accessions, obtained from seed collections (Table 1), for their immune response towards *P. infestans*.

TABLE 1

Accessions with *Phytophthora infestans* Resistance Linked to the Rpi-amr1 Locus

| Accession | Source* | Place of origin | Segregation ratio in F2 (R:S) |
|---|---|---|---|
| 954750184 | RU | unknown | 2:1 |
| sn27 | SBG | China | 3:1 |
| Veg422 | NN | United Kingdom | 3:1 |
| A14750006 | RU | unknown | 3:1 |
| SOLA 425 | IPK | Middle America** | 15:1 |
| Wang 2058 | NHM | China | 3:1 |
| A14750130 | RU | unknown | 3:1 |

*RU - Radboud University, Nijmegen, The Netherlands; IPK - IPK Gatersleben, Germany and NHM - Natural History Museum, London, United Kingdom; SBG - Shanghai Botanical Garden, Shanghai, China; NN - Nickys Nursery, Ltd, United Kingdom.
**Middle America is a region comprising the southern portion of North American and the northern portion of South American and includes Mexico, Belize, Costa Rica, El Salvador, Guatemala, Honduras, Nicaragua, Panama, Colombia and Venezuela.

Pathogen susceptibility was assessed in detached leaf assays (DLAs), using three highly virulent *P. infestans* isolates (06_3928A, 88069 and EC1). Accession 954750186 was susceptible to all tested isolates (supporting mycelial growth and sporulation (Witek et al. ((2016) *Nat Biotechnol* 34: 656)). All other accessions remained fully resistant, with no visible sign of infection or only small sites of hypersensitive response (HR) in the form of local cell death at the site of *P. infestans* inoculation.

To determine the genetic basis of *S. americanum* resistance, we crossed seven resistant accessions, namely 954750184, sn27, Veg422, A14750006, SOLA 425, Wang 2058 and A14750130 as male parents to the susceptible line 954750186. Resistant F1 plants were self-pollinated, and we tested 60 to 100 plants per F2 for the response to 06_3928A and 88069 and found that the progeny of six crosses segregated in a ratio suggesting the presence of a single (semi) dominant resistance gene (fitting 3:1 or 2:1). One cross showed 15:1 segregation, suggesting the presence of two or more unlinked R genes (Table 1).

Example 2: Mapping of the Underlying Resistance Gene in a Population Derived from the Resistant Accession 954750184

We initially focused on F2 and F3 populations derived from crosses of the resistant parent 954750184. Bulked susceptible (BS) Genomic DNA samples were created from 94 of the most susceptible F2 and F3 plants. We subsequently subjected BS gDNA, as well as from resistant (R) and susceptible parent (S) to Illumina-based RenSeq (76 bp PE reads), and additionally RAD-seq experiments. Additionally, we performed Whole Genome Shotgun sequencing (WGS) on R and S samples with Illumina HiSeq 90 bp PE reads. We used our previously published in silico trait mapping pipelines (Jupe et al. ((2013) *Plant J.* 76: 530) and Witek et al. ((2016) *Nat Biotechnol* 34: 656)) to perform single nucleotide polymorphism (SNP) calling and detection of polymorphisms linked to disease resistance. Screening a set of markers derived from these analyses on DNA of 94 susceptible F2 and F3 plants identified 12 markers linked with resistance response that flank the R locus between 7.5 cM to one side and 4.3 cM to the other side. While four markers were found to co-segregate with the resistance, two were found to be located around 1 cM on either side; CAPS marker RAD_3 (BslI) distal and the PCR-marker CLC_I (WGS_I1) to the proximal side (FIG. 1, upper horizontal bar). Both markers were subsequently used to genotype 1793 F2 plants, and identified 259 recombinants (118 homozygous susceptible—heterozygous; 110 homozygous resistant—heterozygous).

The 118 informative recombinants (homozygous susceptible to one side and heterozygous to the other) were further genotyped using the eight linked markers (FIG. 1, middle horizontal bar), and tested in DLAs for their response to *P. infestans* isolates EC1 and 06_3928A. This identified that markers CLC_3 (WGS_3) and RAD1 are flanking with a single recombination event for each marker and CLC_2 (WGS_2), 56766 and 46418 are co-segregating with the resistance locus (FIG. 1, middle horizontal bar).

Example 3: BAC Clone Selection

Comparison of the linkage map with the potato reference genome identified the homogeneous CNL-3 NLR gene sub-family to be within the cosegregating locus. This cluster comprises 18 members on potato reference chromosome 11. Marker WGS_2 was designed on a *S. americanum* WGS data derived NLR sequence, orthologous to the CNL-3 cluster. WGS_2 was then used to probe for two BAC clones (outsourced to BioS&T; Quebec, Canada; see on the World Wide Web: biost.com). While the co-segregating marker WGS_2 was present on both derived BAC clones 5G and 12H, a further co-segregating marker WGS_3 was only present on 12H. Differences between both BAC clones were further identified through the HindIII digestion pattern. Both were subsequently sequenced on the PacBio RS platform and assembled into single contigs of 125,327 bp (5G) and 144.006 bp (12H) and further assembled to a single contig of 192,456 bp.

Figure 1:
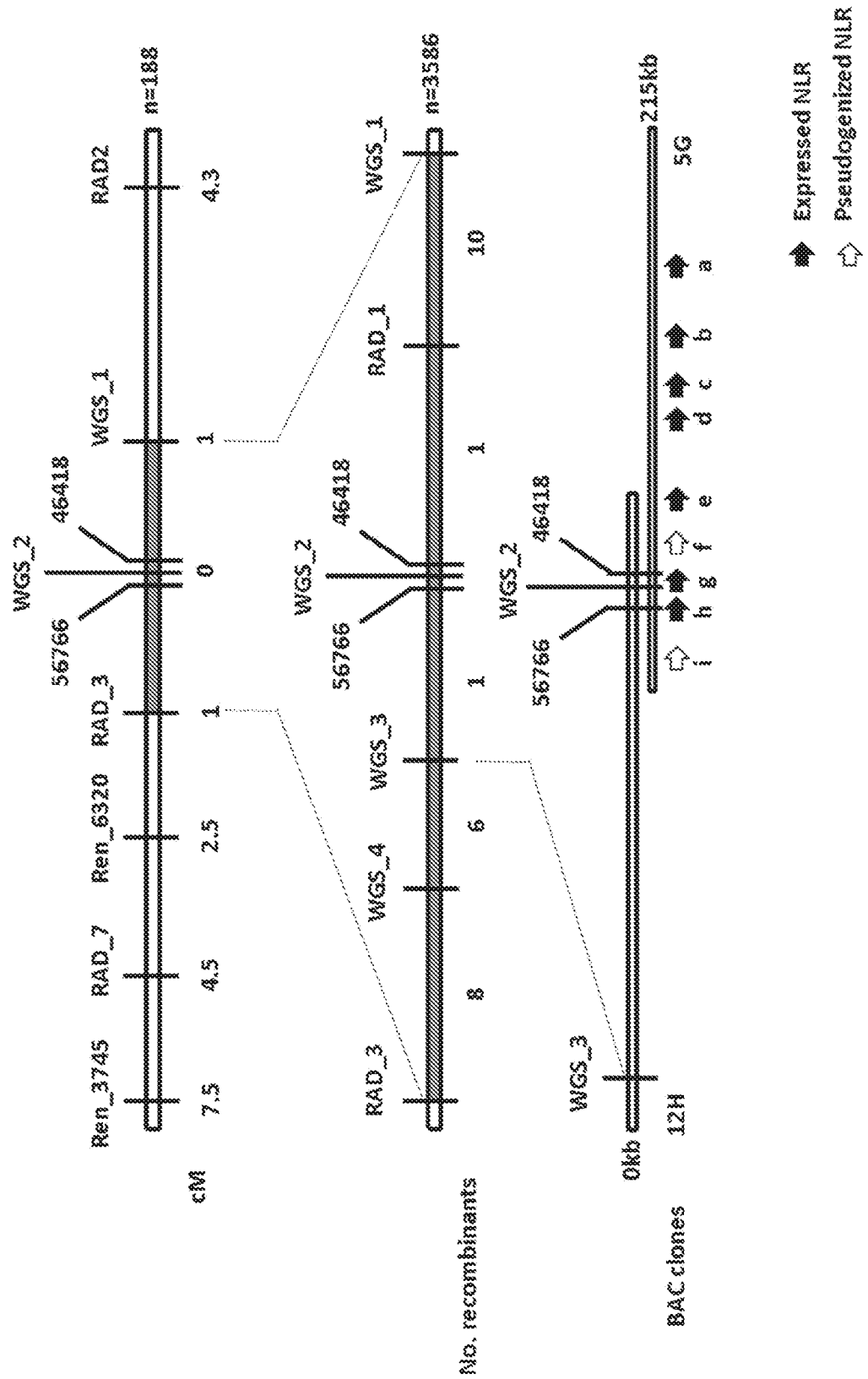
FIG. 1 is a genetic linkage map and map of co-segregating BAC clones. The upper horizontal bar is a representation of a bulked segregant analysis on 94 F2 susceptible plants coupled with RenSeq RAD-seq and Whole Genome Shotgun (WGS) led to development of flanking and co-segregating markers. Markers with only number in the name or beginning with 'Ren' are RenSeq markers, with 'WGS' are WGS derived markers and with 'RAD' are RAD-seq based markers. The middle horizontal bar is a representation of the gend of 1793 F2 plants with markers RAD_3 and WGS_1 identified 118 informative recombinants which were further phenotype and genotyped with additional markers. This analysis confirmed that WGS_2, 56766 and 46418 co-segregates with resistance. The lower horizontal bar is a schematic representation of the contig derived from two BAC clones obtained from BAC library screen with co-segregating marker WGS2. Prediction of open reading frames identified 11 potential coding sequences, nine of which were confirmed to be nucleotide-binding domain, leucine rich containing proteins (NLRs) (a-i). Solid black arrows represent expressed NLRs, white—pseudogenes.

Prediction of open reading frames identified 11 potential coding sequences, nine of which were NLRs, as identified by mapping of R parent RenSeq reads as well as NLR-parser analysis (Steuernagel et al. ((2015) *Bioinformatics* 31: 1665, FIG. 1, lower horizontal bar). All nine sequences have over 80% identity, and belong to the CNL-3 subgroup. Mapping of cDNA RenSeq reads of the R parent, identified 7 NLRs as expressed and they were further considered as candidate NLRs (Rpi-amr1a, b, c, d, e, g and h).

Figure 2:
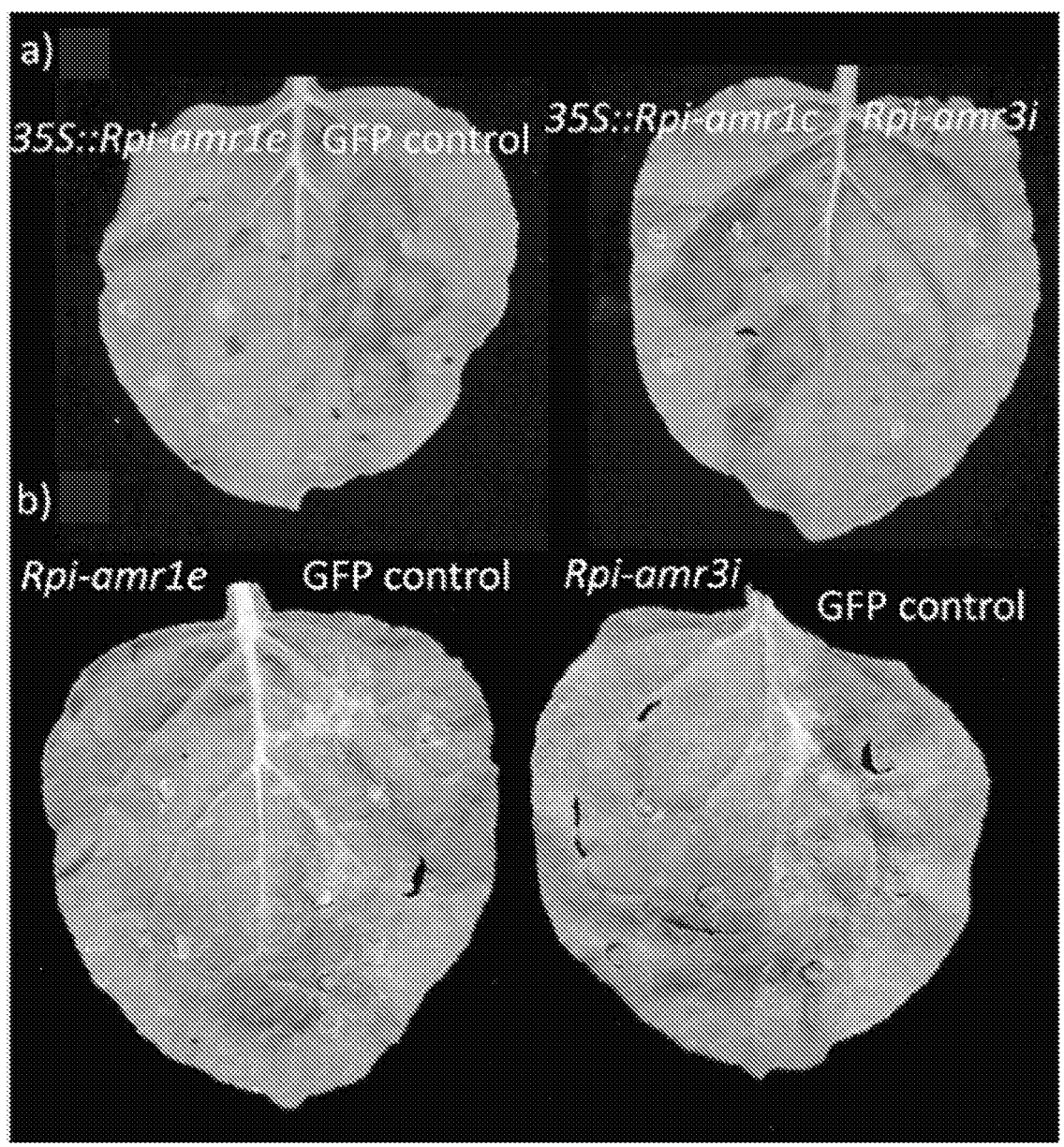
FIG. 2 is a photographic illustration showing that the candidate Rpi-amr1e confers resistance against *P. infestans* in a transient complementation assay in *N. benthamiana* leaves. The upper two leaves are the third leaves of *N. benthamiana* plants that were infiltrated with the vector pICSLUS0003::35S overexpressing Rpi-amr3i (positive control), Rpi-amr1 candidates, or GFP (negative control), and 24 hours later inoculated with the *P. infestans* strain 88069. No *P. infestans* growth was observed for Rpi-amr3i and Rpi-amr1e (pictured), while *P. infestans* growth was unaltered at infiltration sites of all other Rpi-amr1e candidates and the GFP control. The figure shows Rpi-amr1c as an example. Photographs were taken 6 days post inoculation. The lower two leaves are from a transient complementation assay with the Rpi-amr1e genomic construct (native promoter and terminator) with *P. infestans* applied at the same level as under the 35S promoter. A vector overexpressing GFP was used as a negative control. The experiment was performed as described previously (Witek et al. (2016) *Nat. Biotechnol.* 34: 656). The photographs were taken 6 days post inoculation.

Example 4: Transient Expression of Seven Expressed NLR Genes in *Nicotiana benthamiana* Reveals One that Confers *P. Infestans* Resistance We cloned the open reading frames of the 7 candidate NLRs into a binary expression vector under control of a 35S promoter and transformed into *Agrobacterium*. These constructs were transiently expressed in *N. benthamiana* detached leaves, which were subsequently inoculated with the *P. infestans* isolate 88069 as described in Witek et al. ((2016) *Nat Biotechnol* 34: 656). *P. infestans* growth was observed 6 days post inoculation on GFP-infiltrated control leaves and all other constructs, except for the Rpi-amr3i control and the candidate gene Rpi-amr1e. 35S:Rpi-acmr1e infiltrated leaves showed no to small HR at 6 days post inoculation (dpi) (FIG. 2, upper left leaf). Transient delivery of candidate Rpi-amle under its native promoter and terminator elements (1.7 kb 5' and 1.3 kb 3', nucleotides 1 to 1665 and 4429 to 5732, respectively, of SEQ ID NO: 1) followed by *P. infestans* infection (FIG. 2, lower left leaf) showed the same level of resistance as the 35S:Rpi-amr1e construct (FIG. 2, upper left leaf). This transient expression system identified candidate Rpi-amr1e as the functional Rpi-amr1 gene.

Figure 3:
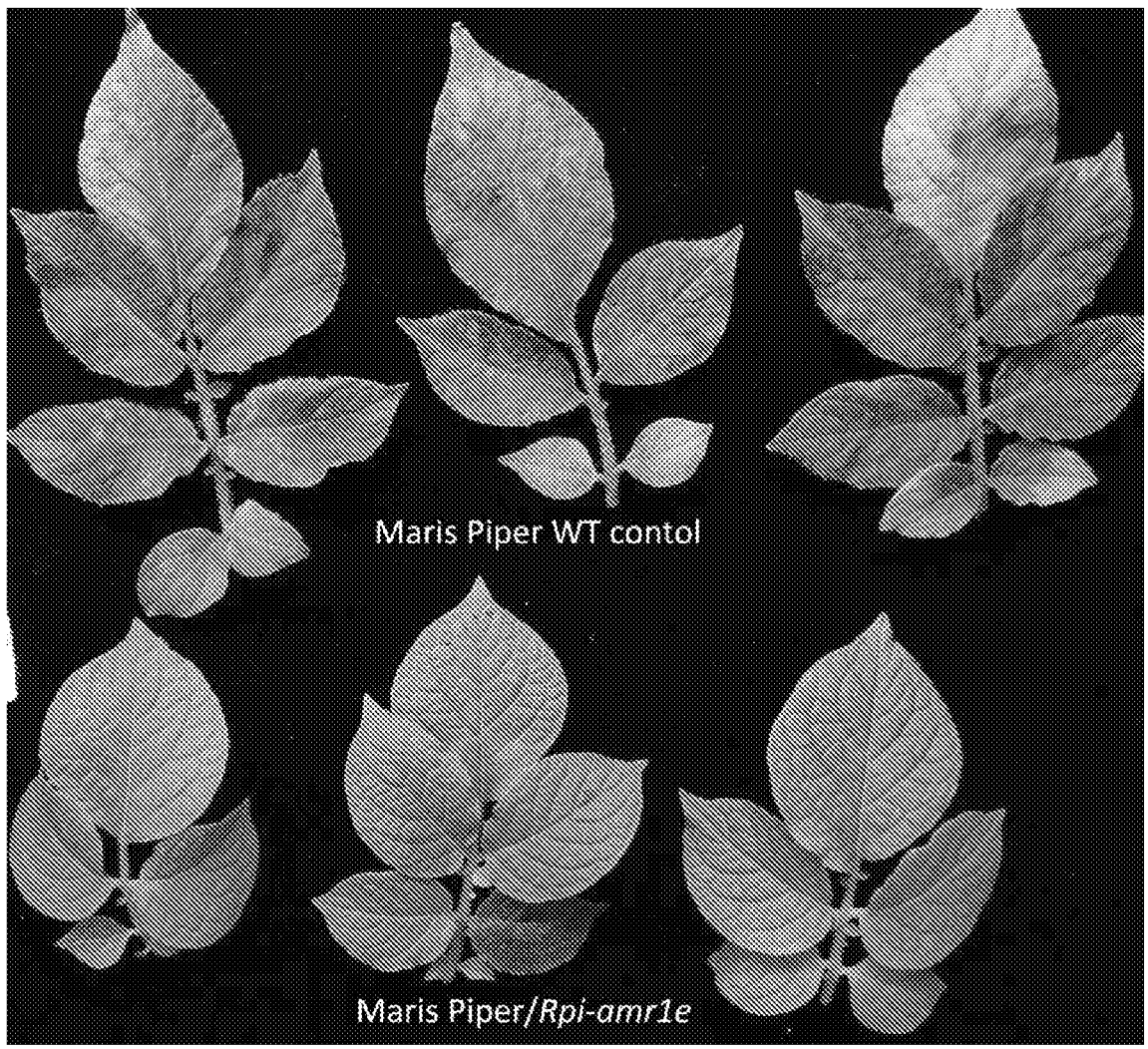
FIG. 3 is a photographic illustration of leaves of stable transgenic potato plants, cultivar *Maris* Piper, carrying Rpi-amr1e under the control of the native regulatory elements demonstrating resistance to *P. infestans* isolate 88069. Transgenic tetraploid potato "*Maris* Piper" which expresses Rpi-amr1e under the native regulatory elements is resistant to *P. infestans* isolate 88069. The transgenic line displays HR at the spot of inoculation. In contrast, the control wild type *Maris* Piper plants show large necrotic lesions and sporulation. Each leaflet was inoculated with a droplet containing 100-200 zoospores. The photographs were taken 6 days post inoculation.

Example 5: Stable Transformed Potato Lines Carrying 35S::Rpi-amr1 are Resistant to Diverse *P. infestans* Strains We created stable transgenic plants with Rpi-amr1e constructs under native regulatory elements in the tetraploid cultivar Maris Piper using the transformation method described in Kumar et al. ((1996) *Plant J.* 9:147). Transgenic plants showed resistance against *P. infestans* race 88069 (FIG. 3). This result confirms that the cloned gene is the functional Rpi-amr1 gene conferring resistance against *P. infestans* in planta.

Example 6: Resistance is Linked to the Rpi-amr1 Locus in Six Additional Populations Genotyping of 10-20 susceptible F2 plants from populations derived from resistant accessions sn27, Veg422, A14750006, SOLA 425, Wang 2058 and A14750130 showed that resistance is linked to the Rpi-amr1 locus. To test whether Rpi-amr1e orthologs confer resistance, we performed SMRT RenSeq on resistant accessions and assembled NLRs as described in Witek et al. ((2016) *Nat Biotechnol* 34: 656). We next mapped all assembled contigs to coding sequence of Rpi-amr1e allowing for 10% mismatches and gaps and selected the closest, transcribed orthologs (Table 2 for % amino acid sequence identity), as identified by mapping the cDNA RenSeq reads. In three resistant parents, namely Veg422, A14750130 and Wang 2058, identified genes showed 100% identity on amino acid level to Rpi-amr1e, while the remaining accessions had above 94% identity to functional Rpi-amr1e (Table 2). We cloned polymorphic genes under control of 35S promoter (sn27 and A14750006) or under native regulatory elements (SOLA425) into binary expression vector. These constructs were transiently expressed in *N. benthamiana* detached leaves and inoculated with *P. infestans* isolate 88069 (24 hours post infiltration) and assessed for resistance at 6 dpi. All tested genes confer enhanced resistance to *P. infestans*, similar to Rpi-amr1e, when compared to GFP control infiltration.

TABLE 2

Percent Amino Acid Sequence Identity of Proteins Encoded by Cloned Rpi-amr1e Orthologs

|  | Rpi-amr1e | A14750130 | Veg422 | Wang2058 | sn27 | SOLA425 | A14750006 |
| --- | --- | --- | --- | --- | --- | --- | --- |
| Rpi-amr1e | — | 100 | 100 | 100 | 95.761 | 94.463 | 94.68 |
| A14750130 | 100 | — | 100 | 100 | 95.761 | 94.463 | 94.68 |
| Veg422 | 100 | 100 | — | 100 | 95.761 | 94.463 | 94.68 |
| Wang2058 | 100 | 100 | 100 | — | 95.761 | 94.463 | 94.68 |
| sn27 | 95.761 | 95.761 | 95.761 | 95.761 | — | 95.652 | 95.109 |
| SOLA425 | 94.463 | 94.463 | 94.463 | 94.463 | 95.652 | — | 97.717 |
| A14750006 | 94.68 | 94.68 | 94.68 | 94.68 | 95.109 | 97.717 | — |

Example 7: Full-Length Rpi-amr1e Confers Strong Resistance Against Multiple Isolates of *P. infestans* in Stable Transgenic Potato Plants We mapped cDNA RenSeq data to BAC contig with TopHat splice junction mapper for RNA-Seq reads (Trapnell et al. (2009) *Bioinformatics* 25:1105-1111) and detected two dominant splice variants for Rpi-amr1e gene (SEQ ID NO: 22). The most abundant version, supported by over 80% of cDNA reads, consists of 4 exons (SEQ ID NO: 23) and encodes a protein of 1013 amino acids (SEQ ID NO: 24). The remaining cDNA reads show that several other splice variants corresponding to various forms of 3' truncation of SEQ ID NO: 23 are possible. We confirmed this by 3' rapid amplification of cDNA ends (RACE) PCR and observed the following CDS sequences: SEQ ID NO: 25, SEQ ID NO: 26, and SEQ ID NO: 27 coding for 1004 amino acids (SEQ ID NO: 28), 925 amino acids (SEQ ID NO: 29) and 868 amino acids (SEQ ID NO: 30) proteins, respectively.

Figure 4:
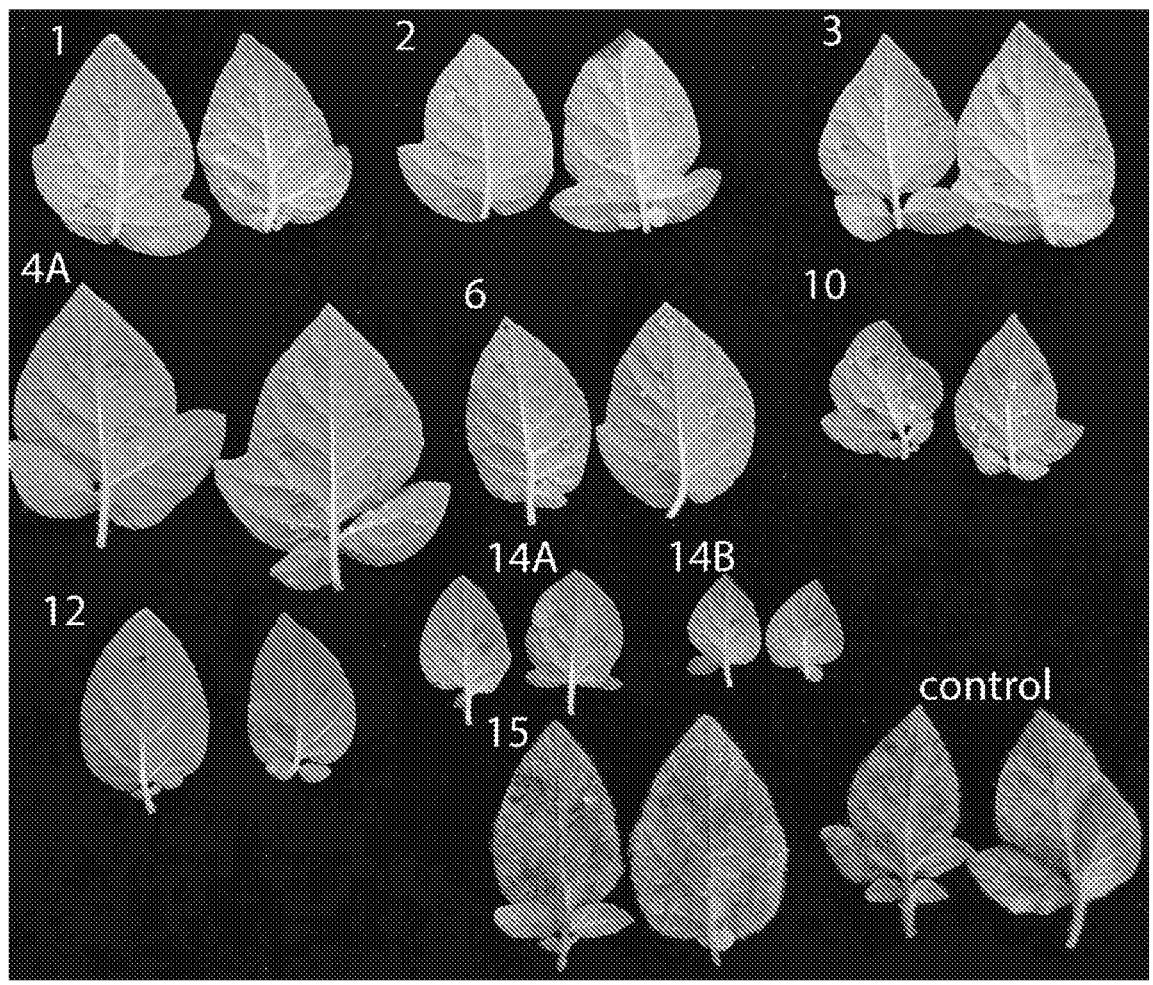
FIG. 4 is a photographic illustration of leaves of stable transgenic potato plants, cv. *Maris* Piper, carrying Rpi-amr1e under the control of the native regulatory elements demonstrating resistance to *P. infestans* isolate 88069.

We used the transformation method as described previously to construct stable transgenic potato plants (cv. Maris Piper) carrying the Rpi-amr1e gene (SEQ ID NO: 23). We recovered 10 transgenic lines where presence of Rpi-amr1e was confirmed by PCR with gene-specific primers. In DLAs, nine lines showed resistance against P. infestans isolate 88069 (FIG. 4). A selected resistant line (line 6) was further phenotyped with additional highly virulent P. infestans isolates US23, EC3626, NL14307, NL14538, NL14518, and NL14327 and showed strong resistance (data not shown).

Figure 5:
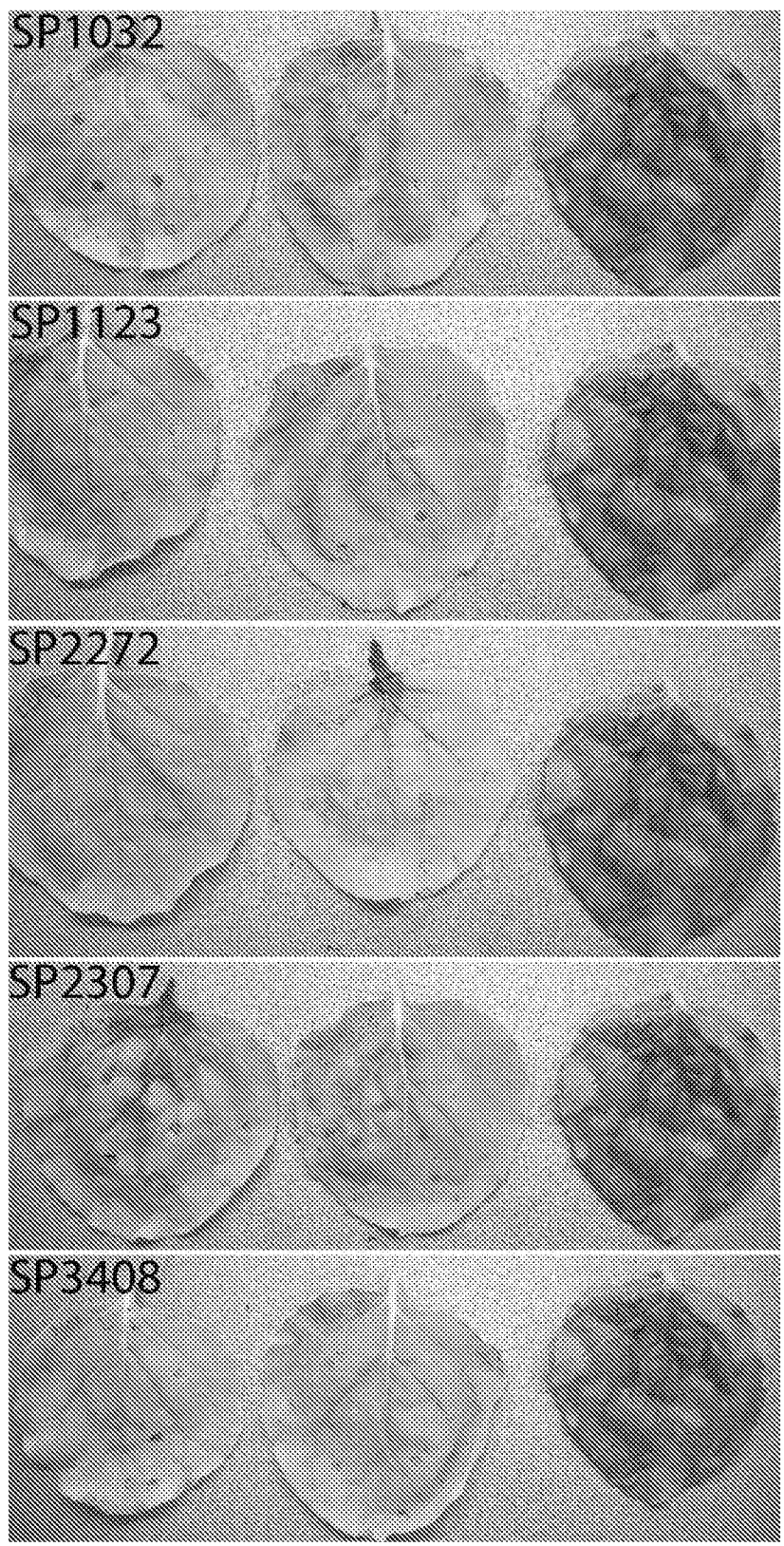
Figure 6:
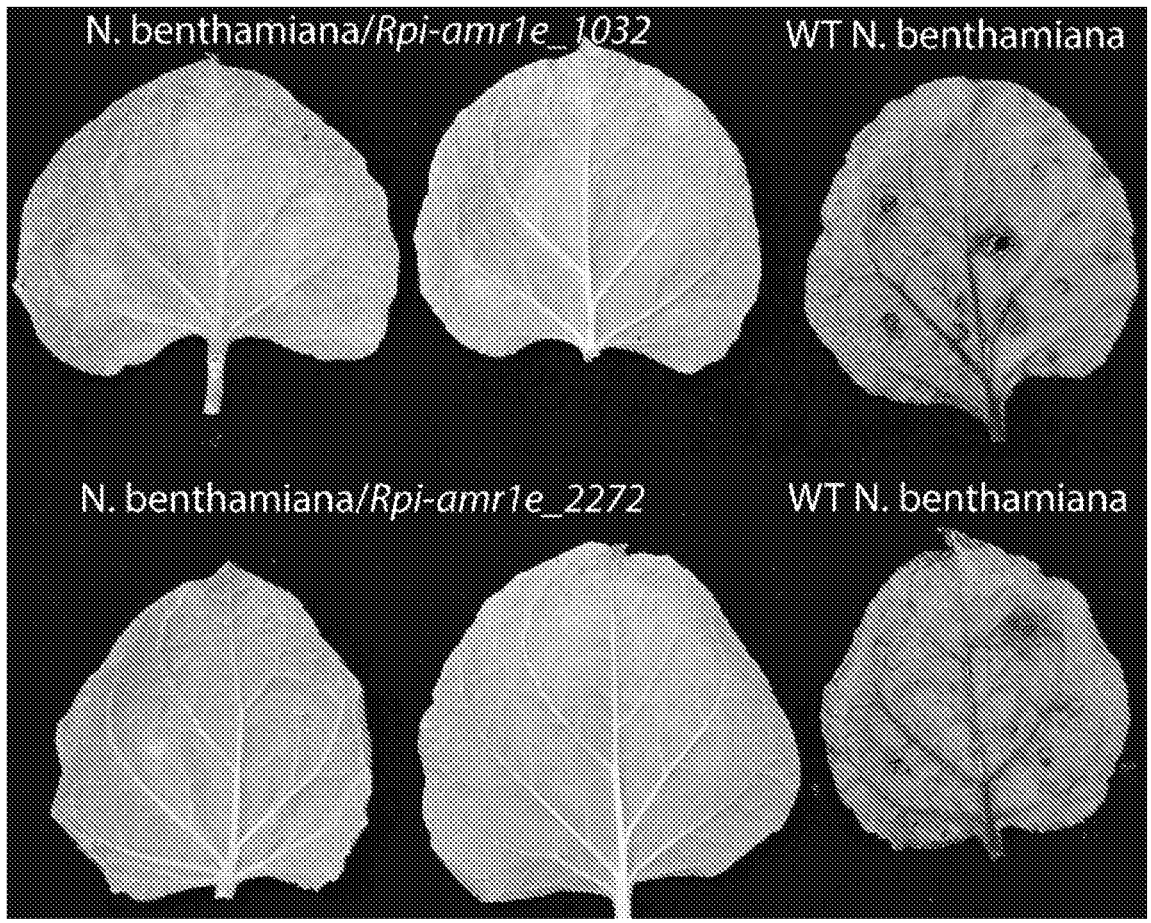

Example 8: Allele Mining Identified 5 Additional Functional Alleles of Rpi-amr1e that Confer Resistance in a Transient Complementation Assay in N. benthamiana Plants In addition to alleles of Rpi-amr1e disclosed above in Example 6 (accession sn27, also referred to herein as SP1032; accession SOLA425, also referred to herein as SP2307; and accession A14750006, also referred to herein as SP1123), we found three more populations, derived from resistant parents 954750174 (also referred to herein as SP2272), A14750130 (SP3400) and 954750172 (SP3408) where resistance co-segregates with the Rpi-amr1e locus. To test if Rpi-amr1e alleles were involved in this resistance, we performed SMRT RenSeq and looked for the closest transcribed homolog of Rpi-amr1e as described in Example 6. The gene from SP3408 showed less than 92.5% identity to Rpi-amr1e. The remaining two candidate sequences were more diverged and showed 89.3% identify on amino acid level to Rpi-amr1e; however, they were 1000/identical to each other. We cloned two new Rpi-amr1e alleles and also three previously reported (SP1032, SOLA425 and SP1123) under their native regulatory elements into a binary vector as described earlier; SP1032 (SEQ ID NO: 31, SP1123 (SEQ ID NO: 32, SP2272 (SEQ ID NO: 33, SP2307 (SEQ ID NO: 34, SP3408 (SEQ ID NO: 35. In transient complementation assays, all genes conferred resistance against P. infestans isolate 88069 (FIG. 5). Additionally, we created stable transgenic N. benthamiana carrying Rpi-amr1e alleles from SP1032 and SP2272 (SEQ ID NO: 31 and SEQ ID NO: 33, respectively). We recovered 12 independent, transgenic lines for each construct and phenotyped them in DLAs with P. infestans isolate 88069. For both constructs 10 out of 12 lines showed strong resistance (FIG. 6).

We annotated coding sequences of the functional Rpi-amr1e alleles using AUGUSTUS gene prediction software (Stanke et al. (2008) Bioinformatics 24: 637-644) and also by alignments with the coding sequence of Rpi-amr1e (SEQ ID NO: 23). The predicted CDS sequences for accessions SP1032 (SEQ ID NO: 36), SP1123 (SEQ ID NO: 37), SP2272 (SEQ ID NO: 38), SP2307 (SEQ ID NO: 39) and SP3408 (SEQ ID NO: 40) encode 986 amino acids (SEQ ID NO: 41), 987 amino acids (SEQ ID NO: 42), 976 amino acids (SEQ ID NO: 43), 986 amino acids (SEQ ID NO: 44) and SP3408 (SEQ ID NO: 45) proteins, respectively.

Example 9: Development of Segregating Population Derived from & Nigrescens Accession A14750423

We investigated the immune response towards P. infestans in S. nigrescens (2n) accession A14750423 (also referred to herein as SP3409; country of origin, Mauritius). In detached leaf assays (DLAs) with the highly virulent P. infestans isolates (06_3928A, 88069, EC1 and NL07434). Plants of the accession SP3409 remained fully resistant (R parent), with no obvious signs of infection or only small sites of hypersensitive response (HR) in the form of local cell death at the site of P. infestans inoculation.

To determine the genetic basis of resistance, we crossed the resistant line SP3409 as a male parent to the susceptible line SP2271 (S parent, reported in Witek et al. (2016) Nat. Biotechnol. 34: 656-660) as a female parent. Heterozygous F1 progeny showed no segregation for resistance to P. infestans isolate 06_3928A and EC1 (6-8 plants were tested for each F1), and were allowed to self-pollinate to generate F2 progenies. We tested 90 F2 progeny for resistance to the P. infestans isolate 88069 and found F2 progenies segregate in a 3:1, suggesting the presence of a single dominant resistance gene, which we named Rpi-amr6. Hence this $F_2$ population was selected for R gene identification.

Example 10: Identification of Candidate Gene by RenSeq Mapping Combined with PacBio and MiSeq Sequencing We successfully applied a previously described method to clone R genes without construction of BAC libraries using a Solanum NLR bait library (Witek et al. (2016) Nat. Biotechnol. 34: 656-660). To define the complement of NLRs from resistant SP3409 parental line, we captured 3-4 kb gDNA fragments and sequenced in two SMRT cells. This resulted in more than 32 k reads of inserts (ROI). De novo assembly of ROI with Geneious and analysis with NLR-parser (Steuernagel et al. (2015) Bioinformatics. 31: 1665-1667) identified 287 full length and 555 partial NLRs. To identify linked candidate NLRs we performed Illumina RenSeq on gDNA from 42 susceptible individuals from F2 plants (bulked susceptible, BS) as described (Jupe et al. ((2013) Plant J. 76: 530-544; Witek et al. (2016) Nat. Biotechnol. 34: 656-660). The Illumina MiSeq run generated 744,943; 2,824,501; 678,099 and 1,597,558 paired-end reads for resistant (R) parent, susceptible (S) parent, bulk susceptible and cDNA of resistant parent respectively. After performing initial QC, we mapped the MiSeq data (R, S parents, and BS) to assembly of PacBio data of R parent. We used our previously published in silico trait mapping pipelines (Jupe et al. ((2013) Plant J. 76: 530) and Witek et al. (2016) Nat. Biotechnol. 34: 656-660)) to perform SNP (calling and detection of polymorphisms linked to disease resistance. Briefly, we called homozygous SNPs between S and R parents, and looked for contigs which showed absence of R specific allele (less than 5% R allele in BS). Transcriptionally active NLRs and their intron/exon structure were annotated with cDNA RenSeq reads as described previously (Andolfo et al. (2014) BMC Plant Biol. 14:120; Witek et al. (2016) Nat. Biotechnol. 34: 656-660). These identified five candidate NLRs for Rpi-amr6. We further confirmed co-segregation of these sequences using gene specific markers (data not shown).

Figure 7:
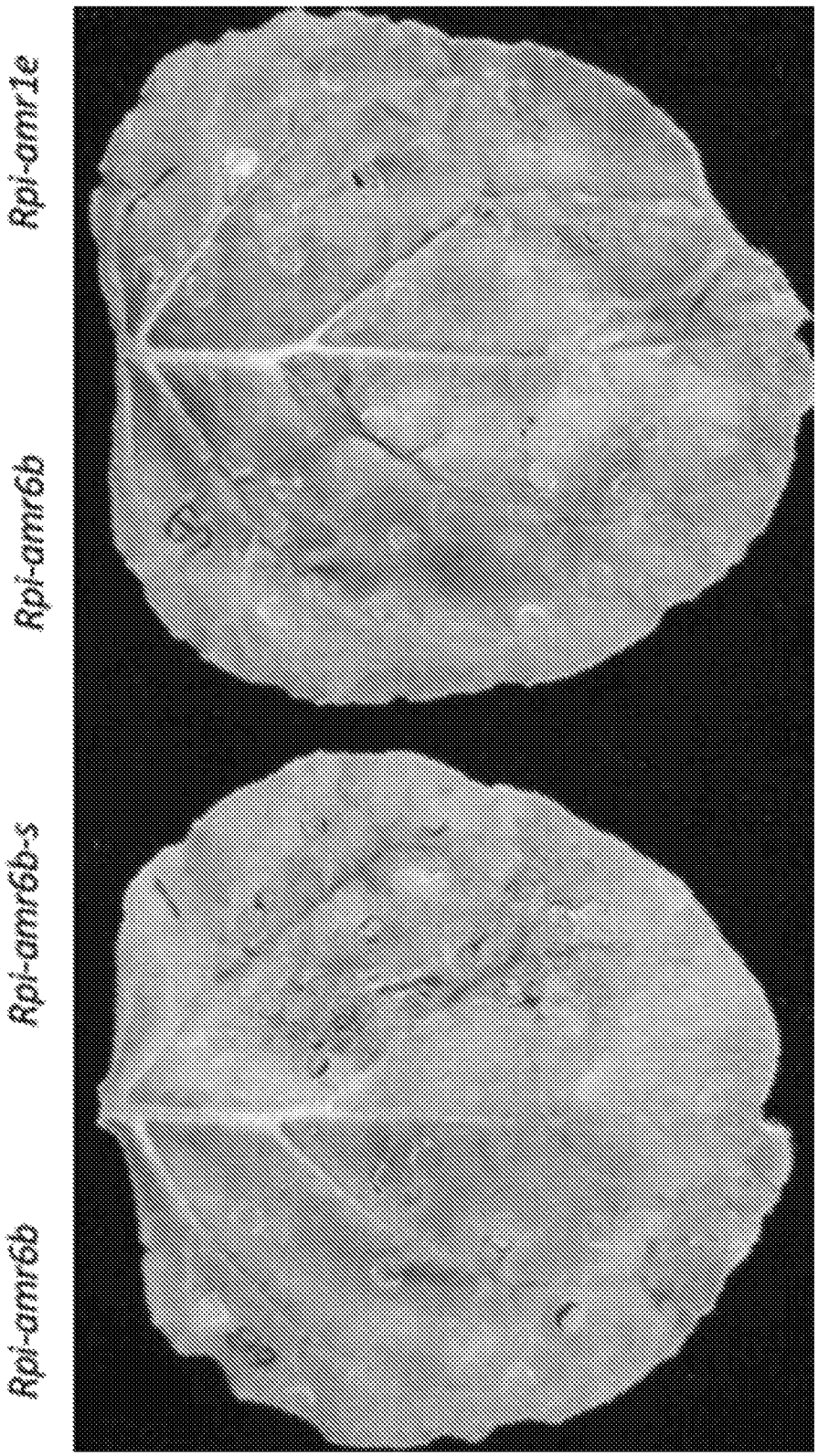
Figure 8:
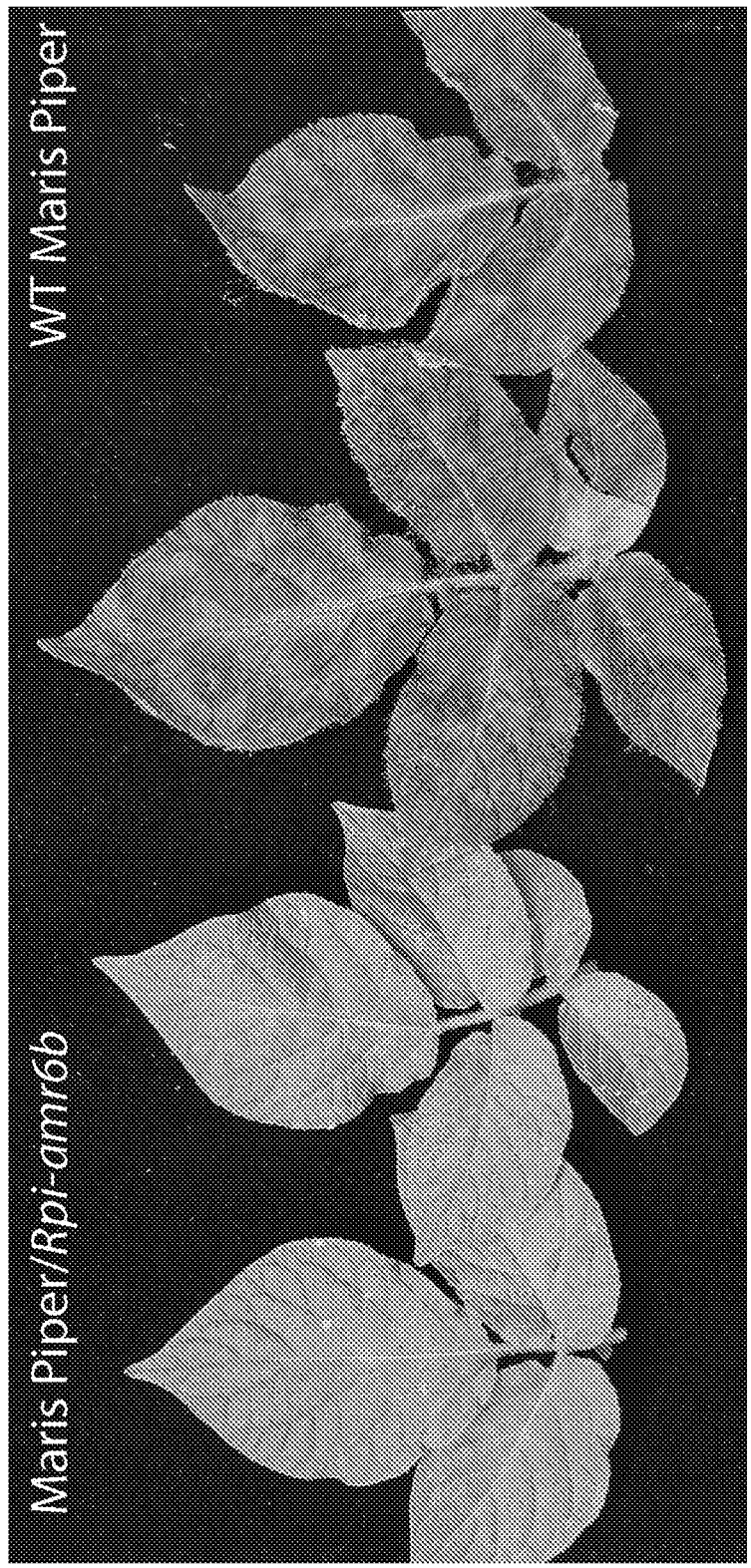
Figure 9:
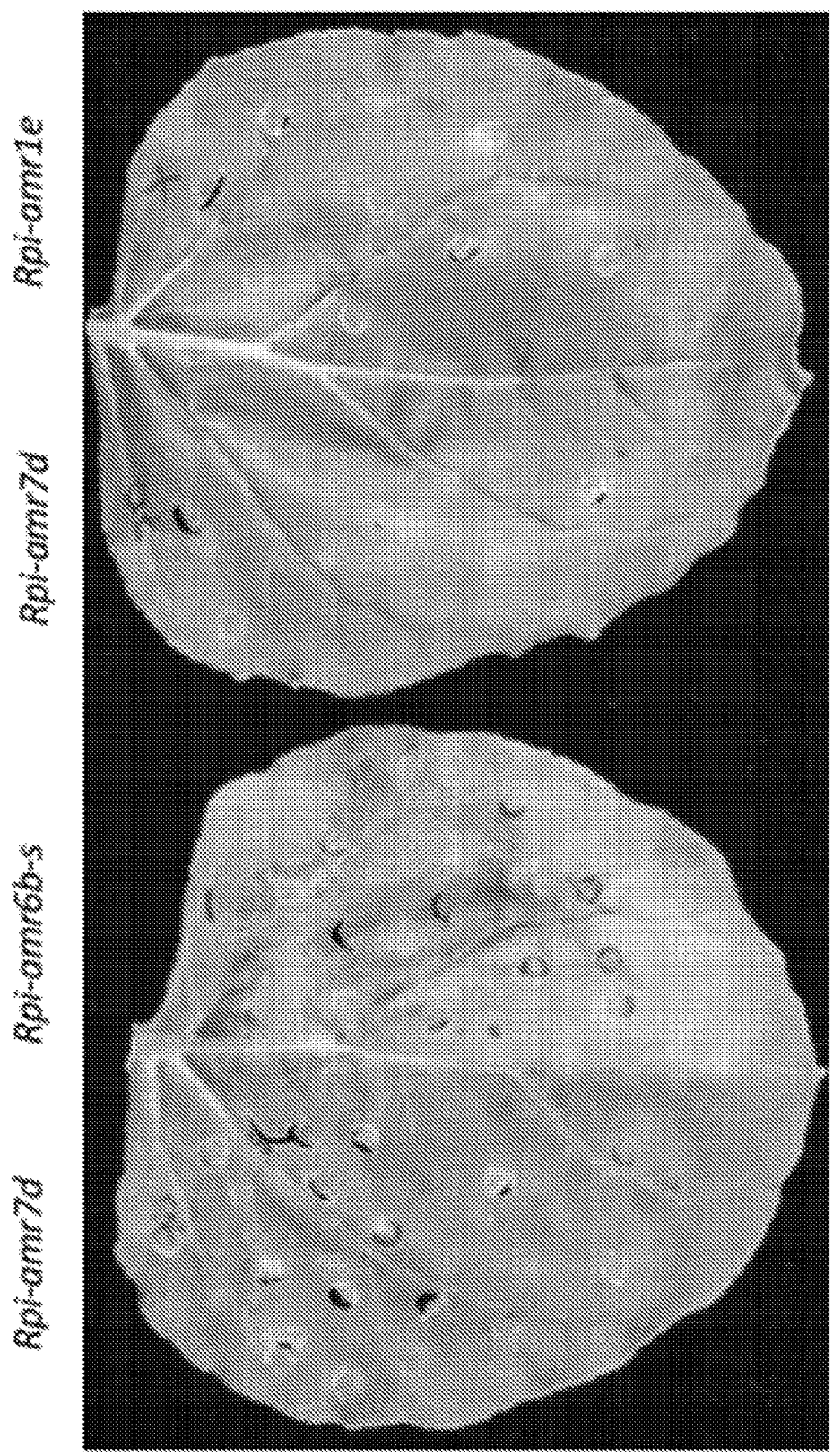
Figure 10:
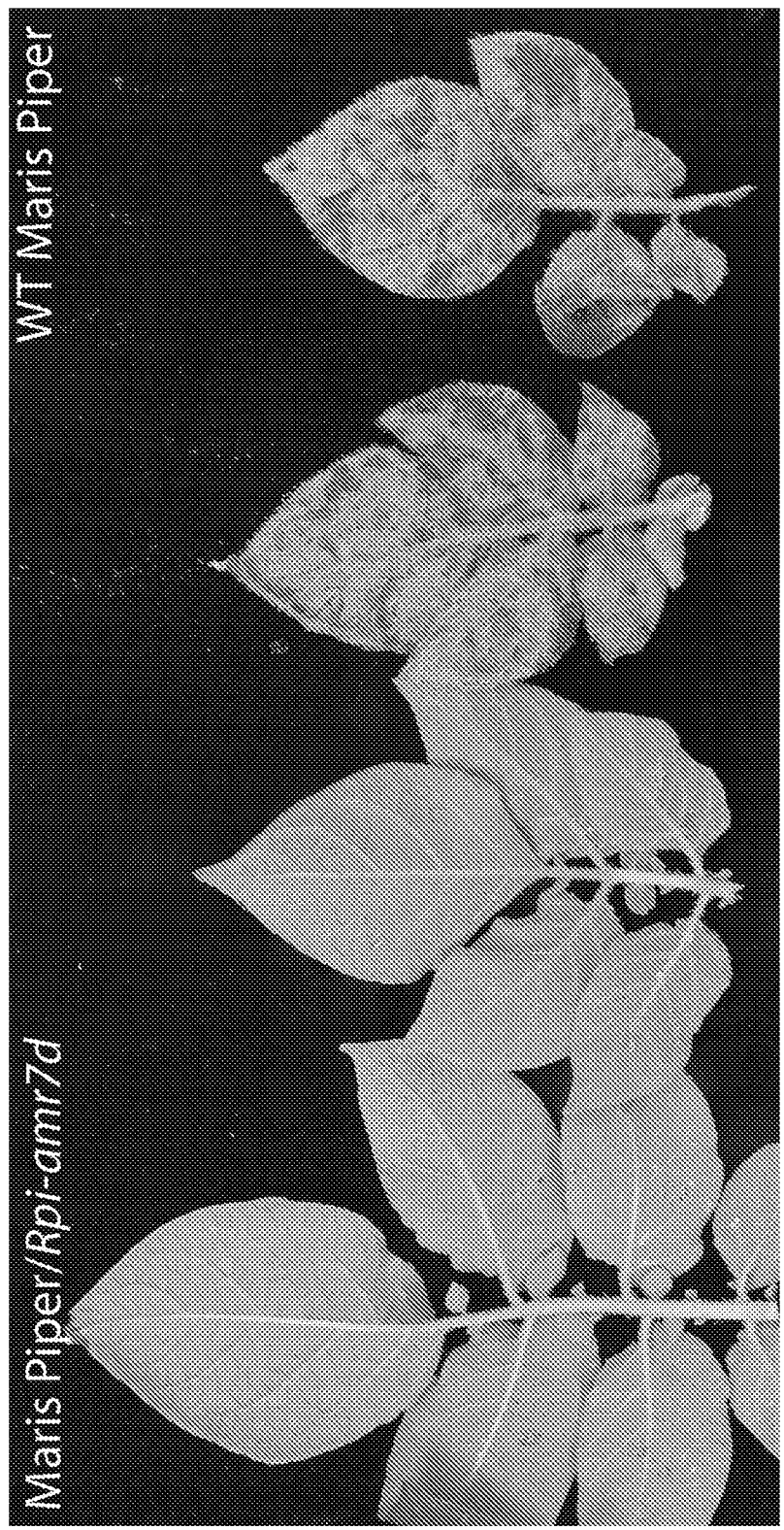
Figure 11:
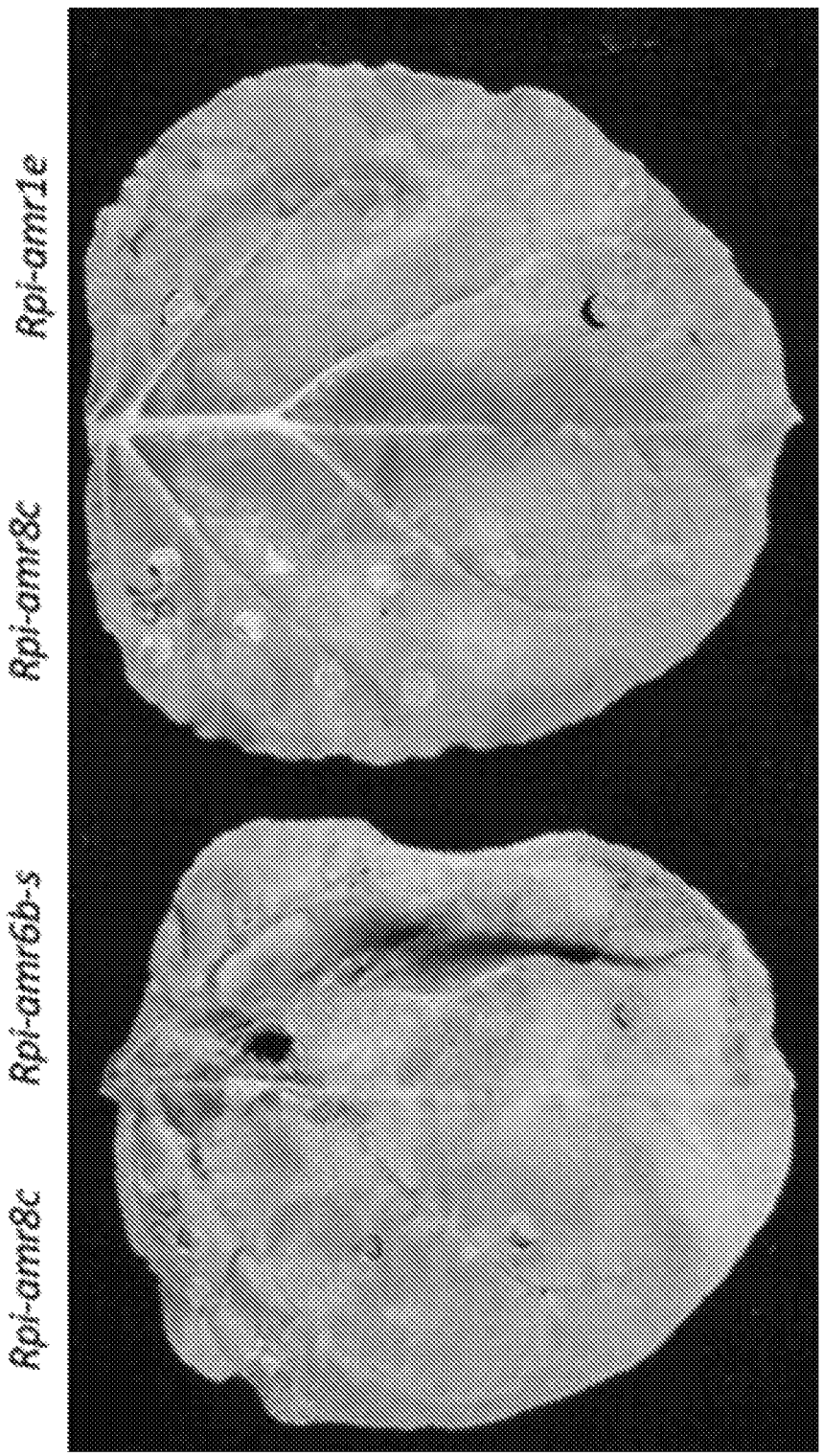
Figure 12:
Figure 13:
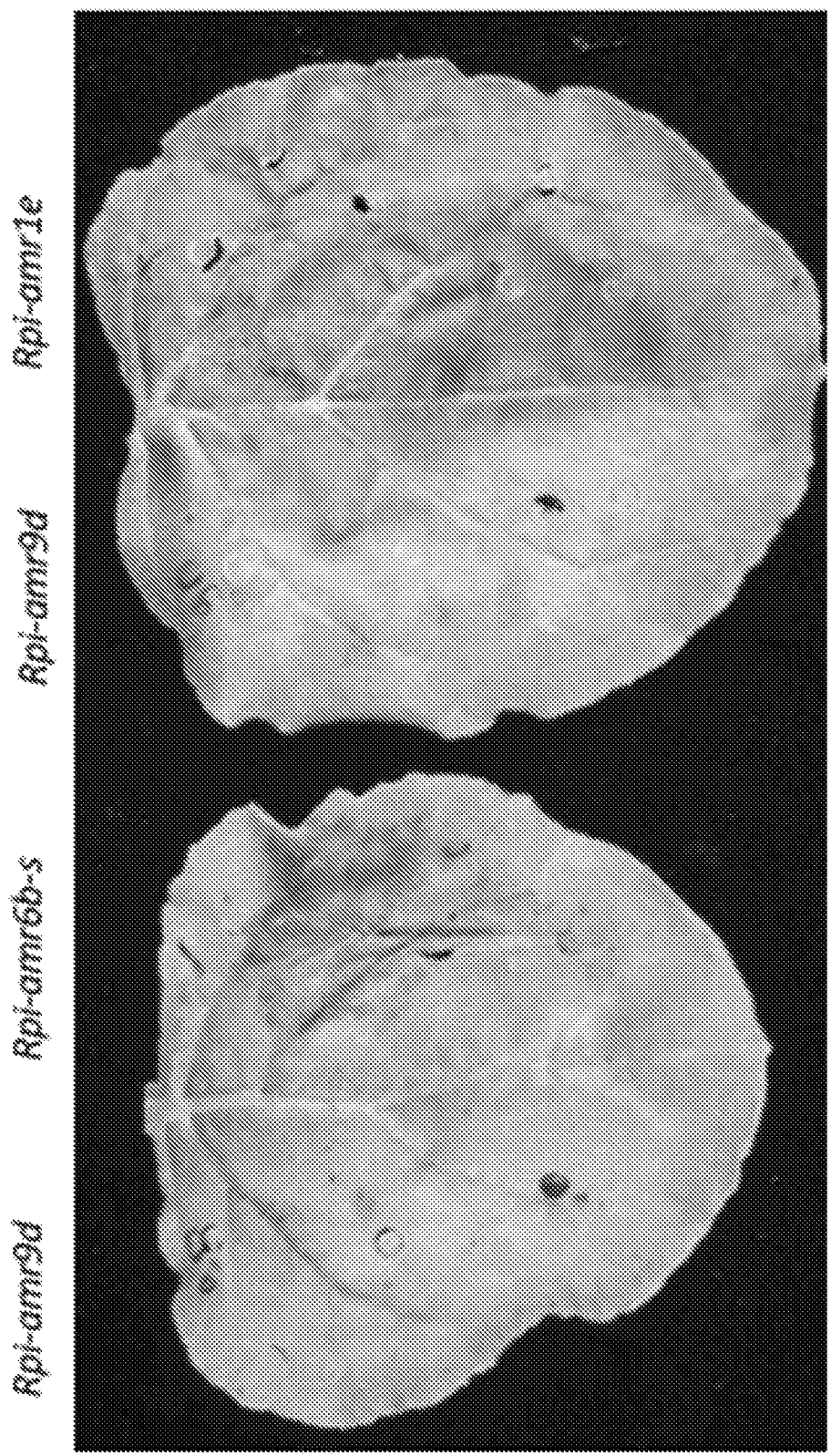

Example 11: Transient Expression of Co-Segregating Expressed NLR Genes in Nicotana benthamiana Reveals P. Infestans Resistance Genes We cloned the open reading frames of the candidate NLRs for Rpi-amr6 into a binary expression vector under native regulatory elements and then introduced the vectors into Agrobacterium tumefaciens strain AGL-1. These constructs were transiently expressed in N. benthamiana leaves which were detached 24 hours later and inoculated with the P. infestans isolates 88069 and US-23 as described in Witek et al. ((2016) *Nat. Biotechnol.* 34: 656-660). At 6 dpi restriction of *P. infestans* growth was observed with candidate construct Rpi-amr6b (SEQ ID NO: 46) and with the Rpi-amr3 positive control construct, while symptoms of *P. infestans* infection were visible on GFP-infiltrated control leaves and remaining candidate genes (FIG. 7). This transient expression system identified candidate Rpi-amr6b as the functional gene.

Example 12: Stable Transformed Potato Lines Carrying Rpi-amr6 and Testing for Resistance to Diverse *P. infestans* Races A construct carrying the Rpi-amr6b gene under its native regulatory elements (SEQ ID NO: 1) in pICSLUS0001 binary vector (Witek et al. (2016) *Nat Biotechnol* 34: 656-660) was used to create stable transgenic potato plants in cv. *Maris* Piper background using transformation method for potato as described in Kumar et al. ((1996) *Plant J,* 9: 147-158). We recovered 5 stable transgenic lines showing presence of transgene in PCR test with Rpi-amr6b specific primers. One line exhibited enhanced resistance to *P. infestans* race 88069 (FIG. 8) and also US23, NL14538 and 14327 (data not shown) as compared to the wild type potato plants.

Example 13: Rpi-amr6b is Homologous to Rpi-amr1e

Rpi-amr6b comprises a 5,131 bp open reading frame (ORF). The mapping pattern of cDNA data suggests that Rpi-amr6b undergoes alternative splicing, and two splice forms can be distinguished. The dominant (i.e. most abundant) transcript variant consists of 5 exons (SEQ ID NO: 49) encoding a protein of 961 amino acids (SEQ ID NO: 47). A longer transcript (SEQ ID NO: 50) was also detected that encodes a protein of 978 amino acids (SEQ ID NO: 48). Both proteins contain typical characteristics of a CC-NB-LRR class resistance protein, including coiled-coil domain (CC; amino acids 4-114), nucleotide binding domain (NB-ARC; amino acids 153-437) and two potential leucine-reach repeats (LRR; amino acids 683-800).

Example 14: GenSeq Mapping Reveals the Map Position Rpi-amr6b on Potato Doubled-Monoploid (DM) Genome To determine chromosomal location of Rpi-amr6b, we used an enrichment-based genotyping, named GenSeq (Chen et al. "Identification and rapid mapping of a gene conferring broad-spectrum late blight resistance in the diploid potato species *Solanum verrucosum* through DNA capture technologies," *Theor. Appl. Genet.*, submitted 2017) with 19,716 biotinylated RNA baits targeting 1,143 conserved ortholog set (COS) (Lindqvist-Kreuze et al. (2013) *BMC Genetics,* 14: 51-51) and 837 single copy genes identified in the potato reference genome (DM) (Potato Genome Sequencing Consortium (2011) *Nature* 475:189-195). Targeted enrichment and Illumina sequencing was performed as described above, which generated 536,335; 1,200,699 and 658,651 paired-end reads for gDNA of R parent (SP3409), S parent (SP2271), and BS, respectively. After performing initial QC, we mapped the MiSeq data to the potato DM sequence. To find the linked region, we annotated homozygous SNPs between S and R parents that were present/absent in BS (less than 5% R allele; Jupe et al. (2013) *Plant J.* 76: 530-544). Based on these SNPs, we developed genetic markers and confirmed that Rpi-amr6b maps to the 78 Mb region of chromosome 1 in the DM sequence, which is different from the position of Rpi-amr1e which maps to the top of chromosome 11 (around 6 Mb in the DM reference genome).

Example 15: Cloning of Rpi-amr7d from *S. americanum* Accession A54750014 Using RenSeq Approach In our screening, *S. americanum* accession A54750014 (also referred to herein as SP1101) showed strong resistance to *P. infestans* isolate 88069 in DLA assay. All 60 plants in F2 progeny derived from the cross with susceptible SP2271 were resistant, suggesting presence of two or more resistant genes. To separate these genes, we back-crossed F1 plants to susceptible SP2271 (BC1) followed by another backcross to SP2271 (BC2). Resistant BC2F1 plants were self-pollinated to generate BC2F2 and segregation ratio was tested on 90 plants in a population. An additional 600 plants for selected population were sown and phenotyped in DLA for *P. infestans* response. gDNA from 133 susceptible plants was isolated and the RenSeq pipeline performed as described above to identify linked candidate genes. Additionally, with the standard SNP calling pipeline described above, we performed RenSeq and SNP calling on bulked resistance (BR) sample (BR, 20 R plants from segregation population) to identify fixed susceptible loci. Briefly, for homozygous SNPs between S and R parents that were absent in BS (criteria as described above) we counted the allele ratio from BR data. SNPs showing less than 5% of R allele were annotated as fixed and excluded from further analysis. This revealed eight NLR-encoding candidate genes which were cloned and tested in transient assay as described above. Candidate Rpi-amr7d (SEQ ID NO: 51) conferred resistance in transient assay (FIG. 9) and was used to generate stable transgenic potato plants in cv. *Maris* Piper background. We recovered 6 lines showing presence of Rpi-amr7d in PCR screening with gene-specific markers. Five-week old plants were assessed in DLA assay with *P. infestans* isolate 8869. US23 and five lines showed strong resistance (FIG. 10).

Rpi-amr7d comprises a 5131 bp ORF. Mapping of cDNA reads suggests that Rpi-amr7d undergoes alternative splicing and two splice forms can be distinguished. The dominant transcript variant consists of 5 exons (SEQ ID NO: 54) encoding a protein of 961 amino acids (SEQ ID NO: 52). An additional transcript (SEQ ID NO: 55) was detected that encoded a protein of 978 amino acids (SEQ ID NO: 53). Both proteins contain typical characteristics of a CC-NB-LRR class resistance protein, including coiled-coil domain (CC; amino acids 2-120), nucleotide binding domain (NB-ARC; amino acids 154-432) and two potential leucine-reach repeats (LRR; amino acids, 683-800).

Example 16: Cloning of Rpi-amr8c from *S. americanum* Accession SOLA 226 Using RenSeq Approach

*S. americanum* accession SOLA 226 (also referred to herein as SP2300) showed strong resistance to *P. infestans* isolate 88069 in DLA assay. In an F2 population derived from cross between resistant SP2300 and susceptible SP2271 plants, we observed a 15:1 segregation ratio (resistant to susceptible), suggesting presence of two unlinked dominant resistant genes. We showed that resistance was co-segregating with previously cloned Rpi-amr3 gene (Witek et al. (2016) *Nat. Biotechnol.* 34: 656-660; see also WO 2016/182881 patent application). Using Rpi-amr3 gene-specific markers we screened F2 population and selected resistant plants which lacked Rpi-amr3. Plants were self-pollinated and resulting F3 populations screened with *P. infestans* isolate 88069 to detect families segregating in ratio 3:1 (resistant to susceptible). From one of the populations segregating 3:1, 600 plants were phenotyped using the DLA for *P. infestans* response, gDNA from 114 susceptible (BS) and 20 resistant (BR) plants was isolated, and the RenSeq pipeline performed as described above to identify linked candidate genes. Additionally, to standard SNP calling pipeline described above, we performed RenSeq and SNP calling on a BR resistance sample to identify fixed susceptible loci. Briefly, for homozygous SNPs between S and R parents that were absent in BS (criteria as described above) we counted the allele ratio from BR data. SNPs showing less than 5% of R allele were annotated as fixed and excluded from further analysis. This resulted in 10 NLR-encoding candidate genes which were cloned and tested in transient assays as described above. Candidate Rpi-amr8c (SEQ ID NO: 56) conferred resistance in a transient assay (FIG. 11) and was used to generate stable transgenic potato plants in cv. *Maris* Piper background as described above. Twelve lines were assessed in the DLA assay with *P. infestans* isolate US23, three lines showed strong resistance (FIG. 12), five lines showed partial resistance with restricted *P. infestans* growth, and the remaining four lines were susceptible.

Rpi-amr8c comprises a 5125 bp ORF. Mapping of cDNA data suggests that Rpi-amr8c undergoes alternative splicing, and two splice forms can be distinguished. The dominant transcript variant consists of 5 exons (SEQ ID NO: 59) encoding a protein of 960 amino acids (SEQ ID NO: 58). An additional transcript (SEQ ID NO: 60) was detected that encodes a protein of 986 amino acids (SEQ ID NO: 57). Both proteins contain typical characteristics of a CC-NB-LRR class resistance protein, including coiled-coil domain (CC: amino acids 2-120), nucleotide binding domain (NB-ARC; amino acids 153-431) and two potential leucine-reach repeats (LRR; amino acids 683-800).

Example 17: Cloning of Rpi-amr9d from *S. americanum* Accession SOLA 425 Using RenSeq Approach

*S. americanum* accession SOLA 425 (also referred to herein as SP2307), showed strong resistance to *P. infestans* isolate 88069 in the DLA assay. In an F2 population derived from a cross between resistant SP2307 and susceptible SP2271 plants, we observed a segregation ratio 9:1 (resistant to susceptible), suggesting the presence of more than one resistance gene. Resistant F2 plants were self-pollinated, and the resulting F3 populations were screened with *P. infestans* isolate 88069 to detect families segregating in ratio 3:1 (resistant to susceptible). From one population showing 3:1 segregation, 600 plants were phenotyped in DLA for *P. infestans* response, gDNA from 117 susceptible (BS) and 20 resistant (BR) plants was isolated and the RenSeq pipeline performed as described above to identify linked candidate genes. In addition to standard SNP calling as described above, we performed RenSeq and SNP calling on a BR sample to identify fixed susceptible loci. Briefly, for homozygous SNPs between S and R parents that were absent in BS (criteria as described above), we counted allele ratios from BR data SNPs showing less than 5% of R allele were annotated as fixed and excluded from further analysis. This resulted in 10 NLR-encoding genes which were cloned and tested in transient assay as described above. Candidate Rpi-amr9d (SEQ ID NO: 61) conferred resistance in a transient assay (FIG. 13) and was used to generate stable transgenic *N. benthamiana* plants. Twelve independent transgenic events were phenotyped using te DLA assay with *P. infestans* isolate 8869, and 11 of these transgenic events showed strong resistance (FIG. 14).

Rpi-amr9d comprises a 7357 bp ORF. Mapping of cDNA data suggests that the gene Rpi-amr9d undergoes alternative splicing and two splice forms can be distinguished. The dominant transcript variant consists of 5 exons (SEQ ID NO: 64) encoding a protein of 986 amino acids (SEQ ID NO: 63). An additional transcript (SEQ ID NO: 65) was detected that encodes a protein of 1011 amino acids (SEQ ID NO: 62). Both proteins contain typical characteristics of a CC-NB-LRR class resistance protein, including coiled-coil domain (SEQ ID NO: 62, amino acids 2-145; SEQ ID NO: 63, amino acids 2-120), nucleotide binding domain (SEQ ID NO: 62, amino acids 179-457; SEQ ID NO: 63, amino acids 154-432 amino acids) and two potential leucine-reach repeats (SEQ ID NO: 62, amino acids 683-800; SEQ ID NO: 63, amino acids 683-986). Alignment of the nucleotide sequence of Rpi-amr9d with homolog of Rpi-amr1e cloned from resistant line SP2307, namely Rpi-amr1_2307 (see Examples 6 and 8, above), showed that these two genes are 100% identical.

Example 18: Rpi-amr1e, Rpi-amr6b, Rpi-amr7d, Rpi-amr8c Belong to the Same Clade of CC-NLRs We aligned full-length amino acid sequences (Table 3) of all Rpi-amr1e functional homologs and also Rpi-amr6b. Rpi-amr7d and Rpi-amr8c and generated a phylogenetic tree (FIG. 15). All genes are closely related and share 88.7% to 97.4% identity. Alignment of NB-ARC domains of these genes with NB-ARC domains of cloned functional NLRs (as described in Witek et al. (2016) *Nat. Biotechnol.* 34: 656-660) showed that these genes belong to a previously uncharacterized clade CNL-3 (not shown).

Our data show that there is an extensive allelic variation for a functional Rpi-amr1e in *S. americanum*, with up to 12% differences between different alleles. Thus, it is highly probable that various alleles can recognize unrelated *P. infestans* effectors. This was shown for a barley mildew resistance locus (MIA), where diverse alleles of Mia immune receptor recognize sequence-unrelated avirulence genes of the cognate pathogen (Lu et al. (2016) *PNAS* 18:E6486-E6495).

TABLE 3

Percent Amino Acid Identity of Full-Length Proteins Encoded by Cloned Rpi-amr1e Homologs

| Rpi-amr | 1e_1123 | 7d | 6b | 1e_2307 | 1e_3408 | 8c | 1e_1032 | 1e |
|---|---|---|---|---|---|---|---|---|
| Rpi-amr7d | 97.4 | | | | | | | |
| Rpi-amr6b | 97.3 | 99.9 | | | | | | |
| Rpi- | 97.2 | 94.7 | 94.8 | | | | | |

TABLE 3-continued Percent Amino Acid Identity of Full-Length Proteins Encoded by Cloned Rpi-amr1e Homologs

| Rpi-amr | 1e__1123 | 7d | 6b | 1e__2307 | 1e__3408 | 8c | 1e__1032 | 1e |
|---|---|---|---|---|---|---|---|---|
| amr1e__2307 | | | | | | | | |
| Rpi-amr1e__3408 | 95.4 | 92.8 | 92.9 | 95.0 | | | | |
| Rpi-amr8c | 92.8 | 95.3 | 95.4 | 92.4 | 96.8 | | | |
| Rpi-amr1e__1032 | 95.4 | 92.8 | 92.9 | 95.2 | 99.4 | 96.3 | | |
| Rpi-amr1e | 91.8 | 89.4 | 89.5 | 91.6 | 92.5 | 90.3 | 92.7 | |
| Rpi-amr1e__2272 | 91.8 | 89.3 | 89.4 | 91.4 | 91.2 | 88.7 | 91.3 | 89.3 |

The article "a" and "an" are used herein to refer to one or more than one (i.e. to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An expression cassette or vector comprising a heterologous promoter operably linked to a nucleic acid molecule comprising a nucleotide sequence selected from the group consisting of:
   (a) a nucleotide sequence encoding the amino acid sequence set forth in SEQ ID NO: 2, 5, 8, 11, 14, 17, 20, 24, 28, 29, 30, 41, 42, 43, 44, 45, 47, 48, 52, 53, 57, 58, 62, or 63;
   (b) the nucleotide sequence set forth in SEQ ID NO: 3, 6, 9, 12, 15, 18, 21, 23, 25, 26, 27, 36, 37, 38, 39, 40, 49, 50, 54, 55, 59, 60, 64, or 65; and
   (c) a nucleic acid molecule comprising a nucleotide sequence encoding an amino acid sequence having at least 90% sequence identity to at least one of the amino acid sequences set forth in SEQ ID NO: 2, 5, 8, 11, 14, 17, 20, 24, 28, 29, 30, 41, 42, 43, 44, 45, 47, 48, 52, 53, 57, 58, 62, and 63, wherein the nucleic acid molecule is capable of conferring resistance to a plant disease caused by at least one race of at least one *Phytophthora* sp. to a plant comprising the nucleic acid.

2. A host cell transformed with the expression cassette or vector of claim 1.

3. A plant comprising stably incorporated in its genome a heterologous polynucleotide comprising a nucleotide sequence selected from the group consisting of:
   (a) the nucleotide sequence set forth in SEQ ID NO: 1, 4, 7, 10, 13, 16, 19, 22, 31, 32, 33, 34, 35, 46, 51, 56, or 61;
   (b) a nucleotide sequence encoding the amino acid sequence set forth in SEQ ID NO: 2, 5, 8, 11, 14, 17, 20, 24, 28, 29, 30, 41, 42, 43, 44, 45, 47, 48, 52, 53, 57, 58, 62, or 63;
   (c) the nucleotide sequence set forth in SEQ ID NO: 3, 6, 9, 12, 15, 18, 21, 23, 25, 26, 27, 36, 37, 38, 39, 40, 49, 50, 54, 55, 59, 60, 64, or 65; and
   (d) a nucleic acid molecule comprising a nucleotide sequence encoding an amino acid sequence having at least 90% sequence identity to at least one of the amino acid sequences set forth in SEQ ID NO: 2, 5, 8, 11, 14, 17, 20, 24, 28, 29, 30, 41, 42, 43, 44, 45, 47, 48, 52, 53, 57, 58, 62, and 63, wherein the nucleic acid molecule is capable of conferring resistance to a plant disease caused by at least one race of at least one *Phytophthora* sp. to a plant comprising the nucleic acid molecule;
   wherein the plant comprises enhanced resistance to a plant disease caused by at least one race of at least one *Phytophthora* sp., relative to a control plant.

4. The plant of claim 3, wherein the heterologous polynucleotide comprises the nucleotide sequence of any one of (b)-(d) and further comprises a promoter operably linked for the expression of the nucleotide sequence in a plant.

5. The plant of claim 3, wherein the plant is a solanaceous plant.

6. The plant of claim 5, wherein the solanaceous plant is selected from the group consisting of potato, tomato, eggplant, pepper, tobacco, and petunia.

7. A fruit, tuber, leaf, or seed of the plant of claim 3, wherein the fruit, tuber, leaf or seed comprises the heterologous polynucleotide.

8. A method for enhancing the resistance of a plant to a plant disease caused by at least one race of at least one *Phytophthora* sp., the method comprising modifying at least one plant cell to comprise a heterologous polynucleotide and regenerating the plant cell into a plant comprising in its genome the heterologous polynucleotide, wherein the heterologous polynucleotide comprises a nucleotide sequence selected from the group consisting:
   (a) the nucleotide sequence set forth in SEQ ID NO: 1, 4, 7, 10, 13, 16, 19, 22, 31, 32, 33, 34, 35, 46, 51, 56, or 61;
   (b) a nucleotide sequence encoding the amino acid sequence set forth in SEQ ID NO: 2, 5, 8, 11, 14, 17, 20, 24, 28, 29, 30, 41, 42, 43, 44, 45, 47, 48, 52, 53, 57, 58, 62, or 63;
   (c) the nucleotide sequence set forth in SEQ ID NO: 3, 6, 9, 12, 15, 18, 21, 23, 25, 26, 27, 36, 37, 38, 39, 40, 49, 50, 54, 55, 59, 60, 64, or 65; and
   (d) a nucleic acid molecule comprising a nucleotide sequence encoding an amino acid sequence having at least 90% sequence identity to at least one of the amino acid sequences set forth in SEQ ID NO: 2, 5, 8, 11, 14, 17, 20, 24, 28, 29, 30, 41, 42, 43, 44, 45, 47, 48, 52, 53, 57, 58, 62, and 63, wherein the nucleic acid molecule is capable of conferring resistance to a plant disease caused by at least one race of at least one *Phytophthora* sp. to a plant comprising the nucleic acid molecule;
   wherein the regenerated plant comprises enhanced resistance to a plant disease caused by at least one race of at least one *Phytophthora* sp., relative to a control plant.

9. The method of claim 8, wherein the heterologous polynucleotide is stably incorporated into the genome of the plant cell.

10. The method of claim 8, wherein modifying at least one plant cell to comprise a heterologous polynucleotide comprises introducing the heterologous polynucleotide into at least one plant cell.

11. The method of claim 8, wherein modifying at least one plant cell to comprise a heterologous polynucleotide comprises using genome editing to modify the nucleotide sequences of a native or non-native gene in the genome of the plant cell to comprise the nucleotide sequence of any one of (a)-(d).

12. A method of limiting a plant disease caused by at least one race of at least one *Phytophthora* sp. in agricultural crop production, the method comprising planting a seedling, tuber, or seed and growing the seedling, tuber, or seed under conditions favorable for the growth and development of a plant resulting therefrom, wherein the seedling, tuber, or seed comprises a heterologous polynucleotide comprising a nucleotide sequence selected from the group consisting of:
- (a) the nucleotide sequence set forth in SEQ ID NO: 1, 4, 7, 10, 13, 16, 19, 22, 31, 32, 33, 34, 35, 46, 51, 56, or 61;
- (b) a nucleotide sequence encoding the amino acid sequence set forth in SEQ ID NO: 2, 5, 8, 11, 14, 17, 20, 24, 28, 29, 30, 41, 42, 43, 44, 45, 47, 48, 52, 53, 57, 58, 62, or 63;
- (c) the nucleotide sequence set forth in SEQ ID NO: 3, 6, 9, 12, 15, 18, 21, 23, 25, 26, 27, 36, 37, 38, 39, 40, 49, 50, 54, 55, 59, 60, 64, or 65; and
- (d) a nucleic acid molecule comprising a nucleotide sequence encoding an amino acid sequence having at least 90% sequence identity to at least one of the amino acid sequences set forth in SEQ ID NO: 2, 5, 8, 11, 14, 17, 20, 24, 28, 29, 30, 41, 42, 43, 44, 45, 47, 48, 52, 53, 57, 58, 62, and 63, wherein the nucleic acid molecule is capable of conferring resistance to a plant disease caused by at least one race of at least one *Phytophthora* sp. to a plant comprising the nucleic acid molecule;

wherein the plant comprises enhanced resistance to a plant disease caused by at least one race of at least one *Phytophthora* sp., relative to a control plant.

13. A method for identifying a solanaceous plant that displays newly conferred or enhanced resistance to a plant disease caused by at least one race of at least one *Phytophthora* sp., the method comprising detecting in the plant, or in at least one part or cell thereof, the presence of an Rpi-amr nucleotide sequence, wherein the Rpi-amr nucleotide sequence is selected from the group consisting of:
- (a) the nucleotide sequence set forth in SEQ ID NO: 1, 4, 7, 10, 13, 16, 19, 22, 31, 32, 33, 34, 35, 46, 51, 56, or 61;
- (b) a nucleotide sequence encoding the amino acid sequence set forth in SEQ ID NO: 2, 5, 8, 11, 14, 17, 20, 24, 28, 29, 30, 41, 42, 43, 44, 45, 47, 48, 52, 53, 57, 58, 62, or 63;
- (c) the nucleotide sequence set forth in SEQ ID NO: 3, 6, 9, 12, 15, 18, 21, 23, 25, 26, 27, 36, 37, 38, 39, 40, 49, 50, 54, 55, 59, 60, 64, or 65; and
- (d) a nucleic acid molecule comprising a nucleotide sequence encoding an amino acid sequence having at least 90% sequence identity to at least one of the amino acid sequences set forth in SEQ ID NO: 2, 5, 8, 11, 14, 17, 20, 24, 28, 29, 30, 41, 42, 43, 44, 45, 47, 48, 52, 53, 57, 58, 62, and 63, wherein the nucleic acid molecule is capable of conferring resistance to a plant disease caused by at least one race of at least one *Phytophthora* sp. to a plant comprising the nucleic acid molecule.

14. A human or animal food product produced using a, plant, a fruit, a tuber, a leaf, or a seed comprising a heterologous polynucleotide comprising a nucleotide sequence selected from the group consisting of:
- (a) the nucleotide sequence set forth in SEQ ID NO: 1, 4, 7, 10, 13, 16, 19, 22, 31, 32, 33, 34, 35, 46, 51, 56, or 61;
- (b) a nucleotide sequence encoding the amino acid sequence set forth in SEQ ID NO: 2, 5, 8, 11, 14, 17, 20, 24, 28, 29, 30, 41, 42, 43, 44, 45, 47, 48, 52, 53, 57, 58, 62, or 63;
- (c) the nucleotide sequence set forth in SEQ ID NO: 3, 6, 9, 12, 15, 18, 21, 23, 25, 26, 27, 36, 37, 38, 39, 40, 49, 50, 54, 55, 59, 60, 64, or 65; and
- (d) a nucleic acid molecule comprising a nucleotide sequence encoding an amino acid sequence having at least 90% sequence identity to at least one of the amino acid sequences set forth in SEQ ID NO: 2, 5, 8, 11, 14, 17, 20, 24, 28, 29, 30, 41, 42, 43, 44, 45, 47, 48, 52, 53, 57, 58, 62, and 63, wherein the nucleic acid molecule is capable of conferring resistance to a plant disease caused by at least one race of at least one *Phytophthora* sp. to a plant comprising the nucleic acid molecule;

wherein the human or animal food product comprises the heterologous polynucleotide.

\* \* \* \* \*

SEQUENCE LISTING

```
<160> NUMBER OF SEQ ID NOS: 65

<210> SEQ ID NO 1
<211> LENGTH: 5732
<212> TYPE: DNA
<213> ORGANISM: Solanum americanum

<400> SEQUENCE: 1
ctacatctat ttgcctacca taaaattacc ggtcaagcaa cgtaatttgt aagtcccata      60
gaatttttaa cagatgcatt ggttcatggt tgaggtgaag aacagatgta gcagtttttt     120
gttgaagccg ttagtttctt gacagactat aacagaggaa tgtaagttgc aacttttgag     180
gatagtttag ggatgatttt tgttcattat gtagtataag gatgtagttt aagtttgagg     240
tataattgag ggatgttttt gctatttact ctacaaaatt ccacacagta ttattaattt     300
tctaaggacc gtttggccat gtgatatgaa atcatgatat gaaattatga aatgaagtta     360
aagttttgtt tggacatgta atttggactt tttatgttgt atgttttctt ataaacataa     420
aaaacccaca agttgtaaaa ttattaaact tgtcccattt ttttattcaa ttttaccaaa     480
taaacaaaaa tttacaaaat cacataatat gctaacacaa aactattctt taaaaaatac     540
aatatttatt gatcaaactt taattcaaca aaaaataaaa ttcaacataa gttgtagtgt     600
actagtcttt aatataattc tcccacatag tacggagcaa ttatatgatc gagtatacaa     660
accaacattg ctactttgag ctataaatgg tttaaaaagt aatgatatga atcataaatt     720
ttattacata tgaaacaaat ggtgagtaga tattttttaa taaaatataa acttatgggt     780
caatttttgt atttgaaaaa tcccaaatca tgatttgaaa ttttcaaatc atgatttttg     840
aagaatttgg gattttatct catgatatga aatcatgaga tgaaatcagc ctgaaatcgc     900
atgtccaaat gctgatttca tctcatgatt tcatatcgtg atatgaaatc gcatgtccaa     960
acgcctacta agtaacttag acacgtcttg acctttata attgctccat ccatcctaat    1020
```

-continued

```
ttacttgtca aatattttct aatttgattc ccctttttact tgtcattttt tacaaatcaa    1080
gaaacgacaa tttttttct ttctattata ccctcaattt attaacattg aattaatgtc      1140
cttgaaaaat atagtaagta aatatgttta aactctatc aaattaatag gggtaaaatg      1200
gtaaactcat taccaatt atttttttt taatagatgc gtcaaatcaa aaattgacaa        1260
gtaaaaagag acggaaagag tatataaatt tcaaagaaaa tttgtattga aagttaattg     1320
tattcgtcca cttgacacat catgtcttaa ttactacaag ttgatttgaa taagaaatgt    1380
gagacatctc tactatcgtg gtgggaccaa tgcttgaaaa gtcgacgaaa actacaagag     1440
tgtctttatt agaaatcagg acaacttgac tctttatttt tcatttcttt tttcttactt    1500
tttcttggtc aatccatagt tttgcatcca taaaccacaa gttctgttta gatattaaat    1560
agaaaattgt ccaaattcat ttagaaaaat gtggacataa atcatttaga caaaacctct    1620
tatagcctaa gcagagacat ttctcttcca gcaaacaaaa gagaaatggc ttatgctgct    1680
cttcttcac ttatctatac attgcaacaa ctcttcaaac ctaatcaatc tttcgtttgt    1740
caaagctgct gtacgcaaca acatgttcaa tctctctgtc aaaatctttc tgctctgcaa    1800
cttttccttg acgatactac aacaaaggat attgaaactc ttaaggtatg taattatcta    1860
atctcttact catcttatat ttattcaata ataattaatt tatcgagttt caattttaag    1920
gttatagaaa agaggatcag agatgtagta tacaaagcag aagataaagt tgattcaagc    1980
ctaagaagca tcattctagc tgattgcaca gagaataaag aaggggcttg taaattcttt    2040
gaggaagaat tgctaaaagt ggaaaaagat gttgattctc tcagcaaaga ggtgatgcag    2100
atcaatgtta caagcatgg aagcagatct gcagaactaa caacaattcc tccctctcca    2160
gaaaaaagta caaatgagga acatactatt gttgggatgg aggatgagta caacaccata    2220
cttgatcgcc tcactgccca aacagacgag ttgactgtca taccaattt tggtatgggc    2280
ggtataggta agacaactct tgccagaaag gtttatgatg attcatctat tcgttctcga    2340
tttgatagac atgtatgggt cactacctct gaagaattca atgagagacg aatgcttctc    2400
gaagttgttt cttcaattac tactggaagc aatcaagaaa agagcgatga tcaactaatg    2460
gagattgtgt atagaggtct taagggtagg agatttctaa ttgtcataga tgatatttgg    2520
agtactgagg cttgggacca aatgcaaaga atatttccaa atgatgacaa taaaagccga    2580
attctactaa ctacacggct caagtatgtt gctgattatg tcagcagtcc tgattttcca    2640
cctcatagta agtcttttct aagtcttgat gatagttgga atctattcac cgaaaaagta    2700
ttcaacaaag atacctgtcc tcctcaccta gaagaaacag gaagcatat tgtacaacaa     2760
tgtcgaggat tacctctctc ggttgttgta gttgctggac ttgttggaaa aatggaccca    2820
acgcatgaca attgggagaa cgttgaggaa aatctgaact cattcattgg tactgtatcc    2880
gaacggtgcc aatcaattct ttctttaagc tacaattact tgccccaata tttgagggct    2940
tgttttctct atgttggatg ttttcctgaa gataaagaga ttgatgtttc caagttgatt    3000
aggctatgga ttgctgagca attcgtaaag gcgagaagca ataaaaggtt agaagtggta    3060
gcagaggagt atctagaaga gttaattgat agaagcctaa ttttgagtgg tagacaaagg    3120
gctaatggaa ggatgaaaac ttgcaaaatt catgatcttc ttcgccaact atgcctaagt    3180
gaagctcata ctgaaaatat tagtcatatc atgaataaga atgtccccgt gtcctcagaa    3240
gccatagatg atcaacggcg agtgattgtt ccattggaac ttgaagagga accagtttat    3300
cctcaagga atagcagtgg tattacaagt acaacccgca cctttatttc aatgaaaata    3360
tgcctaagag aagctcagac cgaagccata tatgatcaac ggcgagtgat ccttctgtct    3420
```

```
aaacgacata ggattgatac aatccgcacc attattccat tcaaagatac ttttccgaaa    3480
gagatttgtt ccattgtttc acagttgaag ttgcttaagg tgttggatgt attatcagtc    3540
tggtacgatg tctcttgtat aatacctcag cttgtacatt tgagatatgt tggtgcagta    3600
attttgaaag ctctttcact acccaaattg agaaatctac agaccataat tcttacaagt    3660
gttgaaacca cagagttgaa gcactcacta gatatctgga gaatgtcaga gataagacat    3720
ttggatattg taccgccact atatatatca atcctcttg aagcagaaca acctttgttt    3780
ctcaataact tgcacacact ttttctccgt tgctctcctt tgttgcgaa atcataaga     3840 agaactccca atctaaaaaa gctaaagatt ttagataaat ctaagcatcc tgactggcct    3900
gatattcttg attctctcaa tcttctagag gagctggaga cactacaaat atcaacagaa    3960
gaaaacattg acccgatgat tttctctggg gatattttcc ctcgtaatct caagcaactg    4020
aaattatcat atacttgtat accatgggaa gatatgaaat tgctggctaa tttacccaat    4080
cttgaggtgt tcaagggtca ttatgcattc aatggaacag attggaaact agatgaagat    4140
gttgtgtttt gcaaattaaa atctctacga ctgtatgagc gtggagattt gcaaaggtgg    4200
gaagctgctg gtagtgataa ttttccaatg cttgagcaac tattattgta tgggttcaaa    4260
aaactggaag agattccgga gagtattgga gaaataatga cactaaaatt tatcaaaaca    4320
gaattttgcg gctctggtgt aaagacaagt gcaagaaaa ttcaagaaga gcaagaaagc    4380
ctgggaaatt atgagcttca agttcaaatt actcctaagg tatgttgaaa ctcaatcttt    4440
gattaatact ctccactcgg ttagatttag gattcaaatt gtctacttac atttatgatc    4500
atcacccttg cggtcttctt atttctttta gtaaatagct tcaaaaactc tacagaaatt    4560
acacataatt aacaattgac aattgattct ctcttattga taatttgtaa ttttctcttt    4620
cagttaagat ttttgatcga aaatttagac gaaataagca tgttgccccc gaatgaagta    4680
gccgaaaaaa tcaaaggttt gtctatttaa ttcctttttt atttcattga agaggttca    4740 gatatattaa acaacttttt aaccttcta tttgattttt tatcgcttag atagatacaa    4800
catttatttt aacatcaatt gttatttga ttcaattatg ttcttttaat atatagtttc    4860
cactcggttc ttcaattctt ttttcaatta tagttttatt ttttaattg cacatggttg    4920 atcgatttaa tttgtgagat tcactttct ttcggtttta cgagttcttc gcgattaatg    4980
ttattcagat ttaggagtat tatatttcaa cttcgatta gatttaggat tcaaattgtc    5040
ttctttcatt tatgatcatc atcctttcga tcttctttat ttcttttagt aaatagcttc    5100
aaaaactcta tagaaattac atataattaa caattgagaa ttgattctct cgtaatttct    5160
catgttctct ttcagttaaa attttgatc aaaaactaaa agagattccg gagagcactg    5220
gacaaataat gacacgaaaa atcatcaaaa cagaattttg cggctctggt gtagagacta    5280
gtgcaaagaa gattcaagaa gagcaagaaa gcttgggaaa ttgtgagctt catcaagttc    5340
aaattactcc taaggtatat taaaactcca tctttgatta ttagccaatt ctttaatttc    5400 atattattc tagactaaat taaaatatta aaagatataa agaatttaat taatttaatt    5460
attcctttaa aatccaaaca tgatgaattt gagtaaatta aatgaatata gttcagattc    5520
atttaactaa taggccattt agttttaata tggcaacgtt ttaggctttt aacattctct    5580
ttgaatgtag gtataatgca ttaagtgcag aaatttaatc tttatttaaa aaatgaaaac    5640
atctcataat aactttggtc tttttactcc aaacatcttg taataaagtg agtgtcttct    5700
acttctccta acatctcata ataaatttct ac                                5732
```

```
<210> SEQ ID NO 2
<211> LENGTH: 920
<212> TYPE: PRT
<213> ORGANISM: Solanum americanum

<400> SEQUENCE: 2

Met Ala Tyr Ala Ala Leu Ser Ser Leu Ile Tyr Thr Leu Gln Gln Leu
1               5                   10                  15

Phe Lys Pro Asn Gln Ser Phe Val Cys Gln Ser Cys Cys Thr Gln Gln
            20                  25                  30

His Val Gln Ser Leu Cys Gln Asn Leu Ser Ala Leu Gln Leu Phe Leu
        35                  40                  45

Asp Asp Thr Thr Thr Lys Asp Ile Glu Thr Leu Lys Val Cys Asn Tyr
    50                  55                  60

Leu Ile Ser Tyr Ser Ser Tyr Ile Tyr Ser Ile Ile Asn Leu Ser
65                  70                  75                  80

Ser Phe Asn Phe Lys Val Ile Glu Lys Arg Ile Arg Asp Val Val Tyr
                85                  90                  95

Lys Ala Glu Asp Lys Val Asp Ser Ser Leu Arg Ser Ile Ile Leu Ala
            100                 105                 110

Asp Cys Thr Glu Asn Lys Glu Gly Ala Cys Lys Phe Phe Glu Glu Glu
        115                 120                 125

Leu Leu Lys Val Glu Lys Asp Val Asp Ser Leu Ser Lys Glu Val Met
130                 135                 140

Gln Ile Asn Val Asn Lys His Gly Ser Arg Ser Ala Glu Leu Thr Thr
145                 150                 155                 160

Ile Pro Pro Ser Pro Glu Lys Ser Thr Asn Glu Glu His Thr Ile Val
                165                 170                 175

Gly Met Glu Asp Glu Tyr Asn Thr Ile Leu Asp Arg Leu Thr Ala Gln
            180                 185                 190

Thr Asp Glu Leu Thr Val Ile Pro Ile Phe Gly Met Gly Gly Ile Gly
        195                 200                 205

Lys Thr Thr Leu Ala Arg Lys Val Tyr Asp Asp Ser Ser Ile Arg Ser
210                 215                 220

Arg Phe Asp Arg His Val Trp Val Thr Thr Ser Glu Glu Phe Asn Glu
225                 230                 235                 240

Arg Arg Met Leu Leu Glu Val Val Ser Ser Ile Thr Thr Gly Ser Asn
                245                 250                 255

Gln Glu Lys Ser Asp Asp Gln Leu Met Glu Ile Val Tyr Arg Gly Leu
            260                 265                 270

Lys Gly Arg Arg Phe Leu Ile Val Ile Asp Asp Ile Trp Ser Thr Glu
        275                 280                 285

Ala Trp Asp Gln Met Gln Arg Ile Phe Pro Asn Asp Asp Asn Lys Ser
    290                 295                 300

Arg Ile Leu Leu Thr Thr Arg Leu Lys Tyr Val Ala Asp Tyr Val Ser
305                 310                 315                 320

Ser Pro Asp Phe Pro Pro His Ser Lys Ser Phe Leu Ser Leu Asp Asp
                325                 330                 335

Ser Trp Asn Leu Phe Thr Glu Lys Val Phe Asn Lys Asp Thr Cys Pro
            340                 345                 350

Pro His Leu Glu Glu Thr Gly Lys His Ile Val Gln Gln Cys Arg Gly
        355                 360                 365

Leu Pro Leu Ser Val Val Val Val Ala Gly Leu Val Gly Lys Met Asp
    370                 375                 380
```

```
Pro Thr His Asp Asn Trp Glu Asn Val Glu Glu Asn Leu Asn Ser Phe
385                 390                 395                 400

Ile Gly Thr Val Ser Glu Arg Cys Gln Ser Ile Leu Ser Leu Ser Tyr
                405                 410                 415

Asn Tyr Leu Pro Gln Tyr Leu Arg Ala Cys Phe Leu Tyr Val Gly Cys
            420                 425                 430

Phe Pro Glu Asp Lys Glu Ile Asp Val Ser Lys Leu Ile Arg Leu Trp
        435                 440                 445

Ile Ala Glu Gln Phe Val Lys Ala Arg Ser Asn Lys Arg Leu Glu Val
    450                 455                 460

Val Ala Glu Glu Tyr Leu Glu Glu Leu Ile Asp Arg Ser Leu Ile Leu
465                 470                 475                 480

Ser Gly Arg Gln Arg Ala Asn Gly Arg Met Lys Thr Cys Lys Ile His
                485                 490                 495

Asp Leu Leu Arg Gln Leu Cys Leu Ser Glu Ala His Thr Glu Asn Ile
            500                 505                 510

Ser His Ile Met Asn Arg Asn Val Pro Val Ser Ser Glu Ala Ile Asp
        515                 520                 525

Asp Gln Arg Arg Val Ile Val Pro Leu Glu Leu Glu Glu Pro Val
    530                 535                 540

Tyr Pro Thr Arg Asn Ser Ser Gly Ile Thr Ser Thr Thr Arg Thr Phe
545                 550                 555                 560

Ile Ser Met Glu Ile Cys Leu Arg Glu Ala Gln Thr Glu Ala Ile Tyr
                565                 570                 575

Asp Gln Arg Arg Val Ile Leu Leu Ser Lys Arg His Arg Ile Asp Thr
            580                 585                 590

Ile Arg Thr Ile Ile Pro Phe Lys Asp Thr Phe Pro Lys Glu Ile Cys
        595                 600                 605

Ser Ile Val Ser Gln Leu Lys Leu Leu Lys Val Leu Asp Val Leu Ser
    610                 615                 620

Val Trp Tyr Asp Val Ser Cys Ile Ile Pro Gln Leu Val His Leu Arg
625                 630                 635                 640

Tyr Val Gly Ala Val Ile Leu Lys Ala Leu Ser Leu Pro Lys Leu Arg
                645                 650                 655

Asn Leu Gln Thr Ile Ile Leu Thr Ser Val Glu Thr Thr Glu Leu Lys
            660                 665                 670

His Ser Leu Asp Ile Trp Arg Met Ser Glu Ile Arg His Leu Asp Ile
        675                 680                 685

Val Pro Pro Leu Tyr Ile Ser Asn Pro Leu Glu Ala Glu Gln Pro Leu
    690                 695                 700

Phe Leu Asn Asn Leu His Thr Leu Phe Leu Arg Cys Ser Pro Phe Val
705                 710                 715                 720

Ala Lys Ile Ile Arg Arg Thr Pro Asn Leu Lys Lys Leu Lys Ile Leu
                725                 730                 735

Asp Lys Ser Lys His Pro Asp Trp Asp Ile Leu Asp Ser Leu Asn
            740                 745                 750

Leu Leu Glu Glu Leu Glu Thr Leu Gln Ile Ser Thr Glu Glu Asn Ile
        755                 760                 765

Asp Pro Met Ile Phe Ser Gly Asp Ile Phe Pro Arg Asn Leu Lys Gln
    770                 775                 780

Leu Lys Leu Ser Tyr Thr Cys Ile Pro Trp Glu Asp Met Lys Leu Leu
785                 790                 795                 800
```

```
Ala Asn Leu Pro Asn Leu Glu Val Phe Lys Gly His Tyr Ala Phe Asn
            805                 810                 815

Gly Thr Asp Trp Lys Leu Asp Glu Asp Val Val Phe Cys Lys Leu Lys
        820                 825                 830

Ser Leu Arg Leu Tyr Glu Arg Gly Asp Leu Gln Arg Trp Glu Ala Ala
    835                 840                 845

Gly Ser Asp Asn Phe Pro Met Leu Glu Gln Leu Leu Leu Tyr Gly Phe
850                 855                 860

Lys Lys Leu Glu Glu Ile Pro Glu Ser Ile Gly Glu Ile Met Thr Leu
865                 870                 875                 880

Lys Phe Ile Lys Thr Glu Phe Cys Gly Ser Gly Val Lys Thr Ser Ala
                885                 890                 895

Lys Lys Ile Gln Glu Glu Gln Glu Ser Leu Gly Asn Tyr Glu Leu Gln
            900                 905                 910

Val Gln Ile Thr Pro Lys Val Cys
        915                 920
```

<210> SEQ ID NO 3
<211> LENGTH: 2760
<212> TYPE: DNA
<213> ORGANISM: Solanum americanum

<400> SEQUENCE: 3

```
atggcttatg ctgctctttc ttcacttatc tatacattgc aacaactctt caaacctaat      60
caatctttcg tttgtcaaag ctgctgtacg caacaacatg ttcaatctct ctgtcaaaat     120
ctttctgctc tgcaactttt ccttgacgat actacaacaa ggatattga aactcttaag      180
gtatgtaatt atctaatctc ttactcatct tatatttatt caataataat taatttatcg     240
agtttcaatt ttaaggttat agaaaagagg atcagagatg tagtatacaa agcagaagat     300
aaagttgatt caagcctaag aagcatcatt ctagctgatt gcacagagaa taaagaaggg     360
gcttgtaaat tctttgagga gaattgcta aaagtggaaa agatgttga ttctctcagc       420
aaagaggtga tgcagatcaa tgttaacaag catggaagca gatctgcaga actaacaaca     480
attcctccct ctccagaaaa aagtacaaat gaggaacata ctattgttgg gatggaggat     540
gagtacaaca ccatacttga tcgcctcact gcccaaacag acgagttgac tgtcatacca     600
attttggta tgggcggtat aggtaagaca actcttgcca gaaaggttta tgatgattca      660
tctattcgtt ctcgatttga tagacatgta tgggtcacta cctctgaaga attcaatgag     720
agacgaatgc ttctcgaagt tgtttcttca attactactg gaagcaatca agaaaagagc     780
gatgatcaac taatggagat tgtgtataga ggtcttaagg gtaggagatt tctaattgtc     840
atagatgata tttggagtac tgaggcttgg gaccaaatgc aaagaatatt tccaaatgat     900
gacaataaaa gccgaattct actaactaca cggctcaagt atgttgctga ttatgtcagc     960
agtcctgatt tccacctca gtaagtct tttctaagtc ttgatgatag ttggaatcta      1020
ttcaccgaaa aagtattcaa caaagatacc tgtcctcctc acctagaaga aacagggaag    1080
catattgtac aacaatgtcg aggattacct ctctcggttg ttgtagttgc tggacttgtt    1140
ggaaaaatgg acccaacgca tgacaattgg gagaacgttg aggaaaatct gaactcattc    1200
attggtactg tatccgaacg gtgccaatca attctttctt aagctacaa ttacttgccc     1260
caatatttga gggcttgttt tctctatgtt ggatgttttc ctgaagataa agagattgat    1320
gtttccaagt tgattaggct atggattgct gagcaattcg taaggcgag aagcaataaa     1380
aggttagaag tggtagcaga ggagtatcta gaagagttaa ttgatagaag cctaatttg    1440
```

```
agtggtagac aaagggctaa tggaaggatg aaaacttgca aaattcatga tcttcttcgc    1500
caactatgcc taagtgaagc tcatactgaa atattagtc atatcatgaa agaaatgtc      1560 cccgtgtcct cagaagccat agatgatcaa cggcgagtga ttgttccatt ggaacttgaa    1620
gaggaaccag tttatcctac aaggaatagc agtggtatta caagtacaac ccgcaccttt    1680
atttcaatgg aaatatgcct aagagaagct cagaccgaag ccatatatga tcaacggcga    1740
gtgatccttc tgtctaaacg acataggatt gatacaatcc gcaccattat tccattcaaa    1800
gatacttttc cgaaagagat ttgttccatt gtttcacagt tgaagttgct taaggtgttg    1860
gatgtattat cagtctggta cgatgtctct tgtataatac ctcagcttgt acatttgaga    1920
tatgttggtg cagtaatttt gaaagctctt tcactaccca aattgagaaa tctacagacc    1980
ataattctta caagtgttga aaccacagag ttgaagcact cactagatat ctggagaatg    2040
tcagagataa gacatttgga tattgtaccg ccactatata tatcaaatcc tcttgaagca    2100
gaacaacctt tgtttctcaa taacttgcac acacttttc tccgttgctc tccttttgtt     2160
gcgaaaatca taagaagaac tcccaatcta aaaaagctaa agatttttaga taaatctaag   2220 catcctgact ggcctgatat tcttgattct ctcaatcttc tagaggagct ggagacacta    2280
caaatatcaa cagaagaaaa cattgacccg atgattttct ctggggatat tttccctcgt    2340
aatctcaagc aactgaaatt atcatatact tgtataccat gggaagatat gaaattgctg    2400
gctaatttac ccaatcttga ggtgttcaag ggtcattatg cattcaatgg aacagattgg    2460
aaactagatg aagatgttgt gttttgcaaa ttaaaatctc tacgactgta tgagcgtgga    2520
gatttgcaaa ggtgggaagc tgctggtagt gataattttc caatgcttga gcaactatta    2580
ttgtatgggt tcaaaaaact ggaagagatt ccggagagta ttggagaaat aatgacacta    2640
aaatttatca aacagaatt ttgcggctct ggtgtaaaga caagtgcaaa gaaaattcaa      2700
gaagagcaag aaagcctggg aaattatgag cttcaagttc aaattactcc taaggtatgt    2760
```

<210> SEQ ID NO 4
<211> LENGTH: 5957
<212> TYPE: DNA
<213> ORGANISM: Solanum americanum

<400> SEQUENCE: 4

```
attggtgatt cgacgtttga attttaaga taattatatc ttttcaatg atacccgcaa        60 gggtgatcga gttggttgag cagataattt ctaaatgggg tcataggttc aaaatcctct     120
acatgtttgc tcggtagctc gtcatatgga acttgcttag tatagtttac cttttcagtg    180
tgatttgcgc gctattacgt tgaagcagtg ttatcgtata cacacctaaa ccctgaagaa    240
tcatgactgc gagcttcctt gacaacaaat ttttttatc tatttcaatg acattactat      300
tagatcaatt tttttatatc acatgatttg atccatccta catctatttg cctaccataa    360
aattaccggt caagcaacgt aatttgtaag tcccatagaa ttttaacag atgcattggt      420 tcatggttga ggtgaagaac agatgtagca gttttttgtt gaagccgtta gtttcttgac    480
agactataac agaggaatgt aagttgcaac tttgaggat agtttaggga tgattttgt      540 tcattatgta gtataaggat gtagtttaag tttgaggtat aattgaggga tgttttgct      600 atttactcta caaaattcca cacagtatta ttaattttct aaggaccgtt tggccatgtg    660
atatgaaatc atgatatgaa attatgaaat gaagttaaag ttttgtttgg acatgtaatt    720 tggactttt atgttgtatg ttttcttata aacataaaaa acccacaagt tgtaaaatta     780
```

```
ttaaacttgt cccattttt tattcaattt taccaaataa acaaaaattt acaaaatcac    840
ataatatgct aacacaaaac tattcttta aaaatacaat atttattgat caaactttaa    900
ttcaacaaaa aataaaattc aacataagtt gtagtgtact agtctttaat ataattctcc   960
cacatagtac ggagcaatta tatgatcgag tatacaaacc aacattgcta ctttgagcta  1020
taaatggttt aaaaagtaat gatatgaatc ataaatttta ttacatatga aacaaatggt  1080
gagtagatat ttttaataa aatataaact tatgggtcaa ttttgtatt tgaaaaatcc    1140
caaatcatga tttgaaattt tcaaatcatg atttttgaag aatttgggat tttatctcat  1200
gatatgaaat catgagatga aatcagcctg aaatcgcatg tccaaatgct gatttcatct  1260
catgatttca tatcgtgata tgaaatcgca tgtccaaacg cctactaagt aacttagaca  1320
cgtcttgacc ttttataatt gctccatcca tcctaattta cttgtcaaat attttctaat  1380
ttgattcccc ttttacttgt cattttttac aaatcaagaa acgacaattt ttttctttc   1440
tattataccc tcaatttatt aacattgaat taatgtcctt gaaaaatata gtaagtaaat  1500
atgtttaaaa ctctatcaaa ttaataggg taaaatggta aactcattat accaattatt   1560
ttttttttaa tagatgcgtc aaatcaaaaa ttgacaagta aaaagagacg gaaagagtat  1620
ataaattca aagaaattt gtattgaaag ttaattgtat tcgtccactt gacacatcat   1680
gtcttaatta ctacaagttg atttgaataa gaaatgtgag acatctctac tatcgtggtg  1740
ggaccaatgc ttgaaaagtc gacgaaaact acaagagtgt ctttattaga aatcaggaca  1800
acttgactct ttatttttca tttctttttt cttactttt cttggtcaat ccatagtttt   1860
gcatccataa accacaagtt ctgtttagat attaaataga aaattgtcca aattcattta  1920
gaaaaatgtg gacataaatc atttagacaa aacctcttat agcctaagca gagacatttc  1980
tcttccagca aacaaagag aaatggctta tgctgctctt tcttcactta tctatacatt   2040
gcaacaactc ttcaaaccta atcaatcttt cgtttgtcaa agctgctgta cgcaacaaca  2100
tgttcaatct ctctgtcaaa atctttctgc tctgcaactt ttccttgacg atactacaac  2160
aaaggatatt gaaactctta aggtatgtaa ttatctaatc tcttactcat cttatattta  2220
ttcaataata attaatttat cgagtttcaa ttttaaggtt atagaaaaga ggatcagaga  2280
tgtagtatac aaagcagaag ataaagttga ttcaagccta agaagcatca ttctagctga  2340
ttgcacagag aataaagaag gggcttgtaa attcttgag gaagaattgc taaaagtgga   2400
aaaagatgtt gattctctca gcaaagaggt gatgcagatc aatgttaaca agcatggaag  2460
cagatctgca gaactaacaa caattcctcc ctctccagaa aaaagtacaa atgaggaaca  2520
tactattgtt gggatggagg atgagtacaa caccatactt gatcgcctca ctgcccaaac  2580
agacgagttg actgtcatac aattttttgg tatgggcggt ataggtaaga caactcttgc  2640
cagaaaggtt tatgatgatt catctattcg ttctcgattt gatagacatg tatgggtcac  2700
tacctctgaa gaattcaatg agagacgaat gcttctcgaa gttgtttctt caattactac  2760
tggaagcaat caagaaaaga gcgatgatca actaatggag attgtgtata gaggtcttaa  2820
gggtaggaga tttctaattg tcatagatga tatttggagt actgaggctt gggaccaaat  2880
gcaaagaata tttccaaatg atgacaataa aagccgaatt ctactaacta cacggctcaa  2940
gtatgttgct gattatgtca gcagtcctga ttttccacct catagtaagt cttttctaag  3000
tcttgatgat agttggaatc tattcaccga aaaagtattc aacaaagata cctgtcctcc  3060
tcacctagaa gaaacaggga agcatattgt acaacaatgt cgaggattac ctctctcggt  3120
tgttgtagtt gctggacttg ttggaaaaat ggacccaacg catgacaatt gggagaacgt  3180
```

```
tgaggaaaat ctgaactcat tcattggtac tgtatccgaa cggtgccaat caattctttc    3240
tttaagctac aattacttgc cccaatattt gagggcttgt tttctctatg ttggatgttt    3300
tcctgaagat aaagagattg atgtttccaa gttgattagg ctatggattg ctgagcaatt    3360
cgtaaaggcg agaagcaata aaaggttaga agtggtagca gaggagtatc tagaagagtt    3420
aattgataga agcctaattt tgagtggtag acaaagggct aatggaagga tgaaaacttg    3480
caaaattcat gatcttcttc gccaactatg cctaagtgaa gctcatactg aaaatattag    3540
tcatatcatg aatagaaatg tccccgtgtc ctcagaagcc atagatgatc aacggcgagt    3600
gattgttcca ttggaacttg aagaggaacc agtttatcct acaaggaata gcagtggtat    3660
tacaagtaca acccgcacct ttatttcaat ggaaatatgc ctaagagaag ctcagaccga    3720
agccatatat gatcaacggc gagtgatcct tctgtctaaa cgacatagga ttgatacaat    3780
ccgcaccatt attccattca agatactttt ccgaaagag atttgttcca ttgtttcaca    3840
gttgaagttg cttaaggtgt tggatgtatt atcagtctgg tacgatgtct cttgtataat    3900
acctcagctt gtacatttga gatatgttgg tgcagtaatt ttgaaagctc tttcactacc    3960
caaattgaga aatctacaga ccataattct tacaagtgtt gaaaccacag agttgaagca    4020
ctcactagat atctggagaa tgtcagagat aagacatttg gatattgtac cgccactata    4080
tatatcaaat cctcttgaag cagaacaacc tttgtttctc aataacttgc acacactttt    4140
tctccgttgc tctcctttg ttgcgaaaat cataagaaga actcccaatc taaaaaagct    4200
aaagatttta gataaatcta agcatcctga ctggcctgat attcttgatt ctctcaatct    4260
tctagaggag ctggagacac tacaaatatc aacagaagaa acattgaccc cgatgatttt    4320
ctctggggat atttttccctc gtaatctcaa gcaactgaaa ttatcatata cttgtatacc    4380
atgggaagat atgaaattgc tggctaattt acccaatctt gaggtgttca agggtcatta    4440
tgcattcaat ggaacagatt ggaaactaga tgaagatgtt gtgttttgca aattaaaatc    4500
tctacgactg tatgagcgtg gagatttgca aaggtgggaa gctgctggta gtgataattt    4560
tccaatgctt gagcaactat tattgtatgg gttcaaaaaa ctggaagaga ttccggagag    4620
tattggagaa ataatgacac taaaatttat caaaacagaa ttttgcggct ctggtgtaaa    4680
gacaagtgca aagaaaattc aagaagagca agaaagcctg ggaaattatg agcttcaagt    4740
tcaaattact cctaaggtat gttgaaactc aatctttgat taatactctc cactcggtta    4800
gatttaggat tcaaattgtc tacttacatt tatgatcatc cccttgcgg tcttcttatt    4860 tcttttagta aatagcttca aaaactctac agaaattaca cataattaac aattgacaat    4920
tgattctctc ttattgataa tttgtaattt tctctttcag ttaagatttt tgatcgaaaa    4980
tttagacgaa ataagcatgt tgcccccgaa tgaagtagcc gaaaaaatca aaggtttgtc    5040
tatttaattc cttttttatt tcattgaaag aggttcagat atattaaaca acttttttaac    5100 ctttctattt gatttttat cgcttagata gatacaacat ttatttttaac atcaattgtt    5160 attttgattc aattatgttc ttttaatata tagttccac tcggttcttc aattcttttt    5220
tcaattatag ttttatttttt ttaattgcac atggttgatc gatttaattt gtgagattca    5280
cttttctttc ggttttacga gttcttcgcg attaatgtta ttcagattta ggagtattat    5340
atttcaactt tcgattagat ttaggattca aattgtcttc tttcatttat gatcatcatc    5400
ctttcgatct tctttatttc ttttagtaaa tagcttcaaa aactctatag aaattacata    5460
taattaacaa ttgagaattg attctctcgt aatttctcat gttctctttc agttaaaatt    5520
```

-continued

```
tttgatcaaa aactaaaaga gattccggag agcactggac aaataatgac acgaaaaatc    5580
atcaaaacag aattttgcgg ctctggtgta gagactagtg caaagaagat tcaagaagag    5640
caagaaagct tgggaaattg tgagcttcat caagttcaaa ttactcctaa ggtatattaa    5700
aactccatct ttgattatta gccaattctt taatttcata ttatttctag actaaattaa    5760
aatattaaaa gatataaaga atttaattaa tttaattatt cctttaaaat ccaaacatga    5820
tgaatttgag taaattaaat gaatatagtt cagattcatt taactaatag gccatttagt    5880
tttaatatgg caacgtttta ggcttttaac attctctttg aatgtaggta taatgcatta    5940
agtgcagaaa tttaatc                                                   5957
```

<210> SEQ ID NO 5
<211> LENGTH: 920
<212> TYPE: PRT
<213> ORGANISM: Solanum americanum

<400> SEQUENCE: 5

```
Met Ala Tyr Ala Ala Leu Ser Ser Leu Ile Tyr Thr Leu Gln Gln Leu
1               5                   10                  15

Phe Lys Pro Asn Gln Ser Phe Val Cys Gln Ser Cys Cys Thr Gln Gln
            20                  25                  30

His Val Gln Ser Leu Cys Gln Asn Leu Ser Ala Leu Gln Leu Phe Leu
        35                  40                  45

Asp Asp Thr Thr Thr Lys Asp Ile Glu Thr Leu Lys Val Cys Asn Tyr
    50                  55                  60

Leu Ile Ser Tyr Ser Ser Tyr Ile Tyr Ser Ile Ile Asn Leu Ser
65                  70                  75                  80

Ser Phe Asn Phe Lys Val Ile Glu Lys Arg Ile Arg Asp Val Tyr
                85                  90                  95

Lys Ala Glu Asp Lys Val Asp Ser Ser Leu Arg Ser Ile Ile Leu Ala
            100                 105                 110

Asp Cys Thr Glu Asn Lys Glu Gly Ala Cys Lys Phe Phe Glu Glu Glu
        115                 120                 125

Leu Leu Lys Val Glu Lys Asp Val Asp Ser Leu Ser Lys Glu Val Met
    130                 135                 140

Gln Ile Asn Val Asn Lys His Gly Ser Arg Ser Ala Glu Leu Thr Thr
145                 150                 155                 160

Ile Pro Pro Ser Pro Glu Lys Ser Thr Asn Glu His Thr Ile Val
                165                 170                 175

Gly Met Glu Asp Glu Tyr Asn Thr Ile Leu Asp Arg Leu Thr Ala Gln
            180                 185                 190

Thr Asp Glu Leu Thr Val Ile Pro Ile Phe Gly Met Gly Gly Ile Gly
        195                 200                 205

Lys Thr Thr Leu Ala Arg Lys Val Tyr Asp Asp Ser Ser Ile Arg Ser
    210                 215                 220

Arg Phe Asp Arg His Val Trp Val Thr Thr Ser Glu Glu Phe Asn Glu
225                 230                 235                 240

Arg Arg Met Leu Leu Glu Val Val Ser Ser Ile Thr Thr Gly Ser Asn
                245                 250                 255

Gln Glu Lys Ser Asp Asp Gln Leu Met Glu Ile Val Tyr Arg Gly Leu
            260                 265                 270

Lys Gly Arg Arg Phe Leu Ile Val Ile Asp Asp Ile Trp Ser Thr Glu
        275                 280                 285

Ala Trp Asp Gln Met Gln Arg Ile Phe Pro Asn Asp Asp Asn Lys Ser
```

```
                290                 295                 300
Arg Ile Leu Leu Thr Thr Arg Leu Lys Tyr Val Ala Asp Tyr Val Ser
305                 310                 315                 320

Ser Pro Asp Phe Pro Pro His Ser Lys Ser Phe Leu Ser Leu Asp Asp
                325                 330                 335

Ser Trp Asn Leu Phe Thr Glu Lys Val Phe Asn Lys Asp Thr Cys Pro
            340                 345                 350

Pro His Leu Glu Glu Thr Gly Lys His Ile Val Gln Gln Cys Arg Gly
        355                 360                 365

Leu Pro Leu Ser Val Val Val Ala Gly Leu Val Gly Lys Met Asp
    370                 375                 380

Pro Thr His Asp Asn Trp Glu Asn Val Glu Glu Asn Leu Asn Ser Phe
385                 390                 395                 400

Ile Gly Thr Val Ser Glu Arg Cys Gln Ser Ile Leu Ser Leu Ser Tyr
                405                 410                 415

Asn Tyr Leu Pro Gln Tyr Leu Arg Ala Cys Phe Leu Tyr Val Gly Cys
                420                 425                 430

Phe Pro Glu Asp Lys Glu Ile Asp Val Ser Lys Leu Ile Arg Leu Trp
            435                 440                 445

Ile Ala Glu Gln Phe Val Lys Ala Arg Ser Asn Lys Arg Leu Glu Val
450                 455                 460

Val Ala Glu Glu Tyr Leu Glu Glu Leu Ile Asp Arg Ser Leu Ile Leu
465                 470                 475                 480

Ser Gly Arg Gln Arg Ala Asn Gly Arg Met Lys Thr Cys Lys Ile His
                485                 490                 495

Asp Leu Leu Arg Gln Leu Cys Leu Ser Glu Ala His Thr Glu Asn Ile
                500                 505                 510

Ser His Ile Met Asn Arg Asn Val Pro Val Ser Ser Glu Ala Ile Asp
            515                 520                 525

Asp Gln Arg Arg Val Ile Val Pro Leu Glu Leu Glu Glu Pro Val
            530                 535                 540

Tyr Pro Thr Arg Asn Ser Ser Gly Ile Thr Ser Thr Thr Arg Thr Phe
545                 550                 555                 560

Ile Ser Met Glu Ile Cys Leu Arg Glu Ala Gln Thr Glu Ala Ile Tyr
                565                 570                 575

Asp Gln Arg Arg Val Ile Leu Leu Ser Lys Arg His Arg Ile Asp Thr
            580                 585                 590

Ile Arg Thr Ile Ile Pro Phe Lys Asp Thr Phe Pro Lys Glu Ile Cys
        595                 600                 605

Ser Ile Val Ser Gln Leu Lys Leu Leu Lys Val Leu Asp Val Leu Ser
    610                 615                 620

Val Trp Tyr Asp Val Ser Cys Ile Ile Pro Gln Leu Val His Leu Arg
625                 630                 635                 640

Tyr Val Gly Ala Val Ile Leu Lys Ala Leu Ser Leu Pro Lys Leu Arg
                645                 650                 655

Asn Leu Gln Thr Ile Ile Leu Thr Ser Val Glu Thr Thr Glu Leu Lys
            660                 665                 670

His Ser Leu Asp Ile Trp Arg Met Ser Glu Ile Arg His Leu Asp Ile
        675                 680                 685

Val Pro Pro Leu Tyr Ile Ser Asn Pro Leu Glu Ala Glu Gln Pro Leu
    690                 695                 700

Phe Leu Asn Asn Leu His Thr Leu Phe Leu Arg Cys Ser Pro Phe Val
705                 710                 715                 720
```

```
Ala Lys Ile Ile Arg Arg Thr Pro Asn Leu Lys Lys Leu Lys Ile Leu
            725                 730                 735
Asp Lys Ser Lys His Pro Asp Trp Pro Asp Ile Leu Asp Ser Leu Asn
        740                 745                 750
Leu Leu Glu Glu Leu Glu Thr Leu Gln Ile Ser Thr Glu Glu Asn Ile
    755                 760                 765
Asp Pro Met Ile Phe Ser Gly Asp Ile Phe Pro Arg Asn Leu Lys Gln
770                 775                 780
Leu Lys Leu Ser Tyr Thr Cys Ile Pro Trp Glu Asp Met Lys Leu Leu
785                 790                 795                 800
Ala Asn Leu Pro Asn Leu Glu Val Phe Lys Gly His Tyr Ala Phe Asn
            805                 810                 815
Gly Thr Asp Trp Lys Leu Asp Glu Asp Val Val Phe Cys Lys Leu Lys
        820                 825                 830
Ser Leu Arg Leu Tyr Glu Arg Gly Asp Leu Gln Arg Trp Glu Ala Ala
    835                 840                 845
Gly Ser Asp Asn Phe Pro Met Leu Glu Gln Leu Leu Leu Tyr Gly Phe
850                 855                 860
Lys Lys Leu Glu Glu Ile Pro Glu Ser Ile Gly Glu Ile Met Thr Leu
865                 870                 875                 880
Lys Phe Ile Lys Thr Glu Phe Cys Gly Ser Gly Val Lys Thr Ser Ala
            885                 890                 895
Lys Lys Ile Gln Glu Glu Gln Glu Ser Leu Gly Asn Tyr Glu Leu Gln
        900                 905                 910
Val Gln Ile Thr Pro Lys Val Cys
    915                 920

<210> SEQ ID NO 6
<211> LENGTH: 2760
<212> TYPE: DNA
<213> ORGANISM: Solanum americanum

<400> SEQUENCE: 6
atggcttatg ctgctctttc ttcacttatc tatacattgc aacaactctt caaacctaat      60
caatctttcg tttgtcaaag ctgctgtacg caacaacatg ttcaatctct ctgtcaaaat     120
ctttctgctc tgcaactttt ccttgacgat actacaacaa aggatattga aactcttaag     180
gtatgtaatt atctaatctc ttactcatct tatatttatt caataataat taatttatcg     240
agtttcaatt ttaaggttat agaaaagagg atcagagatg tagtatacaa agcagaagat     300
aaagttgatt caagcctaag aagcatcatt ctagctgatt gcacagagaa taagaaggg      360 gcttgtaaat tctttgagga agaattgcta aaagtggaaa aagatgttga ttctctcagc     420
aaagaggtga tgcagatcaa tgttaacaag catggaagca gatctgcaga actaacaaca     480
attcctccct ctccagaaaa aagtacaaat gaggaacata ctattgttgg gatggaggat     540
gagtacaaca ccatacttga tcgcctcact gcccaaacag acgagttgac tgtcatacca     600 attttggta tgggcggtat aggtaagaca actcttgcca gaaaggttta tgatgattca     660
tctattcgtt ctcgatttga tagacatgta tgggtcacta cctctgaaga attcaatgag     720
agacgaatgc ttctcgaagt tgtttcttca attactactg gaagcaatca agaaaagagc     780
gatgatcaac taatggagat tgtgtataga ggtcttaagg gtaggagatt tctaattgtc     840
atagatgata tttggagtac tgaggcttgg gaccaaatgc aaagaatatt tccaaatgat     900
gacaataaaa gccgaattct actaactaca cggctcaagt atgttgctga ttatgtcagc     960
```

```
agtcctgatt ttccacctca tagtaagtct tttctaagtc ttgatgatag ttggaatcta    1020
ttcaccgaaa aagtattcaa caaagatacc tgtcctcctc acctagaaga aacagggaag    1080
catattgtac aacaatgtcg aggattacct ctctcggttg ttgtagttgc tggacttgtt    1140
ggaaaaatgg acccaacgca tgacaattgg gagaacgttg aggaaaatct gaactcattc    1200
attggtactg tatccgaacg gtgccaatca attctttctt taagctacaa ttacttgccc    1260
caatatttga gggcttgttt tctctatgtt ggatgttttc ctgaagataa agagattgat    1320
gtttccaagt tgattaggct atggattgct gagcaattcg taaaggcgag aagcaataaa    1380
aggttagaag tggtagcaga ggagtatcta aagagttaa ttgatagaag cctaattttg    1440
agtggtagac aaagggctaa tggaaggatg aaaacttgca aaattcatga tcttcttcgc    1500
caactatgcc taagtgaagc tcatactgaa atattagtc atatcatgaa agaaatgtc    1560 cccgtgtcct cagaagccat agatgatcaa cggcgagtga ttgttccatt ggaacttgaa    1620
gaggaaccag tttatcctac aaggaatagc agtggtatta caagtacaac ccgcaccttt    1680
atttcaatgg aaatatgcct aagagaagct cagaccgaag ccatatatga tcaacggcga    1740
gtgatccttc tgtctaaacg acataggatt gatacaatcc gcaccattat tccattcaaa    1800 gatactttc cgaaagagat ttgttccatt gtttcacagt tgaagttgct taaggtgttg    1860
gatgtattat cagtctggta cgatgtctct tgtataatac ctcagcttgt acatttgaga    1920
tatgttggtg cagtaatttt gaaagctctt tcactaccca aattgagaaa tctacagacc    1980
ataattctta caagtgttga aaccacagag ttgaagcact cactagatat ctggagaatg    2040
tcagagataa gacatttgga tattgtaccg ccactatata tatcaaatcc tcttgaagca    2100
gaacaacctt tgtttctcaa taacttgcac acacttttc tccgttgctc tccttttgtt    2160
gcgaaaatca taagaagaac tcccaatcta aaaaagctaa agatttttaga taaatctaag    2220 catcctgact ggcctgatat tcttgattct ctcaatcttc tagaggagct ggagacacta    2280
caaatatcaa cagaagaaaa cattgacccg atgattttct ctggggatat tttccctcgt    2340
aatctcaagc aactgaaatt atcatatact tgtataccat gggaagatat gaaattgctg    2400
gctaatttac ccaatcttga ggtgttcaag ggtcattatg cattcaatgg aacagattgg    2460
aaactagatg aagatgttgt gttttgcaaa ttaaaatctc tacgactgta tgagcgtgga    2520
gatttgcaaa ggtgggaagc tgctggtagt gataattttc caatgcttga gcaactatta    2580
ttgtatgggt tcaaaaaact ggaagagatt ccggagagta ttggagaaat aatgacacta    2640
aaatttatca aaacagaatt ttgcggctct ggtgtaaaga caagtgcaaa gaaaattcaa    2700
gaagagcaag aaagcctggg aaattatgag cttcaagttc aaattactcc taaggtatgt    2760
```

<210> SEQ ID NO 7
<211> LENGTH: 5948
<212> TYPE: DNA
<213> ORGANISM: Solanum americanum

<400> SEQUENCE: 7

```
ttgcttagta tagtttacct tttcagtgtg atttgcgcgc tattacgttg aagcagtgtt      60
atcgtataca cacctaaacc ctgaagaatc atgactgcga gcttccttga caacaaattt     120
tttttatcta tttcaatgac attactatta gatcaatttt tttatatcac atgatttgat     180
ccatcctaca tctatttgcc taccataaaa ttaccggtca agcaacgtaa tttgtaagtc     240
ccatagaatt tttaacagat gcattggttc atggttgagg tgaagaacag atgtagcagt     300
```

```
tttttgttga agccgttagt ttcttgacag actataacag aggaatgtaa gttgcaactt    360
ttgaggatag tttagggatg attttttgttc attatgtagt ataaggatgt agtttaagtt    420
tgaggtataa ttgagggatg tttttgctat ttactctaca aaattccaca cagtattatt    480
aattttctaa ggaccgtttg gccatgtgat atgaaatcat gatatgaaat tatgaaatga    540
agttaaagtt ttgtttggac atgtaatttg gacttttttat gttgtatgtt ttcttataaa    600
cataaaaaac ccacaagttg taaaattatt aaacttgtcc cattttttta ttcaatttta    660
ccaaataaac aaaaatttac aaaatcacat aatatgctaa cacaaaacta ttctttaaaa    720
aatacaatat ttattgatca aactttaatt caacaaaaaa taaaattcaa cataagttgt    780
agtgtactag tctttaatat aattctccca catagtacgg agcaattata tgatcgagta    840
tacaaaccaa cattgctact ttgagctata aatggtttaa aaagtaatga tatgaatcat    900
aaattttatt acatatgaaa caaatggtga gtagatattt tttaataaaa tataaactta    960
tgggtcaatt tttgtatttg aaaaatccca aatcatgatt tgaaattttc aaatcatgat   1020
ttttgaagaa tttgggattt tatctcatga tatgaaatca tgagatgaaa tcagcctgaa   1080
atcgcatgtc caaatgctga tttcatctca tgatttcata tcgtgatatg aaatcgcatg   1140
tccaaacgcc tactaagtaa cttagacacg tcttgacctt ttataattgc tccatccatc   1200
ctaatttact tgtcaaatat tttctaattt gattccccctt ttacttgtca ttttttacaa   1260
atcaagaaac gacaattttt tttctttcta ttatacccctc aatttattaa cattgaatta   1320
atgtccttga aaatatagt aagtaaatat gtttaaaact ctatcaaatt aatagggggta   1380 aaatggtaaa ctcattatac caattatttt tttttaata gatgcgtcaa atcaaaaatt   1440
gacaagtaaa aagagacgga aagagtatat aaatttcaaa gaaaatttgt attgaaagtt   1500
aattgtattc gtccacttga cacatcatgt cttaattact acaagttgat ttgaataaga   1560
aatgtgagac atctctacta tcgtggtggg accaatgctt gaaaagtcga cgaaaactac   1620
aagagtgtct ttattagaaa tcaggacaac ttgactcttt attttcatt tcttttttct   1680 tactttttct tggtcaatcc atagttttgc atccataaac cacaagttct gtttagatat   1740
taaatagaaa attgtccaaa ttcatttaga aaaatgtgga cataaatcat ttagacaaaa   1800
cctcttatag cctaagcaga gacatttctc ttccagcaaa caaagagaa atggcttatg   1860 ctgctctttc ttcacttatc tatacattgc aacaactctt caaacctaat caatctttcg   1920
tttgtcaaag ctgctgtacg caacaacatg ttcaatctct ctgtcaaaat ctttctgctc   1980
tgcaactttt ccttgacgat actacaacaa aggatattga aactcttaag gtatgtaatt   2040
atctaatctc ttactcatct tatatttatt caataataat taatttatcg agtttcaatt   2100
ttaaggttat agaaaagagg atcagagatg tagtatacaa agcagaagat aaagttgatt   2160
caagcctaag aagcatcatt ctagctgatt gcacagagaa taaagaaggg gcttgtaaat   2220
tctttgagga agaattgcta aaagtggaaa aagatgttga ttctctcagc aaagaggtga   2280
tgcagatcaa tgttaacaag catggaagca gatctgcaga actaacaaca attcctcccct   2340 ctccagaaaa aagtacaaat gaggaacata ctattgttgg gatggaggat gagtacaaca   2400
ccatacttga tcgcctcact gcccaaacag acgagttgac tgtcatacca attttttggta   2460 tgggcggtat aggtaagaca actcttgcca gaaaggttta tgatgattca tctattcgtt   2520
ctcgatttga tagacatgta tgggtcacta cctctgaaga attcaatgag agacgaatgc   2580
ttctcgaagt tgtttcttca attactactg gaagcaatca agaaaagagc gatgatcaac   2640
taatggagat tgtgtataga ggtcttaagg gtaggagatt tctaattgtc atagatgata   2700
```

```
tttggagtac tgaggcttgg gaccaaatgc aaagaatatt tccaaatgat gacaataaaa    2760
gccgaattct actaactaca cggctcaagt atgttgctga ttatgtcagc agtcctgatt    2820
ttccacctca tagtaagtct tttctaagtc ttgatgatag ttggaatcta ttcaccgaaa    2880
aagtattcaa caaagatacc tgtcctcctc acctagaaga aacagggaag catattgtac    2940
aacaatgtcg aggattacct ctctcggttg ttgtagttgc tggacttgtt ggaaaaatgg    3000
acccaacgca tgacaattgg gagaacgttg aggaaaatct gaactcattc attggtactg    3060
tatccgaacg gtgccaatca attctttctt taagctacaa ttacttgccc caatatttga    3120
gggcttgttt tctctatgtt ggatgttttc ctgaagataa agagattgat gtttccaagt    3180
tgattaggct atggattgct gagcaattcg taaaggcgag aagcaataaa aggttagaag    3240
tggtagcaga ggagtatcta gaagagttaa ttgatagaag cctaattttg agtggtagac    3300
aaagggctaa tggaaggatg aaaacttgca aaattcatga tcttcttcgc caactatgcc    3360
taagtgaagc tcatactgaa aatattagtc atatcatgaa tagaaatgtc cccgtgtcct    3420
cagaagccat agatgatcaa cggcgagtga ttgttccatt ggaacttgaa gaggaaccag    3480
tttatcctac aaggaatagc agtggtatta caagtacaac ccgcaccttt atttcaatgg    3540
aaatatgcct aagagaagct cagaccgaag ccatatatga tcaacggcga gtgatccttc    3600
tgtctaaacg acataggatt gatacaatcc gcaccattat tccattcaaa gatacttttc    3660
cgaaagagat ttgttccatt gtttcacagt tgaagttgct taaggtgttg gatgtattat    3720
cagtctggta cgatgtctct tgtataatac ctcagcttgt acatttgaga tatgttggtg    3780
cagtaatttt gaaagctctt tcactaccca aattgagaaa tctacagacc ataattctta    3840
caagtgttga aaccacagag ttgaagcact cactagatat ctggagaatg tcagagataa    3900
gacatttgga tattgtaccg ccactatata tatcaaatcc tcttgaagca gaacaacctt    3960
tgtttctcaa taacttgcac acactttttc tccgttgctc tccttttgtt gcgaaaatca    4020
taagaagaac tcccaatcta aaaaagctaa agattttaga taaatctaag catcctgact    4080
ggcctgatat tcttgattct ctcaatcttc tagaggagct ggagacacta caaatatcaa    4140
cagaagaaaa cattgacccg atgattttct ctggggatat tttccctcgt aatctcaagc    4200
aactgaaatt atcatatact tgtataccat gggaagatat gaaattgctg ctaatttac    4260 ccaatcttga ggtgttcaag ggtcattatg cattcaatgg aacagattgg aaactagatg    4320
aagatgttgt gttttgcaaa ttaaaatctc tacgactgta tgagcgtgga gatttgcaaa    4380
ggtgggaagc tgctggtagt gataattttc caatgcttga gcaactatta ttgtatgggt    4440
tcaaaaaact ggaagagatt ccggagagta ttggagaaat aatgacacta aaatttatca    4500
aaacagaatt ttgcggctct ggtgtaaaga caagtgcaaa gaaaattcaa gaagagcaag    4560
aaagcctggg aaattatgag cttcaagttc aaattactcc taaggtatgt tgaaactcaa    4620
tctttgatta atactctcca ctcggttaga tttaggattc aaattgtcta cttacattta    4680
tgatcatcac ccttgcggtc ttcttatttc ttttagtaaa tagcttcaaa aactctacag    4740
aaattacaca taattaacaa ttgacaattg attctctctt attgataatt tgtaattttc    4800
tctttcagtt aagattttg atcgaaaatt tagacgaaat aagcatgttg cccccgaatg    4860
aagtagccga aaaaatcaaa ggtttgtcta tttaattcct tttttatttc attgaaagag    4920
gttcagatat attaaacaac ttttttaacct ttctatttga ttttttatcg cttagataga    4980
tacaacattt attttaacat caattgttat tttgattcaa ttatgttctt ttaatatata    5040
```

```
gtttccactc ggttcttcaa ttctttttc aattatagtt ttatttttt aattgcacat    5100
ggttgatcga tttaatttgt gagattcact tttctttcgg ttttacgagt tcttcgcgat    5160
taatgttatt cagatttagg agtattatat ttcaactttc gattagattt aggattcaaa    5220
ttgtcttctt tcatttatga tcatcatcct ttcgatcttc tttatttctt ttagtaaata    5280
gcttcaaaaa ctctatagaa attacatata attaacaatt gagaattgat tctctcgtaa    5340
tttctcatgt tctctttcag ttaaaatttt tgatcaaaaa ctaaagaga ttccggagag    5400
cactggacaa ataatgacac gaaaaatcat caaaacagaa ttttgcggct ctggtgtaga    5460
gactagtgca aagaagattc aagaagagca agaaagcttg ggaaattgtg agcttcatca    5520
agttcaaatt actcctaagg tatattaaaa ctccatcttt gattattagc caattcttta    5580
atttcatatt atttctagac taaattaaaa tattaaaaga tataaagaat ttaattaatt    5640
taattattcc tttaaaatcc aaacatgatg aatttgagta aattaaatga atatagttca    5700
gattcattta actaataggc catttagttt taatatggca acgttttagg cttttaacat    5760
tctctttgaa tgtaggtata atgcattaag tgcagaaatt taatctttat ttaaaaaatg    5820
aaaacatctc ataataactt tggtcttttt actccaaaca tcttgtaata aagtgagtgt    5880
cttctacttc tcctaacatc tcataataaa tttctactat tcctaacatc tcattataaa    5940
taagtctt                                                             5948
```

<210> SEQ ID NO 8
<211> LENGTH: 920
<212> TYPE: PRT
<213> ORGANISM: Solanum americanum

<400> SEQUENCE: 8

```
Met Ala Tyr Ala Ala Leu Ser Ser Leu Ile Tyr Thr Leu Gln Gln Leu
1               5                   10                  15

Phe Lys Pro Asn Gln Ser Phe Val Cys Gln Ser Cys Cys Thr Gln Gln
            20                  25                  30

His Val Gln Ser Leu Cys Gln Asn Leu Ser Ala Leu Gln Leu Phe Leu
        35                  40                  45

Asp Asp Thr Thr Thr Lys Asp Ile Glu Thr Leu Lys Val Cys Asn Tyr
    50                  55                  60

Leu Ile Ser Tyr Ser Ser Tyr Ile Tyr Ser Ile Ile Asn Leu Ser
65                  70                  75                  80

Ser Phe Asn Phe Lys Val Ile Glu Lys Arg Ile Arg Asp Val Val Tyr
                85                  90                  95

Lys Ala Glu Asp Lys Val Asp Ser Ser Leu Arg Ser Ile Ile Leu Ala
            100                 105                 110

Asp Cys Thr Glu Asn Lys Glu Gly Ala Cys Lys Phe Phe Glu Glu Glu
        115                 120                 125

Leu Leu Lys Val Glu Lys Asp Val Asp Ser Leu Ser Lys Glu Val Met
    130                 135                 140

Gln Ile Asn Val Asn Lys His Gly Ser Arg Ser Ala Glu Leu Thr Thr
145                 150                 155                 160

Ile Pro Pro Ser Pro Glu Lys Ser Thr Asn Glu Glu His Thr Ile Val
                165                 170                 175

Gly Met Glu Asp Glu Tyr Asn Thr Ile Leu Asp Arg Leu Thr Ala Gln
            180                 185                 190

Thr Asp Glu Leu Thr Val Ile Pro Ile Phe Gly Met Gly Gly Ile Gly
        195                 200                 205
```

-continued

```
Lys Thr Thr Leu Ala Arg Lys Val Tyr Asp Asp Ser Ser Ile Arg Ser
    210                 215                 220

Arg Phe Asp Arg His Val Trp Val Thr Thr Ser Glu Glu Phe Asn Glu
225                 230                 235                 240

Arg Arg Met Leu Leu Glu Val Val Ser Ser Ile Thr Thr Gly Ser Asn
                245                 250                 255

Gln Glu Lys Ser Asp Asp Gln Leu Met Glu Ile Val Tyr Arg Gly Leu
            260                 265                 270

Lys Gly Arg Arg Phe Leu Ile Val Ile Asp Asp Ile Trp Ser Thr Glu
        275                 280                 285

Ala Trp Asp Gln Met Gln Arg Ile Phe Pro Asn Asp Asp Asn Lys Ser
    290                 295                 300

Arg Ile Leu Leu Thr Thr Arg Leu Lys Tyr Val Ala Asp Tyr Val Ser
305                 310                 315                 320

Ser Pro Asp Phe Pro Pro His Ser Lys Ser Phe Leu Ser Leu Asp Asp
                325                 330                 335

Ser Trp Asn Leu Phe Thr Glu Lys Val Phe Asn Lys Asp Thr Cys Pro
            340                 345                 350

Pro His Leu Glu Glu Thr Gly Lys His Ile Val Gln Gln Cys Arg Gly
        355                 360                 365

Leu Pro Leu Ser Val Val Val Ala Gly Leu Val Gly Lys Met Asp
    370                 375                 380

Pro Thr His Asp Asn Trp Glu Asn Val Glu Glu Asn Leu Asn Ser Phe
385                 390                 395                 400

Ile Gly Thr Val Ser Glu Arg Cys Gln Ser Ile Leu Ser Leu Ser Tyr
                405                 410                 415

Asn Tyr Leu Pro Gln Tyr Leu Arg Ala Cys Phe Leu Tyr Val Gly Cys
            420                 425                 430

Phe Pro Glu Asp Lys Glu Ile Asp Val Ser Lys Leu Ile Arg Leu Trp
        435                 440                 445

Ile Ala Glu Gln Phe Val Lys Ala Arg Ser Asn Lys Arg Leu Glu Val
    450                 455                 460

Val Ala Glu Glu Tyr Leu Glu Glu Leu Ile Asp Arg Ser Leu Ile Leu
465                 470                 475                 480

Ser Gly Arg Gln Arg Ala Asn Gly Arg Met Lys Thr Cys Lys Ile His
                485                 490                 495

Asp Leu Leu Arg Gln Leu Cys Leu Ser Glu Ala His Thr Glu Asn Ile
            500                 505                 510

Ser His Ile Met Asn Arg Asn Val Pro Val Ser Ser Glu Ala Ile Asp
        515                 520                 525

Asp Gln Arg Arg Val Ile Val Pro Leu Glu Leu Glu Glu Pro Val
    530                 535                 540

Tyr Pro Thr Arg Asn Ser Ser Gly Ile Thr Ser Thr Thr Arg Thr Phe
545                 550                 555                 560

Ile Ser Met Glu Ile Cys Leu Arg Glu Ala Gln Thr Glu Ala Ile Tyr
                565                 570                 575

Asp Gln Arg Arg Val Ile Leu Leu Ser Lys Arg His Arg Ile Asp Thr
            580                 585                 590

Ile Arg Thr Ile Ile Pro Phe Lys Asp Thr Phe Pro Lys Glu Ile Cys
        595                 600                 605

Ser Ile Val Ser Gln Leu Lys Leu Leu Lys Val Leu Asp Val Leu Ser
    610                 615                 620

Val Trp Tyr Asp Val Ser Cys Ile Ile Pro Gln Leu Val His Leu Arg
```

```
                625           630           635           640

Tyr Val Gly Ala Val Ile Leu Lys Ala Leu Ser Leu Pro Lys Leu Arg
                    645               650               655

Asn Leu Gln Thr Ile Ile Leu Thr Ser Val Glu Thr Thr Glu Leu Lys
                    660               665               670

His Ser Leu Asp Ile Trp Arg Met Ser Glu Ile Arg His Leu Asp Ile
                    675               680               685

Val Pro Pro Leu Tyr Ile Ser Asn Pro Leu Glu Ala Glu Gln Pro Leu
                    690               695               700

Phe Leu Asn Asn Leu His Thr Leu Phe Leu Arg Cys Ser Pro Phe Val
705                 710               715               720

Ala Lys Ile Ile Arg Arg Thr Pro Asn Leu Lys Leu Lys Ile Leu
                    725               730               735

Asp Lys Ser Lys His Pro Asp Trp Pro Asp Ile Leu Asp Ser Leu Asn
                    740               745               750

Leu Leu Glu Glu Leu Glu Thr Leu Gln Ile Ser Thr Glu Asn Ile
                    755               760               765

Asp Pro Met Ile Phe Ser Gly Asp Ile Phe Pro Arg Asn Leu Lys Gln
                    770               775               780

Leu Lys Leu Ser Tyr Thr Cys Ile Pro Trp Glu Asp Met Lys Leu Leu
785                 790               795               800

Ala Asn Leu Pro Asn Leu Glu Val Phe Lys Gly His Tyr Ala Phe Asn
                    805               810               815

Gly Thr Asp Trp Lys Leu Asp Glu Asp Val Val Phe Cys Lys Leu Lys
                    820               825               830

Ser Leu Arg Leu Tyr Glu Arg Gly Asp Leu Gln Arg Trp Glu Ala Ala
                    835               840               845

Gly Ser Asp Asn Phe Pro Met Leu Glu Gln Leu Leu Tyr Gly Phe
                    850               855               860

Lys Lys Leu Glu Glu Ile Pro Glu Ser Ile Gly Glu Ile Met Thr Leu
865                 870               875               880

Lys Phe Ile Lys Thr Glu Phe Cys Gly Ser Gly Val Lys Thr Ser Ala
                    885               890               895

Lys Lys Ile Gln Glu Glu Gln Glu Ser Leu Gly Asn Tyr Glu Leu Gln
                    900               905               910

Val Gln Ile Thr Pro Lys Val Cys
                    915               920

<210> SEQ ID NO 9
<211> LENGTH: 2760
<212> TYPE: DNA
<213> ORGANISM: Solanum americanum

<400> SEQUENCE: 9
atggcttatg ctgctctttc ttcacttatc tatacattgc aacaactctt caaacctaat      60
caatctttcg tttgtcaaag ctgctgtacg caacaacatg ttcaatctct ctgtcaaaat     120
ctttctgctc tgcaactttt ccttgacgat actacaacaa aggatattga aactcttaag     180
gtatgtaatt atctaatctc ttactcatct tatatttatt caataataat taatttatcg     240
agtttcaatt ttaaggttat agaaaagagg atcagagatg tagtatacaa agcagaagat     300
aaagttgatt caagcctaag aagcatcatt ctagctgatt gcacagagaa taaagaaggg     360
gcttgtaaat tctttgagga agaattgcta aaagtggaaa aagatgttga ttctctcagc     420
aaagaggtga tgcagatcaa tgttaacaag catggaagca gatctgcaga actaacaaca     480
```

-continued

```
attcctccct ctccagaaaa aagtacaaat gaggaacata ctattgttgg gatggaggat    540
gagtacaaca ccatacttga tcgcctcact gcccaaacag acgagttgac tgtcatacca    600
atttttggta tgggcggtat aggtaagaca actcttgcca gaaaggttta tgatgattca    660
tctattcgtt ctcgatttga tagacatgta tgggtcacta cctctgaaga attcaatgag    720
agacgaatgc ttctcgaagt tgtttcttca attactactg gaagcaatca agaaaagagc    780
gatgatcaac taatggagat tgtgtataga ggtcttaagg gtaggagatt tctaattgtc    840
atagatgata tttggagtac tgaggcttgg gaccaaatgc aaagaatatt tccaaatgat    900
gacaataaaa gccgaattct actaactaca cggctcaagt atgttgctga ttatgtcagc    960
agtcctgatt ttccacctca tagtaagtct tttctaagtc ttgatgatag ttggaatcta   1020
ttcaccgaaa aagtattcaa caaagatacc tgtcctcctc acctagaaga aacagggaag   1080
catattgtac aacaatgtcg aggattacct ctctcggttg ttgtagttgc tggacttgtt   1140
ggaaaaatgg acccaacgca tgacaattgg gagaacgttg aggaaaatct gaactcattc   1200
attggtactg tatccgaacg gtgccaatca attctttctt taagctacaa ttacttgccc   1260
caatatttga gggcttgttt tctctatgtt ggatgttttc ctgaagataa agagattgat   1320
gtttccaagt tgattaggct atggattgct gagcaattcg taaaggcgag aagcaataaa   1380
aggttagaag tggtagcaga ggagtatcta gaagagttaa ttgatagaag cctaattttg   1440
agtggtagac aaagggctaa tggaaggatg aaaacttgca aaattcatga tcttcttcgc   1500
caactatgcc taagtgaagc tcatactgaa atattagtc atatcatgaa agaaatgtc    1560 cccgtgtcct cagaagccat agatgatcaa cggcgagtga ttgttccatt ggaacttgaa   1620
gaggaaccag tttatcctac aaggaatagc agtggtatta caagtacaac ccgcaccttt   1680
atttcaatgg aaatatgcct aagagaagct cagaccgaag ccatatatga tcaacggcga   1740
gtgatccttc tgtctaaacg acataggatt gatacaatcc gcaccattat tccattcaaa   1800
gatacttttc cgaaagagat tgttccatt gtttcacagt tgaagttgct taaggtgttg    1860
gatgtattat cagtctggta cgatgtctct tgtataatac ctcagcttgt acatttgaga   1920
tatgttggtg cagtaatttt gaaagctctt tcactaccca aattgagaaa tctacagacc   1980
ataattctta caagtgttga aaccacagag ttgaagcact cactagatat ctggagaatg   2040
tcagagataa gacatttgga tattgtaccg ccactatata tatcaaatcc tcttgaagca   2100
gaacaacctt tgtttctcaa taacttgcac acactttttc tccgttgctc tccttttgtt   2160
gcgaaaatca taagaagaac tcccaatcta aaaagctaa agattttaga taaatctaag   2220
catcctgact ggcctgatat tcttgattct ctcaatcttc tagaggagct ggagacacta   2280
caaatatcaa cagaagaaaa cattgacccg atgattttct ctggggatat tttccctcgt   2340
aatctcaagc aactgaaatt atcatatact tgtataccat gggaagatat gaaattgctg   2400
gctaatttac ccaatcttga ggtgttcaag ggtcattatg cattcaatgg aacagattgg   2460
aaactagatg aagatgttgt gttttgcaaa ttaaaatctc tacgactgta tgagcgtgga   2520
gatttgcaaa ggtgggaagc tgctggtagt gataattttc caatgcttga gcaactatta   2580
ttgtatgggt tcaaaaaact ggaagagatt ccggagagta ttggagaaat aatgacacta   2640
aaatttatca aaacagaatt tgcggctct ggtgtaaaga caagtgcaaa gaaaattcaa    2700
gaagagcaag aaagcctggg aaattatgag cttcaagttc aaattactcc taaggtatgt   2760
```

<210> SEQ ID NO 10

<211> LENGTH: 6049
<212> TYPE: DNA
<213> ORGANISM: Solanum americanum

<400> SEQUENCE: 10

| | | | | | |
|---|---|---|---|---|---|
| ggtaatttttt | ttcttatcat | gtataacatt | tctttatat | taatagaggg | gtcacatgtt | 60 |
| attcaaaaac | aagtatggtg | attggtgatt | cgacgtttga | atttttaaga | taattatatc | 120 |
| tttttcaatg | atacccgcaa | gggtgatcga | gttggttgag | cagataattt | ctaaatgggg | 180 |
| tcataggttc | aaaatcctct | acatgtttgc | tcggtagctc | gtcatatgga | acttgcttag | 240 |
| tatagtttac | cttttcagtg | tgatttgcgc | gctattacgt | tgaagcagtg | ttatcgtata | 300 |
| cacacctaaa | ccctgaagaa | tcatgactgc | gagcttcctt | gacaacaaat | ttttttatc | 360 |
| tatttcaatg | acattactat | tagatcaatt | tttttatatc | acatgatttg | atccatccta | 420 |
| catctatttg | cctaccataa | aattaccggt | caagcaacgt | aatttgtaag | tcccatagaa | 480 |
| tttttaacag | atgcattggt | tcatggttga | ggtgaagaac | agatgtagca | gttttttgtt | 540 |
| gaagccgtta | gtttcttgac | agactataac | agaggaatgt | aagttgcaac | ttttgaggat | 600 |
| agtttaggga | tgattttttgt | tcattatgta | gtataaggat | gtagtttaag | tttgaggtat | 660 |
| aattgaggga | tgttttttgct | atttactcta | caaaattcca | cacagtatta | ttaattttct | 720 |
| aaggaccgtt | tggccatgtg | atatgaaatc | atgatatgaa | attatgaaat | gaagttaaag | 780 |
| ttttgtttgg | acatgtaatt | tggacttttt | atgttgtatg | ttttcttata | aacataaaaa | 840 |
| acccacaagt | tgtaaaatta | ttaaacttgt | cccatttttt | tattcaattt | taccaaataa | 900 |
| acaaaaattt | acaaaatcac | ataatatgct | aacacaaaac | tattctttaa | aaaatacaat | 960 |
| atttattgat | caaactttaa | ttcaacaaaa | aataaaattc | aacataagtt | gtagtgtact | 1020 |
| agtcttaat | ataattctcc | cacatagtac | ggagcaatta | tatgatcgag | tatacaaacc | 1080 |
| aacattgcta | ctttgagcta | taaatggttt | aaaaagtaat | gatatgaatc | ataaattta | 1140 |
| ttacatatga | aacaaatggt | gagtagatat | tttttaataa | aatataaact | tatgggtcaa | 1200 |
| tttttgtatt | tgaaaaatcc | caaatcatga | tttgaaattt | tcaaatcatg | attttttgaag | 1260 |
| aatttgggat | tttatctcat | gatatgaaat | catgagatga | aatcagcctg | aaatcgcatg | 1320 |
| tccaaatgct | gatttcatct | catgatttca | tatcgtgata | tgaaatcgca | tgtccaaacg | 1380 |
| cctactaagt | aacttagaca | cgtcttgacc | ttttataatt | gctccatcca | tcctaattta | 1440 |
| cttgtcaaat | attttctaat | ttgattcccc | ttttacttgt | catttttttac | aaatcaagaa | 1500 |
| acgacaattt | ttttttcttc | tattataccc | tcaatttatt | aacattgaat | taatgtcctt | 1560 |
| gaaaaatata | gtaagtaaat | atgtttaaaa | ctctatcaaa | ttaataggggg | taaaatggta | 1620 |
| aactcattat | accaattatt | tttttttttaa | tagatgcgtc | aaatcaaaaa | ttgacaagta | 1680 |
| aaaagagacg | gaaagagtat | ataaatttca | aagaaaattt | gtattgaaag | ttaattgtat | 1740 |
| tcgtccactt | gacacatcat | gtcttaatta | ctacaagttg | atttgaataa | gaaatgtgag | 1800 |
| acatctctac | tatcgtggtg | ggaccaatgc | ttgaaaagtc | gacgaaaact | acaagagtgt | 1860 |
| ctttattaga | aatcaggaca | acttgactct | ttatttttca | tttctttttt | cttactttt | 1920 |
| cttggtcaat | ccatagtttt | gcatccataa | accacaagtt | ctgtttagat | attaaataga | 1980 |
| aaattgtcca | aattcattta | gaaaaatgtg | gacataaatc | atttagacaa | aacctcttat | 2040 |
| agcctaagca | gagacatttc | tcttccagca | aacaaaagag | aaatggctta | tgctgctctt | 2100 |
| tcttcactta | tctatacatt | gcaacaactc | ttcaaaccta | atcaatcttt | cgttgtcaa | 2160 |
| agctgctgta | cgcaacaaca | tgttcaatct | ctctgtcaaa | atctttctgc | tctgcaactt | 2220 |

```
ttccttgacg atactacaac aaaggatatt gaaactctta aggtatgtaa ttatctaatc    2280
tcttactcat cttatattta ttcaataata attaatttat cgagtttcaa ttttaaggtt    2340
atagaaaaga ggatcagaga tgtagtatac aaagcagaag ataaagttga ttcaagccta    2400
agaagcatca ttctagctga ttgcacagag aataaagaag gggcttgtaa attctttgag    2460
gaagaattgc taaaagtgga aaaagatgtt gattctctca gcaaagaggt gatgcagatc    2520
aatgttaaca agcatggaag cagatctgca gaactaacaa caattcctcc ctctccagaa    2580
aaaagtacaa atgaggaaca tactattgtt gggatggagg atgagtacaa caccatactt    2640
gatcgcctca ctgcccaaac agacgagttg actgtcatac caattttggt tatgggcggt    2700
ataggtaaga caactcttgc cagaaaggtt tatgatgatt catctattcg ttctcgattt    2760
gatagacatg tatgggtcac tacctctgaa gaattcaatg agagacgaat gcttctcgaa    2820
gttgtttctt caattactac tggaagcaat caagaaaaga gcgatgatca actaatggag    2880
attgtgtata gaggtcttaa gggtaggaga tttctaattg tcatagatga tatttggagt    2940
actgaggctt gggaccaaat gcaaagaata tttccaaatg atgacaataa aagccgaatt    3000
ctactaacta cacggctcaa gtatgttgct gattatgtca gcagtcctga ttttccacct    3060
catagtaagt cttttctaag tcttgatgat agttggaatc tattcaccga aaaagtattc    3120
aacaaagata cctgtcctcc tcacctagaa gaaacaggga agcatattgt acaacaatgt    3180
cgaggattac ctctctcggt tgttgtagtt gctggacttg ttggaaaaat ggacccaacg    3240
catgacaatt gggagaacgt tgaggaaaat ctgaactcat tcattggtac tgtatccgaa    3300
cggtgccaat caattctttc tttaagctac aattacttgc cccaatattt gagggcttgt    3360
tttctctatg ttggatgttt tcctgaagat aaagagattg atgtttccaa gttgattagg    3420
ctatggattg ctgagcaatt cgtaaaggcg agaagcaata aaaggttaga agtggtagca    3480
gaggagtatc tagaagagtt aattgataga agcctaattt tgagtggtag acaaagggct    3540
aatggaagga tgaaaacttg caaaattcat gatcttcttc gccaactatg cctaagtgaa    3600
gctcatactg aaaatattag tcatatcatg aatagaaatg tccccgtgtc ctcagaagcc    3660
atagatgatc aacggcgagt gattgttcca ttggaacttg aagaggaacc agtttatcct    3720
acaaggaata gcagtggtat tacaagtaca acccgcacct ttatttcaat ggaaatatgc    3780
ctaagagaag ctcagaccga agccatatat gatcaacggc gagtgatcct tctgtctaaa    3840
cgacatagga ttgatacaat ccgcaccatt attccattca agatactttt ccgaaagag    3900 atttgttcca ttgtttcaca gttgaagttg cttaaggtgt tggatgtatt atcagtctgg    3960
tacgatgtct cttgtataat acctcagctt gtacatttga gatatgttgg tgcagtaatt    4020
ttgaaagctc tttcactacc caaattgaga aatctacaga ccataattct tacaagtgtt    4080
gaaaccacag agttgaagca ctcactagat atctggagaa tgtcagagat aagacatttg    4140
gatattgtac cgccactata tatcaaat cctcttgaag cagaacaacc tttgtttctc    4200
aataacttgc acacactttt tctccgttgc tctccttttg ttgcgaaaat cataagaaga    4260
actcccaatc taaaaaagct aaagatttta gataaatcta agcatcctga ctggcctgat    4320
attcttgatt ctctcaatct tctagaggag ctggagacac tacaaatatc aacagaagaa    4380
aacattgacc cgatgatttt ctctggggat attttccctc gtaatctcaa gcaactgaaa    4440
ttatcatata cttgtatacc atgggaagat atgaaattgc tggctaattt acccaatctt    4500
gaggtgttca agggtcatta tgcattcaat ggaacagatt ggaaactaga tgaagatgtt    4560
```

```
gtgttttgca aattaaaatc tctacgactg tatgagcgtg gagatttgca aaggtgggaa    4620
gctgctggta gtgataattt tccaatgctt gagcaactat tattgtatgg gttcaaaaaa    4680
ctggaagaga ttccggagag tattggagaa ataatgacac taaaatttat caaaacagaa    4740
ttttgcggct ctggtgtaaa gacaagtgca agaaaattc aagaagagca agaaagcctg     4800
ggaaattatg agcttcaagt tcaaattact cctaaggtat gttgaaactc aatctttgat    4860
taatactctc cactcggtta gatttaggat tcaaattgtc tacttacatt tatgatcatc    4920
acccttgcgg tcttcttatt tcttttagta aatagcttca aaaactctac agaaattaca    4980
cataattaac aattgacaat tgattctctc ttattgataa tttgtaattt tctctttcag    5040
ttaagatttt tgatcgaaaa tttagacgaa ataagcatgt tgcccccgaa tgaagtagcc    5100
gaaaaaatca aaggtttgtc tatttaattc cttttttatt tcattgaaag aggttcagat    5160
atattaaaca acttttaac ctttctattt gattttttat cgcttagata gatacaacat     5220 ttatttaac atcaattgtt attttgattc aattatgttc ttttaatata tagtttccac     5280
tcggttcttc aattcttttt tcaattatag ttttattttt ttaattgcac atggttgatc    5340
gatttaattt gtgagattca cttttctttc ggttttacga gttcttcgcg attaatgtta    5400
ttcagattta ggagtattat atttcaactt tcgattagat ttaggattca aattgtcttc    5460
tttcatttat gatcatcatc ctttcgatct tctttatttc ttttagtaaa tagcttcaaa    5520
aactctatag aaattacata taattaacaa ttgagaattg attctctcgt aatttctcat    5580
gttctctttc agttaaaatt tttgatcaaa aactaaaaga gattccggag agcactggac    5640
aaataatgac acgaaaaatc atcaaaacag aattttgcgg ctctggtgta gagactagtg    5700
caaagaagat tcaagaagag caagaaagct tgggaaattg tgagcttcat caagttcaaa    5760
ttactcctaa ggtatattaa aactccatct ttgattatta gccaattctt taatttcata    5820
ttatttctag actaaattaa aatattaaaa gatataaaga atttaattaa tttaattatt    5880
cctttaaaat ccaaacatga tgaatttgag taaattaaat gaatatagtt cagattcatt    5940
taactaatag gccatttagt tttaatatgg caacgtttta ggcttttaac attctctttg    6000
aatgtaggta taatgcatta agtgcagaaa tttaatcttt atttaaaaa                6049
```

<210> SEQ ID NO 11
<211> LENGTH: 920
<212> TYPE: PRT
<213> ORGANISM: Solanum americanum

<400> SEQUENCE: 11

```
Met Ala Tyr Ala Ala Leu Ser Ser Leu Ile Tyr Thr Leu Gln Gln Leu
1               5                   10                  15

Phe Lys Pro Asn Gln Ser Phe Val Cys Gln Ser Cys Cys Thr Gln Gln
            20                  25                  30

His Val Gln Ser Leu Cys Gln Asn Leu Ser Ala Leu Gln Leu Phe Leu
        35                  40                  45

Asp Asp Thr Thr Thr Lys Asp Ile Glu Thr Leu Lys Val Cys Asn Tyr
    50                  55                  60

Leu Ile Ser Tyr Ser Ser Tyr Ile Tyr Ser Ile Ile Asn Leu Ser
65                  70                  75                  80

Ser Phe Asn Phe Lys Val Ile Glu Lys Arg Ile Arg Asp Val Tyr
                85                  90                  95

Lys Ala Glu Asp Lys Val Asp Ser Leu Arg Ser Ile Ile Leu Ala
            100                 105                 110
```

```
Asp Cys Thr Glu Asn Lys Glu Gly Ala Cys Lys Phe Phe Glu Glu Glu
            115                 120                 125

Leu Leu Lys Val Glu Lys Asp Val Asp Ser Leu Ser Lys Glu Val Met
        130                 135                 140

Gln Ile Asn Val Asn Lys His Gly Ser Arg Ser Ala Glu Leu Thr Thr
145                 150                 155                 160

Ile Pro Pro Ser Pro Glu Lys Ser Thr Asn Glu Glu His Thr Ile Val
                165                 170                 175

Gly Met Glu Asp Glu Tyr Asn Thr Ile Leu Asp Arg Leu Thr Ala Gln
            180                 185                 190

Thr Asp Glu Leu Thr Val Ile Pro Ile Phe Gly Met Gly Gly Ile Gly
        195                 200                 205

Lys Thr Thr Leu Ala Arg Lys Val Tyr Asp Asp Ser Ser Ile Arg Ser
210                 215                 220

Arg Phe Asp Arg His Val Trp Val Thr Thr Ser Glu Glu Phe Asn Glu
225                 230                 235                 240

Arg Arg Met Leu Leu Glu Val Val Ser Ser Ile Thr Thr Gly Ser Asn
                245                 250                 255

Gln Glu Lys Ser Asp Asp Gln Leu Met Glu Ile Val Tyr Arg Gly Leu
            260                 265                 270

Lys Gly Arg Arg Phe Leu Ile Val Ile Asp Asp Ile Trp Ser Thr Glu
        275                 280                 285

Ala Trp Asp Gln Met Gln Arg Ile Phe Pro Asn Asp Asp Asn Lys Ser
290                 295                 300

Arg Ile Leu Leu Thr Thr Arg Leu Lys Tyr Val Ala Asp Tyr Val Ser
305                 310                 315                 320

Ser Pro Asp Phe Pro Pro His Ser Lys Ser Phe Leu Ser Leu Asp Asp
                325                 330                 335

Ser Trp Asn Leu Phe Thr Glu Lys Val Phe Asn Lys Asp Thr Cys Pro
            340                 345                 350

Pro His Leu Glu Glu Thr Gly Lys His Ile Val Gln Gln Cys Arg Gly
        355                 360                 365

Leu Pro Leu Ser Val Val Val Ala Gly Leu Val Gly Lys Met Asp
370                 375                 380

Pro Thr His Asp Asn Trp Glu Asn Val Glu Glu Asn Leu Asn Ser Phe
385                 390                 395                 400

Ile Gly Thr Val Ser Glu Arg Cys Gln Ser Ile Leu Ser Leu Ser Tyr
                405                 410                 415

Asn Tyr Leu Pro Gln Tyr Leu Arg Ala Cys Phe Leu Tyr Val Gly Cys
            420                 425                 430

Phe Pro Glu Asp Lys Glu Ile Asp Val Ser Lys Leu Ile Arg Leu Trp
        435                 440                 445

Ile Ala Glu Gln Phe Val Lys Ala Arg Ser Asn Lys Arg Leu Glu Val
450                 455                 460

Val Ala Glu Glu Tyr Leu Glu Glu Leu Ile Asp Arg Ser Leu Ile Leu
465                 470                 475                 480

Ser Gly Arg Gln Arg Ala Asn Gly Arg Met Lys Thr Cys Lys Ile His
                485                 490                 495

Asp Leu Leu Arg Gln Leu Cys Leu Ser Glu Ala His Thr Glu Asn Ile
            500                 505                 510

Ser His Ile Met Asn Arg Asn Val Pro Val Ser Ser Glu Ala Ile Asp
        515                 520                 525

Asp Gln Arg Arg Val Ile Val Pro Leu Glu Leu Glu Glu Glu Pro Val
```

```
                530             535             540
Tyr Pro Thr Arg Asn Ser Ser Gly Ile Thr Ser Thr Thr Arg Thr Phe
545                 550             555             560

Ile Ser Met Glu Ile Cys Leu Arg Glu Ala Gln Thr Glu Ala Ile Tyr
                565             570             575

Asp Gln Arg Arg Val Ile Leu Leu Ser Lys Arg His Arg Ile Asp Thr
            580             585             590

Ile Arg Thr Ile Ile Pro Phe Lys Asp Thr Phe Pro Lys Glu Ile Cys
        595             600             605

Ser Ile Val Ser Gln Leu Lys Leu Leu Lys Val Leu Asp Val Leu Ser
    610             615             620

Val Trp Tyr Asp Val Ser Cys Ile Ile Pro Gln Leu Val His Leu Arg
625             630             635             640

Tyr Val Gly Ala Val Ile Leu Lys Ala Leu Ser Leu Pro Lys Leu Arg
                645             650             655

Asn Leu Gln Thr Ile Ile Leu Thr Ser Val Glu Thr Thr Glu Leu Lys
                660             665             670

His Ser Leu Asp Ile Trp Arg Met Ser Glu Ile Arg His Leu Asp Ile
            675             680             685

Val Pro Pro Leu Tyr Ile Ser Asn Pro Leu Glu Ala Glu Gln Pro Leu
        690             695             700

Phe Leu Asn Asn Leu His Thr Leu Phe Leu Arg Cys Ser Pro Phe Val
705             710             715             720

Ala Lys Ile Ile Arg Arg Thr Pro Asn Leu Lys Lys Leu Lys Ile Leu
                725             730             735

Asp Lys Ser Lys His Pro Asp Trp Pro Asp Ile Leu Asp Ser Leu Asn
                740             745             750

Leu Leu Glu Glu Leu Glu Thr Leu Gln Ile Ser Thr Glu Glu Asn Ile
            755             760             765

Asp Pro Met Ile Phe Ser Gly Asp Ile Phe Pro Arg Asn Leu Lys Gln
        770             775             780

Leu Lys Leu Ser Tyr Thr Cys Ile Pro Trp Glu Asp Met Lys Leu Leu
785             790             795             800

Ala Asn Leu Pro Asn Leu Glu Val Phe Lys Gly His Tyr Ala Phe Asn
                805             810             815

Gly Thr Asp Trp Lys Leu Asp Glu Asp Val Val Phe Cys Lys Leu Lys
                820             825             830

Ser Leu Arg Leu Tyr Glu Arg Gly Asp Leu Gln Arg Trp Glu Ala Ala
            835             840             845

Gly Ser Asp Asn Phe Pro Met Leu Glu Gln Leu Leu Leu Tyr Gly Phe
        850             855             860

Lys Lys Leu Glu Glu Ile Pro Glu Ser Ile Gly Glu Ile Met Thr Leu
865             870             875             880

Lys Phe Ile Lys Thr Glu Phe Cys Gly Ser Gly Val Lys Thr Ser Ala
                885             890             895

Lys Lys Ile Gln Glu Glu Gln Glu Ser Leu Gly Asn Tyr Glu Leu Gln
                900             905             910

Val Gln Ile Thr Pro Lys Val Cys
            915             920

<210> SEQ ID NO 12
<211> LENGTH: 2760
<212> TYPE: DNA
<213> ORGANISM: Solanum americanum
```

<400> SEQUENCE: 12

```
atggcttatg ctgctctttc ttcacttatc tatacattgc aacaactctt caaacctaat      60
caatctttcg tttgtcaaag ctgctgtacg caacaacatg ttcaatctct ctgtcaaaat     120
ctttctgctc tgcaactttt ccttgacgat actacaacaa aggatattga aactcttaag     180
gtatgtaatt atctaatctc ttactcatct tatatttatt caataataat taatttatcg     240
agtttcaatt ttaaggttat agaaaagagg atcagagatg tagtatacaa agcagaagat     300
aaagttgatt caagcctaag aagcatcatt ctagctgatt gcacagagaa taaagaaggg     360
gcttgtaaat tctttgagga agaattgcta aaagtggaaa aagatgttga ttctctcagc     420
aaagaggtga tgcagatcaa tgttaacaag catggaagca gatctgcaga actaacaaca     480
attcctccct ctccagaaaa aagtacaaat gaggaacata ctattgttgg gatggaggat     540
gagtacaaca ccatacttga tcgcctcact gcccaaacag acgagttgac tgtcatacca     600
atttttggta tgggcggtat aggtaagaca actcttgcca gaaaggttta tgatgattca     660
tctattcgtt ctcgatttga tagacatgta tgggtcacta cctctgaaga attcaatgag     720
agacgaatgc ttctcgaagt tgtttcttca attactactg gaagcaatca agaaaagagc     780
gatgatcaac taatggagat tgtgtataga ggtcttaagg gtaggagatt tctaattgtc     840
atagatgata tttggagtac tgaggcttgg gaccaaatgc aaagaatatt tccaaatgat     900
gacaataaaa gccgaattct actaactaca cggctcaagt atgttgctga ttatgtcagc     960
agtcctgatt ttccacctca tagtaagtct tttctaagtc ttgatgatag ttggaatcta    1020
ttcaccgaaa agtattcaa caaagatacc tgtcctcctc acctagaaga aacagggaag    1080
catattgtac aacaatgtcg aggattacct ctctcggttg ttgtagttgc tggacttgtt    1140
ggaaaaatgg acccaacgca tgacaattgg gagaacgttg aggaaaatct gaactcattc    1200
attggtactg tatccgaacg gtgccaatca attctttctt taagctacaa ttacttgccc    1260
caatatttga gggcttgttt tctctatgtt ggatgttttc ctgaagataa agagattgat    1320
gtttccaagt tgattaggct atggattgct gagcaattcg taaaggcgag aagcaataaa    1380
aggttagaag tggtagcaga ggagtatcta gaagagttaa ttgatagaag cctaattttg    1440
agtggtagac aaagggctaa tggaaggatg aaaacttgca aaattcatga tcttcttcgc    1500
caactatgcc taagtgaagc tcatactgaa aatattagtc atatcatgaa agaaatgtc    1560
cccgtgtcct cagaagccat agatgatcaa cggcgagtga ttgttccatt ggaacttgaa    1620
gaggaaccag tttatcctac aaggaatagc agtggtatta caagtacaac ccgcaccttt    1680
atttcaatgg aaatatgcct aagagaagct cagaccgaag ccatatatga tcaacggcga    1740
gtgatccttc tgtctaaacg acataggatt gatacaatcc gcaccattat tccattcaaa    1800
gatactttc cgaaagagat ttgttccatt gtttcacagt tgaagttgct taaggtgttg    1860
gatgtattat cagtctggta cgatgtctct tgtataatac ctcagcttgt acatttgaga    1920
tatgttggtg cagtaatttt gaaagctctt tcactaccca aattgagaaa tctacagacc    1980
ataattctta caagtgttga aaccacagag ttgaagcact cactagatat ctggagaatg    2040
tcagagataa gacatttgga tattgtaccg ccactatata tatcaaatcc tcttgaagca    2100
gaacaacctt tgtttctcaa taacttgcac acacttttc tccgttgctc tccttttgtt    2160
gcgaaaatca aagaagaac tcccaatcta aaaaagctaa agattttaga taaatctaag    2220
catcctgact ggcctgatat tcttgattct ctcaatcttc tagaggagct ggagacacta    2280
```

-continued

| | |
|---|---|
| caaatatcaa cagaagaaaa cattgacccg atgattttct ctggggatat tttccctcgt | 2340 |
| aatctcaagc aactgaaatt atcatatact tgtataccat gggaagatat gaaattgctg | 2400 |
| gctaatttac ccaatcttga ggtgttcaag ggtcattatg cattcaatgg aacagattgg | 2460 |
| aaactagatg aagatgttgt gttttgcaaa ttaaaatctc tacgactgta tgagcgtgga | 2520 |
| gatttgcaaa ggtgggaagc tgctggtagt gataattttc caatgcttga gcaactatta | 2580 |
| ttgtatgggt tcaaaaaact ggaagagatt ccggagagta ttggagaaat aatgacacta | 2640 |
| aaatttatca aaacagaatt tgcggctct ggtgtaaaga caagtgcaaa gaaaattcaa | 2700 |
| gaagagcaag aaagcctggg aaattatgag cttcaagttc aaattactcc taaggtatgt | 2760 |

<210> SEQ ID NO 13
<211> LENGTH: 5149
<212> TYPE: DNA
<213> ORGANISM: Solanum americanum

<400> SEQUENCE: 13

| | |
|---|---|
| gaacgctgtg taacatcatc tccaaccaac ctgggtcata tgagtcccaa atgcatttac | 60 |
| agcaacaaag agcaaagcaa agcacaactt tgaaatttga aaaatgatgc aagacaaata | 120 |
| tcaaaattag acagtaaaat tcacaattcc ccttaaaata aatgataaat taagaagac | 180 |
| taaacaatag aaaaccttac aatctcaaag gcagtatgga tcggagtcgt atttggaaga | 240 |
| aattttgata caacttgaag aagattgaag attgttgttc ataaagtata ctgtgggcgg | 300 |
| gttaatctac aacctgtgtg tttttttatca tacaaaattc cacagagtat tattaatttt | 360 |
| ttaaggatcg tttggccatg tgatatgaaa ttatgagatg aagttgacgt tttgtttgga | 420 |
| catgcaattt ggactttta tgttgtatgt tttcttataa acataagttg taaaattatt | 480 |
| aaagttgtcc catttttta ttcaattta ccaaataaac aaaaatttac aaaatcacat | 540 |
| aatatgctaa cacaaaacta ttctttaaaa aatacaatat ttattgatca aactttaatt | 600 |
| caacaaaaaa taaaattcaa cataagttgt agtgtactag tctttaatat aattctccca | 660 |
| cataatacgg acaatctcct cacgttgaac ttgcatttct cgatcatatg attgagtaga | 720 |
| caaaccaaca ttgctacttt gagctataaa tggtttaaaa agtaatgata tgaattataa | 780 |
| atttttattta catatgaaac aaatggtaag taaatataaa tgtggggttg tttttataaa | 840 |
| atataaactt atgggtcaat ttttgtattt gaaaaatccc aaattatgat ttgaaatttt | 900 |
| caaatcatga tttttgaaga attcagtctg aaatcgcatg tccaaatgct gatttcatct | 960 |
| catgatttca tatcgtgata tgaaatcgca tgtccaaacg cctactaagt aacttagaca | 1020 |
| cgtcttgacc ttttataatt actccctcca tcctaattta cttgtcaaat attttctaat | 1080 |
| ttgattcccc ttttacttgt catttttac aaatcaagaa acgacaattt ttttcttcc | 1140 |
| tattataccc tcaatttatt aacattgaat taatgtcctt gaaaaatata ggaagtaaat | 1200 |
| atgtttaaaa ctctatcaaa ttaatatgga taaaatggta aattcattat accaattatt | 1260 |
| attttcttaa tagatgcgtc aaatcaaaaa ttgacaagta atataaattt caaagaaaat | 1320 |
| ttgtattgaa agttaattgt attcgtccac ttgacacatc atgtcttaat tattcaacaa | 1380 |
| gtttgaatcc aatgtatatg aatgtttgaa aagtcttgac gaaaactaca agagtgtctt | 1440 |
| tattagaaat caggacaact tgactcttta ttttcattt ctttttctc actttgactt | 1500 |
| ggtcaatcca tagttttgca tccataaacc acaagttctg tttagatatt aaatagaaaa | 1560 |
| ttgtccaaat tcatttagaa aaatgtggac ataaatcatt tagacaaaac ctcttagcct | 1620 |
| aagcagagac atttctcttc cagcaaacaa aagagaaatg gcatatgctg ctctttcttc | 1680 |

```
acttatctat acattgcaac aactcttgaa acctaatcaa tctttggttt gtcgaagctg    1740
tacacaacaa catcttcaat ctatctatca caatctttct gctctgcaac ttttccttga    1800
cgatactacg acaaggata ttgaaactct taaggtatgt aattatctaa tctcttactc    1860
atcttatatt tattcaataa taattaattt atcgagtttc aattttaagg ttatagaaaa    1920
gaggatcaga gatgtagtat acaaagcaga agataaagtt gattcaagcc taagaaacat    1980
catactagca gattgcacag agaatagaga aggggcttgt aaattctttg aggaagaatt    2040
gctaaaagtg gaaaaagatg ttgattctct caggaaagag gtgatgcaga tcgagtttaa    2100
caagcatggt agcagatctg cagaactaac aacaattctt ccctctccag aaaaaagtac    2160
aattgaggaa catactattg ttgggatgga ggatgagtac aacaccatac ttgatcgcct    2220
cactgcccaa acagacgagt tgactgtcat accaattttt ggtatgggcg gtataggtaa    2280
gacaactcta gccagaaagg tttatgatga ttcatctatt cgttctcgat tgatagaca     2340 tgtatgggtc actacctctg aagaattcaa tgagagacga atgcttctcg aagttgtttc    2400
ttcaattact actggaagca atcaagaaaa gagcgatgat caactaatgg agattgtgta    2460
tagaggtctt aagggtagga gatttctaat tgtcatagat gatatttgga gtactcaggc    2520
ttgggaccaa atgcaaagaa tatttccaaa tgatgacaat aaaagcagaa ttctactaac    2580
tacacggctc aagtatgttg ctgattatgt caacagtcct gatttccac ctcatagtaa     2640 gtcttttcta agtcttgatg atagttggaa tctattcacc gaaaaagtat tcaacaaaga    2700
tacctgtcct cctcacctag aagaaacagg gaagcatatt gtacaacaat gtcgaggatt    2760
acctctctcg gttgttgtag ttgctggact tgttggaaaa atggacccaa cgcatgacaa    2820
ttgggagaac gttgaggaaa atctgaactc attcattggt actgtatctg aacggtgcca    2880
atcaattctt tctttaagct acaattactt gccccagtat ttgagggctt gttttctcta    2940
tgttggatgt tttcctgaag ataaagagat tgatgtttcc aagttgatta ggctatggat    3000
tgctgagcaa ttcgtaaagg cgagaagcaa taaaaattta gaagtggtgg cagaggagta    3060
tctggaagag ttaattgata gaagtctaat tttgagtggt agacaaaggg ctaatggaag    3120
gatgaaaact tgtaaaattc atgatcttct tcgccaacta tgcctaagtg aagctcatac    3180
tgaaaatatt agtcatatca tgaatagaaa tgtcctcgtg tcctcagaag ccatagatga    3240
tcaatggcga gtgattgttc cattggaact cgaagagaaa caagtttatc cgacaaggca    3300
tagcagtggt attacaagta caacccgcac ctttatttca atggaaatat gcctaagaga    3360
agctcagacc gaaaccatat atgatcaacg gcgagtgatc cttctctcta aacgacatag    3420
gattgataca atccgcacca ttattccatt cggagatact tttccaaaag tgatttgttc    3480 catttttttcg cagttgaagt tgcttaaggt gttggatgta ttatcagtct ggtacgatgt    3540
ctcttgtata atacctcagc ttgtacattt gagatatgtt ggtgcagtaa ttttggaagc    3600
tgtttcacta tccaaattga gaatctacag accataatt cttgcaagtg ttgaaaccac     3660
agagttgaag cacccagtag atatctggag aatgtcagag atcagacatt tggatattgt    3720
accgccacta tatatatcaa atcctcttga agcagaacaa cctttgtttc tcaataactt    3780
gcacacgctt tttctccgtt gctctccttt tgttgcgaaa atcataagaa gaactcccaa    3840
tctaaaaaag ctaaagattt tagataaatc taagcatcct gactggcctg atattcttga    3900
ttctctcaat cttctagagg agctggagac actacaaata tcaacagaag aaaacattga    3960
ccggatgatt ttctctgggg atattttccc tcgtaatctc aagcaactga aattatcata    4020
```

```
tacttgtata ccatgggaag atatgaaatt gctggctaat ttacccaatc ttgaggtgtt    4080
caagggtcat tatgcattcg atggaacaga ttggaaacta gatgaagatg ttgtgttttg    4140
caaattaaaa tgtctacgac tgtatgagcg cggagatctg caaaggtggg aagctgctgg    4200
tagtgataat tttccaatgc ttgagcaact attactgtat ggattcaaaa agctggaaga    4260
gattccggag agtattggag aaataatgac actaaaattc attaatacag aattttgcgg    4320
ctctggtgta gagactagtg caagaaaat tcaagaagag caagaaagct tgggaaatta    4380
tgagcttcaa cttcaaatta ctcctaaggt atgttgaaac tcaatctttg attaatactc    4440
tcccccagct agactttca aagtaatatt tcacacgtac aatctccact cggtaagatt    4500
taggattgaa attgtcttct tacatttatg atcatcaccc ttcggttttt tttatttttt    4560
tttagtaaat agcttcatat actctacaaa agttacacat aattaacaat tgacaattga    4620
ttctctctta ttgataattt gtcattttct ctttcagtta agattttga tcgaaaattt    4680 agacgaaaca agcatgttgc catcgaatga agtaatcgaa aaaatcaaag gtttgtctat    4740
ttaattcctt ttattacttc attgaaagag gttcagatat tttaaacaac ttttaacct    4800 ttctatttga atttttatc gctcagatag atacaacatt tattttgacg tcaaattgtt    4860
attttgattt aatcttattc ttttgtata tagtttccac tcggttcttc atttttttt    4920 caattatagt ttaattttt ttaattgcac atggttgatt gatttaattt gtgagattca    4980
cttttctttc gattttagga gttcttcggg attaatgtta ttcagattta ggagtattat    5040
atttcaactt tcggttagat ttaggattca aattgtcttc ttacatttat gatcatcatc    5100
cttttgatgt tatttatttc ttttagtaaa tagcttcaaa aactctata                5149
```

<210> SEQ ID NO 14
<211> LENGTH: 919
<212> TYPE: PRT
<213> ORGANISM: Solanum americanum

<400> SEQUENCE: 14

```
Met Ala Tyr Ala Ala Leu Ser Ser Leu Ile Tyr Thr Leu Gln Gln Leu
1               5                   10                  15

Leu Lys Pro Asn Gln Ser Leu Val Cys Arg Ser Cys Thr Gln His
            20                  25                  30

Leu Gln Ser Ile Tyr His Asn Leu Ser Ala Leu Gln Leu Phe Leu Asp
        35                  40                  45

Asp Thr Thr Lys Asp Ile Glu Thr Leu Lys Val Cys Asn Tyr Leu
    50                  55                  60

Ile Ser Tyr Ser Ser Tyr Ile Tyr Ser Ile Ile Asn Leu Ser Ser
65                  70                  75                  80

Phe Asn Phe Lys Val Ile Glu Lys Arg Ile Arg Asp Val Val Tyr Lys
                85                  90                  95

Ala Glu Asp Lys Val Asp Ser Ser Leu Arg Asn Ile Ile Leu Ala Asp
            100                 105                 110

Cys Thr Glu Asn Arg Glu Gly Ala Cys Lys Phe Phe Glu Glu Leu
        115                 120                 125

Leu Lys Val Glu Lys Asp Val Asp Ser Leu Arg Lys Glu Val Met Gln
    130                 135                 140

Ile Glu Phe Asn Lys His Gly Ser Arg Ser Ala Glu Leu Thr Thr Ile
145                 150                 155                 160

Leu Pro Ser Pro Glu Lys Ser Thr Ile Glu Glu His Thr Ile Val Gly
                165                 170                 175
```

```
Met Glu Asp Glu Tyr Asn Thr Ile Leu Asp Arg Leu Thr Ala Gln Thr
                180                 185                 190
Asp Glu Leu Thr Val Ile Pro Ile Phe Gly Met Gly Gly Ile Gly Lys
            195                 200                 205
Thr Thr Leu Ala Arg Lys Val Tyr Asp Asp Ser Ser Ile Arg Ser Arg
        210                 215                 220
Phe Asp Arg His Val Trp Val Thr Thr Ser Glu Glu Phe Asn Glu Arg
225                 230                 235                 240
Arg Met Leu Leu Glu Val Val Ser Ser Ile Thr Thr Gly Ser Asn Gln
                245                 250                 255
Glu Lys Ser Asp Asp Gln Leu Met Glu Ile Val Tyr Arg Gly Leu Lys
            260                 265                 270
Gly Arg Arg Phe Leu Ile Val Ile Asp Asp Ile Trp Ser Thr Gln Ala
        275                 280                 285
Trp Asp Gln Met Gln Arg Ile Phe Pro Asn Asp Asn Lys Ser Arg
290                 295                 300
Ile Leu Leu Thr Thr Arg Leu Lys Tyr Val Ala Asp Tyr Val Asn Ser
305                 310                 315                 320
Pro Asp Phe Pro Pro His Ser Lys Ser Phe Leu Ser Leu Asp Asp Ser
                325                 330                 335
Trp Asn Leu Phe Thr Glu Lys Val Phe Asn Lys Asp Thr Cys Pro Pro
            340                 345                 350
His Leu Glu Glu Thr Gly Lys His Ile Val Gln Gln Cys Arg Gly Leu
        355                 360                 365
Pro Leu Ser Val Val Val Ala Gly Leu Val Gly Lys Met Asp Pro
370                 375                 380
Thr His Asp Asn Trp Glu Asn Val Glu Glu Asn Leu Asn Ser Phe Ile
385                 390                 395                 400
Gly Thr Val Ser Glu Arg Cys Gln Ser Ile Leu Ser Leu Ser Tyr Asn
                405                 410                 415
Tyr Leu Pro Gln Tyr Leu Arg Ala Cys Phe Leu Tyr Val Gly Cys Phe
            420                 425                 430
Pro Glu Asp Lys Glu Ile Asp Val Ser Lys Leu Ile Arg Leu Trp Ile
        435                 440                 445
Ala Glu Gln Phe Val Lys Ala Arg Ser Asn Lys Asn Leu Glu Val Val
450                 455                 460
Ala Glu Glu Tyr Leu Glu Glu Leu Ile Asp Arg Ser Leu Ile Leu Ser
465                 470                 475                 480
Gly Arg Gln Arg Ala Asn Gly Arg Met Lys Thr Cys Lys Ile His Asp
                485                 490                 495
Leu Leu Arg Gln Leu Cys Leu Ser Glu Ala His Thr Glu Asn Ile Ser
            500                 505                 510
His Ile Met Asn Arg Asn Val Leu Val Ser Ser Glu Ala Ile Asp Asp
        515                 520                 525
Gln Trp Arg Val Ile Val Pro Leu Glu Leu Glu Lys Gln Val Tyr
530                 535                 540
Pro Thr Arg His Ser Ser Gly Ile Thr Ser Thr Thr Arg Thr Phe Ile
545                 550                 555                 560
Ser Met Glu Ile Cys Leu Arg Glu Ala Gln Thr Glu Thr Ile Tyr Asp
                565                 570                 575
Gln Arg Arg Val Ile Leu Leu Ser Lys Arg His Arg Ile Asp Thr Ile
            580                 585                 590
Arg Thr Ile Ile Pro Phe Gly Asp Thr Phe Pro Lys Val Ile Cys Ser
```

```
                  595                 600                 605
        Ile Phe Ser Gln Leu Lys Leu Leu Lys Val Leu Asp Val Leu Ser Val
            610                 615                 620

Trp Tyr Asp Val Ser Cys Ile Ile Pro Gln Leu Val His Leu Arg Tyr
        625                 630                 635                 640

Val Gly Ala Val Ile Leu Glu Ala Val Ser Leu Ser Lys Leu Arg Asn
                        645                 650                 655

Leu Gln Thr Ile Ile Leu Ala Ser Val Glu Thr Thr Glu Leu Lys His
                    660                 665                 670

Pro Val Asp Ile Trp Arg Met Ser Glu Ile Arg His Leu Asp Ile Val
                675                 680                 685

Pro Pro Leu Tyr Ile Ser Asn Pro Leu Glu Ala Glu Gln Pro Leu Phe
            690                 695                 700

Leu Asn Asn Leu His Thr Leu Phe Leu Arg Cys Ser Pro Phe Val Ala
        705                 710                 715                 720

Lys Ile Ile Arg Arg Thr Pro Asn Leu Lys Lys Leu Lys Ile Leu Asp
                        725                 730                 735

Lys Ser Lys His Pro Asp Trp Pro Asp Ile Leu Asp Ser Leu Asn Leu
                    740                 745                 750

Leu Glu Glu Leu Glu Thr Leu Gln Ile Ser Thr Glu Glu Asn Ile Asp
                755                 760                 765

Arg Met Ile Phe Ser Gly Asp Ile Phe Pro Arg Asn Leu Lys Gln Leu
            770                 775                 780

Lys Leu Ser Tyr Thr Cys Ile Pro Trp Glu Asp Met Lys Leu Leu Ala
        785                 790                 795                 800

Asn Leu Pro Asn Leu Glu Val Phe Lys Gly His Tyr Ala Phe Asp Gly
                        805                 810                 815

Thr Asp Trp Lys Leu Asp Glu Asp Val Val Phe Cys Lys Leu Lys Cys
                    820                 825                 830

Leu Arg Leu Tyr Glu Arg Gly Asp Leu Gln Arg Trp Glu Ala Ala Gly
                835                 840                 845

Ser Asp Asn Phe Pro Met Leu Glu Gln Leu Leu Leu Tyr Gly Phe Lys
            850                 855                 860

Lys Leu Glu Glu Ile Pro Glu Ser Ile Gly Glu Ile Met Thr Leu Lys
        865                 870                 875                 880

Phe Ile Asn Thr Glu Phe Cys Gly Ser Gly Val Glu Thr Ser Ala Lys
                        885                 890                 895

Lys Ile Gln Glu Glu Gln Glu Ser Leu Gly Asn Tyr Glu Leu Gln Leu
                    900                 905                 910

Gln Ile Thr Pro Lys Val Cys
                915

<210> SEQ ID NO 15
<211> LENGTH: 2757
<212> TYPE: DNA
<213> ORGANISM: Solanum americanum

<400> SEQUENCE: 15
atggcatatg ctgctctttc ttcacttatc tatacattgc aacaactctt gaaacctaat      60
caatctttgg tttgtcgaag ctgtacacaa caacatcttc aatctatcta tcacaatctt     120
tctgctctgc aacttttcct tgacgatact acgacaaagg atattgaaac tcttaaggta     180
tgtaattatc taatctctta ctcatcttat atttattcaa taataattaa tttatcgagt     240 ttcaattttta aggttataga aaagaggatc agagatgtag tatacaaagc agaagataaa     300
```

```
gttgattcaa gcctaagaaa catcatacta gcagattgca cagagaatag agaagggget     360 tgtaaattct ttgaggaaga attgctaaaa gtggaaaaag atgttgattc tctcaggaaa     420
gaggtgatgc agatcgagtt taacaagcat ggtagcagat ctgcagaact aacaacaatt     480
cttccctctc cagaaaaaag tacaattgag gaacatacta ttgttgggat ggaggatgag     540
tacaacacca tacttgatcg cctcactgcc caaacagacg agttgactgt cataccaatt     600
tttggtatgg gcggtatagg taagacaact ctagccagaa aggtttatga tgattcatct     660
attcgttctc gatttgatag acatgtatgg gtcactacct ctgaagaatt caatgagaga     720
cgaatgcttc tcgaagttgt ttcttcaatt actactggaa gcaatcaaga aaagagcgat     780
gatcaactaa tggagattgt gtatagaggt cttaagggta ggagatttct aattgtcata     840
gatgatattt ggagtactca ggcttgggac caaatgcaaa gaatatttcc aaatgatgac     900
aataaaagca gaattctact aactacacgg ctcaagtatg ttgctgatta tgtcaacagt     960 cctgatttc cacctcatag taagtctttt ctaagtcttg atgatagttg gaatctattc    1020
accgaaaaag tattcaacaa agatacctgt cctcctcacc tagaagaaac agggaagcat    1080
attgtacaac aatgtcgagg attacctctc tcggttgttg tagttgctgg acttgttgga    1140
aaaatggacc caacgcatga caattgggag aacgttgagg aaaatctgaa ctcattcatt    1200
ggtactgtat ctgaacggtg ccaatcaatt cttctcttaa gctacaatta cttgccccag    1260
tatttgaggg cttgttttct ctatgttgga tgttttcctg aagataaaga gattgatgtt    1320
tccaagttga ttaggctatg gattgctgag caattcgtaa aggcgagaag caataaaaat    1380
ttagaagtgg tggcagagga gtatctggaa gagttaattg atagaagtct aattttgagt    1440
ggtagacaaa gggctaatgg aaggatgaaa acttgtaaaa ttcatgatct tcttcgccaa    1500
ctatgcctaa gtgaagctca tactgaaaat attagtcata tcatgaatag aaatgtcctc    1560
gtgtcctcag aagccataga tgatcaatgg cgagtgattg ttccattgga actcgaagag    1620
aaacaagttt atccgacaag gcatagcagt ggtattacaa gtacaacccg cacctttatt    1680
tcaatggaaa tatgcctaag agaagctcag accgaaacca tatatgatca acggcgagtg    1740
atccttctct ctaaacgaca taggattgat acaatccgca ccattattcc attcggagat    1800
acttttccaa aagtgatttg ttccattttt tcgcagttga agttgcttaa ggtgttggat    1860
gtattatcag tctggtacga tgtctcttgt ataatacctc agcttgtaca tttgagatat    1920
gttggtgcag taattttgga agctgtttca ctatccaaat tgagaaatct acagaccata    1980
attcttgcaa gtgttgaaac cacagagttg aagcacccag tagatatctg gagaatgtca    2040
gagatcagac atttggatat tgtaccgcca ctatatatat caaatcctct tgaagcagaa    2100
caacctttgt ttctcaataa cttgcacacg cttttttctcc gttgctctcc ttttgttgcg    2160
aaaatcataa gaagaactcc caatctaaaa aagctaaaga ttttagataa atctaagcat    2220
cctgactggc ctgatattct tgattctctc aatcttctag aggagctgga gacactacaa    2280
atatcaacag aagaaaacat tgaccggatg atttttctctg gggatatttt ccctcgtaat    2340
ctcaagcaac tgaaattatc atatacttgt ataccatggg aagatatgaa attgctggct    2400
aatttaccca atcttgaggt gttcaagggt cattatgcat tcgatggaac agattggaaa    2460
ctagatgaag atgttgtgtt ttgcaaatta aaatgtctac gactgtatga gcgcggagat    2520
ctgcaaaggt gggaagctgc tggtagtgat aattttccaa tgcttgagca actattactg    2580
tatggattca aaaagctgga agagattccg gagagtattg agaaataat gacactaaaa    2640
```

```
ttcattaata cagaattttg cggctctggt gtagagacta gtgcaaagaa aattcaagaa    2700
gagcaagaaa gcttgggaaa ttatgagctt caacttcaaa ttactcctaa ggtatgt      2757

<210> SEQ ID NO 16
<211> LENGTH: 5608
<212> TYPE: DNA
<213> ORGANISM: Solanum americanum

<400> SEQUENCE: 16
aagttggaag cttaactcat ttggctacct catatagttt acccatattt ttacccatga     60
atactcatat ttctatgggt tgaatatggg tataaaccca tattttaccc atctaaaaaa    120
tcactcacca acccattaaa atatgaacag attgggcggg ttaccaaaat atgggctctt    180
tttgccacca ctaacaacaa caaagagcaa agcaaagcac aactttgaaa tttgaaaaat    240
gatgcaagac aaatatcaaa attagacagt aaaattcaca attccccttaa aaataaatga    300 taaattaaag aagactaaac aatagaaaac cttacaatct caaaggcact atggatcgga    360
gtcgtacctg tgtgtttttt atcgtacaat attccacaca gtattattaa ttttttaagg    420
accatttggc catgtgatat gaaattatga gatgaagttg aagttttatt tggacatgca    480
atttgaattt tttatgttgt atgttttctt ataaacataa aaaacccata agttgtaaaa    540
ttattaaact tgtctcattt ttttattcaa ttttaccaaa taaataaaaa tttacaaaat    600
cacataatat gctaacacaa actattctt taaaaaatac aatatttatt gatcaaactt     660
taattcaaca aaaataaaa ttcaacataa gttgtagtgt actagtcttt aatataattc    720
tcccacatag tacggacaat ctcctcacat tgaacttgca tttctcgatc atatgatcga    780
gtagacaaac caacattgct actttgagct ataaatggtt taaaaagtaa tgatatgaat    840
tataaatttt atttacatat gaaacaaatg gtaagtagat ataaatgtgg ggttgttttt    900
ataaaatata aacttatggg tcaattttg tatttgaaaa atctcaaatc atgatttgaa     960 attttaaat catgattttt gaagaatttg ggatttcatc tcatgatatg aaatcatgag   1020
atgaaatcag tctgaaattg catgtccaaa tgctgatttc atctcatgat tcatatcgt    1080 gatatgaaat aaatcgtgat atgaaatcgc atgtccaaac gtctactaaa taacttagac   1140
atgtcttgac cttttataat tactccctcc gtcctaattt acttgtcaaa tattttctaa   1200
tttgattccc cttttacttg tcatttttta caaatcaaga aacgacaatt tttttttctt   1260
cctattatac cctcaattta ttaacattga attaatgtcc ttgaaaaata tagaaagtaa   1320
atatgtttaa aactctatca aattaatagg gataaaatgg taaattcatt ataccaatta   1380
ttattttctt aatagatgcg tcaaatcaaa aattgacaaa taaaaaaaga cgaaagaaaa   1440
tttgtattga agttaattg tattcgtcca cttgacacat catgtcttaa ttattcaaca    1500
agtttgaatc caatgtatat gaatcataaa tgtgagacat ctctactatc gtggtgggc     1560 caatgtttga aaagtgttga cgaaaactac aagagtgtct ttattagaaa tcaggacaac   1620
ttgactcttt atttttcatt tctttttct tactttgact tggtcaatcc atagttttgc    1680
atccataaac cacaagttct gtttagatat taaatagaaa attgtccaaa ttcatttaga   1740
aaaatgtgga cataaatcat ttagacaaaa cctcttagcc taagcagaga catttctctt   1800
ccagcaaaca aaagagaaat ggcatatgct gctctttctt cacttatcta tacattgcaa   1860
caactcttga aacctaatca atctttggtt tgtcgaagct gtacacaaca acatcttcaa   1920
tctatctatc acaatctttc tgctctgcaa cttttccttg acgatactac gacaaaggat   1980
attgaaactc ttaaggtatg taattatcta atctcttact catcttatat ttattcaata   2040
```

```
ataattaatt tatcgagttt caattttaag gttatagaaa agaggatcag agatgtagta    2100
tacaaagcag aagatacagt tgattcaagc ctaagaaaca tcattctagc agattgcaca    2160
gagaatagag aagggcttg taaattcttt gaggaagaat tgctaaaagt ggaaaaagat     2220
gttgattctc tcagcaaaga ggtgatgcag atcgacttta acaagcatgg aagcagatct    2280
gcagaattag caacaactga tccctcctca tcaggaaaaa gtacaattga ggaacatact    2340
attgttggga tggaggatga gtacaacacc atacttgatc gcctcactgc ccaaacagac    2400
gagttgactg tcataccaat ttttggtatg ggcggtatag gtaagacaac tcttgccaga    2460
aaggtttatg atgattcatc tattcgttct cgatttgata gacatgcatg ggtcactacc    2520
tctgaagaat tcaatgagag acgaatgctt ctcgaagttg tttcttcaat tactactgga    2580
agcaatcaag aaagagcga tgatcaacta atggagattg tgtatagaag tctgaagggt    2640
aggagatttc taattgtcat agatgatatt tggagtactc aggcttggga ccaaatgcaa    2700
agaatatttc caaatgatga caataaaagc cgaattctac taactacacg gctcaagtat    2760
gttgctgatt atgtcagcag tcctgatttt ccacctcata gtaagtcttt tctaagtctt    2820
gatgatagtt ggaatctatt caccgaaaaa gtattcaacg aagatacctg tcctcctcac    2880
ctagaagaaa cagggaagca tattgtacaa caatgtcaag gattacctct ctcggttgtt    2940
gtcgttgctg gacttgttgg aaaaatggac ccaacgcatg acaattggga gaatgttgag    3000
gaaaatctga actcattctt tggtactgta tccgaacggt gccactcaat tctttctttg    3060
agctacaatt acttgcccca atatttgagg gcttgttttc tctatgttgg aggttttcct    3120
gaagataaag agattgatgt ttccaagttg attaggctat ggattgctga gcaattcgta    3180
aaggcgagaa gcaataaaag gctagaagtg gtggcagagg agtatctgga agagttaatt    3240
gatagaagtc taattttgag tggtagacaa agggctaatg gaaggatgaa aacttgcaaa    3300
attcatgatc ttcttcgcca actatgccta agtgaagctc atactgaaaa tattagtcat    3360
atcatgaata gaaatgtccc cgtgtcctca gaagccatag atgatcaacg gcgagtgatt    3420
gttccattgg aactcgaaga gaaacaagtt tatcctacaa ggcatagcag tggtattaca    3480
agtacaaccc gcacctttat ttcaatggaa atatgcctaa gagaagctca aaccgaagcc    3540
atatatgatc aacggcgagt gatccttctg tctaaacgac ataggattga tacaatccgc    3600
accattattc cattcggaga tacttttcca aaagagattt gttccatttt ttcagagttc    3660
aagttgctta aggtgttgga tgtattatca gtctggtacg atgtctcttg tataatacct    3720
cagcttgtac atttgagata tgttggtgca gtaattttgg aagctctttc actacccaaa    3780
ttgagaaatc tacagaccat aatgcttaca agtgttgaaa ccacagagtt gaagcactca    3840
ctagatatct ggagaatgtc agagataaga catttggata ttgtaccgcc actatatata    3900
tcaaatcctc ttgaagcaga acaacctttg tttctcaata acttgcacac gcttttctc    3960
cgttgctctc cttttgttgc gaaaatcata agaagaactc cgaatctaaa aaagctaaag    4020
attttagata aatctaagca tcctgactgg cctgatattc ttgattctct caatcttcta    4080
gaggagctgg agacactaca aatatcaaca gaagaaaaca ttgaccggat gattttctct    4140
ggggataatt tccctcgtaa tctcaagcaa ctgaaattat caggtactaa aataccatgg    4200
gaagatatga aattgctggc taatttaccc aatcttgagg tgttcaaggg tcattatgca    4260
ttcgatggaa cagattggaa actagatgaa gatgttgtgt tttgcaaatt aaaatgtcta    4320
cgactgtatg agcgcggaga tctgcaaagg tgggaagcag caggtagtga taattttcct    4380
```

-continued

```
atgcttgagc aactagtact gtatgggttc gaaaaactgg aagagattcc ggagagtatt    4440
ggagaaataa tgacactaaa attcatcaaa acagaatttt gcggctctgg tgtagagaca    4500
agtgcaaaga aaattcaaga agagcaagaa agctggggaa attatgagct tcaacttcta    4560
attactccta tggtatgtta aaactccatc tttgataatt agactcaact atcaactttt    4620
ttcacagaga gtcaattctt tcacaagaag tcactcaact atcaattttt ttcacaaaaa    4680
gtcactcaac tttgattctt tcatagaaag ttactcaact atgggctttt tgcatagaaa    4740
accactcaac ctatttaatt atattttca tatgaaattt ttatttctaa tcaaaatttt    4800
aaaatccaaa tatatatcca tttaaaccat ttaatgaatc acccacacta aatccgatcc    4860
gctaaaaata taatatttac cttttgtttt atccttattc ccctaaatat tctctcctgt    4920
ttcctaaata ttctctcctg tttcctgatt ctttctcttc tgcgttttcc ccctcaattt    4980
cagtctcttc ttttacgtat atatcaacct ctctttctcc ataagcatca tattattgtt    5040
ttctcaactt caaaaacaat ataaattaca acaatctctt gatttacaat ttcaataaaa    5100
aattctatgc acaccatgct tttatcaatt attatgaaaa ctgataaaat taacaaacaa    5160
ggctctcaat ctgcataact acgaatctac gcctatagtt gctctttaat tgcaattatt    5220
cattcaataa aatcaagtga tcaggatagt cctaaatcta gatatagttt gagaaatcga    5280
tggaaaattc ctagttaata gagattttaa aattgagaaa ttaaaaaaaa tgcagtgaat    5340
caggagacgg gagagaatat ttagggagat aaggataaaa caaaagtcaa tattatattt    5400
ttagcggatc gaatttagtg gggtgattca ttaaatggtt taaatggaaa tatatttaga    5460
ttttaaaatt ttgattaaaa ataaaaattt catatgaaaa atataattaa ataggttgag    5520
tgactttcta tgcaaaagcc ccatagttga gtgactttct gtgaaaaaaa ttgatagttg    5580
agtgactttc tgtgaaagta tcaaagtt                                       5608
```

<210> SEQ ID NO 17
<211> LENGTH: 920
<212> TYPE: PRT
<213> ORGANISM: Solanum americanum

<400> SEQUENCE: 17

```
Met Ala Tyr Ala Ala Leu Ser Ser Leu Ile Tyr Thr Leu Gln Gln Leu
1               5                   10                  15

Leu Lys Pro Asn Gln Ser Leu Val Cys Arg Ser Cys Thr Gln Gln His
            20                  25                  30

Leu Gln Ser Ile Tyr His Asn Leu Ser Ala Leu Gln Leu Phe Leu Asp
        35                  40                  45

Asp Thr Thr Lys Asp Ile Glu Thr Leu Lys Val Cys Asn Tyr Leu
    50                  55                  60

Ile Ser Tyr Ser Ser Tyr Ile Tyr Ser Ile Ile Asn Leu Ser Ser
65                  70                  75                  80

Phe Asn Phe Lys Val Ile Glu Lys Arg Ile Arg Asp Val Val Tyr Lys
                85                  90                  95

Ala Glu Asp Thr Val Asp Ser Ser Leu Arg Asn Ile Ile Leu Ala Asp
            100                 105                 110

Cys Thr Glu Asn Arg Glu Gly Ala Cys Lys Phe Phe Glu Glu Leu
        115                 120                 125

Leu Lys Val Glu Lys Asp Val Asp Ser Leu Ser Lys Glu Val Met Gln
    130                 135                 140

Ile Asp Phe Asn Lys His Gly Ser Arg Ser Ala Glu Leu Ala Thr Thr
145                 150                 155                 160
```

```
Asp Pro Ser Ser Ser Gly Lys Ser Thr Ile Glu Glu His Thr Ile Val
            165                 170                 175

Gly Met Glu Asp Glu Tyr Asn Thr Ile Leu Asp Arg Leu Thr Ala Gln
        180                 185                 190

Thr Asp Glu Leu Thr Val Ile Pro Ile Phe Gly Met Gly Gly Ile Gly
        195                 200                 205

Lys Thr Thr Leu Ala Arg Lys Val Tyr Asp Asp Ser Ser Ile Arg Ser
    210                 215                 220

Arg Phe Asp Arg His Ala Trp Val Thr Thr Ser Glu Glu Phe Asn Glu
225                 230                 235                 240

Arg Arg Met Leu Leu Glu Val Val Ser Ser Ile Thr Thr Gly Ser Asn
                245                 250                 255

Gln Gly Lys Ser Asp Asp Gln Leu Met Glu Ile Val Tyr Arg Ser Leu
            260                 265                 270

Lys Gly Arg Arg Phe Leu Ile Val Ile Asp Asp Ile Trp Ser Thr Gln
    275                 280                 285

Ala Trp Asp Gln Met Gln Arg Ile Phe Pro Asn Asp Asp Asn Lys Ser
290                 295                 300

Arg Ile Leu Leu Thr Thr Arg Leu Lys Tyr Val Ala Asp Tyr Val Ser
305                 310                 315                 320

Ser Pro Asp Phe Pro Pro His Ser Lys Ser Phe Leu Ser Leu Asp Asp
                325                 330                 335

Ser Trp Asn Leu Phe Thr Glu Lys Val Phe Asn Glu Asp Thr Cys Pro
            340                 345                 350

Pro His Leu Glu Glu Thr Gly Lys His Ile Val Gln Gln Cys Gln Gly
        355                 360                 365

Leu Pro Leu Ser Val Val Val Ala Gly Leu Val Gly Lys Met Asp
    370                 375                 380

Pro Thr His Asp Asn Trp Glu Asn Val Glu Glu Asn Leu Asn Ser Phe
385                 390                 395                 400

Phe Gly Thr Val Ser Glu Arg Cys His Ser Ile Leu Ser Leu Ser Tyr
                405                 410                 415

Asn Tyr Leu Pro Gln Tyr Leu Arg Ala Cys Phe Leu Tyr Val Gly Gly
            420                 425                 430

Phe Pro Glu Asp Lys Glu Ile Asp Val Ser Lys Leu Ile Arg Leu Trp
        435                 440                 445

Ile Ala Glu Gln Phe Val Lys Ala Arg Ser Asn Lys Arg Leu Glu Val
    450                 455                 460

Val Ala Glu Glu Tyr Leu Glu Glu Leu Ile Asp Arg Ser Leu Ile Leu
465                 470                 475                 480

Ser Gly Arg Gln Arg Ala Asn Gly Arg Met Lys Thr Cys Lys Ile His
                485                 490                 495

Asp Leu Leu Arg Gln Leu Cys Leu Ser Glu Ala His Thr Glu Asn Ile
            500                 505                 510

Ser His Ile Met Asn Arg Asn Val Pro Val Ser Ser Glu Ala Ile Asp
        515                 520                 525

Asp Gln Arg Arg Val Ile Val Pro Leu Glu Leu Glu Glu Lys Gln Val
    530                 535                 540

Tyr Pro Thr Arg His Ser Ser Gly Ile Thr Ser Thr Arg Thr Phe
545                 550                 555                 560

Ile Ser Met Glu Ile Cys Leu Arg Glu Ala Gln Thr Glu Ala Ile Tyr
                565                 570                 575
```

```
Asp Gln Arg Arg Val Ile Leu Leu Ser Lys Arg His Arg Ile Asp Thr
            580                 585                 590
Ile Arg Thr Ile Ile Pro Phe Gly Asp Thr Phe Pro Lys Glu Ile Cys
        595                 600                 605
Ser Ile Phe Ser Glu Phe Lys Leu Leu Lys Val Leu Asp Val Leu Ser
    610                 615                 620
Val Trp Tyr Asp Val Ser Cys Ile Ile Pro Gln Leu Val His Leu Arg
625                 630                 635                 640
Tyr Val Gly Ala Val Ile Leu Glu Ala Leu Ser Leu Pro Lys Leu Arg
                645                 650                 655
Asn Leu Gln Thr Ile Met Leu Thr Ser Val Glu Thr Thr Glu Leu Lys
            660                 665                 670
His Ser Leu Asp Ile Trp Arg Met Ser Glu Ile Arg His Leu Asp Ile
        675                 680                 685
Val Pro Pro Leu Tyr Ile Ser Asn Pro Leu Glu Ala Glu Gln Pro Leu
    690                 695                 700
Phe Leu Asn Asn Leu His Thr Leu Phe Leu Arg Cys Ser Pro Phe Val
705                 710                 715                 720
Ala Lys Ile Ile Arg Arg Thr Pro Asn Leu Lys Lys Leu Lys Ile Leu
                725                 730                 735
Asp Lys Ser Lys His Pro Asp Trp Pro Asp Ile Leu Asp Ser Leu Asn
            740                 745                 750
Leu Leu Glu Glu Leu Glu Thr Leu Gln Ile Ser Thr Glu Glu Asn Ile
        755                 760                 765
Asp Arg Met Ile Phe Ser Gly Asp Asn Phe Pro Arg Asn Leu Lys Gln
    770                 775                 780
Leu Lys Leu Ser Gly Thr Lys Ile Pro Trp Glu Asp Met Lys Leu Leu
785                 790                 795                 800
Ala Asn Leu Pro Asn Leu Glu Val Phe Lys Gly His Tyr Ala Phe Asp
                805                 810                 815
Gly Thr Asp Trp Lys Leu Asp Glu Asp Val Val Phe Cys Lys Leu Lys
            820                 825                 830
Cys Leu Arg Leu Tyr Glu Arg Gly Asp Leu Gln Arg Trp Glu Ala Ala
        835                 840                 845
Gly Ser Asp Asn Phe Pro Met Leu Glu Gln Leu Val Leu Tyr Gly Phe
    850                 855                 860
Glu Lys Leu Glu Glu Ile Pro Glu Ser Ile Gly Glu Ile Met Thr Leu
865                 870                 875                 880
Lys Phe Ile Lys Thr Glu Phe Cys Gly Ser Gly Val Glu Thr Ser Ala
                885                 890                 895
Lys Lys Ile Gln Glu Glu Gln Glu Ser Trp Gly Asn Tyr Glu Leu Gln
            900                 905                 910
Leu Leu Ile Thr Pro Met Val Cys
        915                 920

<210> SEQ ID NO 18
<211> LENGTH: 2760
<212> TYPE: DNA
<213> ORGANISM: Solanum americanum

<400> SEQUENCE: 18
atggcatatg ctgctctttc ttcacttatc tatacattgc aacaactctt gaaacctaat       60
caatctttgg tttgtcgaag ctgtacacaa caacatcttc aatctatcta tcacaatctt      120
tctgctctgc aacttttcct tgacgatact acgacaaagg atattgaaac tcttaaggta      180
```

```
tgtaattatc taatctctta ctcatcttat atttattcaa taataattaa tttatcgagt    240
ttcaatttta aggttataga aaagaggatc agagatgtag tatacaaagc agaagataca    300
gttgattcaa gcctaagaaa catcattcta gcagattgca cagagaatag agaagggct    360 tgtaaattct ttgaggaaga attgctaaaa gtggaaaaag atgttgattc tctcagcaaa    420
gaggtgatgc agatcgactt taacaagcat ggaagcagat ctgcagaatt agcaacaact    480
gatccctcct catcaggaaa aagtacaatt gaggaacata ctattgttgg gatgaggat    540 gagtacaaca ccatacttga tcgcctcact gcccaaacag acgagttgac tgtcatacca    600 attttttggta tgggcggtat aggtaagaca actcttgcca gaaaggttta tgatgattca    660
tctattcgtt ctcgatttga tagacatgca tgggtcacta cctctgaaga attcaatgag    720
agacgaatgc ttctcgaagt tgtttcttca attactactg gaagcaatca aggaaagagc    780
gatgatcaac taatggagat tgtgtataga agtctgaagg gtaggagatt tctaattgtc    840
atagatgata tttggagtac tcaggcttgg gaccaaatgc aaagaatatt ccaaatgat    900 gacaataaaa gccgaattct actaactaca cggctcaagt atgttgctga ttatgtcagc    960
agtcctgatt tccacctca tagtaagtct tttctaagtc ttgatgatag ttggaatcta   1020
ttcaccgaaa agtattcaa cgaagatacc tgtcctcctc acctagaaga aacagggaag   1080
catattgtac aacaatgtca aggattacct ctctcggttg ttgtcgttgc tggacttgtt   1140
ggaaaaatgg acccaacgca tgacaattgg gagaatgttg aggaaaatct gaactcattc   1200
tttggtactg tatccgaacg gtgccactca attctttctt tgagctacaa ttacttgccc   1260
caatatttga gggcttgttt tctctatgtt ggaggtttc ctgaagataa agagattgat   1320
gtttccaagt tgattaggct atggattgct gagcaattcg taaaggcgag aagcaataaa   1380
aggctagaag tggtggcaga ggagtatctg gaagagttaa ttgatagaag tctaattttg   1440
agtggtagac aaagggctaa tggaaggatg aaaacttgca aaattcatga tcttcttcgc   1500
caactatgcc taagtgaagc tcatactgaa atatattagtc atatcatgaa tagaaatgtc   1560
cccgtgtcct cagaagccat agatgatcaa cggcgagtga ttgttccatt ggaactcgaa   1620
gagaaacaag tttatcctac aaggcatagc agtggtatta caagtacaac ccgcaccttt   1680
atttcaatgg aaatatgcct aagagaagct caaaccgaag ccatatatga tcaacggcga   1740
gtgatccttc tgtctaaacg acataggatt gatacaatcc gcaccattat tccattcgga   1800
gatacttttc caaaagagat ttgttccatt ttttcagagt tcaagttgct taaggtgttg   1860
gatgtattat cagtctggta cgatgtctct tgtataatac ctcagcttgt acatttgaga   1920
tatgttggtg cagtaatttt ggaagctctt tcactaccca aattgagaaa tctacagacc   1980
ataatgctta caagtgttga aaccacagag ttgaagcact cactagatat ctggagaatg   2040
tcagagataa gacatttgga tattgtaccg ccactatata tatcaaatcc tcttgaagca   2100
gaacaacctt tgtttctcaa taacttgcac acgcttttttc tccgttgctc tccttttgtt   2160
gcgaaaatca taagaagaac tccgaatcta aaaaagctaa agattttaga taaatctaag   2220
catcctgact ggcctgatat tcttgattct ctcaatcttc tagaggagct ggagacacta   2280
caaatatcaa cagaagaaaa cattgaccgg atgatttttct ctggggataa tttccctcgt   2340
aatctcaagc aactgaaatt atcaggtact aaaataccat gggaagatat gaaattgctg   2400
gctaatttac ccaatcttga ggtgttcaag ggtcattatg cattcgatgg aacagattgg   2460
aaactagatg aagatgttgt gttttgcaaa ttaaaatgtc tacgactgta tgagcgcgga   2520
```

| | |
|---|---|
| gatctgcaaa ggtgggaagc agcaggtagt gataatttc ctatgcttga gcaactagta | 2580 |
| ctgtatgggt tcgaaaaact ggaagagatt ccggagagta ttggagaaat aatgacacta | 2640 |
| aaattcatca aaacagaatt tgcggctct ggtgtagaga caagtgcaaa gaaaattcaa | 2700 |
| gaagagcaag aaagctgggg aaattatgag cttcaacttc taattactcc tatggtatgt | 2760 |

<210> SEQ ID NO 19
<211> LENGTH: 6006
<212> TYPE: DNA
<213> ORGANISM: Solanum americanum

<400> SEQUENCE: 19

| | |
|---|---|
| attcacattc taaaggctat aaatatatcc ttaagtttcc tttgtaaaac ataacacaca | 60 |
| aatacaattc aggagatcgt gagaagaaga aagtatttag tgaggttttt gtagtgagaa | 120 |
| attcttggtg taaattctct ataattctat tcttgtgaaa tagagttgtt tttcctccca | 180 |
| aatattttc atagtgatca gagaataaca acaaatgtgt ctacggactg ttaaaaaata | 240 |
| atggcataag tgggccctct tgtaaacga taatggcatg ggtgagctca atatttagcg | 300 |
| gatgatataa atgaaatctt ttcaaagtt tgattactta tttaagtttt tttcttttta | 360 |
| tttaatttt aattcgatgt ccaatatgca caaccaaatt tccactacaa ccaaaaaaaa | 420 |
| aaaaaagaac gctgtgtaac atcatctcca accaacctgg gtcatatgag tcccaaatgc | 480 |
| atttacagca acaagagca aagcaaagca cgactttgaa atttgaaaaa tgatgcaaga | 540 |
| caaatatcat tcacaattcc ccttaaaata aatgataaat taagaagac taaacaatag | 600 |
| aaaaccttac aatctcaaag gcagtatgga tcggagtcgt atttggaaga attttgata | 660 |
| caacttgaag aagattgaag attgttgttc ataaagtata ctgtgggcgg ttaatctac | 720 |
| aacctgtgtg tttttatca tacaaaattc cacacagtat tattaatttc atgcaatttg | 780 |
| gacttttat gttgtatgtt ttcttataaa cataagttgt aaaattatta aagttgtccc | 840 |
| attttttat tcaattttac caaataaaca aaaatttaca aaatcacata atatgctaac | 900 |
| acaaaactat tctttaaaaa atacaatatt tattgatcaa actttaattc aacaaaaaat | 960 |
| aaaattcaac ataagttgta gtagttgtag tgtactagtc tttaatataa ttctcccaca | 1020 |
| taatacggac aatctcctca cgttgaactt gcatttctcg atcatatgat tgagtagaca | 1080 |
| aaccaacatt gctactttga gctataaatg gtttaaaaag taatgatatg aattataaat | 1140 |
| tttatttaca tatgaaacaa atgataagta aatataaatg tggggttgtt tttataaaat | 1200 |
| ataaacttat gggtcaattt ttgtatttga aaaatcccaa attatgattt gaaattttca | 1260 |
| aatcatgatt tttgaagaat tcagtctgaa atcgcatgtc caaatgctga tttcatctca | 1320 |
| tgatttcata tcgtgatatg aaatcgcatg tccaaacgcc tactaagtaa cttagacacg | 1380 |
| tcttgacctt ttataattat ccctccatcc taatttactt gtcaaatatt ttctaatttg | 1440 |
| attccctttt tacttgtcat tttttacaaa tcaagaaacg acaatttttt tttcttccta | 1500 |
| ttatacccctc aatttattaa cattgaatta atgtccttga aaaatatagt aagtaaatat | 1560 |
| gtttaaaact ctatcaaatt aatagggta aaataataaa ctcattatat taattattat | 1620 |
| tttcttaata gatgcgtcaa atcaaaaatc gacaaagtaa tataaatttc aaagaaaatt | 1680 |
| tgtatcgaaa gttaattgta ttcgtcaagt ttgaatccaa tgtatatgaa tgtttgaaaa | 1740 |
| gtcttgacga aaactacaag agtgtctta ttagaaatca ggacaacttg actctttatt | 1800 |
| tttcatttct tttttctcac tttgacttgg tcaatccata gttttgcatc cataaaccac | 1860 |
| aagttctgtt tagatattaa atagaaaatt gtccaaattt atttagaaaa atgtggacat | 1920 |

```
aaatcattta gacaaaacct cttatagcct aagcagagac atttctcttc cagcaaacaa   1980
aagagaaatg gcttatgctg ctctttcttc acttatgtat acattgcaac aactcttgaa   2040
acctaatcaa tctttcgttt gtcgatactc tacacaacaa cttgttcaat ctctctatca   2100
aaatcttact gctctgcaac ttttccttga ccatactacg acaaaggata ttgaaacact   2160
taaggtatgt aattatctaa tctcttactc atcttatatt tattcaataa taattaattt   2220
atcgagtttc aattttaagg ttatagaaaa gaggatcaga gatgtagtat acaaagcaga   2280
agataaagtt gattcaagcc taagaaacat cattctagca gattgcacag agaatagaga   2340
aggggcttgt aaattctttg aggaagaatt gctaaaagtg gaaaaagatg ttgattctct   2400
cagcaaagag gtgatgcaga tcgagtttaa caagcatgga tgcagatctg cagaattagc   2460
aacaactgat ccctcctcat caggaaaaag tacaattgag gaacatacta ttgttgggat   2520
ggaggatgag tacaacacca tacttgatcg cctcactgcc caaacagacg agttgactgt   2580
cataccaatt tttggtatgg gcggtatagg taagacaact cttgccagaa aggtttatga   2640
tgattcatct attcgttctc gatttgatag acatgcatgg gtcactacct ctgaagaatt   2700
caatgagaga cgaatgcttc tcgaagttgt ttcttcaatt actactggaa gcaatcaagg   2760
aaagagcgat gatcaactaa tggagattgt gtatagaagt ctgaagggta ggagatttct   2820
aattgtcata gatgatattt ggagtactca ggcttgggac caaatgcaaa gaatatttcc   2880
aaatgatgac agtaaaagcc gaattctact aactacacgg ctcaagtatg ttgctgatta   2940
tgtcagcagt cctgatttc cacctcatag taagtcttt ctaagtcttg atgatagttg   3000
gaatctattc accgaaaaag tattcaacga agatacctgt cctcctcacc tagaagaaac   3060
agggaagcat attgtacaac aatgtcaagg attacctctc tcggttgttg tcgttgctgg   3120
acttgttgga aaaatggacc caacgcatga caattgggag aatgttgagg aaaatctgaa   3180
ctcattcttt ggtactgtat ccgaacggtg ccactcaatt cttctcttga gctacaatta   3240
cttgccccaa tatttgaggg cttgttttct ctatgttgga ggttttcctg aagataaaga   3300
gattgatgtt tccaagttga ttaggctatg gattgctgag caattcgtaa aggcgagaag   3360
caataaaagg ctagaagtgg tggcagagga gtatctggaa gagttaattg atagaagtct   3420
aattttgagt ggtagacaaa gggctaatgg aaggatgaaa acttgcaaaa ttcatgatct   3480
tcttcgccaa ctatgcctaa gtgaagctca tactgaaaat attagtcata tcatgaatag   3540
aaatgtcccc gtgtcctcag aagccataga tgatcaacgg cgagtgattg ttccattgga   3600
actcgaagag aaacaatttt atcctacaag gcatagcagt ggtattacaa gtacaacccg   3660
cacctttatt tcaatggaaa tatgcctaag agaagctcaa accgaagcca tatatgatca   3720
acggcgagtg atccttctgt ctaaacgaca taggattgat acaatccgca ccattattcc   3780
attcggagat acttttccaa aagagatttg ttccattttt tcagagttca gttgcttaa   3840 ggtgttggat gtattatcag tctggtacga tgtctcttgt ataatacctc agcttgtaca   3900
tttgagatat gttggtgcag taattttgga agctctttca ctacccaaat tgagaaatct   3960
acagaccata atgcttacaa gtgttgaaac cacagagttg aagcactcac tagatatctg   4020
gagaatgtca gagataagac atttggatat tgtaccgcca ctatatatat caaatcctct   4080
tgaagcagaa caacctttgt ttctcaataa cttgcacacg cttttctcc gttgctctcc   4140 ttttgttgcg aaaatcataa gaagaactcc gaatctaaaa aagctaaaga ttttagataa   4200
atctaagcat cctgactggc ctgatattct tgattctctc aatcttctag aggagctgga   4260
```

```
gacactacaa atatcaacag aagaaaacat tgaccggatg attttctctg gggatatttt    4320
ccctcgtaat ctcaagcaac tgaaattatc atatacttgt ataccatggg aagatatgaa    4380
attgctggct aatttaccca atcttgaggt gttcaagggt cattatgcat tcgatggaac    4440
agattggaaa ctagatgaag atgttgtgtt ttgcaaatta aaatgtctac gactgtatga    4500
gcgcggagat ctgcaaaggt gggaagcagc aggtagtgat aattttccta tgcttgagca    4560
actagtactg tatgggttcg aaaaactgga agagattccg gagagtattg gagaaataat    4620
gacactaaaa ttcattaaaa cagaattttg cggctctggt gtagagacta gtgcaaagaa    4680
aattcaagaa gagcaagaaa gcttgggaaa ttatgagctt caacttcaaa ttactcctaa    4740
ggtatgttga aactcaatct ttgattaata ctctccccca gctagacttt tcaaagtaat    4800
atttcacacg tacaatctcc actcggtaag atttaggatt gaaattgtct tcttacattt    4860
atgatcatca cccttcggtt ttttttattt tttttttagta aatagtttca tatactctac    4920
aaaagttaca cataattaac aattgacaat tgattctctc ttattgataa tttgtcattt    4980
tctctttcag ttaagatttt tgatcgaaaa tttagacgaa acaagcatgt tgccatcgaa    5040
tgaagtaatc gaaaaaatca aaggtttgtc tatttaattc cttttattac ttcattgaaa    5100
gaggttcaga tattttaaac aacttttttaa cctttctatt tgaatttttt atcgctcaga    5160
tagatacaac atttattttg acgtcaaatt gttattttga tttaatctta ttcttttttgt    5220 atatagtttc cactcggttc ttcatttttt tttcaattat agtttaattt ttttttaattg    5280 cacatggttg attgatttaa tttgtgagat tcacttttct ttcgatttta ggagttcttc    5340
gggattaatg ttattcagat ttaggagtat tatatttcaa ctttcggtta gatttaggat    5400
tcaaattgtc ttcttacatt tatgatcatc atccttttga tgttatttat ttcttttagt    5460
aaatagcttc aaaaactcta tagaaattac atataattaa caattgacaa ttgattctct    5520
cttattgata atttctcatg tttctctttc aattaaaatt tttgatcgaa aactaaaaga    5580
gattccggag agtactggac aaataatgac acgaaaaatc atcaaaacag aattttgcag    5640
ctctggtgta gagactagtg caaagaaaat tcaagaagag caagaaagct tgggaaatta    5700
tgagcttcaa gttcaaatta ctcctagggt atgttaaact ccttctttga ttattagcca    5760
attctttaat ttcataatat ttctagacta agagcctgtc tggatggact taaaaaaaat    5820
aacttataag ttgaaaactg tttataagtc aaaaaaaata agtaggtcta ccctaactta    5880 ttttttttg acttataagt tgttttcaac ttttaagctg ttttaaataa gctaagtcaa    5940
atagatccaa ttattttttg ggcttatttt aagcacaaaa tgactttaag ttggccagcc    6000
aaatac                                                              6006
```

<210> SEQ ID NO 20
<211> LENGTH: 920
<212> TYPE: PRT
<213> ORGANISM: Solanum americanum

<400> SEQUENCE: 20

```
Met Ala Tyr Ala Ala Leu Ser Ser Leu Met Tyr Thr Leu Gln Gln Leu
1               5                   10                  15

Leu Lys Pro Asn Gln Ser Phe Val Cys Arg Tyr Ser Thr Gln Gln Leu
            20                  25                  30

Val Gln Ser Leu Tyr Gln Asn Leu Thr Ala Leu Gln Leu Phe Leu Asp
        35                  40                  45

His Thr Thr Thr Lys Asp Ile Glu Thr Leu Lys Val Cys Asn Tyr Leu
    50                  55                  60
```

-continued

```
Ile Ser Tyr Ser Ser Tyr Ile Tyr Ser Ile Ile Asn Leu Ser Ser
 65                  70                  75                  80

Phe Asn Phe Lys Val Ile Glu Lys Arg Ile Arg Asp Val Val Tyr Lys
             85                  90                  95

Ala Glu Asp Lys Val Asp Ser Ser Leu Arg Asn Ile Ile Leu Ala Asp
            100                 105                 110

Cys Thr Glu Asn Arg Glu Gly Ala Cys Lys Phe Phe Glu Glu Glu Leu
            115                 120                 125

Leu Lys Val Glu Lys Asp Val Asp Ser Leu Ser Lys Glu Val Met Gln
130                 135                 140

Ile Glu Phe Asn Lys His Gly Cys Arg Ser Ala Glu Leu Ala Thr Thr
145                 150                 155                 160

Asp Pro Ser Ser Gly Lys Ser Thr Ile Glu Glu His Thr Ile Val
                165                 170                 175

Gly Met Glu Asp Glu Tyr Asn Thr Ile Leu Asp Arg Leu Thr Ala Gln
                180                 185                 190

Thr Asp Glu Leu Thr Val Ile Pro Ile Phe Gly Met Gly Gly Ile Gly
            195                 200                 205

Lys Thr Thr Leu Ala Arg Lys Val Tyr Asp Asp Ser Ser Ile Arg Ser
            210                 215                 220

Arg Phe Asp Arg His Ala Trp Val Thr Ser Glu Glu Phe Asn Glu
225                 230                 235                 240

Arg Arg Met Leu Leu Glu Val Val Ser Ser Ile Thr Thr Gly Ser Asn
                245                 250                 255

Gln Gly Lys Ser Asp Asp Gln Leu Met Glu Ile Val Tyr Arg Ser Leu
            260                 265                 270

Lys Gly Arg Arg Phe Leu Ile Val Ile Asp Asp Ile Trp Ser Thr Gln
            275                 280                 285

Ala Trp Asp Gln Met Gln Arg Ile Phe Pro Asn Asp Ser Lys Ser
290                 295                 300

Arg Ile Leu Leu Thr Thr Arg Leu Lys Tyr Val Ala Asp Tyr Val Ser
305                 310                 315                 320

Ser Pro Asp Phe Pro Pro His Ser Lys Ser Phe Leu Ser Leu Asp Asp
            325                 330                 335

Ser Trp Asn Leu Phe Thr Glu Lys Val Phe Asn Glu Asp Thr Cys Pro
            340                 345                 350

Pro His Leu Glu Glu Thr Gly Lys His Ile Val Gln Gln Cys Gln Gly
            355                 360                 365

Leu Pro Leu Ser Val Val Val Ala Gly Leu Val Gly Lys Met Asp
370                 375                 380

Pro Thr His Asp Asn Trp Glu Asn Val Glu Glu Asn Leu Asn Ser Phe
385                 390                 395                 400

Phe Gly Thr Val Ser Glu Arg Cys His Ser Ile Leu Ser Leu Ser Tyr
            405                 410                 415

Asn Tyr Leu Pro Gln Tyr Leu Arg Ala Cys Phe Leu Tyr Val Gly Gly
            420                 425                 430

Phe Pro Glu Asp Lys Glu Ile Asp Val Ser Lys Leu Ile Arg Leu Trp
            435                 440                 445

Ile Ala Glu Gln Phe Val Lys Ala Arg Ser Asn Lys Arg Leu Glu Val
450                 455                 460

Val Ala Glu Glu Tyr Leu Glu Glu Leu Ile Asp Arg Ser Leu Ile Leu
465                 470                 475                 480
```

Ser Gly Arg Gln Arg Ala Asn Gly Arg Met Lys Thr Cys Lys Ile His
            485                 490                 495

Asp Leu Leu Arg Gln Leu Cys Leu Ser Glu Ala His Thr Glu Asn Ile
            500                 505                 510

Ser His Ile Met Asn Arg Asn Val Pro Val Ser Ser Glu Ala Ile Asp
            515                 520                 525

Asp Gln Arg Arg Val Ile Val Pro Leu Glu Leu Glu Glu Lys Gln Phe
            530                 535                 540

Tyr Pro Thr Arg His Ser Ser Gly Ile Thr Ser Thr Thr Arg Thr Phe
545                 550                 555                 560

Ile Ser Met Glu Ile Cys Leu Arg Glu Ala Gln Thr Glu Ala Ile Tyr
                565                 570                 575

Asp Gln Arg Arg Val Ile Leu Leu Ser Lys Arg His Arg Ile Asp Thr
            580                 585                 590

Ile Arg Thr Ile Ile Pro Phe Gly Asp Thr Phe Pro Lys Glu Ile Cys
            595                 600                 605

Ser Ile Phe Ser Glu Phe Lys Leu Leu Lys Val Leu Asp Val Leu Ser
            610                 615                 620

Val Trp Tyr Asp Val Ser Cys Ile Ile Pro Gln Leu Val His Leu Arg
625                 630                 635                 640

Tyr Val Gly Ala Val Ile Leu Glu Ala Leu Ser Leu Pro Lys Leu Arg
                645                 650                 655

Asn Leu Gln Thr Ile Met Leu Thr Ser Val Glu Thr Thr Glu Leu Lys
            660                 665                 670

His Ser Leu Asp Ile Trp Arg Met Ser Glu Ile Arg His Leu Asp Ile
            675                 680                 685

Val Pro Pro Leu Tyr Ile Ser Asn Pro Leu Glu Ala Glu Gln Pro Leu
690                 695                 700

Phe Leu Asn Asn Leu His Thr Leu Phe Leu Arg Cys Ser Pro Phe Val
705                 710                 715                 720

Ala Lys Ile Ile Arg Arg Thr Pro Asn Leu Lys Lys Leu Lys Ile Leu
            725                 730                 735

Asp Lys Ser Lys His Pro Asp Trp Pro Asp Ile Leu Asp Ser Leu Asn
            740                 745                 750

Leu Leu Glu Glu Leu Glu Thr Leu Gln Ile Ser Thr Glu Glu Asn Ile
            755                 760                 765

Asp Arg Met Ile Phe Ser Gly Asp Ile Phe Pro Arg Asn Leu Lys Gln
            770                 775                 780

Leu Lys Leu Ser Tyr Thr Cys Ile Pro Trp Glu Asp Met Lys Leu Leu
785                 790                 795                 800

Ala Asn Leu Pro Asn Leu Glu Val Phe Lys Gly His Tyr Ala Phe Asp
            805                 810                 815

Gly Thr Asp Trp Lys Leu Asp Glu Asp Val Val Phe Cys Lys Leu Lys
            820                 825                 830

Cys Leu Arg Leu Tyr Glu Arg Gly Asp Leu Gln Arg Trp Glu Ala Ala
            835                 840                 845

Gly Ser Asp Asn Phe Pro Met Leu Glu Gln Leu Val Leu Tyr Gly Phe
            850                 855                 860

Glu Lys Leu Glu Glu Ile Pro Glu Ser Ile Gly Glu Ile Met Thr Leu
865                 870                 875                 880

Lys Phe Ile Lys Thr Glu Phe Cys Gly Ser Gly Val Glu Thr Ser Ala
            885                 890                 895

Lys Lys Ile Gln Glu Glu Gln Glu Ser Leu Gly Asn Tyr Glu Leu Gln

```
             900           905           910
Leu Gln Ile Thr Pro Lys Val Cys
        915           920

<210> SEQ ID NO 21
<211> LENGTH: 2760
<212> TYPE: DNA
<213> ORGANISM: Solanum americanum

<400> SEQUENCE: 21
atggcttatg ctgctctttc ttcacttatg tatacattgc aacaactctt gaaacctaat     60
caatctttcg tttgtcgata ctctacacaa caacttgttc aatctctcta tcaaaatctt    120
actgctctgc aacttttcct tgaccatact acgacaaagg atattgaaac acttaaggta    180
tgtaattatc taatctctta ctcatcttat atttattcaa taataattaa tttatcgagt    240
ttcaatttta aggttataga aagaggatc agagatgtag tatacaaagc agaagataaa     300
gttgattcaa gcctaagaaa catcattcta gcagattgca cagagaatag agaaggggct    360
tgtaaattct ttgaggaaga attgctaaaa gtggaaaaag atgttgattc tctcagcaaa    420
gaggtgatgc agatcgagtt taacaagcat ggatgcagat ctgcagaatt agcaacaact    480
gatccctcct catcaggaaa aagtacaatt gaggaacata ctattgttgg gatggaggat    540
gagtacaaca ccatacttga tcgcctcact gcccaaacag acgagttgac tgtcatacca    600
atttttggta tgggcggtat aggtaagaca actcttgcca gaaaggttta tgatgattca    660
tctattcgtt ctcgatttga tagacatgca tgggtcacta cctctgaaga attcaatgag    720
agacgaatgc ttctcgaagt tgtttcttca attactactg gaagcaatca aggaaagagc    780
gatgatcaac taatggagat tgtgtataga agtctgaagg gtaggagatt tctaattgtc    840
atagatgata tttggagtac tcaggcttgg gaccaaatgc aaagaatatt tccaaatgat    900
gacagtaaaa gccgaattct actaactaca cggctcaagt atgttgctga ttatgtcagc    960
agtcctgatt ttccacctca gtaagtctc tttctaagtc ttgatgatag ttggaatcta   1020
ttcaccgaaa aagtattcaa cgaagatacc tgtcctcctc acctagaaga aacagggaag   1080
catattgtac aacaatgtca aggattacct ctctcggttg ttgtcgttgc tggacttgtt   1140
ggaaaaatgg acccaacgca tgacaattgg gagaatgttg aggaaaatct gaactcattc   1200
tttggtactg tatccgaacg tgccactca attctttctt tgagctacaa ttacttgccc   1260
caatatttga gggcttgttt tctctatgtt ggaggtttc ctgaagataa agagattgat    1320
gtttccaagt tgattaggct atggattgct gagcaattcg taaaggcgag aagcaataaa   1380
aggctagaag tggtggcaga ggagtatctg gaagagttaa ttgatagaag tctaattttg   1440
agtggtagac aaagggctaa tggaaggatg aaaacttgca aaattcatga tcttcttcgc   1500
caactatgcc taagtgaagc tcatactgaa atattagtc atatcatgaa tagaaatgtc    1560
cccgtgtcct cagaagccat agatgatcaa cggcgagtga ttgttccatt ggaactcgaa   1620
gagaaacaat tttatcctac aaggcatagc agtggtatta caagtacaac ccgcaccttt   1680
atttcaatgg aaatatgcct aagagaagct caaaccgaag ccatatatga tcaacggcga   1740
gtgatccttc tgtctaaacg acataggatt gatacaatcc gcaccattat tccattcgga   1800
gatactttc caaaagagat tgttccatt ttttcagagt tcaagttgct taaggtgttg     1860
gatgtattat cagtctggta cgatgtctct tgtataatac ctcagcttgt acatttgaga   1920
tatgttggtg cagtaatttt ggaagctctt tcactaccca aattgagaaa tctacagacc   1980
```

-continued

| | | |
|---|---|---|
| ataatgctta caagtgttga aaccacagag ttgaagcact cactagatat ctggagaatg | 2040 |
| tcagagataa gacatttgga tattgtaccg ccactatata tatcaaatcc tcttgaagca | 2100 |
| gaacaacctt tgtttctcaa taacttgcac acgcttttt tccgttgctc tccttttgtt | 2160 |
| gcgaaaatca taagaagaac tccgaatcta aaaaagctaa agattttaga taaatctaag | 2220 |
| catcctgact ggcctgatat tcttgattct ctcaatcttc tagaggagct ggagacacta | 2280 |
| caaatatcaa cagaagaaaa cattgaccgg atgattttct ctggggatat tttccctcgt | 2340 |
| aatctcaagc aactgaaatt atcatatact tgtataccat gggaagatat gaaattgctg | 2400 |
| gctaatttac ccaatcttga ggtgttcaag ggtcattatg cattcgatgg aacagattgg | 2460 |
| aaactagatg aagatgttgt gttttgcaaa ttaaaatgtc tacgactgta tgagcgcgga | 2520 |
| gatctgcaaa ggtgggaagc agcaggtagt gataattttc ctatgcttga gcaactagta | 2580 |
| ctgtatgggt tcgaaaaact ggaagagatt ccggagagta ttggagaaat aatgacacta | 2640 |
| aaattcatta aaacagaatt tgcggctct ggtgtagaga ctagtgcaaa gaaaattcaa | 2700 |
| gaagagcaag aaagcttggg aaattatgag cttcaacttc aaattactcc taaggtatgt | 2760 |

<210> SEQ ID NO 22
<211> LENGTH: 7349
<212> TYPE: DNA
<213> ORGANISM: Solanum americanum

<400> SEQUENCE: 22

| | | |
|---|---|---|
| caagcaacgt aatttgtaag tcccatagaa ttttaacag atgcattggt tcatggttga | 60 |
| ggtgaagaac agatgtagca gttttttgtt gaagccgtta gtttcttgac agactataac | 120 |
| agaggaatgt aagttgcaac ttttgaggat agtttaggga tgattttgt tcattatgta | 180 |
| gtataaggat gtagtttaag tttgaggtat aattgaggga tgttttgct atttactcta | 240 |
| caaaattcca cacagtatta ttaattttct aaggaccgtt tggccatgtg atatgaaatc | 300 |
| atgatatgaa attatgaaat gaagttaaag ttttgtttgg acatgtaatt tggactttt | 360 |
| atgttgtatg ttttcttata acataaaaa acccacaagt tgtaaaatta ttaaacttgt | 420 |
| cccatttttt tattcaattt taccaaataa acaaaaattt acaaaatcac ataatatgct | 480 |
| aacacaaaac tattctttaa aaaatacaat atttattgat caaactttaa ttcaacaaaa | 540 |
| aataaaattc aacataagtt gtagtgtact agtctttaat ataattctcc cacatagtac | 600 |
| ggagcaatta tatgatcgag tatacaaacc aacattgcta ctttgagcta taaatggttt | 660 |
| aaaaagtaat gatatgaatc ataaatttta ttacatatga acaaatggt gagtagatat | 720 |
| ttttaataa aatataaact tatgggtcaa ttttttgtatt tgaaaaatcc caaatcatga | 780 |
| tttgaaattt tcaaatcatg attttttgaag aatttgggat tttatctcat gatatgaaat | 840 |
| catgagatga aatcagcctg aaatcgcatg tccaaatgct gatttcatct catgatttca | 900 |
| tatcgtgata tgaaatcgca tgtccaaacg cctactaagt aacttagaca cgtcttgacc | 960 |
| ttttataatt gctccatcca tcctaattta cttgtcaaat atttttctaat ttgattcccc | 1020 |
| ttttacttgt catttttttac aaatcaagaa acgacaattt ttttctttc tattataccc | 1080 |
| tcaatttatt aacattgaat taatgtcctt gaaaaatata gtaagtaaat atgtttaaaa | 1140 |
| ctctatcaaa ttaataggg taaaatggta aactcattat accaattatt ttttttttaa | 1200 |
| tagatgcgtc aaatcaaaaa ttgacaagta aaaagagacg gaaagagtat ataaatttca | 1260 |
| aagaaaattt gtattgaaag ttaattgtat tcgtccactt gacacatcat gtcttaatta | 1320 |
| ctacaagttg atttgaataa gaaatgtgag acatctctac tatcgtggtg ggaccaatgc | 1380 |

```
ttgaaaagtc gacgaaaact acaagagtgt ctttattaga aatcaggaca acttgactct    1440 ttattttca tttctttttt cttactttt cttggtcaat ccatagtttt gcatccataa      1500
accacaagtt ctgtttagat attaaataga aaattgtcca aattcattta gaaaaatgtg    1560
gacataaatc atttagacaa aacctcttat agcctaagca gagacatttc tcttccagca    1620
aacaaaagag aaatggctta tgctgctctt tcttcactta tctatacatt gcaacaactc    1680
ttcaaaccta atcaatcttt cgtttgtcaa agctgctgta cgcaacaaca tgttcaatct    1740
ctctgtcaaa atctttctgc tctgcaactt tccttgacg atactacaac aaaggatatt     1800
gaaactctta aggtatgtaa ttatctaatc tcttactcat cttatattta ttcaataata    1860
attaatttat cgagtttcaa ttttaaggtt atagaaaaga ggatcagaga tgtagtatac    1920
aaagcagaag ataagttga ttcaagccta agaagcatca ttctagctga ttgcacagag     1980
aataaagaag gggcttgtaa attctttgag gaagaattgc taaaagtgga aaaagatgtt    2040
gattctctca gcaaagaggt gatgcagatc aatgttaaca agcatggaag cagatctgca    2100
gaactaacaa caattcctcc ctctccagaa aaaagtacaa atgaggaaca tactattgtt    2160
gggatggagg atgagtacaa caccatactt gatcgcctca ctgcccaaac agacgagttg    2220
actgtcatac caattttggg tatgggcggt ataggtaaga caactcttgc cagaaaggtt    2280
tatgatgatt catctattcg ttctcgattt gatagacatg tatgggtcac tacctctgaa    2340
gaattcaatg agagacgaat gcttctcgaa gttgtttctt caattactac tggaagcaat    2400
caagaaaaga gcgatgatca actaatggag attgtgtata gaggtcttaa gggtaggaga    2460
tttctaattg tcatagatga tatttggagt actgaggctt gggaccaaat gcaaagaata    2520
tttccaaatg atgacaataa aagccgaatt ctactaacta cacggctcaa gtatgttgct    2580
gattatgtca gcagtcctga ttttccacct catagtaagt ctttttctaag tcttgatgat    2640 agttggaatc tattcaccga aaagtattc aacaaagata cctgtcctcc tcacctagaa    2700
gaaacaggga agcatattgt acaacaatgt cgaggattac ctctctcggt tgttgtagtt    2760
gctggacttg ttggaaaaat ggacccaacg catgacaatt gggagaacgt tgaggaaaat    2820
ctgaactcat tcattggtac tgtatccgaa cggtgccaat caattctttc tttaagctac    2880
aattacttgc cccaatattt gagggcttgt tttctctatg ttggatgttt tcctgaagat    2940
aaagagattg atgtttccaa gttgattagg ctatggattg ctgagcaatt cgtaaaggcg    3000
agaagcaata aaaggttaga agtggtagca gaggagtatc tagaagagtt aattgataga    3060
agcctaattt tgagtggtag acaaagggct aatggaagga tgaaaacttg caaaattcat    3120
gatcttcttc gccaactatg cctaagtgaa gctcatactg aaaatattag tcatatcatg    3180
aatagaaatg tccccgtgtc ctcagaagcc atagatgatc aacggcgagt gattgttcca    3240
ttggaacttg aagaggaacc agtttatcct acaaggaata gcagtggtat tacaagtaca    3300
acccgcacct ttatttcaat ggaaatatgc ctaagagaag ctcagaccga agccatatat    3360
gatcaacggc gagtgatcct tctgtctaaa cgacatagga ttgatacaat ccgcaccatt    3420
attccattca aagatacttt tccgaaagag atttgttcca ttgtttcaca gttgaagttg    3480
cttaaggtgt tggatgtatt atcagtctgg tacgatgtct cttgtataat acctcagctt    3540
gtacatttga gatatgttgg tgcagtaatt ttgaaagctc tttcactacc caaattgaga    3600
aatctacaga cctaaattct tacaagtgtt gaaaccacag agttgaagca ctcactagat    3660
atctggagaa tgtcagagat aagacatttg gatattgtac cgccactata tatatcaaat    3720
```

```
cctcttgaag cagaacaacc tttgtttctc aataacttgc acacactttt tctccgttgc    3780
tctccttttg ttgcgaaaat cataagaaga actcccaatc taaaaaagct aaagatttta    3840
gataaatcta agcatcctga ctggcctgat attcttgatt ctctcaatct tctagaggag    3900
ctggagacac tacaaatatc aacagaagaa aacattgacc cgatgatttt ctctggggat    3960
attttccctc gtaatctcaa gcaactgaaa ttatcatata cttgtatacc atgggaagat    4020
atgaaattgc tggctaattt acccaatctt gaggtgttca aggtcatta tgcattcaat     4080
ggaacagatt ggaaactaga tgaagatgtt gtgttttgca aattaaaatc tctacgactg    4140
tatgagcgtg gagatttgca aaggtgggaa gctgctggta gtgataattt tccaatgctt    4200
gagcaactat tattgtatgg gttcaaaaaa ctggaagaga ttccggagag tattggagaa    4260
ataatgacac taaaatttat caaaacagaa ttttgcggct ctggtgtaaa gacaagtgca    4320
aagaaaattc aagaagagca agaaagcctg ggaaattatg agcttcaagt tcaaattact    4380
cctaaggtat gttgaaactc aatctttgat taatactctc cactcggtta gatttaggat    4440
tcaaattgtc tacttacatt tatgatcatc acccttgcgg tcttcttatt tcttttagta    4500
aatagcttca aaaactctac agaaattaca cataattaac aattgacaat tgattctctc    4560
ttattgataa tttgtaattt tctctttcag ttaagatttt tgatcgaaaa tttagacgaa    4620
ataagcatgt tgcccccgaa tgaagtagcc gaaaaaatca aggtttgtc tatttaattc     4680
cttttttatt tcattgaaag aggttcagat atattaaaca actttttaac ctttctattt    4740
gattttttat cgcttagata gatacaacat ttatttaac atcaattgtt attttgattc     4800
aattatgttc ttttaatata tagttttccac tcggttcttc aattcttttt tcaattatag   4860
ttttatttt ttaattgcac atggttgatc gatttaattt gtgagattca cttttctttc     4920
ggttttacga gttcttcgcg attaatgtta ttcagattta ggagtattat atttcaactt    4980
tcgattagat ttaggattca aattgtcttc tttcatttat gatcatcatc ctttcgatct    5040
tctttatttc ttttagtaaa tagcttcaaa aactctatag aaattacata taattaacaa    5100
ttgagaattg attctctcgt aatttctcat gttctctttc agttaaaatt tttgatcaaa    5160
aactaaaaga gattccggag agcactggac aaataatgac acgaaaaatc atcaaaacag    5220
aattttgcgg ctctggtgta gagactagtg caaagaagat tcaagaagag caagaaagct    5280
tgggaaattg tgagcttcat caagttcaaa ttactcctaa ggtatattaa aactccatct    5340
ttgattatta gccaattctt taatttcata ttatttctag actaaattaa aatattaaaa    5400
gatataaaga atttaattaa tttaattatt cctttaaaat ccaaacatga tgaatttgag    5460
taaattaaat gaatatagtt cagattcatt taactaatag gccatttagt tttaatatgg    5520
caacgtttta ggcttttaac attctctttg aatgtaggta taatgcatta agtgcagaaa    5580
tttaatcttt atttaaaaaa tgaaaacatc tcataataac tttggtcttt ttactccaaa    5640
catcttgtaa taaagtgagt gtcttctact tctcctaaca tctcataata aatttctact    5700
attcctaaca tctcattata aataagtctt ttctactatt taattttgtt aaaatattca    5760
cattttttgt gtcttatata ttctccaccc ccatcttttt tttgtttact ttcttaatat    5820
tcatatgctt gaatcgaaac aaggttctat gaattctaac gcgcttggat tgatcatgat    5880
gcaattcaat atatgcatca atttagtttt tattttttcat gcataatagt tagtttcaca    5940
agataaaatat ttttatttca atatgtattt atcctttaat taagtactta tatatgtcac   6000
taaagtagca tcaaatttgc aagaatttct aatctcaatt tatgagtttg ttatattttt    6060
tttaattgta ttgctttgat ttttatttta taaccaaaga gaaagtctaa taatatacgt    6120
```

```
gtcattattt attttttaag tattttggga taaacacgaa cacacttaca agttacatta      6180
agagtggaaa gaatcaagtc aaaagtttgt ttaccatttt taacgttgaa aaaagcaagc      6240
cttcatttaa atagttatta tatttgctta cattagaaaa tatattaaaa ttcattagct      6300
ccttaaaatt caatgaatcc aaataattaa acgttattg ccataatttt attttatct       6360 ctttaacttg ctaaatggct ccttcactac atgctttgag aacagaagc gtttgctgag       6420 gaagcaggac ggcactgtgt aacaataatt tgtatggctt cagtgatgag aatattttgt      6480
gtgccatgca gcatagcagt gttcatctaa ctagaaattt tataagaaaa gaaaaatcgt      6540
ccttaatcgt tatttcactc attaaattgt tttttctttc attttccatg gtaatttgaa      6600
tttcgaagtg tggacatgga ctgtgtttgg agcataggtt catatttgtg tagtttaaaa      6660
ttgtatgatt attattttag ttctcttgtc aacgtcctta tcacctttgc agatagttac      6720
tattgagaat gtatttatat tattagttag ttagttacta gtcatgatga ttgtgtgatg      6780
atcagcttag ttagttagat tagtgaattg gttacaactg ttagttacag ttagttaggc      6840
taagtcgctt agtttgttag tgttataaat acacttgtac aaattcattt tcattttgag      6900
aagttcaatt caatgaaaca gttactctca tcttcctctt ctctcaatat tcacttctcc      6960
ttctttgcaa gtttctgcca ttgaagctcc aaagcttggg agctgatttc aagttcttgt      7020
tcttgacatg gtaattcacc acaattacgc ctctggcaat gatgcgacga tatggttgtt      7080
tgcaacaaat tttaaataaa tggaaaatag atctgttcct cccttgattc ttctctccta      7140
aattttctcc gtgattcgag ggccgttagt ggcgtatttc tcgaattagg atgatttaaa      7200
cttgatcttc attgtgattc gagggccgtt agtggcgtat ttctcgaatc catgaaagaa      7260
tttgtggatc ttcttgaaat atttgattat caagaagaca agaaaaattt aacatatttt      7320
gatctctttc tgagatgtct tttcaaggg                                        7349

<210> SEQ ID NO 23
<211> LENGTH: 3039
<212> TYPE: DNA
<213> ORGANISM: Solanum americanum

<400> SEQUENCE: 23
atggcttatg ctgctctttc ttcacttatc tatacattgc aacaactctt caaacctaat        60
caatctttcg tttgtcaaag ctgctgtacg caacaacatg ttcaatctct ctgtcaaaat       120
ctttctgctc tgcaactttt ccttgacgat actacaacaa aggatattga aactcttaag       180
gtatgtaatt atctaatctc ttactcatct tatatttatt caataataat taatttatcg       240
agtttcaatt ttaaggttat agaaagagg atcagagatg tagtatacaa agcagaagat       300
aaagttgatt caagcctaag aagcatcatt ctagctgatt gcacagagaa taagaagg        360 gcttgtaaat tctttgagga agaattgcta aaagtggaaa aagatgttga ttctctcagc       420
aaagaggtga tgcagatcaa tgttaacaag catggaagca gatctgcaga actaacaaca       480
attcctccct ctccagaaaa agtacaaat gaggaacata ctattgttgg gatggaggat       540
gagtacaaca ccatacttga tcgcctcact gcccaaacag acgagttgac tgtcatacca       600 attttggta tgggcggtat aggtaagaca actcttgcca gaaaggttta tgatgattca       660
tctattcgtt ctcgatttga tagacatgta tgggtcacta cctctgaaga attcaatgag       720
agacgaatgc ttctcgaagt tgtttcttca attactactg gaagcaatca agaaaagagc       780
gatgatcaac taatggagat tgtgtataga ggtcttaagg gtaggagatt tctaattgtc       840
```

```
atagatgata tttggagtac tgaggcttgg gaccaaatgc aaagaatatt tccaaatgat    900
gacaataaaa gccgaattct actaactaca cggctcaagt atgttgctga ttatgtcagc    960
agtcctgatt ttccacctca tagtaagtct tttctaagtc ttgatgatag ttggaatcta   1020
ttcaccgaaa aagtattcaa caaagatacc tgtcctcctc acctagaaga aacagggaag   1080
catattgtac aacaatgtcg aggattacct ctctcggttg ttgtagttgc tggacttgtt   1140
ggaaaaatgg acccaacgca tgacaattgg gagaacgttg aggaaaatct gaactcattc   1200
attggtactg tatccgaacg gtgccaatca attctttctt taagctacaa ttacttgccc   1260
caatatttga gggcttgttt tctctatgtt ggatgttttc ctgaagataa agagattgat   1320
gtttccaagt tgattaggct atggattgct gagcaattcg taaaggcgag aagcaataaa   1380
aggttagaag tggtagcaga ggagtatcta aagagttaa ttgatagaag cctaattttg    1440
agtggtagac aaagggctaa tggaaggatg aaaacttgca aaattcatga tcttcttcgc   1500
caactatgcc taagtgaagc tcatactgaa aatattagtc atatcatgaa tagaaatgtc   1560
cccgtgtcct cagaagccat agatgatcaa cggcgagtga ttgttccatt ggaacttgaa   1620
gaggaaccag tttatcctac aaggaatagc agtggtatta caagtacaac ccgcaccttt   1680
atttcaatgg aaatatgcct aagagaagct cagaccgaag ccatatatga tcaacggcga   1740
gtgatccttc tgtctaaacg acataggatt gatacaatcc gcaccattat tccattcaaa   1800
gatactttc cgaaagagat ttgttccatt gtttcacagt tgaagttgct taaggtgttg    1860
gatgtattat cagtctggta cgatgtctct tgtataatac ctcagcttgt acatttgaga   1920
tatgttggtg cagtaatttt gaaagctctt tcactaccca aattgagaaa tctacagacc   1980
ataattctta caagtgttga aaccacagag ttgaagcact cactagatat ctggagaatg   2040
tcagagataa gacatttgga tattgtaccg ccactatata tatcaaatcc tcttgaagca   2100
gaacaacctt tgtttctcaa taacttgcac acacttttc tccgttgctc tccttttgtt    2160
gcgaaaatca taagaagaac tcccaatcta aaaaagctaa agattttaga taaatctaag   2220
catcctgact ggcctgatat tcttgattct ctcaatcttc tagaggagct ggagacacta   2280
caaatatcaa cagaagaaaa cattgacccg atgattttct ctggggatat tttccctcgt   2340
aatctcaagc aactgaaatt atcatatact tgtataccat gggaagatat gaaattgctg   2400
gctaatttac ccaatcttga ggtgttcaag ggtcattatg cattcaatgg aacagattgg   2460
aaactagatg aagatgttgt gttttgcaaa ttaaaatctc tacgactgta tgagcgtgga   2520
gatttgcaaa ggtgggaagc tgctggtagt gataattttc caatgcttga gcaactatta   2580
ttgtatgggt tcaaaaaact ggaagagatt ccggagagta ttggagaaat aatgacacta   2640
aaatttatca aaacagaatt tgcggctctt ggtgtaaaga caagtgcaaa gaaaattcaa   2700
gaagagcaag aaagcctggg aaattatgag cttcaagttc aaattactcc taagttaaga   2760
tttttgatcg aaaatttaga cgaaataagc atgttgcccc cgaatgaagt agccgaaaaa   2820
atcaaagtta aaatttttga tcaaaaacta aaagagattc cggagagcac tggacaaata   2880
atgacacgaa aaatcatcaa aacagaattt tgcggctctg gtgtagagac tagtgcaaag   2940
aagattcaag aagagcaaga aagcttggga aattgtgagc ttcatcaagt tcaaattact   3000
cctaagaagc gtttgctgag gaagcaggac ggcactgtg                          3039
```

<210> SEQ ID NO 24
<211> LENGTH: 1013
<212> TYPE: PRT
<213> ORGANISM: Solanum americanum

<400> SEQUENCE: 24

```
Met Ala Tyr Ala Ala Leu Ser Ser Leu Ile Tyr Thr Leu Gln Gln Leu
1               5                   10                  15

Phe Lys Pro Asn Gln Ser Phe Val Cys Gln Ser Cys Cys Thr Gln Gln
                20                  25                  30

His Val Gln Ser Leu Cys Gln Asn Leu Ser Ala Leu Gln Leu Phe Leu
            35                  40                  45

Asp Asp Thr Thr Thr Lys Asp Ile Glu Thr Leu Lys Val Cys Asn Tyr
    50                  55                  60

Leu Ile Ser Tyr Ser Ser Tyr Ile Tyr Ser Ile Ile Asn Leu Ser
65                  70                  75                  80

Ser Phe Asn Phe Lys Val Ile Glu Lys Arg Ile Arg Asp Val Val Tyr
                85                  90                  95

Lys Ala Glu Asp Lys Val Asp Ser Ser Leu Arg Ser Ile Ile Leu Ala
                100                 105                 110

Asp Cys Thr Glu Asn Lys Glu Gly Ala Cys Lys Phe Phe Glu Glu Glu
            115                 120                 125

Leu Leu Lys Val Glu Lys Asp Val Asp Ser Leu Ser Lys Glu Val Met
130                 135                 140

Gln Ile Asn Val Asn Lys His Gly Ser Arg Ser Ala Glu Leu Thr Thr
145                 150                 155                 160

Ile Pro Pro Ser Pro Glu Lys Ser Thr Asn Glu His Thr Ile Val
                165                 170                 175

Gly Met Glu Asp Glu Tyr Asn Thr Ile Leu Asp Arg Leu Thr Ala Gln
            180                 185                 190

Thr Asp Glu Leu Thr Val Ile Pro Ile Phe Gly Met Gly Gly Ile Gly
        195                 200                 205

Lys Thr Thr Leu Ala Arg Lys Val Tyr Asp Asp Ser Ser Ile Arg Ser
    210                 215                 220

Arg Phe Asp Arg His Val Trp Val Thr Thr Ser Glu Glu Phe Asn Glu
225                 230                 235                 240

Arg Arg Met Leu Leu Glu Val Val Ser Ser Ile Thr Thr Gly Ser Asn
                245                 250                 255

Gln Glu Lys Ser Asp Asp Gln Leu Met Glu Ile Val Tyr Arg Gly Leu
                260                 265                 270

Lys Gly Arg Arg Phe Leu Ile Val Ile Asp Asp Ile Trp Ser Thr Glu
                275                 280                 285

Ala Trp Asp Gln Met Gln Arg Ile Phe Pro Asn Asp Asp Asn Lys Ser
            290                 295                 300

Arg Ile Leu Leu Thr Thr Arg Leu Lys Tyr Val Ala Asp Tyr Val Ser
305                 310                 315                 320

Ser Pro Asp Phe Pro Pro His Ser Lys Ser Phe Leu Ser Leu Asp Asp
                325                 330                 335

Ser Trp Asn Leu Phe Thr Glu Lys Val Phe Asn Lys Asp Thr Cys Pro
            340                 345                 350

Pro His Leu Glu Glu Thr Gly Lys His Ile Val Gln Gln Cys Arg Gly
        355                 360                 365

Leu Pro Leu Ser Val Val Val Ala Gly Leu Val Gly Lys Met Asp
    370                 375                 380

Pro Thr His Asp Asn Trp Glu Asn Val Glu Glu Asn Leu Asn Ser Phe
385                 390                 395                 400

Ile Gly Thr Val Ser Glu Arg Cys Gln Ser Ile Leu Ser Leu Ser Tyr
```

```
            405                 410                 415
Asn Tyr Leu Pro Gln Tyr Leu Arg Ala Cys Phe Leu Tyr Val Gly Cys
            420                 425                 430

Phe Pro Glu Asp Lys Glu Ile Asp Val Ser Lys Leu Ile Arg Leu Trp
            435                 440                 445

Ile Ala Glu Gln Phe Val Lys Ala Arg Ser Asn Lys Arg Leu Glu Val
            450                 455                 460

Val Ala Glu Glu Tyr Leu Glu Glu Leu Ile Asp Arg Ser Leu Ile Leu
465                 470                 475                 480

Ser Gly Arg Gln Arg Ala Asn Gly Arg Met Lys Thr Cys Lys Ile His
            485                 490                 495

Asp Leu Leu Arg Gln Leu Cys Leu Ser Glu Ala His Thr Glu Asn Ile
            500                 505                 510

Ser His Ile Met Asn Arg Asn Val Pro Val Ser Ser Glu Ala Ile Asp
            515                 520                 525

Asp Gln Arg Arg Val Ile Val Pro Leu Glu Leu Glu Glu Glu Pro Val
            530                 535                 540

Tyr Pro Thr Arg Asn Ser Ser Gly Ile Thr Ser Thr Thr Arg Thr Phe
545                 550                 555                 560

Ile Ser Met Glu Ile Cys Leu Arg Glu Ala Gln Thr Glu Ala Ile Tyr
                565                 570                 575

Asp Gln Arg Arg Val Ile Leu Leu Ser Lys Arg His Arg Ile Asp Thr
            580                 585                 590

Ile Arg Thr Ile Ile Pro Phe Lys Asp Thr Phe Pro Lys Glu Ile Cys
            595                 600                 605

Ser Ile Val Ser Gln Leu Lys Leu Leu Lys Val Leu Asp Val Leu Ser
            610                 615                 620

Val Trp Tyr Asp Val Ser Cys Ile Ile Pro Gln Leu Val His Leu Arg
625                 630                 635                 640

Tyr Val Gly Ala Val Ile Leu Lys Ala Leu Ser Leu Pro Lys Leu Arg
                645                 650                 655

Asn Leu Gln Thr Ile Ile Leu Thr Ser Val Glu Thr Thr Glu Leu Lys
            660                 665                 670

His Ser Leu Asp Ile Trp Arg Met Ser Glu Ile Arg His Leu Asp Ile
            675                 680                 685

Val Pro Pro Leu Tyr Ile Ser Asn Pro Leu Glu Ala Glu Gln Pro Leu
            690                 695                 700

Phe Leu Asn Asn Leu His Thr Leu Phe Leu Arg Cys Ser Pro Phe Val
705                 710                 715                 720

Ala Lys Ile Ile Arg Arg Thr Pro Asn Leu Lys Lys Leu Lys Ile Leu
            725                 730                 735

Asp Lys Ser Lys His Pro Asp Trp Asp Ile Leu Asp Ser Leu Asn
            740                 745                 750

Leu Leu Glu Glu Leu Glu Thr Leu Gln Ile Ser Thr Glu Glu Asn Ile
            755                 760                 765

Asp Pro Met Ile Phe Ser Gly Asp Ile Phe Pro Arg Asn Leu Lys Gln
            770                 775                 780

Leu Lys Leu Ser Tyr Thr Cys Ile Pro Trp Glu Asp Met Lys Leu Leu
785                 790                 795                 800

Ala Asn Leu Pro Asn Leu Glu Val Phe Lys Gly His Tyr Ala Phe Asn
                805                 810                 815

Gly Thr Asp Trp Lys Leu Asp Glu Asp Val Val Phe Cys Lys Leu Lys
            820                 825                 830
```

```
Ser Leu Arg Leu Tyr Glu Arg Gly Asp Leu Gln Arg Trp Glu Ala Ala
    835                 840                 845

Gly Ser Asp Asn Phe Pro Met Leu Glu Gln Leu Leu Leu Tyr Gly Phe
    850                 855                 860

Lys Lys Leu Glu Glu Ile Pro Glu Ser Ile Gly Glu Ile Met Thr Leu
865                 870                 875                 880

Lys Phe Ile Lys Thr Glu Phe Cys Gly Ser Gly Val Lys Thr Ser Ala
                885                 890                 895

Lys Lys Ile Gln Glu Glu Gln Glu Ser Leu Gly Asn Tyr Glu Leu Gln
            900                 905                 910

Val Gln Ile Thr Pro Lys Leu Arg Phe Leu Ile Glu Asn Leu Asp Glu
            915                 920                 925

Ile Ser Met Leu Pro Pro Asn Glu Val Ala Gly Lys Ile Lys Val Lys
    930                 935                 940

Ile Phe Asp Gln Lys Leu Lys Glu Ile Pro Glu Ser Thr Gly Gln Ile
945                 950                 955                 960

Met Thr Arg Lys Ile Ile Lys Thr Glu Phe Cys Gly Ser Gly Val Glu
                965                 970                 975

Thr Ser Ala Lys Lys Ile Gln Glu Gln Glu Ser Leu Gly Asn Cys
            980                 985                 990

Glu Leu His Gln Val Gln Ile Thr Pro Lys Lys Arg Leu Leu Arg Lys
    995                 1000                1005

Gln Asp Gly Thr Val
    1010

<210> SEQ ID NO 25
<211> LENGTH: 3012
<212> TYPE: DNA
<213> ORGANISM: Solanum americanum

<400> SEQUENCE: 25
atggcttatg ctgctctttc ttcacttatc tatacattgc aacaactctt caaacctaat      60
caatctttcg tttgtcaaag ctgctgtacg caacaacatg ttcaatctct ctgtcaaaat     120
ctttctgctc tgcaactttt ccttgacgat actacaacaa aggatattga aactcttaag     180
gtatgtaatt atctaatctc ttactcatct tatatttatt caataataat taatttatcg     240
agtttcaatt ttaaggttat agaaaagagg atcagagatg tagtatacaa agcagaagat     300
aaagttgatt caagcctaag aagcatcatt ctagctgatt gcacagagaa taaagaaggg     360
gcttgtaaat tctttgagga agaattgcta aaagtggaaa aagatgttga ttctctcagc     420
aaagaggtga tgcagatcaa tgttaacaag catggaagca atctgcaga actaacaaca     480
attcctccct ctccagaaaa aagtacaaat gaggaacata ctattgttgg gatggaggat     540
gagtacaaca ccatacttga tcgcctcact gcccaaacag acgagttgac tgtcatacca     600
attttggta tgggcggtat aggtaagaca actcttgcca gaaaggttta tgatgattca     660
tctattcgtt ctcgatttga tagacatgta tgggtcacta cctctgaaga attcaatgag     720
agacgaatgc ttctcgaagt tgtttcttca attactactg gaagcaatca agaaagagc     780
gatgatcaac taatggagat tgtgtataga ggtcttaagg gtaggagatt tctaattgtc     840
atagatgata tttggagtac tgaggcttgg gaccaaatgc aaagaatatt ccaaatgat     900
gacaataaaa gccgaattct actaactaca cggctcaagt atgttgctga ttatgtcagc     960
agtcctgatt ttccacctca tagtaagtct tttctaagtc ttgatgatag ttggaatcta    1020
```

| | |
|---|---:|
| ttcaccgaaa aagtattcaa caaagatacc tgtcctcctc acctagaaga aacagggaag | 1080 |
| catattgtac aacaatgtcg aggattacct ctctcggttg ttgtagttgc tggacttgtt | 1140 |
| ggaaaaatgg acccaacgca tgacaattgg gagaacgttg aggaaaatct gaactcattc | 1200 |
| attggtactg tatccgaacg gtgccaatca attctttctt taagctacaa ttacttgccc | 1260 |
| caatatttga gggcttgttt tctctatgtt ggatgttttc ctgaagataa agagattgat | 1320 |
| gtttccaagt tgattaggct atggattgct gagcaattcg taaaggcgag aagcaataaa | 1380 |
| aggttagaag tggtagcaga ggagtatcta gaagagttaa ttgatagaag cctaattttg | 1440 |
| agtggtagac aaagggctaa tggaaggatg aaaacttgca aaattcatga tcttcttcgc | 1500 |
| caactatgcc taagtgaagc tcatactgaa aatattagtc atatcatgaa tagaaatgtc | 1560 |
| cccgtgtcct cagaagccat agatgatcaa cggcgagtga ttgttccatt ggaacttgaa | 1620 |
| gaggaaccag tttatcctac aaggaatagc agtggtatta caagtacaac ccgcaccttt | 1680 |
| atttcaatgg aaatatgcct aagagaagct cagaccgaag ccatatatga tcaacggcga | 1740 |
| gtgatccttc tgtctaaacg acataggatt gatacaatcc gcaccattat tccattcaaa | 1800 |
| gatactttc cgaaagagat tgttccatt gtttcacagt tgaagttgct taaggtgttg | 1860 |
| gatgtattat cagtctggta cgatgtctct tgtataatac ctcagcttgt acatttgaga | 1920 |
| tatgttggtg cagtaatttt gaaagctctt tcactaccca aattgagaaa tctacagacc | 1980 |
| ataattctta caagtgttga aaccacagag ttgaagcact cactagatat ctggagaatg | 2040 |
| tcagagataa gacatttgga tattgtaccg ccactatata tatcaaatcc tcttgaagca | 2100 |
| gaacaacctt tgtttctcaa taacttgcac acactttttc tccgttgctc tccttttgtt | 2160 |
| gcgaaaatca taagaagaac tcccaatcta aaaaagctaa agattttaga taaatctaag | 2220 |
| catcctgact ggcctgatat tcttgattct ctcaatcttc tagaggagct ggagacacta | 2280 |
| caaatatcaa cagaagaaaa cattgacccg atgatttct ctggggatat tttccctcgt | 2340 |
| aatctcaagc aactgaaatt atcatatact tgtataccat gggaagatat gaaattgctg | 2400 |
| gctaatttac ccaatcttga ggtgttcaag ggtcattatg cattcaatgg aacagattgg | 2460 |
| aaactagatg aagatgttgt gttttgcaaa ttaaaatctc tacgactgta tgagcgtgga | 2520 |
| gatttgcaaa ggtgggaagc tgctggtagt gataattttc caatgcttga gcaactatta | 2580 |
| ttgtatgggt tcaaaaaact ggaagagatt ccggagagta ttggagaaat aatgacacta | 2640 |
| aaatttatca aaacagaatt ttgcggctct ggtgtaaaga caagtgcaaa gaaaattcaa | 2700 |
| gaagagcaag aaagcctggg aaattatgag cttcaagttc aaattactcc taagttaaga | 2760 |
| tttttgatcg aaaatttaga cgaaataagc atgttgcccc gaatgaagt agccgaaaaa | 2820 |
| atcaaagtta aaattttga tcaaaaacta aaagagattc cggagagcac tggacaaata | 2880 |
| atgacacgaa aaatcatcaa aacagaattt tgcggctctg gtgtagagac tagtgcaaag | 2940 |
| aagattcaag aagagcaaga aagcttggga aattgtgagc ttcatcaagt tcaaattact | 3000 |
| cctaaggtat at | 3012 |

<210> SEQ ID NO 26
<211> LENGTH: 2775
<212> TYPE: DNA
<213> ORGANISM: Solanum americanum

<400> SEQUENCE: 26

| | |
|---|---:|
| atggcttatg ctgctctttc ttcacttatc tatacattgc aacaactctt caaacctaat | 60 |
| caatctttcg tttgtcaaag ctgctgtacg caacaacatg ttcaatctct ctgtcaaaat | 120 |

```
ctttctgctc tgcaactttt ccttgacgat actacaacaa aggatattga aactcttaag      180
gtatgtaatt atctaatctc ttactcatct tatatttatt caataataat taatttatcg      240
agtttcaatt ttaaggttat agaaaagagg atcagagatg tagtatacaa agcagaagat      300
aaagttgatt caagcctaag aagcatcatt ctagctgatt gcacagagaa taagaaggg       360 gcttgtaaat tctttgagga agaattgcta aaagtggaaa aagatgttga ttctctcagc      420
aaagaggtga tgcagatcaa tgttaacaag catggaagca gatctgcaga actaacaaca      480
attcctccct ctccagaaaa aagtacaaat gaggaacata ctattgttgg gatggaggat      540
gagtacaaca ccatacttga tcgcctcact gcccaaacag acgagttgac tgtcatacca      600
atttttggta tgggcggtat aggtaagaca actcttgcca gaaaggttta tgatgattca      660
tctattcgtt ctcgatttga tagacatgta tgggtcacta cctctgaaga attcaatgag      720
agacgaatgc ttctcgaagt tgtttcttca attactactg gaagcaatca agaaaagagc      780
gatgatcaac taatggagat tgtgtataga ggtcttaagg gtaggagatt tctaattgtc      840
atagatgata tttggagtac tgaggcttgg gaccaaatgc aaagaatatt tccaaatgat      900
gacaataaaa gccgaattct actaactaca cggctcaagt atgttgctga ttatgtcagc      960
agtcctgatt ttccacctca tagtaagtct tttctaagtc ttgatgatag ttggaatcta     1020
ttcaccgaaa aagtattcaa caaagatacc tgtcctcctc acctagaaga aacagggaag     1080
catattgtac aacaatgtcg aggattacct ctctcggttg ttgtagttgc tggacttgtt     1140
ggaaaaatgg acccaacgca tgacaattgg gagaacgttg aggaaaatct gaactcattc     1200
attggtactg tatccgaacg gtgccaatca attctttctt taagctacaa ttacttgccc     1260
caatatttga gggcttgttt tctctatgtt ggatgttttc ctgaagataa agagattgat     1320
gtttccaagt tgattaggct atggattgct gagcaattcg taaaggcgag aagcaataaa     1380
aggttagaag tggtagcaga ggagtatcta gaagagttaa ttgatagaag cctaattttg     1440
agtggtagac aaagggctaa tggaaggatg aaaacttgca aaattcatga tcttcttcgc     1500
caactatgcc taagtgaagc tcatactgaa aatattagtc atatcatgaa tagaaatgtc     1560
cccgtgtcct cagaagccat agatgatcaa cggcgagtga ttgttccatt ggaacttgaa     1620
gaggaaccag tttatcctac aaggaatagc agtggtatta caagtacaac ccgcaccttt     1680
atttcaatgg aaatatgcct aagagaagct cagaccgaag ccatatatga tcaacggcga     1740
gtgatccttc tgtctaaacg acataggatt gatacaatcc gcaccattat tccattcaaa     1800 gatactttc cgaaagagat ttgttccatt gtttcacagt tgaagttgct taaggtgttg     1860
gatgtattat cagtctggta cgatgtctct tgtataatac ctcagcttgt acatttgaga     1920
tatgttggtg cagtaatttt gaaagctctt tcactaccca aattgagaaa tctacagacc     1980
ataattctta caagtgttga accacagag ttgaagcact cactagatat ctggagaatg     2040
tcagagataa gacatttgga tattgtaccg ccactatata tatcaaatcc tcttgaagca     2100 gaacaaccttt tgtttctcaa taacttgcac acacttttc tccgttgctc tcctttttgtt     2160 gcgaaaatca taagaagaac tcccaatcta aaaaagctaa agattttaga taaatctaag     2220
catcctgact ggcctgatat tcttgattct ctcaatcttc tagaggagct ggagacacta     2280
caaatatcaa cagaagaaaa cattgacccg atgattttct ctggggatat tttccctcgt     2340
aatctcaagc aactgaaatt atcatatact tgtataccat gggaagatat gaaattgctg     2400
gctaatttac ccaatcttga ggtgttcaag ggtcattatg cattcaatgg aacagattgg     2460
```

```
aaactagatg aagatgttgt gttttgcaaa ttaaaatctc tacgactgta tgagcgtgga    2520
gatttgcaaa ggtgggaagc tgctggtagt gataattttc caatgcttga gcaactatta    2580
ttgtatgggt tcaaaaaact ggaagagatt ccggagagta ttggagaaat aatgacacta    2640
aaatttatca aaacagaatt ttgcggctct ggtgtaaaga caagtgcaaa gaaaattcaa    2700
gaagagcaag aaagcctggg aaattatgag cttcaagttc aaattactcc taagttaaaa    2760 ttttttgatca aaaac                                                    2775

<210> SEQ ID NO 27
<211> LENGTH: 2601
<212> TYPE: DNA
<213> ORGANISM: Solanum americanum

<400> SEQUENCE: 27
atggcttatg ctgctctttc ttcacttatc tatacattgc aacaactctt caaacctaat      60
caatctttcg tttgtcaaag ctgctgtacg caacaacatg ttcaatctct ctgtcaaaat     120
ctttctgctc tgcaactttt ccttgacgat actacaacaa aggatattga aactcttaag     180
gtatgtaatt atctaatctc ttactcatct tatatttatt caataataat taatttatcg     240
agtttcaatt ttaaggttat agaaaagagg atcagagatg tagtatacaa agcagaagat     300
aaagttgatt caagcctaag aagcatcatt ctagctgatt gcacagagaa taaagaaggg     360
gcttgtaaat tctttgagga gaattgctaa aagtggaaa aagatgttga ttctctcagc     420
aaagaggtga tgcagatcaa tgttaacaag catggaagca gatctgcaga actaacaaca     480
attcctccct ctccagaaaa aagtacaaat gaggaacata ctattgttgg gatggaggat     540
gagtacaaca ccatacttga tcgcctcact gcccaaacag acgagttgac tgtcatacca     600
atttttggta tgggcggtat aggtaagaca actcttgcca gaaaggttta tgatgattca     660
tctattcgtt ctcgatttga tagacatgta tgggtcacta cctctgaaga attcaatgag     720
agacgaatgc ttctcgaagt tgtttcttca attactactg gaagcaatca agaaaagagc     780
gatgatcaac taatggagat tgtgtataga ggtcttaagg gtaggagatt tctaattgtc     840
atagatgata tttggagtac tgaggcttgg gaccaaatgc aaagaatatt tccaaatgat     900
gacaataaaa gccgaattct actaactaca cggctcaagt atgttgctga ttatgtcagc     960
agtcctgatt tccacctca tagtaagtct tttctaagtc ttgatgatag ttggaatcta    1020
ttcaccgaaa aagtattcaa caaagatacc tgtcctcctc acctagaaga aacagggaag    1080
catattgtac aacaatgtcg aggattacct ctctcggttg ttgtagttgc tggacttgtt    1140
ggaaaaatgg acccaacgca tgacaattgg gagaacgttg aggaaaatct gaactcattc    1200
attggtactg tatccgaacg gtgccaatca attctttctt taagctacaa ttacttgccc    1260
caatatttga gggcttgttt tctctatgtt ggatgttttc ctgaagataa agagattgat    1320
gtttccaagt tgattaggct atggattgct gagcaattcg taaaggcgag aagcaataaa    1380
aggttagaag tggtagcaga ggagtatcta gaagagttaa ttgatagaag cctaattttg    1440
agtggtagac aaagggctaa tggaaggatg aaaacttgca aaattcatga tcttcttcgc    1500
caactatgcc taagtgaagc tcatactgaa aatattagtc atatcatgaa tagaaatgtc    1560
cccgtgtcct cagaagccat agatgatcaa cggcgagtga ttgttccatt ggaacttgaa    1620
gaggaaccag tttatcctac aaggaatagc agtggtatta caagtacaac ccgcaccttt    1680
atttcaatgg aaatatgcct aagagaagct cagaccgaag ccatatatga tcaacggcga    1740
gtgatccttc tgtctaaacg acataggatt gatacaatcc gcaccattat tccattcaaa    1800
```

-continued

```
gatactttc cgaaagagat tgttccatt gtttcacagt tgaagttgct taaggtgttg   1860
gatgtattat cagtctggta cgatgtctct tgtataatac ctcagcttgt acatttgaga   1920
tatgttggtg cagtaatttt gaaagctctt tcactaccca aattgagaaa tctacagacc   1980
ataattctta caagtgttga aaccacagag ttgaagcact cactagatat ctggagaatg   2040
tcagagataa gacatttgga tattgtaccg ccactatata tatcaaatcc tcttgaagca   2100
gaacaacctt tgtttctcaa taacttgcac acacttttc tccgttgctc tccttttgtt   2160
gcgaaaatca taagaagaac tcccaatcta aaaagctaa agattttaga taaatctaag   2220
catcctgact ggcctgatat tcttgattct ctcaatcttc tagaggagct ggagacacta   2280
caaatatcaa cagaagaaaa cattgacccg atgattttct ctggggatat tttccctcgt   2340
aatctcaagc aactgaaatt atcatatact tgtataccat gggaagatat gaaattgctg   2400
gctaatttac ccaatcttga ggtgttcaag ggtcattatg cattcaatgg aacagattgg   2460
aaactagatg aagatgttgt gttttgcaaa ttaaaatctc tacgactgta tgagcgtgga   2520
gatttgcaaa gaattttgcg gctctggtgt aaagacaagt gcaagaaaaa ttcaagaaga   2580
gcaagaaagc ctgggaaatt a   2601
```

<210> SEQ ID NO 28
<211> LENGTH: 1004
<212> TYPE: PRT
<213> ORGANISM: Solanum americanum

<400> SEQUENCE: 28

```
Met Ala Tyr Ala Ala Leu Ser Ser Leu Ile Tyr Thr Leu Gln Gln Leu
1               5                   10                  15

Phe Lys Pro Asn Gln Ser Phe Val Cys Gln Ser Cys Cys Thr Gln Gln
            20                  25                  30

His Val Gln Ser Leu Cys Gln Asn Leu Ser Ala Leu Gln Leu Phe Leu
        35                  40                  45

Asp Asp Thr Thr Thr Lys Asp Ile Glu Thr Leu Lys Val Cys Asn Tyr
    50                  55                  60

Leu Ile Ser Tyr Ser Ser Tyr Ile Tyr Ser Ile Ile Asn Leu Ser
65                  70                  75                  80

Ser Phe Asn Phe Lys Val Ile Glu Lys Arg Ile Arg Asp Val Val Tyr
                85                  90                  95

Lys Ala Glu Asp Lys Val Asp Ser Ser Leu Arg Ser Ile Ile Leu Ala
            100                 105                 110

Asp Cys Thr Glu Asn Lys Glu Gly Ala Cys Lys Phe Phe Glu Glu Glu
        115                 120                 125

Leu Leu Lys Val Glu Lys Asp Val Asp Ser Leu Ser Lys Glu Val Met
    130                 135                 140

Gln Ile Asn Val Asn Lys His Gly Ser Arg Ser Ala Glu Leu Thr Thr
145                 150                 155                 160

Ile Pro Pro Ser Pro Glu Lys Ser Thr Asn Glu His Thr Ile Val
                165                 170                 175

Gly Met Glu Asp Glu Tyr Asn Thr Ile Leu Asp Arg Leu Thr Ala Gln
            180                 185                 190

Thr Asp Glu Leu Thr Val Ile Pro Ile Phe Gly Met Gly Gly Ile Gly
        195                 200                 205

Lys Thr Thr Leu Ala Arg Lys Val Tyr Asp Asp Ser Ser Ile Arg Ser
    210                 215                 220
```

Arg Phe Asp Arg His Val Trp Val Thr Thr Ser Glu Glu Phe Asn Glu
225                 230                 235                 240

Arg Arg Met Leu Leu Glu Val Val Ser Ser Ile Thr Thr Gly Ser Asn
            245                 250                 255

Gln Glu Lys Ser Asp Asp Gln Leu Met Glu Ile Val Tyr Arg Gly Leu
        260                 265                 270

Lys Gly Arg Arg Phe Leu Ile Val Ile Asp Asp Ile Trp Ser Thr Glu
    275                 280                 285

Ala Trp Asp Gln Met Gln Arg Ile Phe Pro Asn Asp Asn Lys Ser
290                 295                 300

Arg Ile Leu Leu Thr Thr Arg Leu Lys Tyr Val Ala Asp Tyr Val Ser
305                 310                 315                 320

Ser Pro Asp Phe Pro Pro His Ser Lys Ser Phe Leu Ser Leu Asp Asp
            325                 330                 335

Ser Trp Asn Leu Phe Thr Glu Lys Val Phe Asn Lys Asp Thr Cys Pro
            340                 345                 350

Pro His Leu Glu Glu Thr Gly Lys His Ile Val Gln Gln Cys Arg Gly
        355                 360                 365

Leu Pro Leu Ser Val Val Val Ala Gly Leu Val Gly Lys Met Asp
370                 375                 380

Pro Thr His Asp Asn Trp Glu Asn Val Glu Glu Asn Leu Asn Ser Phe
385                 390                 395                 400

Ile Gly Thr Val Ser Glu Arg Cys Gln Ser Ile Leu Ser Leu Ser Tyr
                405                 410                 415

Asn Tyr Leu Pro Gln Tyr Leu Arg Ala Cys Phe Leu Tyr Val Gly Cys
            420                 425                 430

Phe Pro Glu Asp Lys Glu Ile Asp Val Ser Lys Leu Ile Arg Leu Trp
        435                 440                 445

Ile Ala Glu Gln Phe Val Lys Ala Arg Ser Asn Lys Arg Leu Glu Val
450                 455                 460

Val Ala Glu Glu Tyr Leu Glu Glu Leu Ile Asp Arg Ser Leu Ile Leu
465                 470                 475                 480

Ser Gly Arg Gln Arg Ala Asn Gly Arg Met Lys Thr Cys Lys Ile His
            485                 490                 495

Asp Leu Leu Arg Gln Leu Cys Leu Ser Glu Ala His Thr Glu Asn Ile
            500                 505                 510

Ser His Ile Met Asn Arg Asn Val Pro Val Ser Ser Glu Ala Ile Asp
        515                 520                 525

Asp Gln Arg Arg Val Ile Val Pro Leu Glu Leu Glu Glu Pro Val
530                 535                 540

Tyr Pro Thr Arg Asn Ser Ser Gly Ile Thr Ser Thr Thr Arg Thr Phe
545                 550                 555                 560

Ile Ser Met Glu Ile Cys Leu Arg Glu Ala Gln Thr Glu Ala Ile Tyr
                565                 570                 575

Asp Gln Arg Arg Val Ile Leu Leu Ser Lys Arg His Arg Ile Asp Thr
            580                 585                 590

Ile Arg Thr Ile Ile Pro Phe Lys Asp Thr Phe Pro Lys Glu Ile Cys
        595                 600                 605

Ser Ile Val Ser Gln Leu Lys Leu Leu Lys Val Leu Asp Val Leu Ser
        610                 615                 620

Val Trp Tyr Asp Val Ser Cys Ile Ile Pro Gln Leu Val His Leu Arg
625                 630                 635                 640

Tyr Val Gly Ala Val Ile Leu Lys Ala Leu Ser Leu Pro Lys Leu Arg

```
                      645                 650                 655
Asn Leu Gln Thr Ile Ile Leu Thr Ser Val Glu Thr Thr Glu Leu Lys
                660                 665                 670

His Ser Leu Asp Ile Trp Arg Met Ser Glu Ile Arg His Leu Asp Ile
            675                 680                 685

Val Pro Pro Leu Tyr Ile Ser Asn Pro Leu Glu Ala Glu Gln Pro Leu
        690                 695                 700

Phe Leu Asn Asn Leu His Thr Leu Phe Leu Arg Cys Ser Pro Phe Val
705                 710                 715                 720

Ala Lys Ile Ile Arg Arg Thr Pro Asn Leu Lys Lys Leu Lys Ile Leu
                725                 730                 735

Asp Lys Ser Lys His Pro Asp Trp Pro Asp Ile Leu Asp Ser Leu Asn
            740                 745                 750

Leu Leu Glu Glu Leu Glu Thr Leu Gln Ile Ser Thr Glu Glu Asn Ile
        755                 760                 765

Asp Pro Met Ile Phe Ser Gly Asp Ile Phe Pro Arg Asn Leu Lys Gln
    770                 775                 780

Leu Lys Leu Ser Tyr Thr Cys Ile Pro Trp Glu Asp Met Lys Leu Leu
785                 790                 795                 800

Ala Asn Leu Pro Asn Leu Glu Val Phe Lys Gly His Tyr Ala Phe Asn
                805                 810                 815

Gly Thr Asp Trp Lys Leu Asp Glu Asp Val Val Phe Cys Lys Leu Lys
            820                 825                 830

Ser Leu Arg Leu Tyr Glu Arg Gly Asp Leu Gln Arg Trp Glu Ala Ala
        835                 840                 845

Gly Ser Asp Asn Phe Pro Met Leu Glu Gln Leu Leu Leu Tyr Gly Phe
    850                 855                 860

Lys Lys Leu Glu Glu Ile Pro Glu Ser Ile Gly Glu Ile Met Thr Leu
865                 870                 875                 880

Lys Phe Ile Lys Thr Glu Phe Cys Gly Ser Gly Val Lys Thr Ser Ala
                885                 890                 895

Lys Lys Ile Gln Glu Glu Gln Glu Ser Leu Gly Asn Tyr Glu Leu Gln
            900                 905                 910

Val Gln Ile Thr Pro Lys Leu Arg Phe Leu Ile Glu Asn Leu Asp Glu
        915                 920                 925

Ile Ser Met Leu Pro Pro Asn Glu Val Ala Glu Lys Ile Lys Val Lys
    930                 935                 940

Ile Phe Asp Gln Lys Leu Lys Glu Ile Pro Glu Ser Thr Gly Gln Ile
945                 950                 955                 960

Met Thr Arg Lys Ile Ile Lys Thr Glu Phe Cys Gly Ser Gly Val Glu
                965                 970                 975

Thr Ser Ala Lys Lys Ile Gln Glu Glu Gln Glu Ser Leu Gly Asn Cys
            980                 985                 990

Glu Leu His Gln Val Gln Ile Thr  Pro Lys Val Tyr
        995                 1000

<210> SEQ ID NO 29
<211> LENGTH: 925
<212> TYPE: PRT
<213> ORGANISM: Solanum americanum

<400> SEQUENCE: 29

Met Ala Tyr Ala Ala Leu Ser Ser Leu Ile Tyr Thr Leu Gln Gln Leu
1               5                   10                  15
```

```
Phe Lys Pro Asn Gln Ser Phe Val Cys Gln Ser Cys Cys Thr Gln Gln
             20                  25                  30

His Val Gln Ser Leu Cys Gln Asn Leu Ser Ala Leu Gln Leu Phe Leu
             35                  40                  45

Asp Asp Thr Thr Thr Lys Asp Ile Glu Thr Leu Lys Val Cys Asn Tyr
50                   55                  60

Leu Ile Ser Tyr Ser Ser Tyr Ile Tyr Ser Ile Ile Asn Leu Ser
65                   70                  75                  80

Ser Phe Asn Phe Lys Val Ile Glu Lys Arg Ile Arg Asp Val Val Tyr
                 85                  90                  95

Lys Ala Glu Asp Lys Val Asp Ser Ser Leu Arg Ser Ile Ile Leu Ala
                100                 105                 110

Asp Cys Thr Glu Asn Lys Glu Gly Ala Cys Lys Phe Phe Glu Glu Glu
             115                 120                 125

Leu Leu Lys Val Glu Lys Asp Val Asp Ser Leu Ser Lys Glu Val Met
             130                 135                 140

Gln Ile Asn Val Asn Lys His Gly Ser Arg Ser Ala Glu Leu Thr Thr
145                 150                 155                 160

Ile Pro Pro Ser Pro Glu Lys Ser Thr Asn Glu Glu His Thr Ile Val
                165                 170                 175

Gly Met Glu Asp Glu Tyr Asn Thr Ile Leu Asp Arg Leu Thr Ala Gln
             180                 185                 190

Thr Asp Glu Leu Thr Val Ile Pro Ile Phe Gly Met Gly Gly Ile Gly
             195                 200                 205

Lys Thr Thr Leu Ala Arg Lys Val Tyr Asp Asp Ser Ser Ile Arg Ser
210                 215                 220

Arg Phe Asp Arg His Val Trp Val Thr Thr Ser Glu Glu Phe Asn Glu
225                 230                 235                 240

Arg Arg Met Leu Leu Glu Val Val Ser Ser Ile Thr Thr Gly Ser Asn
             245                 250                 255

Gln Glu Lys Ser Asp Asp Gln Leu Met Glu Ile Val Tyr Arg Gly Leu
             260                 265                 270

Lys Gly Arg Arg Phe Leu Ile Val Ile Asp Asp Ile Trp Ser Thr Glu
             275                 280                 285

Ala Trp Asp Gln Met Gln Arg Ile Phe Pro Asn Asp Asn Lys Ser
290                 295                 300

Arg Ile Leu Leu Thr Thr Arg Leu Lys Tyr Val Ala Asp Tyr Val Ser
305                 310                 315                 320

Ser Pro Asp Phe Pro His Ser Lys Ser Phe Leu Ser Leu Asp Asp
             325                 330                 335

Ser Trp Asn Leu Phe Thr Glu Lys Val Phe Asn Lys Asp Thr Cys Pro
             340                 345                 350

Pro His Leu Glu Glu Thr Gly Lys His Ile Val Gln Gln Cys Arg Gly
             355                 360                 365

Leu Pro Leu Ser Val Val Val Ala Gly Leu Val Gly Lys Met Asp
             370                 375                 380

Pro Thr His Asp Asn Trp Glu Asn Val Glu Glu Asn Leu Asn Ser Phe
385                 390                 395                 400

Ile Gly Thr Val Ser Glu Arg Cys Gln Ser Ile Leu Ser Leu Ser Tyr
                405                 410                 415

Asn Tyr Leu Pro Gln Tyr Leu Arg Ala Cys Phe Leu Tyr Val Gly Cys
             420                 425                 430

Phe Pro Glu Asp Lys Glu Ile Asp Val Ser Lys Leu Ile Arg Leu Trp
```

-continued

```
            435                 440                 445
Ile Ala Glu Gln Phe Val Lys Ala Arg Ser Asn Lys Arg Leu Glu Val
450                 455                 460
Val Ala Glu Glu Tyr Leu Glu Glu Leu Ile Asp Arg Ser Leu Ile Leu
465                 470                 475                 480
Ser Gly Arg Gln Arg Ala Asn Gly Arg Met Lys Thr Cys Lys Ile His
                    485                 490                 495
Asp Leu Leu Arg Gln Leu Cys Leu Ser Glu Ala His Thr Glu Asn Ile
                500                 505                 510
Ser His Ile Met Asn Arg Asn Val Pro Val Ser Ser Glu Ala Ile Asp
            515                 520                 525
Asp Gln Arg Arg Val Ile Val Pro Leu Glu Leu Glu Glu Pro Val
            530                 535                 540
Tyr Pro Thr Arg Asn Ser Ser Gly Ile Thr Ser Thr Thr Arg Thr Phe
545                 550                 555                 560
Ile Ser Met Glu Ile Cys Leu Arg Glu Ala Gln Thr Glu Ala Ile Tyr
                565                 570                 575
Asp Gln Arg Arg Val Ile Leu Leu Ser Lys Arg His Arg Ile Asp Thr
                580                 585                 590
Ile Arg Thr Ile Ile Pro Phe Lys Asp Thr Phe Pro Lys Glu Ile Cys
            595                 600                 605
Ser Ile Val Ser Gln Leu Lys Leu Leu Lys Val Leu Asp Val Leu Ser
610                 615                 620
Val Trp Tyr Asp Val Ser Cys Ile Ile Pro Gln Leu Val His Leu Arg
625                 630                 635                 640
Tyr Val Gly Ala Val Ile Leu Lys Ala Leu Ser Leu Pro Lys Leu Arg
                645                 650                 655
Asn Leu Gln Thr Ile Ile Leu Thr Ser Val Glu Thr Thr Glu Leu Lys
                660                 665                 670
His Ser Leu Asp Ile Trp Arg Met Ser Glu Ile Arg His Leu Asp Ile
            675                 680                 685
Val Pro Pro Leu Tyr Ile Ser Asn Pro Leu Glu Ala Glu Gln Pro Leu
            690                 695                 700
Phe Leu Asn Asn Leu His Thr Leu Phe Leu Arg Cys Ser Pro Phe Val
705                 710                 715                 720
Ala Lys Ile Ile Arg Arg Thr Pro Asn Leu Lys Lys Leu Lys Ile Leu
                725                 730                 735
Asp Lys Ser Lys His Pro Asp Trp Pro Asp Ile Leu Asp Ser Leu Asn
                740                 745                 750
Leu Leu Glu Glu Leu Glu Thr Leu Gln Ile Ser Thr Glu Glu Asn Ile
            755                 760                 765
Asp Pro Met Ile Phe Ser Gly Asp Ile Phe Pro Arg Asn Leu Lys Gln
            770                 775                 780
Leu Lys Leu Ser Tyr Thr Cys Ile Pro Trp Glu Asp Met Lys Leu Leu
785                 790                 795                 800
Ala Asn Leu Pro Asn Leu Glu Val Phe Lys Gly His Tyr Ala Phe Asn
                805                 810                 815
Gly Thr Asp Trp Lys Leu Asp Glu Asp Val Val Phe Cys Lys Leu Lys
                820                 825                 830
Ser Leu Arg Leu Tyr Glu Arg Gly Asp Leu Gln Arg Trp Glu Ala Ala
            835                 840                 845
Gly Ser Asp Asn Phe Pro Met Leu Glu Gln Leu Leu Leu Tyr Gly Phe
            850                 855                 860
```

```
Lys Leu Glu Glu Ile Pro Glu Ser Ile Gly Glu Ile Met Thr Leu
865                 870                 875                 880

Lys Phe Ile Lys Thr Glu Phe Cys Gly Ser Gly Val Lys Thr Ser Ala
                885                 890                 895

Lys Lys Ile Gln Glu Gln Glu Ser Leu Gly Asn Tyr Glu Leu Gln
            900                 905                 910

Val Gln Ile Thr Pro Lys Leu Lys Phe Leu Ile Lys Asn
        915                 920                 925

<210> SEQ ID NO 30
<211> LENGTH: 867
<212> TYPE: PRT
<213> ORGANISM: Solanum americanum

<400> SEQUENCE: 30

Met Ala Tyr Ala Ala Leu Ser Ser Leu Ile Tyr Thr Leu Gln Gln Leu
1               5                   10                  15

Phe Lys Pro Asn Gln Ser Phe Val Cys Gln Ser Cys Cys Thr Gln Gln
            20                  25                  30

His Val Gln Ser Leu Cys Gln Asn Leu Ser Ala Leu Gln Leu Phe Leu
        35                  40                  45

Asp Asp Thr Thr Thr Lys Asp Ile Glu Thr Leu Lys Val Cys Asn Tyr
    50                  55                  60

Leu Ile Ser Tyr Ser Ser Tyr Ile Tyr Ser Ile Ile Asn Leu Ser
65                  70                  75                  80

Ser Phe Asn Phe Lys Val Ile Glu Lys Arg Ile Arg Asp Val Val Tyr
                85                  90                  95

Lys Ala Glu Asp Lys Val Asp Ser Ser Leu Arg Ser Ile Ile Leu Ala
            100                 105                 110

Asp Cys Thr Glu Asn Lys Glu Gly Ala Cys Lys Phe Phe Glu Glu Glu
        115                 120                 125

Leu Leu Lys Val Glu Lys Asp Val Asp Ser Leu Ser Lys Glu Val Met
    130                 135                 140

Gln Ile Asn Val Asn Lys His Gly Ser Arg Ser Ala Glu Leu Thr Thr
145                 150                 155                 160

Ile Pro Pro Ser Pro Glu Lys Ser Thr Asn Glu Glu His Thr Ile Val
                165                 170                 175

Gly Met Glu Asp Glu Tyr Asn Thr Ile Leu Asp Arg Leu Thr Ala Gln
            180                 185                 190

Thr Asp Glu Leu Thr Val Ile Pro Ile Phe Gly Met Gly Gly Ile Gly
        195                 200                 205

Lys Thr Thr Leu Ala Arg Lys Val Tyr Asp Asp Ser Ser Ile Arg Ser
    210                 215                 220

Arg Phe Asp Arg His Val Trp Val Thr Thr Ser Glu Glu Phe Asn Glu
225                 230                 235                 240

Arg Arg Met Leu Leu Glu Val Val Ser Ser Ile Thr Thr Gly Ser Asn
                245                 250                 255

Gln Glu Lys Ser Asp Asp Gln Leu Met Glu Ile Val Tyr Arg Gly Leu
            260                 265                 270

Lys Gly Arg Arg Phe Leu Ile Val Ile Asp Asp Ile Trp Ser Thr Glu
        275                 280                 285

Ala Trp Asp Gln Met Gln Arg Ile Phe Pro Asn Asp Asp Asn Lys Ser
    290                 295                 300

Arg Ile Leu Leu Thr Thr Arg Leu Lys Tyr Val Ala Asp Tyr Val Ser
```

```
            305                 310                 315                 320
        Ser Pro Asp Phe Pro His Ser Lys Ser Phe Leu Ser Leu Asp Asp
                        325                 330                 335

Ser Trp Asn Leu Phe Thr Glu Lys Val Phe Asn Lys Asp Thr Cys Pro
                        340                 345                 350

Pro His Leu Glu Glu Thr Gly Lys His Ile Val Gln Gln Cys Arg Gly
                        355                 360                 365

Leu Pro Leu Ser Val Val Val Ala Gly Leu Val Gly Lys Met Asp
        370                 375                 380

Pro Thr His Asp Asn Trp Glu Asn Val Glu Glu Asn Leu Asn Ser Phe
        385                 390                 395                 400

Ile Gly Thr Val Ser Glu Arg Cys Gln Ser Ile Leu Ser Leu Ser Tyr
                        405                 410                 415

Asn Tyr Leu Pro Gln Tyr Leu Arg Ala Cys Phe Leu Tyr Val Gly Cys
                        420                 425                 430

Phe Pro Glu Asp Lys Glu Ile Asp Val Ser Lys Leu Ile Arg Leu Trp
                        435                 440                 445

Ile Ala Glu Gln Phe Val Lys Ala Arg Ser Asn Lys Arg Leu Glu Val
                        450                 455                 460

Val Ala Glu Glu Tyr Leu Glu Glu Leu Ile Asp Arg Ser Leu Ile Leu
        465                 470                 475                 480

Ser Gly Arg Gln Arg Ala Asn Gly Arg Met Lys Thr Cys Lys Ile His
                        485                 490                 495

Asp Leu Leu Arg Gln Leu Cys Leu Ser Glu Ala His Thr Glu Asn Ile
                        500                 505                 510

Ser His Ile Met Asn Arg Asn Val Pro Val Ser Ser Glu Ala Ile Asp
                        515                 520                 525

Asp Gln Arg Arg Val Ile Val Pro Leu Glu Leu Glu Glu Pro Val
                        530                 535                 540

Tyr Pro Thr Arg Asn Ser Ser Gly Ile Thr Ser Thr Thr Arg Thr Phe
        545                 550                 555                 560

Ile Ser Met Glu Ile Cys Leu Arg Glu Ala Gln Thr Glu Ala Ile Tyr
                        565                 570                 575

Asp Gln Arg Arg Val Ile Leu Leu Ser Lys Arg His Arg Ile Asp Thr
                        580                 585                 590

Ile Arg Thr Ile Ile Pro Phe Lys Asp Thr Phe Pro Lys Glu Ile Cys
                        595                 600                 605

Ser Ile Val Ser Gln Leu Lys Leu Leu Lys Val Leu Asp Val Leu Ser
                        610                 615                 620

Val Trp Tyr Asp Val Ser Cys Ile Ile Pro Gln Leu Val His Leu Arg
        625                 630                 635                 640

Tyr Val Gly Ala Val Ile Leu Lys Ala Leu Ser Leu Pro Lys Leu Arg
                        645                 650                 655

Asn Leu Gln Thr Ile Ile Leu Thr Ser Val Glu Thr Thr Glu Leu Lys
                        660                 665                 670

His Ser Leu Asp Ile Trp Arg Met Ser Glu Ile Arg His Leu Asp Ile
                        675                 680                 685

Val Pro Pro Leu Tyr Ile Ser Asn Pro Leu Glu Ala Glu Gln Pro Leu
                        690                 695                 700

Phe Leu Asn Asn Leu His Thr Leu Phe Leu Arg Cys Ser Pro Phe Val
        705                 710                 715                 720

Ala Lys Ile Ile Arg Arg Thr Pro Asn Leu Lys Lys Leu Lys Ile Leu
                        725                 730                 735
```

```
Asp Lys Ser Lys His Pro Asp Trp Pro Asp Ile Leu Asp Ser Leu Asn
                740                 745                 750
Leu Leu Glu Glu Leu Glu Thr Leu Gln Ile Ser Thr Glu Glu Asn Ile
            755                 760                 765
Asp Pro Met Ile Phe Ser Gly Asp Ile Phe Pro Arg Asn Leu Lys Gln
        770                 775                 780
Leu Lys Leu Ser Tyr Thr Cys Ile Pro Trp Glu Asp Met Lys Leu Leu
785                 790                 795                 800
Ala Asn Leu Pro Asn Leu Glu Val Phe Lys Gly His Tyr Ala Phe Asn
                805                 810                 815
Gly Thr Asp Trp Lys Leu Asp Glu Asp Val Val Phe Cys Lys Leu Lys
            820                 825                 830
Ser Leu Arg Leu Tyr Glu Arg Gly Asp Leu Gln Arg Ile Leu Arg Leu
        835                 840                 845
Trp Cys Lys Asp Lys Cys Lys Glu Asn Ser Arg Arg Ala Arg Lys Pro
    850                 855                 860
Gly Lys Leu
865

<210> SEQ ID NO 31
<211> LENGTH: 7913
<212> TYPE: DNA
<213> ORGANISM: Solanum americanum

<400> SEQUENCE: 31
ctttgtaaac gataatggca tgggtgagct caatatttag cggatgatat aaatgaaatt      60
tttttcaaag tttgattact tatttaagtt ttttttcttt tatttaattt ttaattcgat     120
gtccaatatg cacaaccaaa tttccactac aaccaaaaaa aaaaaagaac gctgtgtaac     180
atcatctcca accaacctgg gtcatatgag tcccaaatgc atttacagca acaaagagca     240
aagcaaagca caactttgaa atttgaaaaa tgatgcaaga caaatatcaa aattagacag     300
taaaattcac aattcccctt aaaataaatg ataaattaaa gaagactaaa caatagaaaa     360
ccttacaatc tcaaaggcag tatggatcgg agtcgtattt ggaagaaatt ttgatacaac     420
ttgaagaaga ttgaagattg ttgttcataa agtatactgt gggcgggtta atctacaacc     480
tgtgtgtttt ttatcataca aaattccaca gagtattatt aatttttttaa ggatcgtttg     540 gccatgtgat atgaaattat gagatgaagt tgacgttttg tttggacatg caatttggac     600 ttttatgtt gtatgttttc ttataaacat aagttgtaaa attattaaag ttgtcccatt     660
tttttattca attttaccaa ataaacaaaa atttacaaaa tcacataata tgctaacaca     720
aaactattct ttaaaaaata caatatttat tgatcaaact ttaattcaac aaaaaataaa     780
attcaacata agttgtagtg tactagtctt taatataatt ctcccacata atacggacaa     840
tctcctcacg ttgaacttgc atttctcgat catatgattg agtagacaaa ccaacattgc     900
tactttgagc tataaatggt ttaaaaagta atgatatgaa ttataaattt tatttacata     960
tgaaacaaat ggtaagtaaa tataaatgtg gggttgtttt tataaaatat aaacttatgg    1020
gtcaattttt gtatttgaaa atcccaaat tatgatttga aattttcaaa tcatgatttt    1080
tgaagaattc agtctgaaat cgcatgtcca aatgctgatt catctcatg atttcatatc     1140 gtgatatgaa atcgcatgtc caaacgccta ctaagtaact tagacacgtc ttgaccttt     1200 ataattactc cctccatcct aatttacttg tcaaatattt tctaatttga ttccccttt     1260 acttgtcatt tttacaaaat caagaaacga caatttttt tcttcctatt ataccctcaa    1320
```

-continued

```
tttattaaca ttgaattaat gtccttgaaa aatataggaa gtaaatatgt ttaaaactct   1380
atcaaattaa tatggataaa atggtaaatt cattatacca attattattt tcttaataga   1440
tgcgtcaaat caaaaattga caagtaatat aaatttcaaa gaaatttgt attgaaagtt    1500
aattgtattc gtccacttga cacatcatgt cttaattatt caacaagttt gaatccaatg   1560
tatatgaatg tttgaaaagt cttgacgaaa actacaagag tgtctttatt agaaatcagg   1620
acaacttgac tctttatttt tcatttcttt tttctcactt tgacttggtc aatccatagt   1680
tttgcatcca taaaccacaa gttctgttta gatattaaat agaaaattgt ccaaattcat   1740
ttagaaaaat gtggacataa atcatttaga caaaacctct tagcctaagc agagacattt   1800
ctcttccagc aaacaaaaga gaaatggcat atgctgctct ttcttcactt atctatacat   1860
tgcaacaact cttgaaacct aatcaatctt tggtttgtcg aagctgtaca caacaacatc   1920
ttcaatctat ctatcacaat ctttctgctc tgcaacttt ccttgacgat actacgacaa    1980
aggatattga aactcttaag gtatgtaatt atctaatctc ttactcatct tatatttatt   2040
caataataat taatttatcg agtttcaatt ttaaggttat agaaagagg atcagagatg     2100
tagtatacaa agcagaagat aaagttgatt caagcctaag aaacatcata ctagcagatt   2160
gcacagagaa tagagaaggg gcttgtaaat tctttgagga agaattgcta aaagtggaaa   2220
aagatgttga ttctctcagg aaagaggtga tgcagatcga gtttaacaag catggtagca   2280
gatctgcaga actaacaaca attcttccct ctccagaaaa aagtacaatt gaggaacata   2340
ctattgttgg gatggaggat gagtacaaca ccatacttga tcgcctcact gcccaaacag   2400
acgagttgac tgtcatacca attttggta tgggcggtat aggtaagaca actctagcca    2460
gaaaggttta tgatgattca tctattcgtt ctcgatttga tagacatgta tgggtcacta   2520
cctctgaaga attcaatgag agacgaatgc ttctcgaagt tgtttcttca attactactg   2580
gaagcaatca agaaaagagc gatgatcaac taatggagat tgtgtataga ggtcttaagg   2640
gtaggagatt tctaattgtc atagatgata tttggagtac tcaggcttgg gaccaaatgc   2700
aaagaatatt tccaaatgat gacaataaaa gcagaattct actaactaca cggctcaagt   2760
atgttgctga ttatgtcaac agtcctgatt ttccacctca tagtaagtct tttctaagtc   2820
ttgatgatag ttggaatcta ttcaccgaaa aagtattcaa caaagatacc tgtcctcctc   2880
acctagaaga aacagggaag catattgtac aacaatgtcg aggattacct ctctcggttg   2940
ttgtagttgc tggacttgtt ggaaaaatgg acccaacgca tgacaattgg gagaacgttg   3000
aggaaaatct gaactcattc attggtactg tatctgaacg gtgccaatca attctttctt   3060
taagctacaa ttacttgccc cagtatttga gggcttgttt tctctatgtt ggatgttttc   3120
ctgaagataa agagattgat gtttccaagt tgattaggct atggattgct gagcaattcg   3180
taaaggcgag aagcaataaa aatttagaag tggtggcaga ggagtatctg gaagagttaa   3240
ttgatagaag tctaattttg agtggtagac aaagggctaa tggaaggatg aaaacttgta   3300
aaattcatga tcttcttcgc caactatgcc taagtgaagc tcatactgaa aatattagtc   3360
atatcatgaa tagaaatgtc ctcgtgtcct cagaagccat agatgatcaa tggcgagtga   3420
ttgttccatt ggaactcgaa gagaaacaag tttatccgac aaggcatagc agtggtatta   3480
caagtacaac ccgcaccttt atttcaatgg aaatatgcct aagagaagct cagaccgaaa   3540
ccatatatga tcaacggcga gtgatccttc tctctaaacg acataggatt gatacaatcc   3600
gcaccattat tccattcgga gatacttttc caaaagtgat ttgttccatt ttttcgcagt   3660
```

```
tgaagttgct taaggtgttg gatgtattat cagtctggta cgatgtctct tgtataatac    3720
ctcagcttgt acatttgaga tatgttggtg cagtaatttt ggaagctgtt tcactatcca    3780
aattgagaaa tctacagacc ataattcttg caagtgttga aaccacagag ttgaagcacc    3840
cagtagatat ctggagaatg tcagagatca gacatttgga tattgtaccg ccactatata    3900
tatcaaatcc tcttgaagca gaacaacctt tgtttctcaa taacttgcac acgcttttc    3960
tccgttgctc tccttttgtt gcgaaaatca taagaagaac tcccaatcta aaaaagctaa    4020
agattttaga taaatctaag catcctgact ggcctgatat tcttgattct ctcaatcttc    4080
tagaggagct ggagacacta caaatatcaa cagaagaaaa cattgaccgg atgatttttct   4140
ctggggatat tttccctcgt aatctcaagc aactgaaatt atcatatact tgtataccat    4200
gggaagatat gaaattgctg gctaatttac ccaatcttga ggtgttcaag gtcattatg     4260
cattcgatgg aacagattgg aaactagatg aagatgttgt gttttgcaaa ttaaaatgtc    4320
tacgactgta tgagcgcgga gatctgcaaa ggtgggaagc tgctggtagt gataattttc    4380
caatgcttga gcaactatta ctgtatggat tcaaaaagct ggaagagatt ccggagagta    4440
ttggagaaat aatgacacta aaattcatta atacagaatt ttgcggctct ggtgtagaga    4500
ctagtgcaaa gaaaattcaa aagagcaag aaagcttggg aaattatgag cttcaacttc     4560
aaattactcc taaggtatgt tgaaactcaa tctttgatta atactctccc ccagctagac    4620
ttttcaaagt aatatttcac acgtacaatc tccactcggt aagatttagg attgaaattg    4680
tcttcttaca tttatgatca tcacccttcg gttttttta tttttttta gtaaatagct      4740
tcatatactc tacaaaagtt acacataatt aacaattgac aattgattct ctcttattga    4800
taatttgtca ttttctcttt cagttaagat ttttgatcga aaatttagac gaaacaagca    4860
tgttgccatc gaatgaagta atcgaaaaaa tcaaaggttt gtctatttaa ttccttttat    4920
tacttcattg aaagaggttc agatatttta aacaacttt taaccttct atttgaattt      4980
tttatcgctc agatagatac aacatttatt ttgacgtcaa attgttattt tgatttaatc    5040
ttattctttt tgtatatagt ttccactcgg ttcttcattt tttttcaat tatagtttaa     5100
ttttttttaa ttgcacatgg ttgattgatt taatttgtga gattcacttt tctttcgatt    5160
ttaggagttc ttcgggatta atgttattca gatttaggag tattatattt caactttcgg    5220
ttagatttag gattcaaatt gtcttcttac atttatgatc atcatccttt tgatgttatt    5280
tatttctttt agtaaatagc ttcaaaaact ctatagaaat tacatataat taacaattga    5340
caattgattt tctcttattg ataatttctc atgtttctct ttcaattaaa atttttgatc    5400
gaaaactaaa agagattccg gagagtactg gacaaataat gacacgaaaa atcatcaaaa    5460
cagaattttg cagctctggt gtagagacta gtgcaaagaa aattcaagaa gagcaagaaa    5520
gcttgggaaa ttatgagctt caagttcaaa ttactcctag gtatgttaa actcctttga     5580
ttattagcca attctttaat ttcataatat ttctagacta agagcctgtc tggatggact    5640
taaaaaaaat aacttataag ttgaaaacta tttataagtc aaaaaaaata agtaggtcta    5700
ccctaactta ttttttttg acttataagt tgttttcaac ttttaagctg ttttaaataa     5760
gctaagtcaa atagacccaa ttatttttg ggcttatttt aagcacaaaa tgactttaag     5820
ttggccagcc aaatactaaa aaaaactaaa aacaacttat aagttacttt taagccaatt    5880
caaacgggct ctaaattaaa atattaaaag atataaagaa tttaattaat ttaattattc    5940
ctttgaaatc caaacatgat gaatttgagt aaattaaatg aaatatagtt cagattcatt    6000
taactaatag gtcatttact tttaatccgg caacgtttta ggcttttagc attctctttg    6060
```

```
aatgtaggta taatgcatta agtgcagaaa tttaattttt atttaaaaaa tgaaaacatc    6120
tcataataac tttggtcttt ttactccaaa catcttataa taaagtgagt ctcttctact    6180
tctcctaaca tctcataata aatttctgct attcctaaca tctcataata aataagtctt    6240
ttctactatt taattttgtt aaaatattca caatttttgt gtcttattct ccaccccat     6300 cttttttttt ttactttctt aatattcata tgcttgaatc aaaacaaggt tctatgaatt    6360
ctaacgcgct tggattgatc atgatgcaat tcaatatatg catcaattta attttattt     6420 ttcatgcata atagttagtt tcacaagata aatattttta tttcaatatg tatttatcct    6480
ttaattaaag tactatatat gtcactaaag tagcatcaaa tttgcaagaa tttctaatct    6540
caatttatga gtttgttata ttttttttatt gtattgcttt gattttatt ttataaccaa    6600 agagaaagtc taataatata cgtgtcatta tttatttttt aagtattttg ggataaacac    6660
gaacacacat acaagttaca ttaaagtgga agaatcaag tcaaaagttt gtttaccatt     6720
tttaacgttg aaaaaagcaa gccttcattt aaatagttat tatattgctt acattagaaa    6780
atatattaaa attcattagc tccttaaaat tcaatgaatc caaataatta acgtttatt     6840 gccataattt tatttttatc tctttaactt gctaaatggc tccttcacta catgctttga    6900
ggaacagaag cgtttgctga ggaagcagga cggcactgtg taacaataat ttgtatggct    6960
tcagtgatga gaatattttg tgtgccacgc agcatagcag tgttcatcta actataaatt    7020
ttataagaaa agaaaaatcg tccttaatcg ttatttcact cattaaattg tttttttctt    7080
cattttccat ggtaatttga atttcgaagt gtggacatgg actgtgtttg gagcataggt    7140
tcatatttgt gtagtttaaa attgtatgat tattatttta gttctcttgt yaacgtcctt    7200
atcacctttg cagatagtta ctattgagaa tgtatttata ctattagtta gttagttact    7260
agtcatgatg attgtgtgat gatcagctta gttagttaga ttagtgaatt ggttacagct    7320
gttagttaca gttagttagg ctaagtcgct tagtttgtta gtgttataaa tacacttgta    7380
cagattcatt ttcattttga gaagttcaat tcaatgaaac agttactctc atcttcctct    7440
tctctcaata ttcacttctc ctcctttgca agtttccgcc attgaagctc caaagcttgg    7500
gagctgattt caagttcttg ttcttgacat ggtaattcac cacaattacg cctctggcaa    7560
agatgcgacg atatggttgt ttgcaacaaa ttttaaataa atggaaaata gatcaaccat    7620
aaataaaata tgaagaaaca ataatatttt attgataaat atgcgggtac aagatctgtt    7680
cctcccttga ttcttctctc ctaaattttc tccgtgattc gagggccgtt agtggcgtat    7740
ttctcgaatt aggatgattt aaacttgatc ttcattgtga ttcgagggcc gttagtggcg    7800
tatttctcga atccatgaaa gaatttgtgg atcttcttga aatatttgat tatcaagaag    7860
acaagaagaa tttaacatat tttgatctct ttctgagatg tcttttcaaa gga           7913
```

<210> SEQ ID NO 32
<211> LENGTH: 7804
<212> TYPE: DNA
<213> ORGANISM: Solanum americanum

<400> SEQUENCE: 32

```
caaaaaaaaa aaaagaaacg ctgtgtaaca tcatctccaa ccaacctggg tcatatgagt      60
cccaaatgca tttacagcaa caaagagcaa agcaaagcac gactttgaaa tttgaaaaat     120
gatgcaagac aaatatcatt cacaattccc cttaaaataa atgataaatt aaagaagact    180
aaacaataga aaaccttaca atctcaaagg cagtatggat cggagtcgta tttggaagaa    240
```

```
attttgatac aacttgaaga agattgaaga ttgttgttca taaagtatac tgtgggcggg      300
ttaatctaca acctgtgtgt tttttatcat acaaaattcc acacagtatt attaatttca      360
tgcaatttgg acttttttatg ttgtatgttt tcttataaac ataagttgta aaattattaa     420
agttgtccca ttttttttatt caattttacc aaataaacaa aaatttacaa aatcacataa     480
tatgctaaca caaaactatt cttaaaaaa tacaatattt attgatcaaa ctttaattca       540
acaaaaaata aaattcaaca taagttgtag tagttgtagt gtactagtct ttaatataat      600
tctcccacat aatacggaca atctcctcac gttgaacttg catttctcga tcatatgatt      660
gagtagacaa accaacattg ctactttgag ctataaatgg tttaaaaagt aatgatatga      720
attataaatt ttatttacat atgaaacaaa tgataagtaa atataaatgt ggggttgttt      780
ttataaaata taaacttatg ggtcaatttt tgtatttgaa aaatcccaaa ttatgatttg      840
aaattttcaa atcatgattt ttgaagaatt cagtctgaaa tcgcatgtcc aaatgctgat      900
ttcatctcat gatttcatat cgtgatatga aatcgcatgt ccaaacgcct actaagtaac      960
ttagacacgt cttgaccttt tataattatc cctccatcct aatttacttg tcaaatattt     1020
tctaatttga ttcccttttt acttgtcatt ttttacaaat caagaaacga caattttttt     1080
ttcttcctat tatacccctca atttattaac attgaattaa tgtccttgaa aaatatagta   1140
agtaaatatg tttaaaactc tatcaaatta atagggtaa aataataaac tcattatatt      1200
aattattatt ttcttaatag atgcgtcaaa tcaaaaatcg acaaagtaat ataaatttca     1260
aagaaaattt gtatcgaaag ttaattgtat tcgtcaagtt tgaatccaat gtatatgaat     1320
gtttgaaaag tcttgacgaa aactacaaga gtgtctttat tagaaatcag gacaacttga     1380
ctctttatttt ttcatttctt ttttctcact ttgacttggt caatccatag ttttgcatcc    1440
ataaccaca agttctgttt agatattaaa tagaaaattg tccaaattta tttagaaaaa      1500
tgtggacata aatcatttag acaaaacctc ttatagccta agcagagaca tttctcttcc     1560
agcaaacaaa agagaaatgg cttatgctgc tcttttcttca cttatgtata cattgcaaca    1620
actcttgaaa cctaatcaat ctttcgtttg tcgatactct acacaacaac ttgttcaatc     1680
tctctatcaa aatcttactg ctctgcaact tttccttgac catactacga caaaggatat     1740
tgaaacactt aaggtatgta attatctaat ctcttactca tcttatattt attcaataat     1800
aattaattta tcgagtttca atttttaaggt tatagaaaag aggatcagag atgtagtata    1860
caaagcagaa gataaagttg attcaagcct aagaaacatc attctagcag attgcacaga    1920
gaatagagaa ggggcttgta aattctttga ggaagaattg ctaaaagtgg aaaaagatgt    1980
tgattctctc agcaaagagg tgatgcagat cgagtttaac aagcatggat gcagatctgc    2040
agaattagca acaactgatc cctcctcatc aggaaaaagt acaattgagg aacatactat    2100
tgttgggatg gaggatgagt acaacaccat acttgatcgc ctcactgccc aaacagacga    2160
gttgactgtc ataccaattt ttggtatggg cggtataggg aagacaactc ttgccagaaa    2220
ggtttatgat gattcatcta ttcgttctcg atttgataga catgcatggg tcactacctc    2280
tgaagaattc aatgagagac gaatgcttct cgaagttgtt tcttcaatta ctactggaag    2340
caatcaagga aagagcgatg atcaactaat ggagattgtg tatagaagtc tgaagggtag    2400
gagatttcta attgtcatag atgatatttg gagtactcag gcttgggacc aaatgcaaag    2460
aatatttcca aatgatgaca gtaaaagccg aattctacta actacacggc tcaagtatgt    2520
tgctgattat gtcagcagtc ctgattttcc acctcatagt aagtcttttc taagtcttga    2580
tgatagttgg aatctattca ccgaaaaagt attcaacgaa gatacctgtc ctcctcacct    2640
```

```
agaagaaaca gggaagcata ttgtacaaca atgtcaagga ttacctctct cggttgttgt    2700
cgttgctgga cttgttggaa aaatggaccc aacgcatgac aattgggaga atgttgagga    2760
aaatctgaac tcattctttg gtactgtatc cgaacggtgc cactcaattc tttctttgag    2820
ctacaattac ttgccccaat atttgagggc ttgttttctc tatgttggag gttttcctga    2880
agataaagag attgatgttt ccaagttgat taggctatgg attgctgagc aattcgtaaa    2940
ggcgagaagc aataaaaggc tagaagtggt ggcagaggag tatctggaag agttaattga    3000
tagaagtcta attttgagtg gtagacaaag ggctaatgga aggatgaaaa cttgcaaaat    3060
tcatgatctt cttcgccaac tatgcctaag tgaagctcat actgaaaata ttagtcatat    3120
catgaataga aatgtccccg tgtcctcaga agccatagat gatcaacggc gagtgattgt    3180
tccattggaa ctcgaagaga aacaatttta tcctacaagg catagcagtg gtattacaag    3240
tacaacccgc acctttattt caatggaaat atgcctaaga gaagctcaaa ccgaagccat    3300
atatgatcaa cggcgagtga tccttctgtc taaacgacat aggattgata caatccgcac    3360
cattattcca ttcggagata cttttccaaa agagatttgt tccattttt cagagttcaa    3420 gttgcttaag gtgttggatg tattatcagt ctggtacgat gtctcttgta taatacctca    3480
gcttgtacat ttgagatatg ttggtgcagt aattttggaa gctcttttcac tacccaaatt    3540 gagaaatcta cagaccataa tgcttacaag tgttgaaacc acagagttga agcactcact    3600
agatatctgg agaatgtcag agataagaca tttggatatt gtaccgccac tatatatatc    3660
aaatcctctt gaagcagaac aacctttgtt tctcaataac ttgcacacgc ttttctccg    3720 ttgctctcct tttgttgcga aaatcataag aagaactccg aatctaaaaa agctaaagat    3780
tttagataaa tctaagcatc ctgactggcc tgatattctt gattctctca atcttctaga    3840
ggagctggag acactacaaa tatcaacaga agaaaacatt gaccggatga ttttctctgg    3900
ggatattttc cctcgtaatc tcaagcaact gaaattatca tatacttgta taccatggga    3960
agatatgaaa ttgctggcta atttacccaa tcttgaggtg ttcaagggtc attatgcatt    4020
cgatggaaca gattggaaac tagatgaaga tgttgtgttt tgcaaattaa aatgtctacg    4080
actgtatgag cgcggagatc tgcaaaggtg ggaagcagca ggtagtgata attttcctat    4140
gcttgagcaa ctagtactgt atgggttcga aaaactggaa gagattccgg agagtattgg    4200
agaaataatg acactaaaat tcattaaaac agaattttgc ggctctggtg tagagactag    4260
tgcaaagaaa attcaagaag agcaagaaag cttgggaaat tatgagcttc aacttcaaat    4320
tactcctaag gtatgttgaa actcaatctt tgattaatac tctcccccag ctagactttt    4380
caaagtaata tttcacacgt acaatctcca ctcggtaaga tttaggattg aaattgtctt    4440
cttacattta tgatcatcac ccttcggttt tttttatttt tttttagtaa atagtttcat    4500
atactctaca aaagttacac ataattaaca attgacaatt gattctctct tattgataat    4560
ttgtcatttt ctctttcagt taagattttt gatcgaaaat ttagacgaaa caagcatgtt    4620
gccatcgaat gaagtaatcg aaaaaatcaa aggtttgtct atttaattcc ttttattact    4680
tcattgaaag aggttcagat attttaaaca acttttttaac ctttctattt gaattttta    4740 tcgctcagat agatacaaca tttatttga cgtcaaattg ttattttgat ttaatcttat    4800 tcttttttgta tatagttttcc actcggttct tcattttttt ttcaattata gtttaatttt    4860
ttttaattgc acatggttga ttgatttaat ttgtgagatt cacttttctt tcgatttag    4920 gagttcttcg ggattaatgt tattcagatt taggagtatt atatttcaac tttcggttag    4980
```

```
atttaggatt caaattgtct tcttacattt atgatcatca tccttttgat gttatttatt      5040
tcttttagta aatagcttca aaaactctat agaaattaca tataattaac aattgacaat      5100
tgattctctc ttattgataa tttctcatgt ttctctttca attaaaattt ttgatcgaaa      5160
actaaaagag attccggaga gtactggaca aataatgaca cgaaaaatca tcaaaacaga      5220
attttgcagc tctggtgtag agactagtgc aaagaaaatt caagaagagc aagaaagctt      5280
gggaaattat gagcttcaag ttcaaattac tcctagggta tgttaaactc cttctttgat      5340
tattagccaa ttctttaatt tcataatatt tctagactaa gagcctgtct ggatggactt      5400
aaaaaaaata acttataagt tgaaaactgt ttataagtca aaaaaaataa gtaggtctac      5460
cctaacttat ttttttttga cttataagtt gttttcaact tttaagctgt tttaaataag      5520
ctaagtcaaa tagatccaat tattttttgg gcttatttta agcacaaaat gactttaagt      5580
tggccagcca aatactaaaa aaagctaaaa acaacttata agttactttt aagccaatcc      5640
aaacgaactc taaattaaaa tattaaaaga tataaagaat ttaattaatt taattattcc      5700
tttgaaatcc aaacatgatg aatttgagta aattaaatga aatatagttc agattcattt      5760
aactaatagg tcatttactt ttaatccggc aacgttttag gcttttagca ttctctttga      5820
atgtaggtat aatgcattaa gtgcagaaat ttaattttta tttaaaaaat gaaacatct      5880
cataataact ttggtctttt tactccaaac atcttataat aaagtgagtc tcttctactt      5940
ctcctaacat ctcataataa atttctacta ttcctaacat ctcataataa ataagtcttt      6000
tctactattt aattttgtta aaatattcac aattttgtg tcttattctc caccccatc      6060
ttttttttt tactttctta atattcatat gcttgaatca aaacaaggtt ctatgaattc      6120
taacgcgctt ggattgatca tgatgcaatt caatatatgc atcaatttaa ttttttattt      6180
tcatgcataa tagttagttt cacaagataa atatttttat ttcaatatgt atttatcctt      6240
taattaaagt actatatatg tcactaaagt agcatcaaat ttgcaagaat ttctaatctc      6300
aatttatgag tttgttatat ttttttttatt gtattgcttt gatttttatt ttataaccaa      6360
agagaaagtc taataatata cgtgtcatta tttattttt aagtattttg ggataaacac      6420
gaacacacgt acaagttaca ttaaaagcgg aaagaatcaa gtcaaagtt tgtttaccat      6480
ttttaacgtt gaaaaagca agccttcatt taaatagtta ttatattgct tacattagaa      6540
aatatattaa aattcattag ctcccttaaaa ttcaatgaat ccaaataatt aaacgtttat      6600
tgccataatt ttatttttat ctctttaact tgctaaatgg ctccttcact acatgctttg      6660
aggaacagaa gcgtttgctg aggaagcagg acggcactgt gtaacaataa tttgtatggc      6720
ttcagtgatg agaatatttt gtgtgccacg cagcatagca gtgttcatct aactataaat      6780
tttataagaa aagaaaaatc gttcttaatc gttatttcac tcattaaatt gttttttctt      6840
tcattttcca tggtaatttg aatttcgaag tgtggacatg gactgtgttt ggagcatagg      6900
ttcatatttg tgtagtttaa aattgtatga ttattatttt agttctcttg tcaacgtcct      6960
tatcacccttt gcagatagtt actattgaga atgtatttat actattagtt agttagttac      7020
tagtcatgat gattgtgtga tgatcagctt agttagttag attagtgaat tggttacagc      7080
tgttagttac agttagttag gctaagtcgc ttagtttgtt agtgttataa atacacttgt      7140
acagattcat aaagttcaat tcaatgaaac agttactctc atcttcctct tctctcaata      7200
ttcacttctc cttctttgca agtttccgcc attgaagctc caaagcttgg gagctgattt      7260
caagttcttg ttcttgacat ggtaattcac cacaattacg cctctggcaa agatgcgacg      7320
atatggttgt ttgcaacaaa ttttaaataa atggaaaata gatcaaccat aaataaaata      7380
```

| | |
|---|---|
| tgaagaaaca ataatatttt actgataaat atgcgggtac aagatctgtt cctcccttga | 7440 |
| ttcttctctc ctaaattttc tccgtgattc gagggccgtt aatggcgtat ttctcgaatt | 7500 |
| aggatgattt aaacttgatc ttcattgtga ttcgaggacc gttagtggcg tatttctcga | 7560 |
| atccatgaaa gaatttgtgg atcttcttga aatatttgat tatcaagaag acaagaagaa | 7620 |
| tttaacatat tttgatctct ttctgagatg tcttttcaag ggaatataat acccttttat | 7680 |
| ataggcacaa attagggttt agagtagagt agcctccaag taaccctaat tgaaatagga | 7740 |
| ctcgtctagt agagttctac aaaatttaga tgtctacaat ggttacttca tggatcctca | 7800 |
| attc | 7804 |

<210> SEQ ID NO 33
<211> LENGTH: 7771
<212> TYPE: DNA
<213> ORGANISM: Solanum americanum

<400> SEQUENCE: 33

| | |
|---|---|
| aacgcatggt taatagtata tcctaacata aacttcatat catgattccg tatctgttga | 60 |
| aagttgagtc attatggaat gaagtgcatt taatgtttca tatggtttta atgcagtaat | 120 |
| aggagtgtgt agaaggcttt ccagctctag ttggaaaatt tgctggtgta aacacagagt | 180 |
| aaatgagaga gcattttgaa tctttgatcc taaaaggtgt tttggagagt tttgtttttt | 240 |
| tcttcttcgt aatcagattt gtattggagc ttgtaatagt taagattgat tgaacatttt | 300 |
| gaatacttga tttactcaag tgtattacct tatttaggga agttgaacaa ggactcaatt | 360 |
| gtatgaatat gtaaaatata ggattttcaa atcctagcaa aaaaggaagg aacatattta | 420 |
| ctcaatttag tgaattaata gaatttcata tactcaatct catatataga tacatagaga | 480 |
| attctggaga aagtcgtatt tgatgaaagt catatgtacg gtttggaagg agatctttca | 540 |
| tatcgttaat aatggttgag attcaatgtg gatatcctag tctagtcctc ttggattgca | 600 |
| agggagttct ctgttagttc tttgagtgtt gtcttgtact agtactttca ggtgcaattt | 660 |
| ctacgtttac ccacaatctt ctctcttgat acattgtctc accaataata tatttcctct | 720 |
| ctactctctt ttgtttacat agtaactcat acaaaaattg taatctttga tagagaaggc | 780 |
| aacccaaacg aattgatctt ggaaagagga attgatccct ttccaagaat agtgtggctt | 840 |
| gctcgacttc aattggtaag tttttacgta agcataattc ataaatatgc cctttaactt | 900 |
| ggcctcattt cacatttatg tcctccaaat ttgagtgtgc acaagtagac acttaaactt | 960 |
| gtataaaatt gaacaagtgt ccatgtgtac tacgtggcac aatacacgta ggacaccacg | 1020 |
| taggatcaat ttccaatgta gggtgtcatg tcaaacgaat gtgtctattt gttcaagtat | 1080 |
| tagatagtta aagtgtctac ttgtgcacta gtaaagttag aggtcatagt tgaccgttga | 1140 |
| agccaagtta aaatcatatt tatgtattat gccttttacg tctattaatt tcatcactaa | 1200 |
| aatcaaattt ttgaacatat ttgtcctttt attatgactt gaaaaggttt taaaatctgt | 1260 |
| tatcttgcaa ttatttgatg taattggaga aactgtgata ataagaaaaa gataaaaatg | 1320 |
| attttgaaaa gaatcaaaga aatttcaaag aaaatttgta ctgaaattta attatattgg | 1380 |
| tccaacttga cacatgatgt ctttattatt caatttgata acagagttta atctctctaa | 1440 |
| caagttggaa tccaatgtat atgaatcaga atctgagac atctctaccc tcgtgatggg | 1500 |
| accaatgttt gaaaagtttt gaggaaaact acaagactct ctttattctt cattataatt | 1560 |
| aggacaactt gactctttat ttttcatttc ttttttctca ctttgacttg gtcaatccat | 1620 |

```
agttctgttt agatgttaaa tagaaaattg tccaaattca ttattagaaa aatgtggaca    1680
taaatcattt agacaaaacc tcctagccta agcagagaca tttctcttcc agcaaacaaa    1740
gagaaatggc ttatgctgct ctttcttcac ttatctatac attggaacaa ctcttgaaac    1800
ctaatcaatc tttcgtttgt cgaagctcta cacaacaaaa tgttgaatca atccatcaaa    1860
atctttgtgc tatgcaactt ttccttgacg atactacgac aaaggatatt gaaactctta    1920
aggtaagtag ttcactagta taattatcta aatcttttac tcatcttgta tatattttgt    1980
aatatttaat ttatcgagtt tcaacttcaa ggttatagaa aagaggatca gagatgtagt    2040
atacaaagca gaagataaag ttgattcaag tctaagaaac atcattctag cagattgcac    2100
agagaatcga gaaggtgctt gtaaattctt cgaggaagaa ttgctaaaag tggaaaaaga    2160
tgttgattca ctcaggaaag aggtgatgca gatcgacttt aacaagcatg gaagcagatc    2220
tggagaacta gcaagaactg gtccctcctc acaagaaaaa agtacaattg aggaaaatac    2280
tattgttggg atggaggatg agtacaaacac catacttgat cgcctcactg cccaaacaga    2340
cgagttaact gtcataacaa ttttggtat gggcggtata ggtaagacaa ctcttgccag    2400
aaaagtttat gatgattcat atattcattc tcgatttgat aaacatgcat ggatcactat    2460
ctctgaagaa tacaatcaga gacaaatgct tcttcaagtt gtctcttcaa ttactactgg    2520
aagcaatgga gaaatgagcg atgatcaact aatggagatt gtgtatagag gtctcaaggg    2580
taggagattt ctgattgtca tagatgatat ttggagtact gaggcttggg accaaatgca    2640
aagaatattt ccaaatgata acaataaaag ccgaattcta ctaaccactc ggctcaagta    2700
tgttgctgat tatgtcagtt gtcctgattt tccatctcat tgcaagtctt ttctaagtct    2760
tgatgatagt tggaatctat tcaccgaaaa agtattcaaa aaagatccct gccctcctca    2820
cctagaagaa acagggaagc acattgtaca acaatgccaa ggattacctc tctcggttgt    2880
tgtcgtcgct ggacttgttg gaaaaatgga cccaacgcat gacaattggg agaacgttga    2940
ggaaaatctg aactcattct ttggtacggt atccgaacgg tgccaatcaa ttctttcttt    3000
gagctacaat tacttgcccc aatatttgag ggcttgtttt ctctacgttg gaggttttcc    3060
tgaagataaa gagattgatg tttccaagtt gattaggcta tggattgctg agcaattcgt    3120
aaaggcgaga agcaataaaa ggttagaagt ggtggcagag gagtatcttg aagagttaat    3180
tgatagaagt ctaattttga ctggtagaca aagggttaat ggaaggatga aaacttgcaa    3240
aattcatgat cttcttcgcc aactatgcct aagtgaagct catactgaaa atattagtca    3300
tatcatgaat agaaatgtcc ccgtgtcctc agaagccatt gaagagaaac aagtttatcc    3360
tacaaggcat agcaggggta tttcaagtaa aacccgcacc tttatttcaa tggaaatatg    3420
cctaagagaa gcccagaccg aagcaatata tgatcaacgg cgagtgatcc ttctgtctaa    3480
acgacatagg attgatacaa tccgcaccat tattccattc ggagatactt ttccaaaaga    3540
gatttgttcc attttttcac agttgaagtt gcttaaggtg ttggatgtat tatcagtctg    3600
gtacgatgtc tcttgtataa tacctcagct tgtacatttg agatatgttg gtgcagtaat    3660
tgaggaagct ctttcactat ccaaattgag aaatctacag accataatgc ttacaagtgt    3720
tgaaaccaca gagttgaagc actcactaga tatctggaga atgtcagaga taagacattt    3780
ggatattgta ccgccattat atatatcaaa tcctcttgaa gcagaacaac ctttgtttct    3840
caataacttg caaacgcttt atctccgttg ctctcctttt gttgcgaaaa tcataagaag    3900
aactcccaat ctaaaaaagc taagatttt agataaatct aagcatcctg actggcctga    3960
tattcttgat tctctcaatc ttctagagga gctggagaca ctacaaatat caacagaaga    4020
```

```
aaacattgac ccgatgattt tctctgggga tattttccct cgtaatctca agcaactgaa   4080
attatcatat acttgtatac catgggaaga tatgaaattg ctggctaatt tacccaatct   4140
tgaggtgttc aagggtcatt atgcattcga tggaacagat tggaaactag atgaagatgt   4200
tgtgttttgc aaattaaaat gtctacgact gtatgagcgt ggagatttgc aaaggtggga   4260
agctgctggt agtgataatt ttccaatgct tgagcaacta ttattgtatg ggttcaaaaa   4320
actggaagag attccggaga gtattggaga ataatgaca ctaaaattta tcaaaacaga   4380
attttgcggc tctggtgtag agacaagtgc aaagaaaatt caagaagagc aagaaagcct   4440
gggaaattat gagcttcaag ttcaaattac tcctaaggta tgttgaaact caatctttga   4500
ttaatactct ccactcggtt agatttagga ttcaaattgt ctacttacat ttatgatcat   4560
catccttgcg gtcttcttat ttcttttagt aaatagcttc aaaaactcta cagaaattac   4620
aaatattaac aattgacaat tgattctctc ttattgataa tttgtaattt tctcttttcag  4680 ttaagatttt tgatcgaaaa tttagacgaa ataagcatgt tgccaccgaa tgaagtagcc   4740
gaaaaaatca aggtttgtc tatttaattc cttttttatt tcattgaaag aggttcagat    4800
atattaaaca acttttttaac cttttctattt gattttttat cgcttagata gatcaaacat  4860 ttatttttagg cataatacat aatttggacc ctaaacttgg cttcaaattt taagtttgac   4920
ctcaaacttt catagtgcac aagtaggcac tttaactatc taacacttca agaaaaaaac   4980
acttaaactt tcatagtgca caagtgccca cgtgttccta cttgtttaag tgttttttttg   5040 ttaaagtgtt ggatagttaa agtgcctatt tgtgcactat gaaaattaaa ggtcaaagtt   5100
aaaatttgaa gccaagttta gggtccaatt tatatattgt gcctttattt taacatcaat   5160
tgttattttg attcaattat gttcttttaa tatatagttt ccactcggtt cttcaattct   5220
tttttcaatt atagttttat tttttttaatt gcacatggta gatcgattta atttgtgaga   5280 ttcactttttc tttcggtttt acgagttctt cgcgattaat gttattcaga tttaggagta   5340
ttatatttca actttcgatt agatttagga ttcaaattgt cttcttacat ttatgatcat   5400
catcctttcg atcttcttta tttcttttag taaatagctt caaaaactct atagaaatta   5460
catataatta acaattgaga attgattctc tcgtaatttc tcatatttct ctttcagtta   5520 aaattttttga tcaaaaacta aaagagattc cggagagtac tggacaaata atgcacgaa   5580 aaatcatcaa aacagaattt tgcggctctg gtgtagagac tagtgcaaag aaaattcaag   5640
aagagcaaga aagcttggga aattgtgagc ttcatcaagt tcaaattact cctaaggtat   5700
attaaaactc catctttgat tttagccaat tctttaattt catattattt ctagactaaa   5760
ttaaaatatt aaaagatata aagaatttaa ttaatttaat tattcctttta aaatccaaac   5820 atgatgaatt tgagtaaatt aaatgaatat agtattcatt taactaatag gccatttagt   5880
tttaatctgg caacgtttta ggcttttaac attctctttg aatgtaggta taatgcatta   5940
agtgcagaaa tttaatcttt atttaaaaaa tgaaaacatc tcataataac tttggtctttt  6000 ttactccaaa catcttgtaa taaagtgagt gtcttctact tctcctaaca tctcataata   6060
aatttctact attcctaaca tctcattata ataagtctt ttctactatt taattttgtt    6120
aaaatattca cattttgtg tcttatatat tctccacccc catctttttt ttgtttactt    6180
tcttaatatt catatgcttg aatcgaaaca aggttctatg aattctaacg cgcttggatt   6240
gatcatgatg caattcaata tatgcatcaa tttagttttt atttaatagt tagtttcaca   6300
agataaatat ttttattttca atatgtattt atcctttaat taaagtacta tatatgtcac   6360
```

| | |
|---|---|
| taaagtagca tcaaatttgc aagaatttct aatctcaatt tatgagtttg ttatatttt | 6420 |
| ttaattgtat tgctttgatt tttattttat aaccaaagag aaagtctaat aatatacgtg | 6480 |
| tcattattta ttttttaaat attttgggat aaacacgaac acacttacaa gttacattaa | 6540 |
| gagtggaaag aatcaagtca aaagtttgtt taccatttt aacgttgaaa aaagcaagcc | 6600 |
| ttcatttaaa tagttattat atttgcttac attagaaaat atattaaaat tcattagctc | 6660 |
| cttaaaattc aatgaatcca ataattaaa cgtttattgc cataatttta tttttatccc | 6720 |
| tttaacttgc taaatggctc cttcactaca tgctttgagg aacagaagcg tttgctgagg | 6780 |
| aagcaggacg gcactgtgta acaataattt gtatggcttc agtgatgaga atattttgtg | 6840 |
| tgccacgcag catagcagtg ttcatctaac tagaaattt ataagaaaag aaaaatcgtc | 6900 |
| cttaatcgtt atttcactca ttaaattgtt tttctttca ttttccatgg taatttgaat | 6960 |
| ttcgaagtgt ggacatggac tgtgtttgga gcataggttc atatttgtgt agtttaaaat | 7020 |
| tgtatgatta ttattttagt tctcttgtca acgtccttat caccttttgca gatagttact | 7080 |
| attgagaatg tatttatatt attagttagt tagttactag tcatgatgat tgtgtgatga | 7140 |
| tcagcttagt tagttagatt agtgaattgg ttacaactgt tagttacagt tagttaggct | 7200 |
| aagtcgctta gtttgttagt gttataaata cacttgtaca gattcatttt cattttgaga | 7260 |
| agttcaattc aatgaaacag ttactctcat cttcctcttc tctcaatatt cacttctcct | 7320 |
| tctttgcaag tttccgccat tgaagctcca aagcttggga gctgatttca agttcttgtt | 7380 |
| cttgacatgg taattcacta caattacgcc tctggcaaag atgcgacgat atggttgttt | 7440 |
| gcaacaaatt ttaataaat agaaaataga tcaaccataa ataaaatatg aagaaacagt | 7500 |
| aatattttat tgataaatat gcgggtacaa gatctattcc tcccttgatt cttctctcct | 7560 |
| aaattttctc cttgattcga gggccgttag tggcgtattt ctcgaattag gatgatttaa | 7620 |
| acttgatctt cattgtgatt cgagggccgt tagtggcata tttctcgaat ccatgaaaga | 7680 |
| atttgtggat cttcttgaaa tatttgatta tcaagaagac aagaagaatt taacatattt | 7740 |
| tgatctcttt ctgagatgtc ttttcaaggg a | 7771 |

<210> SEQ ID NO 34
<211> LENGTH: 9596
<212> TYPE: DNA
<213> ORGANISM: Solanum americanum

<400> SEQUENCE: 34

| | |
|---|---|
| ttatatgggt aaaaatgggt tgggtaaaaa atggattggg taaaatacta gtttacccat | 60 |
| atttacccat attttcatga gtaataatac tctacttcat aattcaatat ggagaaacat | 120 |
| tatagtcttt tttgaatgaa aaagttgta agggtgatat catgaatgaa taaaagttgg | 180 |
| aagcttaact catttggcta cctcatatag tttacccata ttttaccca tgaatactca | 240 |
| tatttctatg ggttgaatat gggtataaac ccatatttta cccatctaaa aaatcactca | 300 |
| ccaacccatt aaaatatgaa cagattgggc gggttaccaa aatatgggct cttttgcca | 360 |
| ccactaacaa caacaaagag caaagcaaag cacaactttg aaatttgaaa atgatgcaa | 420 |
| gacaaatatc aaaattagac agtaaaattc acaattcccc ttaaaataaa tgataaatta | 480 |
| aagaagacta acaatagaa aaccttacaa tctcaaaggc actatggatc ggagtcgtac | 540 |
| ctgtgtgttt tttatcgtac aatattccac acagtattat taattttta aggaccattt | 600 |
| ggccatgtga tatgaaatta tgagatgaag ttgaagtttt atttggacat gcaatttgaa | 660 |
| ttttttatgt tgtatgttt cttataaaca taaaaaaccc ataagttgta aaattattaa | 720 |

```
acttgtctca ttttttatt caattttacc aaataaataa aaatttacaa aatcacataa      780
tatgctaaca caaaactatt ctttaaaaaa tacaatattt attgatcaaa ctttaattca      840
acaaaaaata aaattcaaca taagttgtag tgtactagtc tttaatataa ttctcccaca      900
tagtacggac aatctcctca cattgaactt gcatttctcg atcatatgat cgagtagaca      960
aaccaacatt gctactttga gctataaatg gtttaaaaag taatgatatg aattataaat     1020
tttatttaca tatgaaacaa atggtaagta gatataaatg tggggttgtt tttataaaat     1080
ataaacttat gggtcaattt ttgtatttga aaaatctcaa atcatgattt gaaatttta      1140 aatcatgatt tttgaagaat ttgggatttc atctcatgat atgaaatcat gagatgaaat     1200
cagtctgaaa ttgcatgtcc aaatgctgat ttcatctcat gatttcatat cgtgatatga     1260
aataaatcgt gatatgaaat cgcatgtcca aacgtctact aaataactta gacatgtctt     1320
gaccttttat aattactccc tccgtcctaa tttacttgtc aaatattttc taatttgatt     1380 cccctttac ttgtcatttt ttacaaatca agaaacgaca atttttttt cttcctatta     1440 taccctcaat ttattaacat tgaattaatg tccttgaaaa atatagaaag taaatatgtt     1500
taaaactcta tcaaattaat agggataaaa tggtaaattc attataccaa ttattatttt     1560
cttaatagat gcgtcaaatc aaaaattgac aaataaaaaa agacgaaaga aaatttgtat     1620
tgaaagttaa ttgtattcgt ccacttgaca catcatgtct taattattca acaagtttga     1680
atccaatgta tatgaatcat aaatgtgaga catctctact atcgtggtgg ggccaatgtt     1740 tgaaagtgt tgacgaaaac tacaagagtg tctttattag aaatcaggac aacttgactc     1800
tttatttttc atttctttt tcttactttg acttggtcaa tccatagttt tgcatccata     1860
aaccacaagt tctgtttaga tattaaatag aaaattgtcc aaattcattt agaaaaatgt     1920
ggacataaat catttagaca aaacctctta gcctaagcag agacatttct cttccagcaa     1980
acaaaagaga aatggcatat gctgctcttt cttcacttat ctatacattg caacaactct     2040
tgaaacctaa tcaatctttg gtttgtcgaa gctgtacaca acaacatctt caatctatct     2100
atcacaatct ttctgctctg caacttttcc ttgacgatac tacgacaaag gatattgaaa     2160
ctcttaaggt atgtaattat ctaatctctt actcatctta tatttattca ataataatta     2220
atttatcgag tttcaattt aaggttatag aaaagaggat cagagatgta gtatacaaag     2280
cagaagatac agttgattca agcctaagaa acatcattct agcagattgc acagagaata     2340 gagaagggc ttgtaaattc tttgaggaag aattgctaaa agtggaaaaa gatgttgatt     2400
ctctcagcaa agaggtgatg cagatcgact ttaacaagca tggaagcaga tctgcagaat     2460
tagcaacaac tgatccctcc tcatcaggaa aaagtacaat tgaggaacat actattgttg     2520
ggatggagga tgagtacaac accatacttg atcgcctcac tgcccaaaca gacgagttga     2580
ctgtcatacc aattttttggt atgggcggta taggtaagac aactcttgcc agaaaggttt     2640
atgatgattc atctattcgt tctcgatttg atagacatgc atgggtcact acctctgaag     2700
aattcaatga gagacgaatg cttctcgaag ttgtttcttc aattactact ggaagcaatc     2760
aaggaaagag cgatgatcaa ctaatggaga ttgtgtatag aagtctgaag ggtaggagat     2820
ttctaattgt catagatgat atttggagta ctcaggcttg ggaccaaatg caaagaatat     2880
ttccaaatga tgacaataaa agccgaattc tactaactac acggctcaag tatgttgctg     2940
attatgtcag cagtcctgat tttccacctc atagtaagtc ttttctaagt cttgatgata     3000
gttggaatct attcaccgaa aaagtattca acgaagatac ctgtcctcct cacctagaag     3060
```

```
aaacagggaa gcatattgta caacaatgtc aaggattacc tctctcggtt gttgtcgttg    3120
ctggacttgt tggaaaaatg gacccaacgc atgacaattg ggagaatgtt gaggaaaatc    3180
tgaactcatt ctttggtact gtatccgaac ggtgccactc aattctttct ttgagctaca    3240
attacttgcc ccaatatttg agggcttgtt ttctctatgt tggaggtttt cctgaagata    3300
aagagattga tgtttccaag ttgattaggc tatggattgc tgagcaattc gtaaaggcga    3360
gaagcaataa aaggctagaa gtggtggcag aggagtatct ggaagagtta attgatagaa    3420
gtctaatttt gagtggtaga caaagggcta atggaaggat gaaaacttgc aaaattcatg    3480
atcttcttcg ccaactatgc ctaagtgaag ctcatactga aaatattagt catatcatga    3540
atagaaatgt ccccgtgtcc tcagaagcca tagatgatca acggcgagtg attgttccat    3600
tggaactcga agagaaacaa gtttatccta caaggcatag cagtggtatt acaagtacaa    3660
cccgcacctt tatttcaatg gaaatatgcc taagagaagc tcaaaccgaa gccatatatg    3720
atcaacggcg agtgatcctt ctgtctaaac gacataggat tgatacaatc cgcaccatta    3780
ttccattcgg agatactttt ccaaaagaga tttgttccat tttttcagag ttcaagttgc    3840
ttaaggtgtt ggatgtatta tcagtctggt acgatgtctc ttgtataata cctcagcttg    3900
tacatttgag atatgttggt gcagtaattt tggaagctct ttcactaccc aaattgagaa    3960
atctacagac cataatgctt acaagtgttg aaaccacaga gttgaagcac tcactagata    4020
tctggagaat gtcagagata agacatttgg atattgtacc gccactatat atcaaaatc    4080 ctcttgaagc agaacaacct ttgtttctca ataacttgca cacgcttttt ctccgttgct    4140 ctcctttgt tgcgaaaatc ataagaagaa ctccgaatct aaaaaagcta agatttttag    4200
ataaatctaa gcatcctgac tggcctgata ttcttgattc tctcaatctt ctagaggagc    4260
tggagacact acaaatatca acagaagaaa acattgaccg gatgattttc tctgggata    4320 atttccctcg taatctcaag caactgaaat tatcaggtac taaaatacca tgggaagata    4380
tgaaattgct ggctaattta cccaatcttg aggtgttcaa gggtcattat gcattcgatg    4440
gaacagattg gaaactagat gaagatgttg tgttttgcaa attaaaatgt ctacgactgt    4500
atgagcgcgg agatctgcaa aggtgggaag cagcaggtag tgataatttt cctatgcttg    4560
agcaactagt actgtatggg ttcgaaaaac tggaagagat tccggagagt attggagaaa    4620
taatgacact aaaattcatc aaaacagaat tttgcggctc tggtgtagag acaagtgcaa    4680
agaaaattca agaagagcaa gaaagctggg gaaattatga gcttcaactt ctaattactc    4740
ctatggtatg ttaaaactcc atctttgata attagactca actatcaact tttttcacag    4800
agagtcaatt ctttcacaag aagtcactca actatcaatt tttttcacaa aaagtcactc    4860
aactttgatt ctttcataga aagttactca actatgggct ttttgcatag aaaaccactc    4920
aacctattta attatatttt tcatatgaaa tttttatttc taatcaaaat tttaaaatcc    4980
aaatatatat ccatttaaac catttaatga atcacccaca ctaaatccga tccgctaaaa    5040
atataatatt taccttttgt tttatcctta ttcccctaaa tattctctcc tgtttcctaa    5100
atattctctc ctgtttcctg attctttctc ttctgcgttt tccccctcaa tttcagtctc    5160 ttctttacg tatatatcaa cctctctttc tccataagca tcatattatt gttttctcaa    5220
cttcaaaaac aatataaatt acaacaatct cttgatttac aatttcaata aaaaattcta    5280
tgcacaccat gctttttatca attattatga aaactgataa aattaacaaa caaggctctc    5340
aatctgcata actacgaatc tacgcctata gttgctcttt aattgcaatt attcattcaa    5400
taaaatcaag tgatcaggat agtcctaaat ctagatatag tttgagaaat cgatggaaaa    5460
```

```
ttcctagtta atagagattt taaaattgag aaattaaaaa aaatgcagtg aatcaggaga    5520
cgggagagaa tatttaggga gataaggata aaacaaaagt caatattata tttttagcgg    5580
atcgaattta gtggggtgat tcattaaatg gtttaaatgg aaatatattt agattttaaa    5640
attttgatta aaaataaaaa tttcatatga aaaatataat taaataggtt gagtgacttt    5700
ctatgcaaaa gccccatagt tgagtgactt tctgtgaaaa aaattgatag ttgagtgact    5760
ttctgtgaaa gtatcaaagt tgagtgactt tctgtgaaag aatttgatag ttgagtgacc    5820
atcaaagata ttaactcggt gaattgctag attgttttgg acaaattttg tgtcgctata    5880
ttactaattt catatttgtt ttcacatgct agattcctaa catctcatta taaataaatc    5940
ttttctacta tttaatttgg ttaaaatatt cacaattctt gggtcttctt ctccacccca    6000
tctttttttt ttgtttactt tcttaatatt catatgtttg aatcaaaaca aggttctatg    6060
acttctaacg tgtttggatt gatcatgatg cgattcaata tatgcatcaa tttaattttt    6120 attttttccta cataatagtt aattatattt cacaagataa atattcttat ttcaatattt    6180
atttatctgt aaattaaagt attatatatg tcaccaaaat agcatcaaat ttgcaagaat    6240
ttctagtctc aatttatgag tttttttttat ttttttttatt gtattgcttt gattttttatt    6300 ttaataacac tgagaaagtc ttataatata cgtgtcattt aaaatttatc atttgtaata    6360
taaaatttat tttaagtatt ttgtgataaa catgcaacac acgtactggt ctatatctat    6420
ctatattata tttaaagtgt tgtttgaatt ttttattctt cattaaaagg cttttcttta    6480
gacaatacca tcatttacta ttttcttaaa tacttgtctt ttaattatta tcctaatatt    6540
taagacttta aattgattaa agttgtaact attaaaactt tacttatttta taataggtaa    6600 gaactaatat ttagtaattt aaatttttttt acttcttaca tctttcctta ttttcttatt    6660
tgaacttatg aaaagaaag tatttttttt tgtcataagt catacctgtc gtgtgtgttt    6720
ttttgtagtt aaatactact tttgttttttg aacttaggat tcactttagg tttttttatac    6780 cattaatact ctcccccagc tagactttcc aaagtaatat ttcacacgta caatctccac    6840
tcggttcttc aattcttttt tctattatag tttaattttt tttaattgca catggttgat    6900
cgatttaatt tgtgggattc acttttcttt cggttttaga agttcttcgc gatgaatgtt    6960
attcagatat aggagtgtta tatttcaact ttcgattaga tttaggattc aaattatctt    7020
cttacattta tgatcgtcac cctttcggta ttctttatt tttttttagt aaatagcttc    7080
aaaaactcta caaaaattac acataattaa caattgacaa ttgattctct cttattgata    7140
atttgtaatt ttctctttca gttaagattt ttgatcgaaa atttagacga aataagcatg    7200
ttgccaccgg atgaagtagc cgaaaaaatc aaaggtttgt ctatttaatt ccttttttat    7260
ttcattgaaa gaggttcaga tattttaaac aacttttttaa cctttctatt tgaattttttt    7320 atcgctaaga tagatacaac atttatttta acatcaaatg ttattttgat ttaattttgt    7380 tcttttttata tatatagttt ccactcggtt cttcaattct ttttcaatta tagtttttttt    7440 ttttaattgc acatatggtt gatcgattta atttgtgaga ttcacttttc ttttggtttt    7500
aggagttctt cgcgattaat gttattcaga tttaggagta ttatatttca actttcggtt    7560
agatttagga ttcaaattgt cttcttacat ttatgatcat catccttttg atgttatttta    7620 tttctttttag taaatagctt caaaaactct atagaaatta catataatta acaattgaca    7680
attgattctc tcttattgat aatttctcat gtttctcttt cagttaaaat ttttgatcga    7740
aaactaaaag agattctgga gagtactgga caaataatga cacgaaaaat cattaaaacg    7800
```

```
gaattttgca gctctggtgt agagactagt gcaaagaaaa ttcaagagca agaaagcttg      7860
ggaaattatg agcttcaagt tcaaattact cctagggtat gttaaactcc ttctttgatt      7920
attagccaat tctttaattt cataatattt ctagactaag agcctgtctg gatggactta      7980
aaaaagtaa cttataagtt gaaaactgtt tataagtcaa aaaaaaaaat aagtaggtct      8040
accctaactt atttttttt gatttataag ttgttttcaa cttttaagct gttttaaata      8100
agctaagtca aatagaccca attatttttt gggcttattt taagcataaa atgactttaa      8160
gttggccagc caaatactaa aaaaagctaa aaacaactta aagttactt ttaagccaat      8220
ccaaacgggc tctaaattaa aatattaaaa tatataaaga atttaattaa tttaattatt      8280
cctttgaaat ccaaacatga tgaatttgag taaattaaat gaaatatagt tcagattcat      8340
ttaactaata ggtcatttac ttttaatctg gcaacgtttt aggcttttag cattctcttt      8400
gaatgtaggt ataatgcatt aagtgtagaa atttaatttt tatttaaaaa atgaaaacat      8460
ctcataataa ctttggtctt tttactccaa acatcttata ataaagtgag tctcttctac      8520
ttctcctaac atctcataat aaattctac tattcctaac atctcataat aaataagtct      8580
tttctactat ttaattttgt taaaatattc acatttttg tgtcttattc tccacccca      8640
tctttttttt gtttactttc ttaatattca tatgcttgaa tcgaaacaag gttctatgaa      8700
ttctaacgcg cttggattga ttatgatgcg attcaatata tgcatgaatt tagtttttat      8760
ttttcatgca taataattag tttcacaaga taaatatttt tatttcaata tgtatttatc      8820
ctttaattaa agtactatat atgtcactaa agtagcatca aatttgcaag aatttctaat      8880
ctcaatttat gagtttgtta tatttttttt tattgtattg ctttgatttt tatttttataa      8940
ccaaagagaa agtctaataa tatacgtatt ttgggataaa catgcgacac acgtttaagt      9000
tacattataa gtaagaagaa tcaagtcaaa agtttgttta tcattttaa cgttgaaaaa      9060
agcaagcctt catttaaata gttattatat tgcttacatt agaaaatata ttaaaattca      9120
ttagctcctt aaaattcaat gaatccaaat aattaaacgt ttattgccat aattttattt      9180
ttatctcttt aacttgctaa atggctcctt cactacatgc tttgaggaac agaagcgttt      9240
gctgaggaag caggacggca ctgtgtaaca ataatttgta tggcttcagt gatgagaata      9300
ttttgtgtgc cacgcagcat agcagtgttc atctaactag aaattttata agaaaagaaa      9360
aatcgtcctt aatcgttatt tcactcatta aattgttttt tctttcattt tccatggtaa      9420
tttgaatttc gaagtgtgga catggactgt gtttggagca taggttcata tttgtgtagt      9480
ttgaaattgt atgattatta ttttagttct cttgtcaacg tccttgtcac ctttgcagat      9540
agttactatt gagaatgtat ttatactatt agttagttag ttactagtca tgatga         9596
```

<210> SEQ ID NO 35
<211> LENGTH: 8441
<212> TYPE: DNA
<213> ORGANISM: Solanum americanum

<400> SEQUENCE: 35

```
tgaacactct gtgggtctca gcaagctgag gccttaatct ttgtaaacga taatggcatg        60
ggtgaactca attttttttt tttttttttt tttaaattg ggggtagggg aaggggaaat      120
ggggagggg attacaatgt ggggtcctca ccaacaaggt gggagttcag gtagtcaacc       180
aactaagcta ctaagattcc ccgaactcaa tatttaacga atgtcataaa tgaatttttt       240
ttcaaagttt gattacctat atatttaagt ttttttcttt ttatttaatt ttttattcga       300
tgttcaatat ccacaaccaa atttccacta caaccaaaaa aaaaaaaaga aggctgtgta       360
```

```
acatcatctc caaccaacct gggtcatatg agtcccaaat gcatttacag caacaaagag    420
caaagcaaag cacaactttg aaatttgaaa aatgatgcaa gacaaatatc aaattagaca    480
gtaaaattca caattccctt aaaataaata ataaattaaa gaaaacctta caatgtcaaa    540
agcactatgg atcggagtcg tatttggaag aaatttttgat acaacttgaa gaagattgaa    600
gattgctgtt cataaagtag actgtgggcg ggttaatcta caacctgtgt gttttttatg    660
tacaaaattc cacactagta ttattaattt tttaagtaac ttcgacacgt cttgaccttt    720
tataattact ccctccgtcc taatttactt gtcaaatttt ttttaatttg attccccttt    780
tacttttcat tttttaaaaa tcaagaaacg ataattttt ttcttcctat tataccatca    840
atttattaac attgaattaa tgttcttgaa aaatatagta agtaaatatg tttaaaactc    900
tatcaaatta atagggtaa aatgataaac tcatcctatc aattattatt ttcttaatag    960
atgcgtcaaa tcaaaaattg acaagtaaaa agagatggaa agagtatata aatttcaaag    1020
aaaatttgta ttgaaagtta attgtattcg tccacttgac acatcatgtc ttaattattc    1080
aacaagtttg aatccaatgt atatgaatca gaaatgtgag acatctctac taatcgtggt    1140
ggggccaatg tttgaaaagt cttgacgaaa actacaagag tgtctttatt agaaatcagg    1200
acaacttgac tctttatttt tcatttcttt tttcttactt tttcttggtc aatccatagt    1260
tttgcatcca taaccacaa gttctgttta gatattaaat agaaaattgt ccaaattcat    1320
ttagaaaaat gtggacataa atcatttaga caaaacctct tatagcctaa gcagagacat    1380
ttctcttcca gcaaacaaaa cagaaatggc ttatgctgct cttttcttcac ttatctatac    1440 attgcaacaa ctcttgaaac ctaatcaatc tttggtttgt cgaagctcta cacaacaaca    1500
tcttcaatct atctatcaca atctttctgc tctgcaactt ttccttgacg atactacgac    1560
aaaggatatt gaaactctta aggtatgtaa ttatgtaatc tcttactcat cttatatta    1620 ttaaataata attaatttat cgagtttcaa ttttaaggtt atagaaaaga ggatcagaga    1680
tgtagtatac aaagcagaag ataaagttga ttcaagccta agaaacatca ttctagctga    1740
ttgcacagag aatagagaag cggcttgtaa attctttgag gaagaattgc taaaagtgga    1800
aaaagatgtt cattctctca ggaaagaggt gatgcagatc gagtttaaca agcatggtag    1860
cagatctgca gaactaacaa caattcttcc ctcgccagaa aaaagtacaa ttgaggaaca    1920
tactattgtt gggatggagg atgagtacaa caccatactt gatcgcctca ctgcccaaac    1980
agacgagtta actgtcatac caatatttgg tatgggcggt ataggtaaga caactcttgc    2040
cagaaaggtt tatgatgatt catctattcg ttctcgattt gatagacatg tatgggtcac    2100
tacctctgaa gaattcaatg agagacgaat gcttctcgaa gttgtttctt caattactac    2160
tggaagcaat caagaaaaga gcgatgatca actaatggag attgtgtata gaggtcttaa    2220
gggtaggaga tttctaattg tcatagatga tatttggagt actcaggctt gggaccaaat    2280
gcaaagaata tttccaaatg atgacaataa aagcagaatt ctactaacta cacggctcaa    2340
gtatgttgct gattatgtca acagtcctga ttttccacct catagtaagt cttttctaag    2400
tcttgatgat agttggaatc tattcaccga aaaagtattc aacaaagata cctgtcctcc    2460
tcacctagaa gaaacaggga agcatattgt acaacaatgt cgaggattac ctctctcggt    2520
tgttgtagtt gctggacttg ttggaaaaat ggacccaacg catgacaatt gggagaacgt    2580
tgaggaaaat ctgaactcat tcattggtac tgtatcggaa cggtgccaat caattctttc    2640
tttaagctac aattacttgc cccagtattt gagggcttgt tttctctatg ttggatgttt    2700
```

```
tcctgaagat aaagagattg atgtttccaa gttgattagg ctatggattg ctgagcaatt     2760
cgtaaaggcg agaagcaata aaaatttaga agtggtggca gaggagtatc tggaagagtt     2820
aattgataga agtctaatatt tgagtggtag acaaagggct aatggaagga tgaaaacttg    2880
taaaattcat gatcttcttc gccaactatg cctaagtgaa gctcatactg aaaatattag     2940
tcatatcatg aatagaaatg tcctcgtgtc ctcagaagcc atagatgatc aacggcgagt    3000
gattgttcca ttggaactcg aagagaaaca agtttatccg acaaggcata gcagtggtat    3060
tacaagtaca acccgcacct ttatttcaat ggaaatatgc ctaagagaag ctcagaccga    3120
aaccatatat gatcaacggc gagtgatcct tctctctaaa cgacatagga ttgatacaat    3180
ccgcaccatt attccattcg gagatacttt tccaaaagtg atttgttcca ttttttcgca    3240
gttgaagttg cttaaggtgt tggatgtatt atcagtctgg tacgatgtct cttgtataat    3300
acctcagctt gtacatttga gatatgttgg tgcagtaatt ttggaagctg tttcactatc    3360
caaattgaga aatctacaga ccataattct tgcaagtgtt gaaaccacag agttgaagca    3420
cccagtagat atctggagaa tgtcagagat cagacatttg gatattgtac cgccactata    3480
tatatcaaat cctcttgaag cagaacaacc tttgtttctc aataacttgc acacgctttt    3540
tctccgttgc tctccttttg ttgcgaaaat cataagaaga actcccaatc taaaaaagct    3600
aaagatttta gataaatcta agcatcctga ctggcctgat attcttgatt ctctcaatct    3660
tctagaggag ctggagacac tacaaatatc aacagaagaa aacattgacc ggatgatttt    3720
ctctggggat attttccctc gtaatctcaa gcaactgaaa ttatcatata cttgtatacc    3780
atgggaagat atgaaattgc tggctaattt acccaatctt gaggtgttca agggtcatta    3840
tgcattcgat ggaacagatt ggaaactaga tgaagatgtt gtgttttgca aattaaaatg    3900
tctacgactg tatgagcgcg gagatctgca aaggtgggaa gctgctggta gtgataattt    3960
tccaatgctt gagcaactat tactgtatgg attcaaaaag ctggaagaga ttccggagag    4020
tattggagaa ataatgacac taaaattcat taaaacagaa ttttgcggct ctggtgtaga    4080
gactagtgca aagaaaattc aacaagagca agaaagcttg ggaaattatg agcttcaact    4140
tcaaattact cctaaggtat gttgaaactc aatctttgat taatactctc ccccagctag    4200
acttttcaaa gtaatatttc acacgtacaa tctccactcg gtaagattta ggattgaaat    4260
tgtcttctta catttatgat catcacccct cggtttttt  tattttttt  tagtaaatag     4320 cttcatatac tctacaaaag ttacacataa ttaacaattg acaattgatt ctctcttatt    4380 gataaatttgt catttctct  ttcagttaag atttttgatc gaaatttag acgaaacaag    4440 catgttgcca tcgaatgaag taatcgaaaa aatcaaaggt tgtctattt  aattcctttt     4500 attacttctt tgaaagaggt tcagatattt taaacaactt tttaaccttt ctatttgaat    4560
tttttatcgc tcagatagat acaacattta ttttgacgtc aaattgttat tttgatttaa    4620
tcttattctt tttgtatata gtttccactc agttcttcat ttttttttc aattatagtt     4680 taattttttt taattgcaca tggttgattg atttaatttg tgagattcac tttttctttcg    4740 attttaggag ttcttcgcga ttaatgttat tcagatttag gagtattata tttcaacttt    4800
cggttagatt taggattcaa attgtcttct tacatttatg atcatcatcc ttttgatgtt    4860
atttatttct tttagtaaat agcttcaaaa actctataga aattacatat aattaacaat    4920
tgacaattga ttctctctta ttgataattt ttcatgtttt tctttcagtt aaaattttg     4980 atcgaaaact aaaagagatt ccggagagta ctggacaaat aatgacacga aaatcatca    5040 aaacagaatt ttgcagctct ggtgtagaga ctagtgcaaa gaaaattcaa gaagagcaag    5100
```

```
aaagcttggg aaattatgag cttcaagttc aaattactcc tagggtatgt taaactcttc    5160
tttgattatt agccaattct ttaatttcat aatatttcta gactaagagc ctgtctggat    5220
ggacttaaaa aaagtaactt ataaattgaa aactgtttat aagtcaaaaa aaataagtag    5280
gtctacccta acttatttt tttgacttat aagttgtttt caacttttaa gctgttttaa    5340
ataagctaag tcaaatagac ccaattattt ttgggctta ttttaagcac aaaatgactt    5400
taagttggcc agccaaatac taaaaaaagc taaaaacacc ttataagtta cttttaagcc    5460
aatccaaacg ggctctaaat taaaatatta aagatataa agaatttaat taatttaatt    5520
attcctttga aatccaaaca tgatgaattt gagtaaatta aatgaaatat agttcagatt    5580
catttaacta ataggtcatt tactttaat ccggcaacgt tttaggcttt tagcattctc    5640
tttgaatgta ggtataatgc attaagtgca gaaatttaat ttttatttaa aaaatgaaaa    5700
catctcataa taactttggt cttttactc caaacatctt ataataaagt gagtctcttc    5760
tacttctcct aacatctcat aataaatttc tactattcct aacatctcat aataaataag    5820
tcttttctac tatttaattt tgttaaaata ttcacaattt ttgtgtctta ttctccaccc    5880
ccatcttttt tttttactt tcttaatatt catatgcttg aatcaaaaca aggttctatg    5940
aattctaacg cgcttggatt gatcatgatg caattcaata tatgcatcaa tttaattttt    6000 attttttcatg cataatagtt agtttcacaa gataaatatt tttatttcaa tatgtattta    6060
tcctttaatt aaagtactat atatgtcact aaagtagcat caaatttgca agaatttcta    6120
atcttttttt ttttccaaat ttataccact agacaagtgt ctagcagcct tttattaaaa    6180
gataaaaaac ctcacggaca agtacaagca agggggggcta ggccttacct taccaatcct    6240
aatgaattaa cgaacttcta ctaattaaca aacatggaga aaataagagc tagagaggac    6300
tagatatttt atgatcatca cagagtttgt aatacactct atgatgatat tacaactgag    6360
gatgcttaga taatgcaaaa atataaaagc caagaagaaa gttgagtttt caaactcaag    6420 cttccttta caaatgtata aactaaaaaa gagagattgc caatctgttg taacctgaag    6480
tattgtcctc ttgtcttctt cttcaaatct atccaacaac aattgatagt tcatcatttc    6540
ttcttggatt tattggatct tgttgaatct attgacactg tcatatgatt ctgctttgcc    6600
agtcgcattg gtaggtgtct tggaataaac tccccagtca ctttaccatc ccaactacgt    6660
tgccttccat gtgtcttctt tttattttg ttgcttccac ttctttgttg cctaggtgag    6720
atatctccat ccctagccac tttatcaaag catatgtcta acatattgtc ttcctcgtcc    6780
tctgaaagaa aatccttgtc tatatcaata gcatacacac tatttgaact aagtcctgcc    6840
gctaaggtcc ctgactcatt cttctttgca atcacaaatt cttttttgtcc caaatgccct    6900 tgagctagtt gttcccctag agaattcatc aattcttgtc cttttttcatt actcttaggc    6960 acaaaaattg gggcattatg gttgagatta ctgcccgaaa tttgtgagct attatcctgt    7020 aatcttctc ttccgctatc atcattttga tattcttcat cttcagcctg ttctgcccat    7080
gtcttggact tggacgaaac cacatcaatt acctgaatta agtcattatt tagttatatt    7140
ttcaatttat gagtctaatc tcaatttatg agtttgttat attttttta ttgtattgct    7200 ttgatttta ttttataacc aaagagaaag tctaataata tacgtgtcat tatttatttt    7260
ttaagtattt tgggataaac acgaacacac gtacaagtta cattaaaagt ggaaagaatc    7320
aagtcaaaag tttgtttacc attttaacg ttgaaaaag caagccttca tttaaatagt    7380
tattatattg cttacattag aaaatatatt aaaattcatt agctccttaa aattcaatga    7440
```

-continued

```
atccaaataa ttaaacgttt attgccataa ttttattttt atctctttaa cttgctaaat    7500
ggctccttca ctacatgctt tgaggtacag aagcgtttgc tgaggaagca ggacggcact    7560
gtgtaacaat aatttgtatg gcttcagtga tgagaatatt ttgtgtgcca cgcagcatag    7620
cagtgttcat ctaactataa attttataag aaaagaaaaa tcgtccttaa tcgttatttc    7680
actcattaaa ttgttttttc tttcattttc catggtaatt tgaatttcga agtgtggaca    7740
tggactgtgt ttggagcata ggttcatatt tgtgtagttt aaaattgtat gattattatt    7800
ttagttctct tgtcaacgtc cttatcacct ttgcagatag ttactattga gaatgtattt    7860
atactattag ttagttagtt actagtcatg atgattgtgt gatgatcagc ttagttagtt    7920
agattagtga attggttaca gctgttagtt acagttagtt aggctaagtc gcttagttta    7980
ttagtgttat aaatacactt gtacagattc attttcattt tgagaagttc aattcaatga    8040
aacagttact ctcatcttcc tcttctctca atattcactt ctccttcttt gcaagtttcc    8100
gccattgaag ctccaaagct tgggagctga tttcaagttc ttgttcttga catggtaatt    8160
caccacaatt acgcctctgg caaagatgcg acgatatggt tgtttgcaac aaattttaaa    8220
taaatggaaa atagatcaac cataaataaa atatgaagaa acaataatat tttcttcata    8280
ttttattgat aaatatgcgg gtacaagatc tgttcctccc ttgattcttc tctcctaaat    8340
tttctccgtg attcgagggc tgttagtggc gtatttctcg aattaggatg atttaaacat    8400
taaacctcag cttacagaga ccatgggaca cgaagtgatc c                        8441
```

<210> SEQ ID NO 36
<211> LENGTH: 2958
<212> TYPE: DNA
<213> ORGANISM: Solanum americanum

<400> SEQUENCE: 36

```
atggcatatg ctgctctttc ttcacttatc tatacattgc aacaactctt gaaacctaat      60
caatctttgg tttgtcgaag ctgtacacaa caacatcttc aatctatcta tcacaatctt     120
tctgctctgc aacttttcct tgacgatact acgacaaagg atattgaaac tcttaaggtt     180
atagaaaaga ggatcagaga tgtagtatac aaagcagaag ataaagttga ttcaagccta     240
agaaacatca tactagcaga ttgcacagag aatagagaag gggcttgtaa attctttgag     300
gaagaattgc taaagtggaa aaagatgtt gattctctca ggaaagaggt gatgcagatc     360
gagtttaaca agcatggtag cagatctgca gaactaacaa caattcttcc ctctccagaa     420
aaaagtacaa ttgaggaaca tactattgtt gggatggagg atgagtacaa caccatactt     480
gatcgcctca ctgcccaaac agacgagttg actgtcatac cattttttgg tatgggcggt     540
ataggtaaga caactctagc cagaaaggtt tatgatgatt catctattcg ttctcgatt    600 gatagacatg tatgggtcac tacctctgaa gaattcaatg agagacgaat gcttctcgaa     660
gttgtttctt caattactac tggaagcaat caagaaaaga gcgatgatca actaatggag     720
attgtgtata gaggtcttaa gggtaggaga tttctaattg tcatagatga tatttggagt     780
actcaggctt gggaccaaat gcaaagaata tttccaaatg atgacaataa agcagaatt     840 ctactaacta cacggctcaa gtatgttgct gattatgtca acagtcctga ttttccacct     900
catagtaagt cttttctaag tcttgatgat agttggaatc tattcaccga aaagtattc     960 aacaaagata cctgtcctcc tcacctagaa gaaacaggga agcatattgt acaacaatgt    1020
cgaggattac ctctctcggt tgttgtagtt gctggacttg ttggaaaaat ggacccaacg    1080
catgacaatt gggagaacgt tgaggaaaat ctgaactcat tcattggtac tgtatctgaa    1140
```

```
cggtgccaat caattctttc tttaagctac aattacttgc cccagtattt gagggcttgt    1200
tttctctatg ttggatgttt tcctgaagat aaagagattg atgtttccaa gttgattagg    1260
ctatggattg ctgagcaatt cgtaaaggcg agaagcaata aaatttaga agtggtggca    1320 gaggagtatc tggaagagtt aattgataga agtctaattt tgagtggtag acaaagggct    1380
aatggaagga tgaaaacttg taaaattcat gatcttcttc gccaactatg cctaagtgaa    1440
gctcatactg aaaatattag tcatatcatg aatagaaatg tcctcgtgtc ctcagaagcc    1500
atagatgatc aatggcgagt gattgttcca ttggaactcg aagagaaaca agtttatccg    1560
acaaggcata gcagtggtat tacaagtaca acccgcacct ttatttcaat ggaaatatgc    1620
ctaagagaag ctcagaccga aaccatatat gatcaacggc gagtgatcct tctctctaaa    1680
cgacatagga ttgatacaat ccgcaccatt attccattcg agatactttt ccaaaagtg    1740 atttgttcca ttttttcgca gttgaagttg cttaaggtgt tggatgtatt atcagtctgg    1800
tacgatgtct cttgtataat acctcagctt gtacatttga gatatgttgg tgcagtaatt    1860
ttggaagctg tttcactatc caaattgaga atctacaga ccataattct tgcaagtgtt    1920
gaaaccacag agttgaagca cccagtagat atctggagaa tgtcagagat cagacatttg    1980
gatattgtac cgccactata tatcaaat cctcttgaag cagaacaacc tttgtttctc    2040
aataacttgc acacgctttt tctccgttgc tctcctttg ttgcgaaaat cataagaaga    2100
actcccaatc taaaaaagct aaagattta gataaatcta agcatcctga ctggcctgat    2160
attcttgatt ctctcaatct tctagaggag ctggagacac tacaaatatc aacagaagaa    2220
aacattgacc ggatgatttt ctctggggat attttccctc gtaatctcaa gcaactgaaa    2280
ttatcatata cttgtatacc atgggaagat atgaaattgc tggctaattt acccaatctt    2340
gaggtgttca agggtcatta tgcattcgat ggaacagatt ggaaactaga tgaagatgtt    2400
gtgttttgca aattaaaatg tctacgactg tatgagcgcg gagatctgca aaggtgggaa    2460
gctgctggta gtgataattt tccaatgctt gagcaactat tactgtatgg attcaaaaag    2520
ctggaagaga ttccggagag tattggagaa ataatgacac taaaattcat taatacagaa    2580
ttttgcggct ctggtgtaga gactagtgca aagaaaattc aagaagagca agaaagcttg    2640
ggaaattatg agcttcaact tcaaattact cctaagttaa gattttttgat cgaaaattta    2700 gacgaaacaa gcatgttgcc atcgaatgaa gtaatcgaaa aaatcaaagg taaaattttt    2760
gatcgaaaac taaaagagat tccggagagt actggacaaa taatgacacg aaaaatcatc    2820
aaaacagaat tttgcagctc tggtgtagag actagtgcaa agaaaattca agaagagcaa    2880
gaaagcttgg gaaattatga gcttcaagtt caaattactc ctaggaagcg tttgctgagg    2940
aagcaggacg gcactgtg                                                  2958
```

<210> SEQ ID NO 37
<211> LENGTH: 2961
<212> TYPE: DNA
<213> ORGANISM: Solanum americanum

<400> SEQUENCE: 37

```
atggcttatg ctgctctttc ttcacttatg tatacattgc aacaactctt gaaacctaat      60
caatctttcg tttgtcgata ctctacacaa caacttgttc aatctctcta tcaaaatctt     120
actgctctgc aacttttcct tgaccatact acgacaaagg atattgaaac acttaaggtt     180
atagaaaaga ggatcagaga tgtagtatac aaagcagaag ataagttga ttcaagccta      240
```

```
agaaacatca ttctagcaga ttgcacagag aatagagaag gggcttgtaa attctttgag    300
gaagaattgc taaaagtgga aaaagatgtt gattctctca gcaaagaggt gatgcagatc    360
gagtttaaca agcatggatg cagatctgca gaattagcaa caactgatcc ctcctcatca    420
ggaaaaagta caattgagga acatactatt gttgggatgg aggatgagta caacaccata    480
cttgatcgcc tcactgccca acagacgag ttgactgtca taccaatttt tggtatgggc     540
ggtataggta agacaactct tgccagaaag gtttatgatg attcatctat tcgttctcga    600
tttgatagac atgcatgggt cactacctct gaagaattca tgagagacg aatgcttctc     660
gaagttgttt cttcaattac tactggaagc aatcaaggaa agagcgatga tcaactaatg    720
gagattgtgt atagaagtct gaagggtagg agatttctaa ttgtcataga tgatatttgg    780
agtactcagg cttgggacca aatgcaaaga atatttccaa atgatgacag taaaagccga    840
attctactaa ctacacggct caagtatgtt gctgattatg tcagcagtcc tgattttcca    900
cctcatagta agtcttttct aagtcttgat gatagttgga atctattcac cgaaaaagta    960
ttcaacgaag atacctgtcc tcctcaccta gaagaaacag ggaagcatat tgtacaacaa   1020
tgtcaaggat tacctctctc ggttgttgtc gttgctggac ttgttggaaa aatggaccca   1080
acgcatgaca attgggagaa tgttgaggaa aatctgaact cattctttgg tactgtatcc   1140
gaacggtgcc actcaattct ttcttttgagc tacaattact tgccccaata tttgagggct   1200
tgttttctct atgttggagg ttttcctgaa gataaagaga ttgatgtttc caagttgatt   1260
aggctatgga ttgctgagca attcgtaaag gcgagaagca ataaaaggct agaagtggtg   1320
gcagaggagt atctggaaga gttaattgat agaagtctaa ttttgagtgg tagacaaagg   1380
gctaatggaa ggatgaaaac ttgcaaaatt catgatcttc ttcgccaact atgcctaagt   1440
gaagctcata ctgaaaatat tagtcatatc atgaatagaa atgtcccgt gtcctcagaa    1500
gccatagatg atcaacggcg agtgattgtt ccattggaac tcgaagagaa acaattttat   1560
cctacaaggc atagcagtgg tattacaagt acaacccgca cctttatttc aatgaaaata   1620
tgcctaagag aagctcaaac cgaagccata tatgatcaac ggcgagtgat ccttctgtct   1680
aaacgacata ggattgatac aatccgcacc attattccat tcggagatac ttttccaaaa   1740
gagatttgtt ccattttttc agagttcaag ttgcttaagg tgttggatgt attatcagtc   1800
tggtacgatg tctcttgtat aataccctcag cttgtacatt tgagatatgt tggtgcagta   1860
attttggaag ctctttcact acccaaattg agaaatctac agaccataat gcttacaagt   1920
gttgaaacca cagagttgaa gcactcacta gatatctgga gaatgtcaga gataagacat   1980
ttggatattg taccgccact atatatatca atcctcttg aagcagaaca acctttgttt    2040
ctcaataact tgcacacgct ttttctccgt tgctctcctt ttgttgcgaa aatcataaga   2100
agaactccga atctaaaaaa gctaaagatt ttagataaat ctaagcatcc tgactggcct   2160
gatattcttg attctctcaa tcttctagag gagctggaga cactacaaat atcaacagaa   2220
gaaaacattg accggatgat tttctctggg gatattttcc ctcgtaatct caagcaactg   2280
aaattatcat atacttgtat accatgggaa gatatgaaat tgctggctaa tttacccaat   2340
cttgaggtgt tcaagggtca ttatgcattc gatggaacag attggaaact agatgaagat   2400
gttgtgtttt gcaaattaaa atgtctacga ctgtatgagc gcggagatct gcaaaggtgg   2460
gaagcagcag gtagtgataa ttttcctatg cttgagcaac tagtactgta tgggttcgaa   2520
aaactggaag agattccgga gagtattgga gaaataatga cactaaaatt cattaaaaca   2580
gaattttgcg gctctggtgt agagactagt gcaaagaaaa ttcaagaaga gcaagaaagc   2640
```

```
ttgggaaatt atgagcttca acttcaaatt actcctaagt taagattttt gatcgaaaat    2700
ttagacgaaa caagcatgtt gccatcgaat gaagtaatcg aaaaaatcaa aggtaaaatt    2760
tttgatcgaa aactaaaaga gattccggag agtactggac aaataatgac acgaaaaatc    2820
atcaaaacag aattttgcag ctctggtgta gagactagtg caaagaaaat tcaagaagag    2880
caagaaagct tgggaaatta tgagcttcaa gttcaaatta ctcctaggaa gcgtttgctg    2940
aggaagcagg acggcactgt g                                              2961
```

<210> SEQ ID NO 38
<211> LENGTH: 2928
<212> TYPE: DNA
<213> ORGANISM: Solanum americanum

<400> SEQUENCE: 38

```
atggcttatg ctgctctttc ttcacttatc tatacattgg aacaactctt gaaacctaat      60
caatctttcg tttgtcgaag ctctacacaa caaaatgttg aatcaatcca tcaaaatctt     120
tgtgctatgc aacttttcct tgacgatact acgacaaagg atattgaaac tcttaaggtt     180
atagaaaaga ggatcagaga gtagtatac aaagcagaag ataaagttga ttcaagtcta     240
agaaacatca ttctagcaga ttgcacagag aatcgagaag gtgcttgtaa attcttcgag     300
gaagaattgc taaagtggaa aaagatgtt gattcactca ggaaagaggt gatgcagatc     360
gactttaaca agcatggaag cagatctgga gaactagcaa gaactggtcc ctcctcacaa     420
gaaaaagta caattgagga aaatactatt gttgggatgg aggatgagta caacaccata     480
cttgatcgcc tcactgccca acagacgag ttaactgtca taacaatttt tggtatgggc     540
ggtataggta agacaactct tgccagaaaa gtttatgatg attcatatat tcattctcga     600
tttgataaac atgcatggat cactatctct gaagaataca atcagagaca aatgcttctt     660
caagttgtct cttcaattac tactggaagc aatggagaaa tgagcgatga tcaactaatg     720
gagattgtgt atagaggtct caagggtagg agatttctga ttgtcataga tgatatttgg     780
agtactgagg cttgggacca aatgcaaaga atatttccaa atgataacaa taaaagccga     840
attctactaa ccactcggct caagtatgtt gctgattatg tcagttgtcc tgattttcca     900
tctcattgca gtcttttct aagtcttgat gatagttgga atctattcac cgaaaaagta     960
ttcaaaaaag atccctgccc tcctcaccta aagaaacag ggaagcacat tgtacaacaa    1020
tgccaaggat tacctctctc ggttgttgtc gtcgctggac ttgttggaaa aatggaccca    1080
acgcatgaca attgggagaa cgttgaggaa aatctgaact cattctttgg tacggtatcc    1140
gaacggtgcc aatcaattct ttctttgagc tacaattact tgccccaata tttgagggct    1200
tgttttctct acgttggagg ttttcctgaa gataaagaga ttgatgtttc caagttgatt    1260
aggctatgga ttgctgagca attcgtaaag gcgagaagca ataaaaggtt agaagtggtg    1320
gcagaggagt atcttgaaga gttaattgat agaagtctaa ttttgactgg tagacaaagg    1380
gttaatggaa ggatgaaaac ttgcaaaatt catgatcttc ttcgccaact atgcctaagt    1440
gaagctcata ctgaaaatat tagtcatatc atgaatagaa atgtccccgt gtcctcagaa    1500
gccattgaag agaaacaagt ttatcctaca aggcatagca ggggtatttc aagtaaaacc    1560
cgcacctta tttcaatgga atatgccta agagaagccc agaccgaagc aatatatgat    1620
caacggcgag tgatccttct gtctaaacga cataggattg atacaatccg caccattatt    1680
ccattcggag atactttcc aaaagagatt tgttccattt tttcacagtt gaagttgctt    1740
```

```
aaggtgttgg atgtattatc agtctggtac gatgtctctt gtataatacc tcagcttgta   1800
catttgagat atgttggtgc agtaattgag gaagctcttt cactatccaa attgagaaat   1860
ctacagacca taatgcttac aagtgttgaa accacagagt tgaagcactc actagatatc   1920
tggagaatgt cagagataag acatttggat attgtaccgc cattatatat atcaaatcct   1980
cttgaagcag aacaaccttt gtttctcaat aacttgcaaa cgctttatct ccgttgctct   2040
ccttttgttg cgaaaatcat aagaagaact cccaatctaa aaaagctaaa gattttagat   2100
aaatctaagc atcctgactg gcctgatatt cttgattctc tcaatcttct agaggagctg   2160
gagacactac aaatatcaac agaagaaaac attgacccga tgattttctc tggggatatt   2220
ttccctcgta atctcaagca actgaaatta tcatatactt gtataccatg ggaagatatg   2280
aaattgctgg ctaatttacc caatcttgag gtgttcaagg tcattatgc attcgatgga    2340 acagattgga aactagatga agatgttgtg ttttgcaaat taaaatgtct acgactgtat   2400
gagcgtggag atttgcaaag gtgggaagct gctggtagtg ataattttcc aatgcttgag   2460
caactattat tgtatggggtt caaaaaactg gaagagattc cggagagtat tggagaaata   2520 atgcacactaa aatttatcaa aacagaattt tgcggctctg gtgtagagac aagtgcaaag   2580
aaaattcaag aagagcaaga aagcctggga aattatgagc ttcaagttca aattactcct   2640
aagttaagat ttttgatcga aaatttagac gaaataagca tgttgccacc gaatgaagta   2700
gccgaaaaaa tcaaaggtaa aatttttgat caaaaactaa aagagattcc ggagagtact   2760
ggacaaataa tgacacgaaa aatcatcaaa acagaatttt gcggctctgg tgtagagact   2820
agtgcaaaga aaattcaaga agagcaagaa agcttgggaa attgtgagct tcatcaagtt   2880
caaattactc ctaaggagcg tttgctgagg aagcaggacg cactgtg              2928
```

<210> SEQ ID NO 39
<211> LENGTH: 2961
<212> TYPE: DNA
<213> ORGANISM: Solanum americanum

<400> SEQUENCE: 39

```
atggcatatg ctgctctttc ttcacttatc tatacattgc aacaactctt gaaacctaat     60
caatctttgg tttgtcgaag ctgtacacaa caacatcttc aatctatcta tcacaatctt    120
tctgctctgc aactttttcct tgacgatact acgacaaagg atattgaaac tcttaaggtt    180
atagaaaaga ggatcagaga tgtagtatac aaagcagaag atacagttga ttcaagccta    240
agaaacatca ttctagcaga ttgcacagag aatagagaag gggcttgtaa attctttgag    300
gaagaattgc taaagtgga aaaagatgtt gattctctca gcaaagaggt gatgcagatc    360
gactttaaca agcatggaag cagatctgca gaattagcaa caactgatcc ctcctcatca    420
ggaaaaagta caattgagga acatactatt gttgggatgg aggatgagta caacaccata    480
cttgatcgcc tcactgccca aacagacgag ttgactgtca taccaatttt tggtatgggc    540
ggtataggta agacaactct tgccagaaag gtttatgatg attcatctat tcgttctcga    600
tttgatagac atgcatgggt cactacctct gaagaattca tgagagacg aatgcttctc     660 gaagttgttt cttcaattac tactggaagc aatcaaggaa agagcgatga tcaactaatg    720
gagattgtgt atagaagtct gaagggtagg agatttctaa ttgtcataga tgatatttgg    780
agtactcagg cttgggacca aatgcaaaga atatttccaa atgatgacaa taaaagccga    840
attctactaa ctacacggct caagtatgtt gctgattatg tcagcagtcc tgattttcca    900
cctcatagta agtcttttct aagtcttgat gatagttgga atctattcac cgaaaaagta    960
```

| | |
|---|---|
| ttcaacgaag atacctgtcc tcctcaccta gaagaaacag ggaagcatat tgtacaacaa | 1020 |
| tgtcaaggat tacctctctc ggttgttgtc gttgctggac tgttggaaa aatggaccca | 1080 |
| acgcatgaca attgggagaa tgttgaggaa aatctgaact cattctttgg tactgtatcc | 1140 |
| gaacggtgcc actcaattct ttctttgagc tacaattact tgccccaata tttgagggct | 1200 |
| tgttttctct atgttggagg ttttcctgaa gataaagaga ttgatgtttc caagttgatt | 1260 |
| aggctatgga ttgctgagca attcgtaaag gcgagaagca ataaaaggct agaagtggtg | 1320 |
| gcagaggagt atctggaaga gttaattgat agaagtctaa ttttgagtgg tagacaaagg | 1380 |
| gctaatggaa ggatgaaaac ttgcaaaatt catgatcttc ttcgccaact atgcctaagt | 1440 |
| gaagctcata ctgaaaatat tagtcatatc atgaatagaa atgtccccgt gtcctcagaa | 1500 |
| gccatagatg atcaacggcg agtgattgtt ccattggaac tcgaagagaa acaagtttat | 1560 |
| cctacaaggc atagcagtgg tattacaagt acaacccgca cctttatttc aatggaaata | 1620 |
| tgcctaagag aagctcaaac cgaagccata tatgatcaac ggcgagtgat ccttctgtct | 1680 |
| aaacgacata ggattgatac aatccgcacc attattccat tcggagatac ttttccaaaa | 1740 |
| gagatttgtt ccattttttc agagttcaag ttgcttaagg tgttggatgt attatcagtc | 1800 |
| tggtacgatg tctcttgtat aatacctcag cttgtacatt tgagatatgt tggtgcagta | 1860 |
| attttggaag ctctttcact acccaaattg agaaatctac agaccataat gcttacaagt | 1920 |
| gttgaaacca cagagttgaa gcactcacta gatatctgga gaatgtcaga gataagacat | 1980 |
| ttggatattg taccgccact atatatatca aatcctcttg aagcagaaca acctttgttt | 2040 |
| ctcaataact tgcacacgct ttttctccgt tgctctcctt ttgttgcgaa aatcataaga | 2100 |
| agaactccga atctaaaaaa gctaaagatt ttagataaat ctaagcatcc tgactggcct | 2160 |
| gatattcttg attctctcaa tcttctagag gagctggaga cactacaaat atcaacagaa | 2220 |
| gaaaacattg accggatgat tttctctggg gataatttcc ctcgtaatct caagcaactg | 2280 |
| aaattatcag gtactaaaat accatgggaa gatatgaaat tgctggctaa tttacccaat | 2340 |
| cttgaggtgt tcaagggtca ttatgcattc gatggaacag attggaaact agatgaagat | 2400 |
| gttgtgtttt gcaaattaaa atgtctacga ctgtatgagc gcggagatct gcaaaggtgg | 2460 |
| gaagcagcag gtagtgataa тттттcctatg cttgagcaac tagtactgta tgggttcgaa | 2520 |
| aaactggaag agattccgga gagtattgga gaaataatga cactaaaatt catcaaaaca | 2580 |
| gaattttgcg gctctggtgt agagacaagt gcaagaaaaa ttcaagaaga gcaagaaagc | 2640 |
| tggggaaatt atgagcttca acttctaatt actcctatgt taagattttt gatcgaaaat | 2700 |
| ttagacgaaa taagcatgtt gccaccggat gaagtagccg aaaaaatcaa agttaaaatt | 2760 |
| tttgatcgaa aactaaaaga gattctggag agtactggac aaataatgac acgaaaaatc | 2820 |
| attaaaacgg aattttgcag ctctggtgta gagactagtg caagaaaat tcaagagcaa | 2880 |
| gaaagcttgg gaaattatga gcttcaagtt caaattactc ctaggaagcg tttgctgagg | 2940 |
| aagcaggacg gcactgtgta a | 2961 |

<210> SEQ ID NO 40
<211> LENGTH: 2958
<212> TYPE: DNA
<213> ORGANISM: Solanum americanum

<400> SEQUENCE: 40

| | |
|---|---|
| atggcttatg ctgctctttc ttcacttatc tatacattgc aacaactctt gaaacctaat | 60 |

```
caatctttgg tttgtcgaag ctctacacaa caacatcttc aatctatcta tcacaatctt    120
tctgctctgc aacttttcct tgacgatact acgacaaagg atattgaaac tcttaaggtt    180
atagaaaaga ggatcagaga tgtagtatac aaagcagaag ataaagttga ttcaagccta    240
agaaacatca ttctagctga ttgcacagag aatagaagaa cggcttgtaa attctttgag    300
gaagaattgc taaaagtgga aaaagatgtt cattctctca ggaaagaggt gatgcagatc    360
gagtttaaca agcatggtag cagatctgca gaactaacaa caattcttcc ctcgccagaa    420
aaaagtacaa ttgaggaaca tactattgtt gggatggagg atgagtacaa caccatactt    480
gatcgcctca ctgcccaaac agacgagtta actgtcatac caatatttgg tatgggcggt    540
ataggtaaga caactcttgc cagaaaggtt tatgatgatt catctattcg ttctcgattt    600
gatagacatg tatgggtcac tacctctgaa gaattcaatg agagacgaat gcttctcgaa    660
gttgtttctt caattactac tggaagcaat caagaaaaga gcgatgatca actaatggag    720
attgtgtata gaggtcttaa gggtaggaga tttctaattg tcatagatga tatttggagt    780
actcaggctt gggaccaaat gcaaagaata tttccaaatg atgacaataa aagcagaatt    840
ctactaacta cacggctcaa gtatgttgct gattatgtca acagtcctga ttttccacct    900
catagtaagt cttttctaag tcttgatgat agttggaatc tattcaccga aaaagtattc    960
aacaaagata cctgtcctcc tcacctagaa gaaacaggga agcatattgt acaacaatgt    1020
cgaggattac ctctctcggt tgttgtagtt gctggacttg ttggaaaaat ggacccaacg    1080
catgacaatt gggagaacgt tgaggaaaat ctgaactcat tcattggtac tgtatcggaa    1140
cggtgccaat caattctttc tttaagctac aattacttgc cccagtattt gagggcttgt    1200
tttctctatg ttggatgttt tcctgaagat aaagagattg atgtttccaa gttgattagg    1260
ctatggattg ctgagcaatt cgtaaaggcg agaagcaata aaaatttaga agtggtggca    1320
gaggagtatc tggaagagtt aattgataga agtctaattt tgagtggtag acaaagggct    1380
aatgaaagga tgaaaacttg taaaattcat gatcttcttc gccaactatg cctaagtgaa    1440
gctcatactg aaaatattag tcatatcatg aatagaaatg tcctcgtgtc ctcagaagcc    1500
atagatgatc aacggcgagt gattgttcca ttggaactcg aagagaaaca agtttatccg    1560
acaaggcata gcagtggtat tacaagtaca acccgcacct ttatttcaat ggaaatatgc    1620
ctaagagaag ctcagaccga aaccatatat gatcaacggc gagtgatcct tctctctaaa    1680
cgacatagga ttgatacaat ccgcaccatt attccattcg gagatacttt tccaaaagtg    1740
atttgttcca ttttttcgca gttgaagttg cttaaggtgt tggatgtatt atcagtctgg    1800
tacgatgtct cttgtataat acctcagctt gtacatttga gatatgttgg tgcagtaatt    1860
ttggaagctg tttcactatc caaattgaga aatctacaga ccataattct tgcaagtgtt    1920
gaaaccacag agttgaagca cccagtagat atctggagaa tgtcagagat cagacatttg    1980
gatattgtac cgccactata tatcaaat cctcttgaag cagaacaacc tttgtttctc    2040
aataacttgc acacgctttt tctccgttgc tctccttttg ttgcgaaaat cataagaaga    2100
actcccaatc taaaaaagct aaagatttta gataaatcta agcatcctga ctggcctgat    2160
attcttgatt ctctcaatct tctagaggag ctggagacac tacaaatatc aacgaagaa    2220 aacattgacc ggatgatttt ctctggggat attttccctc gtaatctcaa gcaactgaaa    2280
ttatcatata cttgtatacc atgggaagat atgaaattgc tggctaattt acccaatctt    2340
gaggtgttca agggtcatta tgcattcgat ggaacagatt ggaaactaga tgaagatgtt    2400
gtgttttgca aattaaaatg tctacgactg tatgagcgcg gagatctgca aaggtgggaa    2460
```

```
gctgctggta gtgataattt tccaatgctt gagcaactat tactgtatgg attcaaaaag    2520
ctggaagaga ttccggagag tattggagaa ataatgacac taaaattcat taaaacagaa    2580
ttttgcggct ctggtgtaga gactagtgca agaaaattc aacaagagca agaaagcttg    2640
ggaaattatg agcttcaact tcaaattact cctaagttaa gattttgat cgaaaattta    2700 gacgaaacaa gcatgttgcc atcgaatgaa gtaatcgaaa aaatcaaagg taaaatttt    2760 gatcgaaaac taaagagat tccggagagt actggacaaa taatgacacg aaaaatcatc    2820
aaaacagaat tttgcagctc tggtgtagag actagtgcaa agaaaattca agaagagcaa    2880
gaaagcttgg gaaattatga gcttcaagtt caaattactc ctaggaagcg tttgctgagg    2940
aagcaggacg gcactgtg                                                  2958

<210> SEQ ID NO 41
<211> LENGTH: 986
<212> TYPE: PRT
<213> ORGANISM: Solanum americanum

<400> SEQUENCE: 41

Met Ala Tyr Ala Ala Leu Ser Ser Leu Ile Tyr Thr Leu Gln Gln Leu
1               5                   10                  15

Leu Lys Pro Asn Gln Ser Leu Val Cys Arg Ser Cys Thr Gln Gln His
            20                  25                  30

Leu Gln Ser Ile Tyr His Asn Leu Ser Ala Leu Gln Leu Phe Leu Asp
        35                  40                  45

Asp Thr Thr Thr Lys Asp Ile Glu Thr Leu Lys Val Ile Glu Lys Arg
    50                  55                  60

Ile Arg Asp Val Val Tyr Lys Ala Glu Asp Lys Val Asp Ser Ser Leu
65                  70                  75                  80

Arg Asn Ile Ile Leu Ala Asp Cys Thr Glu Asn Arg Glu Gly Ala Cys
                85                  90                  95

Lys Phe Phe Glu Glu Glu Leu Leu Lys Val Glu Lys Asp Val Asp Ser
            100                 105                 110

Leu Arg Lys Glu Val Met Gln Ile Glu Phe Asn Lys His Gly Ser Arg
        115                 120                 125

Ser Ala Glu Leu Thr Thr Ile Leu Pro Ser Pro Glu Lys Ser Thr Ile
    130                 135                 140

Glu Glu His Thr Ile Val Gly Met Glu Asp Glu Tyr Asn Thr Ile Leu
145                 150                 155                 160

Asp Arg Leu Thr Ala Gln Thr Asp Glu Leu Thr Val Ile Pro Ile Phe
                165                 170                 175

Gly Met Gly Gly Ile Gly Lys Thr Thr Leu Ala Arg Lys Val Tyr Asp
            180                 185                 190

Asp Ser Ser Ile Arg Ser Arg Phe Asp Arg His Val Trp Val Thr Thr
        195                 200                 205

Ser Glu Glu Phe Asn Glu Arg Arg Met Leu Leu Glu Val Val Ser Ser
    210                 215                 220

Ile Thr Thr Gly Ser Asn Gln Glu Lys Ser Asp Asp Gln Leu Met Glu
225                 230                 235                 240

Ile Val Tyr Arg Gly Leu Lys Gly Arg Arg Phe Leu Ile Val Ile Asp
                245                 250                 255

Asp Ile Trp Ser Thr Gln Ala Trp Asp Gln Met Gln Arg Ile Phe Pro
            260                 265                 270

Asn Asp Asp Asn Lys Ser Arg Ile Leu Leu Thr Thr Arg Leu Lys Tyr
```

-continued

```
            275                 280                 285
Val Ala Asp Tyr Val Asn Ser Pro Asp Phe Pro His Ser Lys Ser
290                 295                 300
Phe Leu Ser Leu Asp Asp Ser Trp Asn Leu Phe Thr Glu Lys Val Phe
305                 310                 315                 320
Asn Lys Asp Thr Cys Pro Pro His Leu Glu Thr Gly Lys His Ile
                325                 330                 335
Val Gln Gln Cys Arg Gly Leu Pro Leu Ser Val Val Val Ala Gly
                340                 345                 350
Leu Val Gly Lys Met Asp Pro Thr His Asp Asn Trp Glu Asn Val Glu
                355                 360                 365
Glu Asn Leu Asn Ser Phe Ile Gly Thr Val Ser Glu Arg Cys Gln Ser
370                 375                 380
Ile Leu Ser Leu Ser Tyr Asn Tyr Leu Pro Gln Tyr Leu Arg Ala Cys
385                 390                 395                 400
Phe Leu Tyr Val Gly Cys Phe Pro Glu Asp Lys Glu Ile Asp Val Ser
                405                 410                 415
Lys Leu Ile Arg Leu Trp Ile Ala Glu Gln Phe Val Lys Ala Arg Ser
                420                 425                 430
Asn Lys Asn Leu Glu Val Val Ala Glu Glu Tyr Leu Glu Glu Leu Ile
                435                 440                 445
Asp Arg Ser Leu Ile Leu Ser Gly Arg Gln Arg Ala Asn Gly Arg Met
450                 455                 460
Lys Thr Cys Lys Ile His Asp Leu Leu Arg Gln Leu Cys Leu Ser Glu
465                 470                 475                 480
Ala His Thr Glu Asn Ile Ser His Ile Met Asn Arg Asn Val Leu Val
                485                 490                 495
Ser Ser Glu Ala Ile Asp Asp Gln Trp Arg Val Ile Val Pro Leu Glu
                500                 505                 510
Leu Glu Glu Lys Gln Val Tyr Pro Thr Arg His Ser Ser Gly Ile Thr
                515                 520                 525
Ser Thr Thr Arg Thr Phe Ile Ser Met Glu Ile Cys Leu Arg Glu Ala
530                 535                 540
Gln Thr Glu Thr Ile Tyr Asp Gln Arg Arg Val Ile Leu Leu Ser Lys
545                 550                 555                 560
Arg His Arg Ile Asp Thr Ile Arg Thr Ile Ile Pro Phe Gly Asp Thr
                565                 570                 575
Phe Pro Lys Val Ile Cys Ser Ile Phe Ser Gln Leu Lys Leu Leu Lys
                580                 585                 590
Val Leu Asp Val Leu Ser Val Trp Tyr Asp Val Ser Cys Ile Ile Pro
                595                 600                 605
Gln Leu Val His Leu Arg Tyr Val Gly Ala Val Ile Leu Glu Ala Val
                610                 615                 620
Ser Leu Ser Lys Leu Arg Asn Leu Gln Thr Ile Ile Leu Ala Ser Val
625                 630                 635                 640
Glu Thr Thr Glu Leu Lys His Pro Val Asp Ile Trp Arg Met Ser Glu
                645                 650                 655
Ile Arg His Leu Asp Ile Val Pro Pro Leu Tyr Ile Ser Asn Pro Leu
                660                 665                 670
Glu Ala Glu Gln Pro Leu Phe Leu Asn Asn Leu His Thr Leu Phe Leu
                675                 680                 685
Arg Cys Ser Pro Phe Val Ala Lys Ile Ile Arg Arg Thr Pro Asn Leu
                690                 695                 700
```

Lys Lys Leu Lys Ile Leu Asp Lys Ser Lys His Pro Asp Trp Pro Asp
705                 710                 715                 720

Ile Leu Asp Ser Leu Asn Leu Glu Glu Leu Glu Thr Leu Gln Ile
            725                 730                 735

Ser Thr Glu Glu Asn Ile Asp Arg Met Ile Phe Ser Gly Asp Ile Phe
            740                 745                 750

Pro Arg Asn Leu Lys Gln Leu Lys Leu Ser Tyr Thr Cys Ile Pro Trp
        755                 760                 765

Glu Asp Met Lys Leu Leu Ala Asn Leu Pro Asn Leu Glu Val Phe Lys
        770                 775                 780

Gly His Tyr Ala Phe Asp Gly Thr Asp Trp Lys Leu Asp Glu Asp Val
785                 790                 795                 800

Val Phe Cys Lys Leu Lys Cys Leu Arg Leu Tyr Glu Arg Gly Asp Leu
            805                 810                 815

Gln Arg Trp Glu Ala Ala Gly Ser Asp Asn Phe Pro Met Leu Glu Gln
            820                 825                 830

Leu Leu Leu Tyr Gly Phe Lys Lys Leu Glu Glu Ile Pro Glu Ser Ile
        835                 840                 845

Gly Glu Ile Met Thr Leu Lys Phe Ile Asn Thr Glu Phe Cys Gly Ser
850                 855                 860

Gly Val Glu Thr Ser Ala Lys Lys Ile Gln Glu Gln Ser Leu
865                 870                 875                 880

Gly Asn Tyr Glu Leu Gln Leu Gln Ile Thr Pro Lys Leu Arg Phe Leu
            885                 890                 895

Ile Glu Asn Leu Asp Glu Thr Ser Met Leu Pro Ser Asn Glu Val Ile
            900                 905                 910

Glu Lys Ile Lys Gly Lys Ile Phe Asp Arg Lys Leu Lys Glu Ile Pro
        915                 920                 925

Glu Ser Thr Gly Gln Ile Met Thr Arg Lys Ile Ile Lys Thr Glu Phe
930                 935                 940

Cys Ser Ser Gly Val Glu Thr Ser Ala Lys Lys Ile Gln Glu Glu Gln
945                 950                 955                 960

Glu Ser Leu Gly Asn Tyr Glu Leu Gln Val Gln Ile Thr Pro Arg Lys
            965                 970                 975

Arg Leu Leu Arg Lys Gln Asp Gly Thr Val
        980                 985

<210> SEQ ID NO 42
<211> LENGTH: 987
<212> TYPE: PRT
<213> ORGANISM: Solanum americanum

<400> SEQUENCE: 42

Met Ala Tyr Ala Ala Leu Ser Ser Leu Met Tyr Thr Leu Gln Gln Leu
1               5                   10                  15

Leu Lys Pro Asn Gln Ser Phe Val Cys Arg Tyr Ser Thr Gln Gln Leu
            20                  25                  30

Val Gln Ser Leu Tyr Gln Asn Leu Thr Ala Leu Gln Leu Phe Leu Asp
        35                  40                  45

His Thr Thr Thr Lys Asp Ile Glu Thr Leu Lys Val Ile Glu Lys Arg
    50                  55                  60

Ile Arg Asp Val Val Tyr Lys Ala Glu Asp Lys Val Asp Ser Ser Leu
65                  70                  75                  80

Arg Asn Ile Ile Leu Ala Asp Cys Thr Glu Asn Arg Glu Gly Ala Cys

-continued

```
                85                  90                  95
Lys Phe Phe Glu Glu Leu Leu Lys Val Glu Lys Asp Val Asp Ser
                100                 105                 110

Leu Ser Lys Glu Val Met Gln Ile Glu Phe Asn Lys His Gly Cys Arg
            115                 120                 125

Ser Ala Glu Leu Ala Thr Thr Asp Pro Ser Ser Gly Lys Ser Thr
        130                 135                 140

Ile Glu Glu His Thr Ile Val Gly Met Glu Asp Glu Tyr Asn Thr Ile
145                 150                 155                 160

Leu Asp Arg Leu Thr Ala Gln Thr Asp Glu Leu Thr Val Ile Pro Ile
                165                 170                 175

Phe Gly Met Gly Gly Ile Gly Lys Thr Thr Leu Ala Arg Lys Val Tyr
            180                 185                 190

Asp Asp Ser Ser Ile Arg Ser Arg Phe Asp Arg His Ala Trp Val Thr
        195                 200                 205

Thr Ser Glu Glu Phe Asn Glu Arg Arg Met Leu Leu Glu Val Val Ser
210                 215                 220

Ser Ile Thr Thr Gly Ser Asn Gln Gly Lys Ser Asp Asp Gln Leu Met
225                 230                 235                 240

Glu Ile Val Tyr Arg Ser Leu Lys Gly Arg Phe Leu Ile Val Ile
                245                 250                 255

Asp Asp Ile Trp Ser Thr Gln Ala Trp Asp Gln Met Gln Arg Ile Phe
            260                 265                 270

Pro Asn Asp Asp Ser Lys Ser Arg Ile Leu Leu Thr Thr Arg Leu Lys
        275                 280                 285

Tyr Val Ala Asp Tyr Val Ser Ser Pro Asp Phe Pro Pro His Ser Lys
    290                 295                 300

Ser Phe Leu Ser Leu Asp Asp Ser Trp Asn Leu Phe Thr Glu Lys Val
305                 310                 315                 320

Phe Asn Glu Asp Thr Cys Pro Pro His Leu Glu Glu Thr Gly Lys His
                325                 330                 335

Ile Val Gln Gln Cys Gln Gly Leu Pro Leu Ser Val Val Val Ala
            340                 345                 350

Gly Leu Val Gly Lys Met Asp Pro Thr His Asp Asn Trp Glu Asn Val
        355                 360                 365

Glu Glu Asn Leu Asn Ser Phe Phe Gly Thr Val Ser Glu Arg Cys His
    370                 375                 380

Ser Ile Leu Ser Leu Ser Tyr Asn Tyr Leu Pro Gln Tyr Leu Arg Ala
385                 390                 395                 400

Cys Phe Leu Tyr Val Gly Phe Pro Glu Asp Lys Glu Ile Asp Val
                405                 410                 415

Ser Lys Leu Ile Arg Leu Trp Ile Ala Glu Gln Phe Val Lys Ala Arg
            420                 425                 430

Ser Asn Lys Arg Leu Glu Val Val Ala Glu Glu Tyr Leu Glu Glu Leu
        435                 440                 445

Ile Asp Arg Ser Leu Ile Leu Ser Gly Arg Gln Arg Ala Asn Gly Arg
    450                 455                 460

Met Lys Thr Cys Lys Ile His Asp Leu Leu Arg Gln Leu Cys Leu Ser
465                 470                 475                 480

Glu Ala His Thr Glu Asn Ile Ser His Ile Met Asn Arg Asn Val Pro
                485                 490                 495

Val Ser Ser Glu Ala Ile Asp Asp Gln Arg Arg Val Ile Val Pro Leu
            500                 505                 510
```

```
Glu Leu Glu Glu Lys Gln Phe Tyr Pro Thr Arg His Ser Ser Gly Ile
            515                 520                 525

Thr Ser Thr Thr Arg Thr Phe Ile Ser Met Glu Ile Cys Leu Arg Glu
        530                 535                 540

Ala Gln Thr Glu Ala Ile Tyr Asp Gln Arg Arg Val Ile Leu Leu Ser
545                 550                 555                 560

Lys Arg His Arg Ile Asp Thr Ile Arg Thr Ile Ile Pro Phe Gly Asp
                565                 570                 575

Thr Phe Pro Lys Glu Ile Cys Ser Ile Phe Ser Glu Phe Lys Leu Leu
            580                 585                 590

Lys Val Leu Asp Val Leu Ser Val Trp Tyr Asp Val Ser Cys Ile Ile
        595                 600                 605

Pro Gln Leu Val His Leu Arg Tyr Val Gly Ala Val Ile Leu Glu Ala
610                 615                 620

Leu Ser Leu Pro Lys Leu Arg Asn Leu Gln Thr Ile Met Leu Thr Ser
625                 630                 635                 640

Val Glu Thr Thr Glu Leu Lys His Ser Leu Asp Ile Trp Arg Met Ser
                645                 650                 655

Glu Ile Arg His Leu Asp Ile Val Pro Pro Leu Tyr Ile Ser Asn Pro
            660                 665                 670

Leu Glu Ala Glu Gln Pro Leu Phe Leu Asn Asn Leu His Thr Leu Phe
        675                 680                 685

Leu Arg Cys Ser Pro Phe Val Ala Lys Ile Ile Arg Arg Thr Pro Asn
690                 695                 700

Leu Lys Lys Leu Lys Ile Leu Asp Lys Ser Lys His Pro Asp Trp Pro
705                 710                 715                 720

Asp Ile Leu Asp Ser Leu Asn Leu Leu Glu Glu Leu Glu Thr Leu Gln
                725                 730                 735

Ile Ser Thr Glu Glu Asn Ile Asp Arg Met Ile Phe Ser Gly Asp Ile
            740                 745                 750

Phe Pro Arg Asn Leu Lys Gln Leu Lys Leu Ser Tyr Thr Cys Ile Pro
        755                 760                 765

Trp Glu Asp Met Lys Leu Leu Ala Asn Leu Pro Asn Leu Glu Val Phe
770                 775                 780

Lys Gly His Tyr Ala Phe Asp Gly Thr Asp Trp Lys Leu Asp Glu Asp
785                 790                 795                 800

Val Val Phe Cys Lys Leu Lys Cys Leu Arg Leu Tyr Glu Arg Gly Asp
                805                 810                 815

Leu Gln Arg Trp Glu Ala Ala Gly Ser Asp Asn Phe Pro Met Leu Glu
            820                 825                 830

Gln Leu Val Leu Tyr Gly Phe Glu Lys Leu Glu Glu Ile Pro Glu Ser
        835                 840                 845

Ile Gly Glu Ile Met Thr Leu Lys Phe Ile Lys Thr Glu Phe Cys Gly
850                 855                 860

Ser Gly Val Glu Thr Ser Ala Lys Lys Ile Gln Glu Gln Glu Gln Ser
865                 870                 875                 880

Leu Gly Asn Tyr Glu Leu Gln Leu Gln Ile Thr Pro Lys Leu Arg Phe
                885                 890                 895

Leu Ile Glu Asn Leu Asp Glu Thr Ser Met Leu Pro Ser Asn Glu Val
            900                 905                 910

Ile Glu Lys Ile Lys Gly Lys Ile Phe Asp Arg Lys Leu Lys Glu Ile
        915                 920                 925
```

```
Pro Glu Ser Thr Gly Gln Ile Met Thr Arg Lys Ile Ile Lys Thr Glu
            930                 935                 940

Phe Cys Ser Ser Gly Val Glu Thr Ser Ala Lys Lys Ile Gln Glu Glu
945                 950                 955                 960

Gln Glu Ser Leu Gly Asn Tyr Glu Leu Gln Val Gln Ile Thr Pro Arg
                965                 970                 975

Lys Arg Leu Leu Arg Lys Gln Asp Gly Thr Val
                980                 985

<210> SEQ ID NO 43
<211> LENGTH: 976
<212> TYPE: PRT
<213> ORGANISM: Solanum americanum

<400> SEQUENCE: 43

Met Ala Tyr Ala Ala Leu Ser Ser Leu Ile Tyr Thr Leu Glu Gln Leu
1               5                   10                  15

Leu Lys Pro Asn Gln Ser Phe Val Cys Arg Ser Ser Thr Gln Gln Asn
                20                  25                  30

Val Glu Ser Ile His Gln Asn Leu Cys Ala Met Gln Leu Phe Leu Asp
            35                  40                  45

Asp Thr Thr Lys Asp Ile Glu Thr Leu Lys Val Ile Glu Lys Arg
        50                  55                  60

Ile Arg Asp Val Val Tyr Lys Ala Glu Asp Lys Val Asp Ser Ser Leu
65                  70                  75                  80

Arg Asn Ile Ile Leu Ala Asp Cys Thr Glu Asn Arg Glu Gly Ala Cys
                85                  90                  95

Lys Phe Phe Glu Glu Glu Leu Leu Lys Val Glu Lys Asp Val Asp Ser
            100                 105                 110

Leu Arg Lys Glu Val Met Gln Ile Asp Phe Asn Lys His Gly Ser Arg
        115                 120                 125

Ser Gly Glu Leu Ala Arg Thr Gly Pro Ser Ser Gln Glu Lys Ser Thr
    130                 135                 140

Ile Glu Glu Asn Thr Ile Val Gly Met Glu Asp Glu Tyr Asn Thr Ile
145                 150                 155                 160

Leu Asp Arg Leu Thr Ala Gln Thr Asp Glu Leu Thr Val Ile Thr Ile
                165                 170                 175

Phe Gly Met Gly Gly Ile Gly Lys Thr Thr Leu Ala Arg Lys Val Tyr
            180                 185                 190

Asp Asp Ser Tyr Ile His Ser Arg Phe Asp Lys His Ala Trp Ile Thr
        195                 200                 205

Ile Ser Glu Glu Tyr Asn Gln Arg Gln Met Leu Leu Gln Val Val Ser
    210                 215                 220

Ser Ile Thr Thr Gly Ser Asn Gly Glu Met Ser Asp Asp Gln Leu Met
225                 230                 235                 240

Glu Ile Val Tyr Arg Gly Leu Lys Gly Arg Arg Phe Leu Ile Val Ile
                245                 250                 255

Asp Asp Ile Trp Ser Thr Glu Ala Trp Asp Gln Met Gln Arg Ile Phe
            260                 265                 270

Pro Asn Asp Asn Lys Ser Arg Ile Leu Leu Thr Thr Arg Leu Lys
        275                 280                 285

Tyr Val Ala Asp Tyr Val Ser Cys Pro Asp Phe Pro Ser His Cys Lys
    290                 295                 300

Ser Phe Leu Ser Leu Asp Asp Ser Trp Asn Leu Phe Thr Glu Lys Val
305                 310                 315                 320
```

```
Phe Lys Lys Asp Pro Cys Pro Pro His Leu Glu Thr Gly Lys His
                325                 330                 335

Ile Val Gln Gln Cys Gln Gly Leu Pro Leu Ser Val Val Val Ala
                340                 345                 350

Gly Leu Val Gly Lys Met Asp Pro Thr His Asp Asn Trp Glu Asn Val
                355                 360                 365

Glu Glu Asn Leu Asn Ser Phe Phe Gly Thr Val Ser Glu Arg Cys Gln
            370                 375                 380

Ser Ile Leu Ser Leu Ser Tyr Asn Tyr Leu Pro Gln Tyr Leu Arg Ala
385                 390                 395                 400

Cys Phe Leu Tyr Val Gly Gly Phe Pro Glu Asp Lys Glu Ile Asp Val
                405                 410                 415

Ser Lys Leu Ile Arg Leu Trp Ile Ala Glu Gln Phe Val Lys Ala Arg
                420                 425                 430

Ser Asn Lys Arg Leu Glu Val Val Ala Glu Glu Tyr Leu Glu Glu Leu
            435                 440                 445

Ile Asp Arg Ser Leu Ile Leu Thr Gly Arg Gln Arg Val Asn Gly Arg
        450                 455                 460

Met Lys Thr Cys Lys Ile His Asp Leu Leu Arg Gln Leu Cys Leu Ser
465                 470                 475                 480

Glu Ala His Thr Glu Asn Ile Ser His Ile Met Asn Arg Asn Val Pro
                485                 490                 495

Val Ser Ser Glu Ala Ile Glu Glu Lys Gln Val Tyr Pro Thr Arg His
                500                 505                 510

Ser Arg Gly Ile Ser Ser Lys Thr Arg Thr Phe Ile Ser Met Glu Ile
            515                 520                 525

Cys Leu Arg Glu Ala Gln Thr Glu Ala Ile Tyr Asp Gln Arg Arg Val
            530                 535                 540

Ile Leu Leu Ser Lys Arg His Arg Ile Asp Thr Ile Arg Thr Ile Ile
545                 550                 555                 560

Pro Phe Gly Asp Thr Phe Pro Lys Glu Ile Cys Ser Ile Phe Ser Gln
                565                 570                 575

Leu Lys Leu Leu Lys Val Leu Asp Val Leu Ser Val Trp Tyr Asp Val
                580                 585                 590

Ser Cys Ile Ile Pro Gln Leu Val His Leu Arg Tyr Val Gly Ala Val
            595                 600                 605

Ile Glu Glu Ala Leu Ser Leu Ser Lys Leu Arg Asn Leu Gln Thr Ile
        610                 615                 620

Met Leu Thr Ser Val Glu Thr Thr Glu Leu Lys His Ser Leu Asp Ile
625                 630                 635                 640

Trp Arg Met Ser Glu Ile Arg His Leu Asp Ile Val Pro Pro Leu Tyr
                645                 650                 655

Ile Ser Asn Pro Leu Glu Ala Glu Gln Pro Leu Phe Leu Asn Asn Leu
                660                 665                 670

Gln Thr Leu Tyr Leu Arg Cys Ser Pro Phe Val Ala Lys Ile Ile Arg
            675                 680                 685

Arg Thr Pro Asn Leu Lys Lys Leu Lys Ile Leu Asp Lys Ser Lys His
        690                 695                 700

Pro Asp Trp Pro Asp Ile Leu Asp Ser Leu Asn Leu Leu Glu Glu Leu
705                 710                 715                 720

Glu Thr Leu Gln Ile Ser Thr Glu Glu Asn Ile Asp Pro Met Ile Phe
                725                 730                 735
```

```
Ser Gly Asp Ile Phe Pro Arg Asn Leu Lys Gln Leu Lys Leu Ser Tyr
            740                 745                 750

Thr Cys Ile Pro Trp Glu Asp Met Lys Leu Leu Ala Asn Leu Pro Asn
        755                 760                 765

Leu Glu Val Phe Lys Gly His Tyr Ala Phe Asp Gly Thr Asp Trp Lys
    770                 775                 780

Leu Asp Glu Asp Val Val Phe Cys Lys Leu Lys Cys Leu Arg Leu Tyr
785                 790                 795                 800

Glu Arg Gly Asp Leu Gln Arg Trp Glu Ala Ala Gly Ser Asp Asn Phe
                805                 810                 815

Pro Met Leu Glu Gln Leu Leu Leu Tyr Gly Phe Lys Lys Leu Glu Glu
            820                 825                 830

Ile Pro Glu Ser Ile Gly Glu Ile Met Thr Leu Lys Phe Ile Lys Thr
        835                 840                 845

Glu Phe Cys Gly Ser Gly Val Glu Thr Ser Ala Lys Lys Ile Gln Glu
    850                 855                 860

Glu Gln Glu Ser Leu Gly Asn Tyr Glu Leu Gln Val Gln Ile Thr Pro
865                 870                 875                 880

Lys Leu Arg Phe Leu Ile Glu Asn Leu Asp Glu Ile Ser Met Leu Pro
                885                 890                 895

Pro Asn Glu Val Ala Glu Lys Ile Lys Gly Lys Ile Phe Asp Gln Lys
            900                 905                 910

Leu Lys Glu Ile Pro Glu Ser Thr Gly Gln Ile Met Thr Arg Lys Ile
        915                 920                 925

Ile Lys Thr Glu Phe Cys Gly Ser Gly Val Glu Thr Ser Ala Lys Lys
    930                 935                 940

Ile Gln Glu Glu Gln Glu Ser Leu Gly Asn Cys Glu Leu His Gln Val
945                 950                 955                 960

Gln Ile Thr Pro Lys Glu Arg Leu Leu Arg Lys Gln Asp Gly Thr Val
                965                 970                 975

<210> SEQ ID NO 44
<211> LENGTH: 986
<212> TYPE: PRT
<213> ORGANISM: Solanum americanum

<400> SEQUENCE: 44

Met Ala Tyr Ala Ala Leu Ser Ser Leu Ile Tyr Thr Leu Gln Gln Leu
1               5                   10                  15

Leu Lys Pro Asn Gln Ser Leu Val Cys Arg Ser Cys Thr Gln Gln His
            20                  25                  30

Leu Gln Ser Ile Tyr His Asn Leu Ser Ala Leu Gln Leu Phe Leu Asp
        35                  40                  45

Asp Thr Thr Lys Asp Ile Glu Thr Leu Lys Val Ile Glu Lys Arg
    50                  55                  60

Ile Arg Asp Val Val Tyr Lys Ala Glu Asp Thr Val Asp Ser Ser Leu
65                  70                  75                  80

Arg Asn Ile Ile Leu Ala Asp Cys Thr Glu Asn Arg Glu Gly Ala Cys
                85                  90                  95

Lys Phe Phe Glu Glu Glu Leu Leu Lys Val Lys Asp Val Asp Ser
            100                 105                 110

Leu Ser Lys Glu Val Met Gln Ile Asp Phe Asn Lys His Gly Ser Arg
        115                 120                 125

Ser Ala Glu Leu Ala Thr Thr Asp Pro Ser Ser Ser Gly Lys Ser Thr
    130                 135                 140
```

```
Ile Glu Glu His Thr Ile Val Gly Met Glu Asp Glu Tyr Asn Thr Ile
145                 150                 155                 160

Leu Asp Arg Leu Thr Ala Gln Thr Asp Glu Leu Thr Val Ile Pro Ile
            165                 170                 175

Phe Gly Met Gly Gly Ile Gly Lys Thr Thr Leu Ala Arg Lys Val Tyr
        180                 185                 190

Asp Asp Ser Ser Ile Arg Ser Arg Phe Asp Arg His Ala Trp Val Thr
            195                 200                 205

Thr Ser Glu Glu Phe Asn Glu Arg Arg Met Leu Leu Glu Val Val Ser
    210                 215                 220

Ser Ile Thr Thr Gly Ser Asn Gln Gly Lys Ser Asp Asp Gln Leu Met
225                 230                 235                 240

Glu Ile Val Tyr Arg Ser Leu Lys Gly Arg Arg Phe Leu Ile Val Ile
                245                 250                 255

Asp Asp Ile Trp Ser Thr Gln Ala Trp Asp Gln Met Gln Arg Ile Phe
            260                 265                 270

Pro Asn Asp Asp Asn Lys Ser Arg Ile Leu Leu Thr Thr Arg Leu Lys
        275                 280                 285

Tyr Val Ala Asp Tyr Val Ser Ser Pro Asp Phe Pro Pro His Ser Lys
    290                 295                 300

Ser Phe Leu Ser Leu Asp Asp Ser Trp Asn Leu Phe Thr Glu Lys Val
305                 310                 315                 320

Phe Asn Glu Asp Thr Cys Pro Pro His Leu Glu Glu Thr Gly Lys His
                325                 330                 335

Ile Val Gln Gln Cys Gln Gly Leu Pro Leu Ser Val Val Val Val Ala
            340                 345                 350

Gly Leu Val Gly Lys Met Asp Pro Thr His Asp Asn Trp Glu Asn Val
        355                 360                 365

Glu Glu Asn Leu Asn Ser Phe Phe Gly Thr Val Ser Glu Arg Cys His
    370                 375                 380

Ser Ile Leu Ser Leu Ser Tyr Asn Tyr Leu Pro Gln Tyr Leu Arg Ala
385                 390                 395                 400

Cys Phe Leu Tyr Val Gly Gly Phe Pro Glu Asp Lys Glu Ile Asp Val
                405                 410                 415

Ser Lys Leu Ile Arg Leu Trp Ile Ala Glu Gln Phe Val Lys Ala Arg
            420                 425                 430

Ser Asn Lys Arg Leu Glu Val Val Ala Glu Glu Tyr Leu Glu Glu Leu
        435                 440                 445

Ile Asp Arg Ser Leu Ile Leu Ser Gly Arg Gln Arg Ala Asn Gly Arg
    450                 455                 460

Met Lys Thr Cys Lys Ile His Asp Leu Leu Arg Gln Leu Cys Leu Ser
465                 470                 475                 480

Glu Ala His Thr Glu Asn Ile Ser His Ile Met Asn Arg Asn Val Pro
                485                 490                 495

Val Ser Ser Glu Ala Ile Asp Asp Gln Arg Arg Val Ile Val Pro Leu
            500                 505                 510

Glu Leu Glu Glu Lys Gln Val Tyr Pro Thr Arg His Ser Ser Gly Ile
        515                 520                 525

Thr Ser Thr Thr Arg Thr Phe Ile Ser Met Glu Ile Cys Leu Arg Glu
    530                 535                 540

Ala Gln Thr Glu Ala Ile Tyr Asp Gln Arg Arg Val Ile Leu Leu Ser
545                 550                 555                 560
```

-continued

```
Lys Arg His Arg Ile Asp Thr Ile Arg Thr Ile Pro Phe Gly Asp
                565                 570                 575
Thr Phe Pro Lys Glu Ile Cys Ser Ile Phe Ser Glu Phe Lys Leu Leu
            580                 585                 590
Lys Val Leu Asp Val Leu Ser Val Trp Tyr Asp Val Ser Cys Ile Ile
        595                 600                 605
Pro Gln Leu Val His Leu Arg Tyr Val Gly Ala Val Ile Leu Glu Ala
    610                 615                 620
Leu Ser Leu Pro Lys Leu Arg Asn Leu Gln Thr Ile Met Leu Thr Ser
625                 630                 635                 640
Val Glu Thr Thr Glu Leu Lys His Ser Leu Asp Ile Trp Arg Met Ser
                645                 650                 655
Glu Ile Arg His Leu Asp Ile Val Pro Pro Leu Tyr Ile Ser Asn Pro
            660                 665                 670
Leu Glu Ala Glu Gln Pro Leu Phe Leu Asn Asn Leu His Thr Leu Phe
        675                 680                 685
Leu Arg Cys Ser Pro Phe Val Ala Lys Ile Ile Arg Arg Thr Pro Asn
    690                 695                 700
Leu Lys Lys Leu Lys Ile Leu Asp Lys Ser Lys His Pro Asp Trp Pro
705                 710                 715                 720
Asp Ile Leu Asp Ser Leu Asn Leu Leu Glu Glu Leu Glu Thr Leu Gln
                725                 730                 735
Ile Ser Thr Glu Glu Asn Ile Asp Arg Met Ile Phe Ser Gly Asp Asn
            740                 745                 750
Phe Pro Arg Asn Leu Lys Gln Leu Lys Leu Ser Gly Thr Lys Ile Pro
        755                 760                 765
Trp Glu Asp Met Lys Leu Leu Ala Asn Leu Pro Asn Leu Glu Val Phe
    770                 775                 780
Lys Gly His Tyr Ala Phe Asp Gly Thr Asp Trp Lys Leu Asp Glu Asp
785                 790                 795                 800
Val Val Phe Cys Lys Leu Lys Cys Leu Arg Leu Tyr Glu Arg Gly Asp
                805                 810                 815
Leu Gln Arg Trp Glu Ala Ala Gly Ser Asp Asn Phe Pro Met Leu Glu
            820                 825                 830
Gln Leu Val Leu Tyr Gly Phe Glu Lys Leu Glu Glu Ile Pro Glu Ser
        835                 840                 845
Ile Gly Glu Ile Met Thr Leu Lys Phe Ile Lys Thr Glu Phe Cys Gly
    850                 855                 860
Ser Gly Val Glu Thr Ser Ala Lys Lys Ile Gln Glu Glu Gln Glu Ser
865                 870                 875                 880
Trp Gly Asn Tyr Glu Leu Gln Leu Leu Ile Thr Pro Met Leu Arg Phe
                885                 890                 895
Leu Ile Glu Asn Leu Asp Glu Ile Ser Met Leu Pro Pro Asp Glu Val
            900                 905                 910
Ala Glu Lys Ile Lys Val Lys Ile Phe Asp Arg Lys Leu Lys Glu Ile
        915                 920                 925
Leu Glu Ser Thr Gly Gln Ile Met Thr Arg Lys Ile Ile Lys Thr Glu
    930                 935                 940
Phe Cys Ser Ser Gly Val Glu Thr Ser Ala Lys Lys Ile Gln Glu Gln
945                 950                 955                 960
Glu Ser Leu Gly Asn Tyr Glu Leu Gln Val Gln Ile Thr Pro Arg Lys
                965                 970                 975
Arg Leu Leu Arg Lys Gln Asp Gly Thr Val
```

<210> SEQ ID NO 45
<211> LENGTH: 986
<212> TYPE: PRT
<213> ORGANISM: Solanum americanum

<400> SEQUENCE: 45

```
Met Ala Tyr Ala Ala Leu Ser Ser Leu Ile Tyr Thr Leu Gln Gln Leu
1               5                   10                  15

Leu Lys Pro Asn Gln Ser Leu Val Cys Arg Ser Ser Thr Gln Gln His
            20                  25                  30

Leu Gln Ser Ile Tyr His Asn Leu Ser Ala Leu Gln Leu Phe Leu Asp
        35                  40                  45

Asp Thr Thr Thr Lys Asp Ile Glu Thr Leu Lys Val Ile Glu Lys Arg
    50                  55                  60

Ile Arg Asp Val Val Tyr Lys Ala Glu Asp Lys Val Asp Ser Ser Leu
65                  70                  75                  80

Arg Asn Ile Ile Leu Ala Asp Cys Thr Glu Asn Arg Glu Ala Ala Cys
                85                  90                  95

Lys Phe Phe Glu Glu Glu Leu Leu Lys Val Glu Lys Asp Val His Ser
            100                 105                 110

Leu Arg Lys Glu Val Met Gln Ile Glu Phe Asn Lys His Gly Ser Arg
        115                 120                 125

Ser Ala Glu Leu Thr Thr Ile Leu Pro Ser Pro Glu Lys Ser Thr Ile
    130                 135                 140

Glu Glu His Thr Ile Val Gly Met Glu Asp Tyr Asn Thr Ile Leu
145                 150                 155                 160

Asp Arg Leu Thr Ala Gln Thr Asp Glu Leu Thr Val Ile Pro Ile Phe
                165                 170                 175

Gly Met Gly Gly Ile Gly Lys Thr Thr Leu Ala Arg Lys Val Tyr Asp
            180                 185                 190

Asp Ser Ser Ile Arg Ser Arg Phe Asp Arg His Val Trp Val Thr Thr
        195                 200                 205

Ser Glu Glu Phe Asn Glu Arg Arg Met Leu Leu Glu Val Val Ser Ser
    210                 215                 220

Ile Thr Thr Gly Ser Asn Gln Glu Lys Ser Asp Asp Gln Leu Met Glu
225                 230                 235                 240

Ile Val Tyr Arg Gly Leu Lys Gly Arg Arg Phe Leu Ile Val Ile Asp
                245                 250                 255

Asp Ile Trp Ser Thr Gln Ala Trp Asp Gln Met Gln Arg Ile Phe Pro
            260                 265                 270

Asn Asp Asp Asn Lys Ser Arg Ile Leu Leu Thr Thr Arg Leu Lys Tyr
        275                 280                 285

Val Ala Asp Tyr Val Asn Ser Pro Asp Phe Pro Pro His Ser Lys Ser
    290                 295                 300

Phe Leu Ser Leu Asp Asp Ser Trp Asn Leu Phe Thr Glu Lys Val Phe
305                 310                 315                 320

Asn Lys Asp Thr Cys Pro Pro His Leu Glu Glu Thr Gly Lys His Ile
                325                 330                 335

Val Gln Gln Cys Arg Gly Leu Pro Leu Ser Val Val Val Ala Gly
            340                 345                 350

Leu Val Gly Lys Met Asp Pro Thr His Asp Asn Trp Glu Asn Val Glu
        355                 360                 365
```

```
Glu Asn Leu Asn Ser Phe Ile Gly Thr Val Ser Glu Arg Cys Gln Ser
    370                 375                 380

Ile Leu Ser Leu Ser Tyr Asn Tyr Leu Pro Gln Tyr Leu Arg Ala Cys
385                 390                 395                 400

Phe Leu Tyr Val Gly Cys Phe Pro Asp Lys Glu Ile Asp Val Ser
            405                 410                 415

Lys Leu Ile Arg Leu Trp Ile Ala Glu Gln Phe Val Lys Ala Arg Ser
            420                 425                 430

Asn Lys Asn Leu Glu Val Val Ala Glu Glu Tyr Leu Glu Glu Leu Ile
        435                 440                 445

Asp Arg Ser Leu Ile Leu Ser Gly Arg Gln Arg Ala Asn Gly Arg Met
450                 455                 460

Lys Thr Cys Lys Ile His Asp Leu Leu Arg Gln Leu Cys Leu Ser Glu
465                 470                 475                 480

Ala His Thr Glu Asn Ile Ser His Ile Met Asn Arg Asn Val Leu Val
                485                 490                 495

Ser Ser Glu Ala Ile Asp Asp Gln Arg Arg Val Ile Val Pro Leu Glu
            500                 505                 510

Leu Glu Glu Lys Gln Val Tyr Pro Thr Arg His Ser Ser Gly Ile Thr
        515                 520                 525

Ser Thr Thr Arg Thr Phe Ile Ser Met Glu Ile Cys Leu Arg Glu Ala
    530                 535                 540

Gln Thr Glu Thr Ile Tyr Asp Gln Arg Arg Val Ile Leu Leu Ser Lys
545                 550                 555                 560

Arg His Arg Ile Asp Thr Ile Arg Thr Ile Pro Phe Gly Asp Thr
            565                 570                 575

Phe Pro Lys Val Ile Cys Ser Ile Phe Ser Gln Leu Lys Leu Leu Lys
            580                 585                 590

Val Leu Asp Val Leu Ser Val Trp Tyr Asp Val Ser Cys Ile Ile Pro
        595                 600                 605

Gln Leu Val His Leu Arg Tyr Val Gly Ala Val Ile Leu Glu Ala Val
    610                 615                 620

Ser Leu Ser Lys Leu Arg Asn Leu Gln Thr Ile Ile Leu Ala Ser Val
625                 630                 635                 640

Glu Thr Thr Glu Leu Lys His Pro Val Asp Ile Trp Arg Met Ser Glu
                645                 650                 655

Ile Arg His Leu Asp Ile Val Pro Pro Leu Tyr Ile Ser Asn Pro Leu
            660                 665                 670

Glu Ala Glu Gln Pro Leu Phe Leu Asn Asn Leu His Thr Leu Phe Leu
        675                 680                 685

Arg Cys Ser Pro Phe Val Ala Lys Ile Ile Arg Arg Thr Pro Asn Leu
690                 695                 700

Lys Lys Leu Lys Ile Leu Asp Lys Ser Lys His Pro Asp Trp Pro Asp
705                 710                 715                 720

Ile Leu Asp Ser Leu Asn Leu Leu Glu Glu Leu Glu Thr Leu Gln Ile
            725                 730                 735

Ser Thr Glu Glu Asn Ile Asp Arg Met Ile Phe Ser Gly Asp Ile Phe
        740                 745                 750

Pro Arg Asn Leu Lys Gln Leu Lys Leu Ser Tyr Thr Cys Ile Pro Trp
            755                 760                 765

Glu Asp Met Lys Leu Leu Ala Asn Leu Pro Asn Leu Glu Val Phe Lys
770                 775                 780

Gly His Tyr Ala Phe Asp Gly Thr Asp Trp Lys Leu Asp Glu Asp Val
```

Val Phe Cys Lys Leu Lys Cys Leu Arg Leu Tyr Glu Arg Gly Asp Leu
                805                 810                 815

Gln Arg Trp Glu Ala Ala Gly Ser Asp Asn Phe Pro Met Leu Glu Gln
            820                 825                 830

Leu Leu Leu Tyr Gly Phe Lys Lys Leu Glu Glu Ile Pro Glu Ser Ile
            835                 840                 845

Gly Glu Ile Met Thr Leu Lys Phe Ile Lys Thr Glu Phe Cys Gly Ser
        850                 855                 860

Gly Val Glu Thr Ser Ala Lys Lys Ile Gln Gln Glu Gln Ser Leu
865                 870                 875                 880

Gly Asn Tyr Glu Leu Gln Leu Gln Ile Thr Pro Lys Leu Arg Phe Leu
            885                 890                 895

Ile Glu Asn Leu Asp Glu Thr Ser Met Leu Pro Ser Asn Glu Val Ile
        900                 905                 910

Glu Lys Ile Lys Gly Lys Ile Phe Asp Arg Lys Leu Lys Glu Ile Pro
        915                 920                 925

Glu Ser Thr Gly Gln Ile Met Thr Arg Lys Ile Ile Lys Thr Glu Phe
        930                 935                 940

Cys Ser Ser Gly Val Glu Thr Ser Ala Lys Lys Ile Gln Glu Glu Gln
945                 950                 955                 960

Glu Ser Leu Gly Asn Tyr Glu Leu Gln Val Gln Ile Thr Pro Arg Lys
            965                 970                 975

Arg Leu Leu Arg Lys Gln Asp Gly Thr Val
            980                 985

<210> SEQ ID NO 46
<211> LENGTH: 8005
<212> TYPE: DNA
<213> ORGANISM: Solanum nigrescens

<400> SEQUENCE: 46

```
aagtttcctt tgtaaaacat aacacacaaa tacaattcag gagatcgtga gaagaagaaa     60
gtatttagtg aggttttttgt agtgagaaat tcttggtgta aattctctat aattctattc    120
ttgtgaaata gagttgtttt tcctcccaaa tatttttcat agtgatcaga gaataacaac    180
aaatgtgtct acggactgtt aaaaaataat ggcataagtg ggccctcttt gtaaacgata    240
atggcatggg tgagctcaat atttagcgga tgatataaat gaatttttt tcaaagtttg    300
attactatt taagtttttt tcttttatt taattttaa ttcgatgtcc aatatgcaca    360
accaaatttc cactacaacc aaaaaaaaa aaaagaacg ctgtgtaaca tcatctccaa    420
ccaacctggg tcatatgagt cccaaatgca tttacagcaa caagagcaa agcaaagcac    480
aactttgaaa tttgaaaaat gatgcaagac aaatatcatt cacaattccc cttaaaataa    540
atgataaatt aaagaagact aaacaataga aaaccttaca atctcaaagg cagtatggat    600
cggagtcgta tttggaagaa attttgatac aacttgaaga agattgaaga ttgttgttca    660
taaagtatac tgtgggcggg ttaatctaca acctgtgtgt ttttatcat acaaaattcc    720
acacagtatt attaatttt taaggatcgt tgtccatgt gatatgaaat tatgatatga    780
aattatgaga tgaagttgac attttgtttg gacatgcaat ttggactttt tatgttgtat    840
gttttcttat aaacataagt tgtaaaatta ttaaagttgt cccatttttt tattcaattt    900
taccaaataa acaaaaattt acaaaatcac ataatatgct accacaaaac tattctttaa    960
aaaatacaat atttattgat caaactttaa ttcaacaaaa aataaaattc aacataagtt   1020
```

```
gtagtagttg tagtgtacta gtctttaata taattctccc acataatacg acaatctcc    1080 tcacgttgaa cttgcatttc tcgatcatat gattgagtag acaaaccaac attgctactt    1140
tgagctataa atggtttaaa aagtaatgat atgaattata aatttttattt acatatgaaa    1200 caaatgataa gtaaatataa atgtggggtt gtttttataa aatataaact tatgggtcaa    1260
tttttgtatt tgaaaaatcc caaattatga tttgaaattt tcaaatcatg attttttgaag   1320 aattcagtct gaaatcgcat gtccaaatgc tgatttcatc tcatgatttc atatcgtgat    1380
atgaaatcgc atgtctaaac gcctactaag taacttagac acgtcttgac cttttataat    1440
tatccctcca tcctaatttta cttgtcaaat attttctaat ttgattccct ttttacttgt    1500
cattttttac aaatcaagaa acgacaattt ttttttcttc ctattatacc ctcaatttat    1560
taacattgaa ttaatgtcct tgaaaaatat agtaagtaaa tatgtttaaa actctatcaa    1620
attaataggg gtaaaataat aaactcatta tattaattat tattttctta atagatgcgt    1680
caaatcaaaa atcgacaaag taatataaat ttcaaacaaa atttgtatcg aaagttaatt    1740
gtattcgtca agtttgaatc caatgtatat gaatgtttga aaagtcttga cgaaaactac    1800
aagagtgtct ttattagaaa tcaggacaac ttgactcttt attttttcatt tcttttttct    1860 cactttgact tggtcaatcc atagttttgc atccataaac cacaagttct gtttagatat    1920
taaatagaaa attgtccaaa tttatttaga aaaatgtgga cataaatcat ttagacaaaa    1980
cctcttatag cctaagcaga gacatttctc ttccagcaaa caaagagaaa atggcttatg    2040
ctgctctttc ttcacttatg tatacattgc aacaactctt gaaacctaat caatctttcg    2100
tttgtcgata ctctacacaa caacttgttc aatctctcta tcaaaatctt actgctctgc    2160 aactttttcct tgaccatact acgacaaagg atattgaaac acttaaggta tgtaattatc    2220
taatctctta ctcatcttat atttattcaa taataattaa tttatcgagt ttcaattttta    2280 aggttataga aaagaggatc agagatgtag tatacaaagc agaagataaa gttgattcaa    2340
gcctaagaaa catcattcta gcagattgca cagagaatag agaaggggct tgtaaattct    2400
ttgaggaaga attgctaaaa gtggaaaaag atgttgattc tctcagcaaa gaggtgatgc    2460
agatcgagtt taacaagcat ggatgcagat ctgcagaatt agcaacaact gatccctcct    2520
catcaggaaa aagtacaatt gaggaacata ctattgttgg gatggaggat gagtacaaca    2580
ccatacttga tcgcctcact gcccaaacag acgagttgac tgtcatacca attttttggta   2640 tgggcggtat aggtaagaca actcttgcca gaaaggttta tgatgattca tctattcgtt    2700
ctcgatttga tagacatgca tgggtcacta cctttgaaga attcaatgag agacgaatgc    2760
ttctcgaagt tgtttcttca attactactg gaagcaatca aggaaagagc gatgatcaac    2820
taatggagat tgtgtataga agtctgaagg gtaggagatt tctaattgtc atagatgata    2880
tttggagtac tcaggcttgg gaccaaatgc aaagaatatt tccaaatgat gacagtaaaa    2940
gccgaattct actaactaca cggctcaagt atgttgctga ttatgtcagc agtcctgatt    3000
ttccacctca tagtaagtct tttctaagtc ttgatgatag ttggaatcta ttcaccgaaa    3060
aagtattcaa cgaagatacc tgtcctcctc acctagaaga aacagggaag catattgtac    3120
aacaatgtca aggattacct ctctcggttg ttgtcgttgc tggacttgtt ggaaaaatgg    3180
acccaacgca tgacaattgg gagaatgttg aggaaaatct gaactcattc tttggtactg    3240
tatccgaacg gtgccactca attctttctt tgagctacaa ttacttgccc caatatttga    3300
gggcttgttt tctctatgtt ggaggttttc ctgaagataa agagattgat gtttccaagt    3360
```

```
tgattaggct atggattgct gagcaattcg taaaggcgag aagcaataaa aggctagaag      3420
tggtggcaga ggagtatctg gaagagttaa ttgatagaag tctaattttg agtggtagac      3480
aaagggctaa tggaaggatg aaaacttgca aaattcatga tcttcttcgc caactatgcc      3540
taagtgaagc tcatactgaa aatattagtc atatcatgaa tagaaatgtc cccgtgtcct      3600
cagaagccat agatgatcaa cggcgagtga ttgttccatt ggaactcgaa gagaaacaag      3660
tttatcctac aaggcatagc agtggtatta caagtacaac ccgcaccttt atttcaatgg      3720
aaatatgcct aagagaagct caaaccgaag ccatatatga tcaacggcga gtgatccttc      3780
tgtctaaacg acataggatt gatacaatcc gcaccattat tccattcgga gatacttttc      3840
caaaagagat ttgttccatt ttttcagagt tcaagttgct taaggtgttg gatgtattat      3900
cagtctggta cgatgtctct tgtataatac ctcagcttgt acatttgaga tatgttggtg      3960
cagtaatttt ggaagctctt tcactaccca aattgagaaa tctacagacc ataatgctta      4020
caagtgttga accacagag ttgaagcact cactagatat ctggagaatg tcagagataa      4080
gacatttgga tattgtaccg ccactatata tatcaaatcc tcttgaagca gaacaacctt      4140
tgtttctcaa taacttgcac acgcttttc tccgttgctc tccttttgtt gcgaaaatca      4200
taagaagaac tccgaatcta aaaaagctaa agatttagga taaatctaag catcctgact      4260
ggcctgatat tcttgattct ctcaatcttc tagaggagct ggagacacta caaatatcaa      4320
cagaagaaaa cattgaccgg atgattttct ctggggatat tttccctcgt aatctcaagc      4380
aactgaaatt atcatatact tgtataccat gggaagatat gaaattgctg gctaatttac      4440
ccaatcttga ggtgttcaag ggtcattatg cattcgatgg aacagattgg aaaactagatg      4500 aagatgttgt gttttgcaaa ttaaaatgtc tacgactgta tgagcgcgga gatctgcaaa      4560
ggtgggaagc agcaggtagt gataattttc ctatgcttga gcaactagta ctgtatgggt      4620
tcgaaaaact ggaagagatt ccggagagta ttggagaaat aatgacacta aaattcatta      4680
aaacagaatt ttgcggctct ggtgtagaga ctagtgcaaa gaaaattcaa gaagagcaag      4740
aaagctgggg aaattatgag cttcaacttc aaattactcc taaggtatgt tgaaaactcaa      4800 tctttgatta atactctccc ccagctagac ttttcaaagt aatatttcac acgtacaatc      4860
tccactcggt aagatttagg attgaaattg tcttcttaca tttatgatca tcacccttcg      4920 gttttttta tttttttta gtaaatagtt tcatatactc tacaaaagtt acacataatt      4980
aacaattgac aattgattct ctcttattga taatttgtca ttttctcttt cagttaagat      5040
ttttgatcga aaatttagac gaaacaagca tgttgccatc gaatgaagta atcgaaaaaa      5100
tcaaaggttt gtctatttaa ttcctttat tacttcattg aaagaggttc agatattta      5160 aacaactttt taacctttct atttgaattt tttatcgctc agatagatac aacatttatt      5220
ttgacgtcaa attgttatt tgatttaatc ttattctttt tgtatatagt ttccactcgg      5280
ttcttcattt tttttttcaa ttatagttta attttttta attgcacatg ttgattgat      5340 ttaatttgtg agattcactt ttctttcgat tttaggagtt cttcgggatt aatgttattc      5400
agatttagga gtattatatt tcaactttcg gttagattta ggattcaaat tgtcttctta      5460
catttatgat catcatcctt ttgatgttat ttatttcttt tagtaaatag cttcaaaaac      5520
tctatagaaa ttacatataa ttaacaattg acaattgatt ctctcttatt gataatttct      5580
catgtttctc tttcaattaa aattttttgat cgaaaactaa aagagattcc ggagagtact      5640
ggacaaaata tgcacgaaa aatcatcaaa acagaatttt gcagctctgg tgtagagact      5700
agtgcaaaga aaattcaaga agagcaagaa agcttgggaa attatgagct tcaagttcaa      5760
```

```
attactcccta gggtatgtta aactccttct ttgattatta gccaattctt taatttcata    5820
atatttctag actaagagcc tgtctggatg gacttaaaaa aataacctta taagttgaaa    5880
actgtttata agtcaaaaaa aataagtagg tctaccctaa cttatttttt tttgacttat    5940
aagttgtttt caacttttaa gctgttttaa ataagctaag tcaaatagat ccaattattt    6000
tttgggctta ttttaagcac aaaatgactt taagttggcc agccaaatac taaaaaaagc    6060
taaaaacaac ttataagtta cttttaagcc aatccaaacg aactctaaat taaaatatta    6120
aaagatataa agaatttaat taatttaatt attcctttga aatccaaaca tgatgaattt    6180
gagtaaatta aatgaaatat agttcagatt cattcaacta ataggtcatt tacttttaat    6240
ccggcaacgt tttaggcttt tagcattctc tttgaatgta ggtataatgc attaagtgca    6300
gaaatttaat tttatttaa aaaatgaaaa catctcataa taactttggt ctttttactc     6360
caaacatctt ataataaagt gagtctcttc tacttctcct aacatctcat aataaatttc    6420
tactattcct aacatctcat aataaataag tcttttctac tatttaattt tgttaaaata    6480
ttcacaattt ttgtgtctta ttctccaccc ccatctttt tttttttttac tttcttaata    6540 ttcatatgct tgaatcaaaa caaggttcta tgaattctaa cgcgcttgga ttgatcatga    6600
tgcaattcaa tatatgcatc aatttaattt ttattttca tgcataatag ttagttcac     6660 aagataaata ttttttatttc aatatgtatt tatccttaa ttaaagtact atatatgtca    6720
ctaaagtagc atcaaatttg caagaatttc taatctcaat ttatgagttt gttatattt    6780 ttttattgta ttgctttgat ttttattta taaccaaaga gaaagtctaa taatatacgt    6840
gtcattattt atttttaag tattttggga taaacacgaa cacacgtaca agttacatta    6900
aaagcggaaa gaatcaagtc aaagtttat ttaccatttt taacgttgaa aaaagcaagc    6960
cttcatttaa atagttatta tattgcttac attagaaaat atattaaaat tcattagctc    7020
cttaaaattc aatgaatcca aataattaaa cgtttattgc cataatttta tttttatctc    7080
tttaacttgc taaatggctc cttcactaca tgctttgagg aacagaagcg tttgctgagg    7140
aagcaggacg gcactgtgta acaataattt gtatggcttc agtgatgaga atattttgtg    7200
tgccacgcag catagcagtg ttcatctaac tataaaattt ataagaaaag aaaaatcgtt    7260
cttaatcgtt atttcactca ttaaattgtt ttttcttca ttttccatgg taatttgaat     7320
ttcgaagtgt ggacatggac tgtgtttgga gcataggttc atatttgtgt agttaaaat    7380 tgtatgatta ttatttagt tctcttgtca acgtccttat caccttgca gatagttact      7440 attgagaatg tatttatact attagttagt tagttactag tcatgatgat tgtgtgatga    7500
tcagcttagt tagttagatt agtgaattgg ttacagctgt tagttacagt tagttaggct    7560
aagtcgctta gtttgttagt gttataaata cacttgtaca gattcataaa gttcaattca    7620
atgaaacagt tactctcatc ttcctcttct ctcaatattc acttctcctt ctttgcaagt    7680
ttccgccatt gaagctccaa agcttgggag ctgatttcaa gttcttgttc ttgacatggt    7740
aattcaccac aattacgcct ctggcaaaga tgcgacgata tggttgtttg caacaaattt    7800
taaataaatg gaaatagat caaccataaa taaaatatga agaaacaata atattttact     7860
gataaatatg cgggtacaag atctgttcct cccttgattc ttctctccta aattttctcc    7920
gtgattcgag gaccgttagt aattaaacct cagcttacag agaccatggg acacgaagtg    7980
atccgtttaa actatcagtg tttga                                          8005
```

<210> SEQ ID NO 47

```
<211> LENGTH: 961
<212> TYPE: PRT
<213> ORGANISM: Solanum nigrescens

<400> SEQUENCE: 47

Met Ala Tyr Ala Ala Leu Ser Ser Leu Met Tyr Thr Leu Gln Gln Leu
1               5                   10                  15

Leu Lys Pro Asn Gln Ser Phe Val Cys Arg Tyr Ser Thr Gln Gln Leu
            20                  25                  30

Val Gln Ser Leu Tyr Gln Asn Leu Thr Ala Leu Gln Leu Phe Leu Asp
        35                  40                  45

His Thr Thr Thr Lys Asp Ile Glu Thr Leu Lys Val Ile Glu Lys Arg
50                  55                  60

Ile Arg Asp Val Val Tyr Lys Ala Glu Asp Lys Val Asp Ser Ser Leu
65                  70                  75                  80

Arg Asn Ile Ile Leu Ala Asp Cys Thr Glu Asn Arg Glu Gly Ala Cys
                85                  90                  95

Lys Phe Phe Glu Glu Glu Leu Leu Lys Val Glu Lys Asp Val Asp Ser
            100                 105                 110

Leu Ser Lys Glu Val Met Gln Ile Glu Phe Asn Lys His Gly Cys Arg
        115                 120                 125

Ser Ala Glu Leu Ala Thr Thr Asp Pro Ser Ser Ser Gly Lys Ser Thr
    130                 135                 140

Ile Glu Glu His Thr Ile Val Gly Met Glu Asp Glu Tyr Asn Thr Ile
145                 150                 155                 160

Leu Asp Arg Leu Thr Ala Gln Thr Asp Glu Leu Thr Val Ile Pro Ile
                165                 170                 175

Phe Gly Met Gly Gly Ile Gly Lys Thr Thr Leu Ala Arg Lys Val Tyr
            180                 185                 190

Asp Asp Ser Ser Ile Arg Ser Arg Phe Asp Arg His Ala Trp Val Thr
        195                 200                 205

Thr Ser Glu Glu Phe Asn Glu Arg Arg Met Leu Leu Glu Val Val Ser
    210                 215                 220

Ser Ile Thr Thr Gly Ser Asn Gln Gly Lys Ser Asp Asp Gln Leu Met
225                 230                 235                 240

Glu Ile Val Tyr Arg Ser Leu Lys Gly Arg Arg Phe Leu Ile Val Ile
                245                 250                 255

Asp Asp Ile Trp Ser Thr Gln Ala Trp Asp Gln Met Gln Arg Ile Phe
            260                 265                 270

Pro Asn Asp Asp Ser Lys Ser Arg Ile Leu Leu Thr Thr Arg Leu Lys
        275                 280                 285

Tyr Val Ala Asp Tyr Val Ser Ser Pro Asp Phe Pro Pro His Ser Lys
    290                 295                 300

Ser Phe Leu Ser Leu Asp Asp Ser Trp Asn Leu Phe Thr Glu Lys Val
305                 310                 315                 320

Phe Asn Glu Asp Thr Cys Pro Pro His Leu Glu Thr Gly Lys His
                325                 330                 335

Ile Val Gln Gln Cys Gln Gly Leu Pro Leu Ser Val Val Val Ala
            340                 345                 350

Gly Leu Val Gly Lys Met Asp Pro Thr His Asp Asn Trp Glu Asn Val
        355                 360                 365

Glu Glu Asn Leu Asn Ser Phe Phe Gly Thr Val Ser Glu Arg Cys His
    370                 375                 380

Ser Ile Leu Ser Leu Ser Tyr Asn Tyr Leu Pro Gln Tyr Leu Arg Ala
```

```
385                 390                 395                 400
Cys Phe Leu Tyr Val Gly Gly Phe Pro Glu Asp Lys Glu Ile Asp Val
                405                 410                 415
Ser Lys Leu Ile Arg Leu Trp Ile Ala Glu Gln Phe Val Lys Ala Arg
                420                 425                 430
Ser Asn Lys Arg Leu Glu Val Ala Glu Glu Tyr Leu Glu Glu Leu
                435                 440                 445
Ile Asp Arg Ser Leu Ile Leu Ser Gly Arg Gln Arg Ala Asn Gly Arg
                450                 455                 460
Met Lys Thr Cys Lys Ile His Asp Leu Leu Arg Gln Leu Cys Leu Ser
465                 470                 475                 480
Glu Ala His Thr Glu Asn Ile Ser His Ile Met Asn Arg Asn Val Pro
                    485                 490                 495
Val Ser Ser Glu Ala Ile Asp Asp Gln Arg Arg Val Ile Val Pro Leu
                500                 505                 510
Glu Leu Glu Glu Lys Gln Val Tyr Pro Thr Arg His Ser Ser Gly Ile
                515                 520                 525
Thr Ser Thr Thr Arg Thr Phe Ile Ser Met Glu Ile Cys Leu Arg Glu
                530                 535                 540
Ala Gln Thr Glu Ala Ile Tyr Asp Gln Arg Arg Val Ile Leu Leu Ser
545                 550                 555                 560
Lys Arg His Arg Ile Asp Thr Ile Arg Thr Ile Ile Pro Phe Gly Asp
                    565                 570                 575
Thr Phe Pro Lys Glu Ile Cys Ser Ile Phe Ser Glu Phe Lys Leu Leu
                580                 585                 590
Lys Val Leu Asp Val Leu Ser Val Trp Tyr Asp Val Ser Cys Ile Ile
                595                 600                 605
Pro Gln Leu Val His Leu Arg Tyr Val Gly Ala Val Ile Leu Glu Ala
                610                 615                 620
Leu Ser Leu Pro Lys Leu Arg Asn Leu Gln Thr Ile Met Leu Thr Ser
625                 630                 635                 640
Val Glu Thr Thr Glu Leu Lys His Ser Leu Asp Ile Trp Arg Met Ser
                    645                 650                 655
Glu Ile Arg His Leu Asp Ile Val Pro Pro Leu Tyr Ile Ser Asn Pro
                660                 665                 670
Leu Glu Ala Glu Gln Pro Leu Phe Leu Asn Asn Leu His Thr Leu Phe
                675                 680                 685
Leu Arg Cys Ser Pro Phe Val Ala Lys Ile Ile Arg Arg Thr Pro Asn
                690                 695                 700
Leu Lys Lys Leu Lys Ile Leu Asp Lys Ser Lys His Pro Asp Trp Pro
705                 710                 715                 720
Asp Ile Leu Asp Ser Leu Asn Leu Leu Glu Leu Glu Thr Leu Gln
                    725                 730                 735
Ile Ser Thr Glu Glu Asn Ile Asp Arg Met Ile Phe Ser Gly Asp Ile
                    740                 745                 750
Phe Pro Arg Asn Leu Lys Gln Leu Lys Leu Ser Tyr Thr Cys Ile Pro
                755                 760                 765
Trp Glu Asp Met Lys Leu Leu Ala Asn Leu Pro Asn Leu Glu Val Phe
                770                 775                 780
Lys Gly His Tyr Ala Phe Asp Gly Thr Asp Trp Lys Leu Asp Glu Asp
785                 790                 795                 800
Val Val Phe Cys Lys Leu Lys Cys Leu Arg Leu Tyr Glu Arg Gly Asp
                    805                 810                 815
```

```
Leu Gln Arg Trp Glu Ala Ala Gly Ser Asp Asn Phe Pro Met Leu Glu
            820                 825                 830

Gln Leu Val Leu Tyr Gly Phe Glu Lys Leu Glu Ile Pro Glu Ser
        835                 840                 845

Ile Gly Glu Ile Met Thr Leu Lys Phe Ile Lys Thr Glu Phe Cys Gly
850                 855                 860

Ser Gly Val Glu Thr Ser Ala Lys Lys Ile Gln Glu Glu Gln Glu Ser
865                 870                 875                 880

Leu Gly Asn Tyr Glu Leu Gln Leu Gln Ile Thr Pro Lys Leu Arg Phe
                885                 890                 895

Leu Ile Glu Asn Leu Asp Glu Thr Ser Met Leu Pro Ser Asn Glu Val
                900                 905                 910

Ile Glu Lys Ile Lys Glu Phe Cys Ser Ser Gly Val Glu Thr Ser Ala
                915                 920                 925

Lys Lys Ile Gln Glu Glu Gln Glu Ser Leu Gly Asn Tyr Glu Leu Gln
        930                 935                 940

Val Gln Ile Thr Pro Arg Lys Arg Leu Leu Arg Lys Gln Asp Gly Thr
945                 950                 955                 960

Val

<210> SEQ ID NO 48
<211> LENGTH: 978
<212> TYPE: PRT
<213> ORGANISM: Solanum nigrescens

<400> SEQUENCE: 48

Met Ala Tyr Ala Ala Leu Ser Ser Leu Met Tyr Thr Leu Gln Gln Leu
1               5                   10                  15

Leu Lys Pro Asn Gln Ser Phe Val Cys Arg Tyr Ser Thr Gln Gln Leu
                20                  25                  30

Val Gln Ser Leu Tyr Gln Asn Leu Thr Ala Leu Gln Leu Phe Leu Asp
            35                  40                  45

His Thr Thr Thr Lys Asp Ile Glu Thr Leu Lys Val Ile Glu Lys Arg
50                  55                  60

Ile Arg Asp Val Val Tyr Lys Ala Glu Asp Lys Val Asp Ser Ser Leu
65                  70                  75                  80

Arg Asn Ile Ile Leu Ala Asp Cys Thr Glu Asn Arg Glu Gly Ala Cys
                85                  90                  95

Lys Phe Phe Glu Glu Glu Leu Leu Lys Val Glu Lys Asp Val Asp Ser
                100                 105                 110

Leu Ser Lys Glu Val Met Gln Ile Glu Phe Asn Lys His Gly Cys Arg
            115                 120                 125

Ser Ala Glu Leu Ala Thr Thr Asp Pro Ser Ser Gly Lys Ser Thr
            130                 135                 140

Ile Glu Glu His Thr Ile Val Gly Met Glu Asp Glu Tyr Asn Thr Ile
145                 150                 155                 160

Leu Asp Arg Leu Thr Ala Gln Thr Asp Glu Leu Thr Val Ile Pro Ile
                165                 170                 175

Phe Gly Met Gly Gly Ile Gly Lys Thr Thr Leu Ala Arg Lys Val Tyr
                180                 185                 190

Asp Asp Ser Ser Ile Arg Ser Arg Phe Asp Arg His Ala Trp Val Thr
            195                 200                 205

Thr Ser Glu Glu Phe Asn Glu Arg Arg Met Leu Leu Glu Val Val Ser
        210                 215                 220
```

Ser Ile Thr Thr Gly Ser Asn Gln Gly Lys Ser Asp Asp Gln Leu Met
225                 230                 235                 240

Glu Ile Val Tyr Arg Ser Leu Lys Gly Arg Arg Phe Leu Ile Val Ile
            245                 250                 255

Asp Asp Ile Trp Ser Thr Gln Ala Trp Asp Gln Met Gln Arg Ile Phe
            260                 265                 270

Pro Asn Asp Asp Ser Lys Ser Arg Ile Leu Leu Thr Thr Arg Leu Lys
            275                 280                 285

Tyr Val Ala Asp Tyr Val Ser Ser Pro Asp Phe Pro Pro His Ser Lys
            290                 295                 300

Ser Phe Leu Ser Leu Asp Asp Ser Trp Asn Leu Phe Thr Glu Lys Val
305                 310                 315                 320

Phe Asn Glu Asp Thr Cys Pro Pro His Leu Glu Glu Thr Gly Lys His
            325                 330                 335

Ile Val Gln Gln Cys Gln Gly Leu Pro Leu Ser Val Val Val Val Ala
            340                 345                 350

Gly Leu Val Gly Lys Met Asp Pro Thr His Asp Asn Trp Glu Asn Val
            355                 360                 365

Glu Glu Asn Leu Asn Ser Phe Phe Gly Thr Val Ser Glu Arg Cys His
370                 375                 380

Ser Ile Leu Ser Leu Ser Tyr Asn Tyr Leu Pro Gln Tyr Leu Arg Ala
385                 390                 395                 400

Cys Phe Leu Tyr Val Gly Gly Phe Pro Glu Asp Lys Glu Ile Asp Val
            405                 410                 415

Ser Lys Leu Ile Arg Leu Trp Ile Ala Glu Gln Phe Val Lys Ala Arg
            420                 425                 430

Ser Asn Lys Arg Leu Glu Val Val Ala Glu Glu Tyr Leu Glu Glu Leu
            435                 440                 445

Ile Asp Arg Ser Leu Ile Leu Ser Gly Arg Gln Arg Ala Asn Gly Arg
            450                 455                 460

Met Lys Thr Cys Lys Ile His Asp Leu Leu Arg Gln Leu Cys Leu Ser
465                 470                 475                 480

Glu Ala His Thr Glu Asn Ile Ser His Ile Met Asn Arg Asn Val Pro
            485                 490                 495

Val Ser Ser Glu Ala Ile Asp Asp Gln Arg Arg Val Ile Val Pro Leu
            500                 505                 510

Glu Leu Glu Glu Lys Gln Val Tyr Pro Thr Arg His Ser Ser Gly Ile
            515                 520                 525

Thr Ser Thr Thr Arg Thr Phe Ile Ser Met Glu Ile Cys Leu Arg Glu
            530                 535                 540

Ala Gln Thr Glu Ala Ile Tyr Asp Gln Arg Arg Val Ile Leu Leu Ser
545                 550                 555                 560

Lys Arg His Arg Ile Asp Thr Ile Arg Thr Ile Ile Pro Phe Gly Asp
            565                 570                 575

Thr Phe Pro Lys Glu Ile Cys Ser Ile Phe Ser Glu Phe Lys Leu Leu
            580                 585                 590

Lys Val Leu Asp Val Leu Ser Val Trp Tyr Asp Val Ser Cys Ile Ile
            595                 600                 605

Pro Gln Leu Val His Leu Arg Tyr Val Gly Ala Val Ile Leu Glu Ala
            610                 615                 620

Leu Ser Leu Pro Lys Leu Arg Asn Leu Gln Thr Ile Met Leu Thr Ser
625                 630                 635                 640

| | | | | | | | | | | | | |
|---|---|---|---|---|---|---|---|---|---|---|---|---|
| Val | Glu | Thr | Thr | Glu 645 | Leu | Lys | His | Ser 650 | Leu | Asp | Ile | Trp | Arg | Met 655 | Ser |

Val Glu Thr Thr Glu Leu Lys His Ser Leu Asp Ile Trp Arg Met Ser
                 645             650                 655

Glu Ile Arg His Leu Asp Ile Val Pro Pro Leu Tyr Ile Ser Asn Pro
             660             665             670

Leu Glu Ala Glu Gln Pro Leu Phe Leu Asn Asn Leu His Thr Leu Phe
             675             680             685

Leu Arg Cys Ser Pro Phe Val Ala Lys Ile Ile Arg Arg Thr Pro Asn
             690             695             700

Leu Lys Lys Leu Lys Ile Leu Asp Lys Ser Lys His Pro Asp Trp Pro
705             710             715             720

Asp Ile Leu Asp Ser Leu Asn Leu Leu Glu Glu Leu Glu Thr Leu Gln
             725             730             735

Ile Ser Thr Glu Glu Asn Ile Asp Arg Met Ile Phe Ser Gly Asp Ile
             740             745             750

Phe Pro Arg Asn Leu Lys Gln Leu Lys Leu Ser Tyr Thr Cys Ile Pro
             755             760             765

Trp Glu Asp Met Lys Leu Leu Ala Asn Leu Pro Asn Leu Glu Val Phe
             770             775             780

Lys Gly His Tyr Ala Phe Asp Gly Thr Asp Trp Lys Leu Asp Glu Asp
785             790             795             800

Val Val Phe Cys Lys Leu Lys Cys Leu Arg Leu Tyr Glu Arg Gly Asp
             805             810             815

Leu Gln Arg Trp Glu Ala Ala Gly Ser Asp Asn Phe Pro Met Leu Glu
             820             825             830

Gln Leu Val Leu Tyr Gly Phe Glu Lys Leu Glu Glu Ile Pro Glu Ser
             835             840             845

Ile Gly Glu Ile Met Thr Leu Lys Phe Ile Lys Thr Glu Phe Cys Gly
850             855             860

Ser Gly Val Glu Thr Ser Ala Lys Lys Ile Gln Glu Glu Gln Glu Ser
865             870             875             880

Leu Gly Asn Tyr Glu Leu Gln Leu Gln Ile Thr Pro Lys Leu Arg Phe
             885             890             895

Leu Ile Glu Asn Leu Asp Glu Thr Ser Met Leu Pro Ser Asn Glu Val
             900             905             910

Ile Glu Lys Ile Lys Glu Ile Pro Glu Ser Thr Gly Gln Ile Met Thr
             915             920             925

Arg Lys Ile Ile Lys Thr Glu Phe Cys Ser Ser Gly Val Glu Thr Ser
             930             935             940

Ala Lys Lys Ile Gln Glu Gln Glu Ser Leu Gly Asn Tyr Glu Leu
945             950             955             960

Gln Val Gln Ile Thr Pro Arg Lys Arg Leu Leu Arg Lys Gln Asp Gly
             965             970             975

Thr Val

<210> SEQ ID NO 49
<211> LENGTH: 2883
<212> TYPE: DNA
<213> ORGANISM: Solanum nigrescens

<400> SEQUENCE: 49
atggcttatg ctgctctttc ttcacttatg tatacattgc aacaactctt gaaacctaat     60
caatctttcg tttgtcgata ctctacacaa caacttgttc aatctctcta tcaaaatctt    120
actgctctgc aacttttcct tgaccatact acgacaaagg atattgaaac acttaaggtt    180

```
atagaaaaga ggatcagaga tgtagtatac aaagcagaag ataaagttga ttcaagccta    240
agaaacatca ttctagcaga ttgcacagag aatagagaag gggcttgtaa attcttgag    300 gaagaattgc taaaagtgga aaaagatgtt gattctctca gcaaagaggt gatgcagatc    360
gagtttaaca agcatggatg cagatctgca gaattagcaa caactgatcc ctcctcatca    420
ggaaaaagta caattgagga acatactatt gttgggatgg aggatgagta caacaccata    480
cttgatcgcc tcactgccca aacagacgag ttgactgtca taccaatttt tggtatgggc    540
ggtataggta agacaactct tgccagaaag gtttatgatg attcatctat tcgttctcga    600
tttgatagac atgcatgggt cactacctct gaagaattca atgagagacg aatgcttctc    660
gaagttgttt cttcaattac tactggaagc aatcaaggaa agagcgatga tcaactaatg    720
gagattgtgt atagaagtct gaagggtagg agatttctaa ttgtcataga tgatatttgg    780
agtactcagg cttgggacca aatgcaaaga atatttccaa atgatgacag taaaagccga    840
attctactaa ctacacggct caagtatgtt gctgattatg tcagcagtcc tgattttcca    900
cctcatagta agtcttttct aagtcttgat gatagttgga atctattcac cgaaaaagta    960
ttcaacgaag atacctgtcc tcctcaccta aagaaacag ggaagcatat tgtacaacaa    1020
tgtcaaggat tacctctctc ggttgttgtc gttgctggac ttgttggaaa aatggaccca    1080
acgcatgaca attgggagaa tgttgaggaa aatctgaact cattctttgg tactgtatcc    1140
gaacggtgcc actcaattct ttcttttgagc tacaattact tgccccaata tttgagggct    1200
tgttttctct atgttggagg ttttcctgaa gataaagaga ttgatgtttc caagttgatt    1260
aggctatgga ttgctgagca attcgtaaag gcgagaagca taaaaggct agaagtggtg    1320 gcagaggagt atctggaaga gttaattgat agaagtctaa ttttgagtgg tagacaaagg    1380
gctaatggaa ggatgaaaac ttgcaaaatt catgatcttc ttcgccaact atgcctaagt    1440
gaagctcata ctgaaaatat tagtcatatc atgaataaga atgtccccgt gtcctcagaa    1500
gccatagatg atcaacggcg agtgattgtt ccattggaac tcgaagagaa acaagtttat    1560
cctacaaggc atagcagtgg tattacaagt acaacccgca cctttatttc aatggaaata    1620
tgcctaagag aagctcaaac cgaagccata tatgatcaac ggcgagtgat ccttctgtct    1680
aaacgacata ggattgatac aatccgcacc attattccat tcggagatac ttttccaaaa    1740
gagatttgtt ccatttttc agagttcaag ttgcttaagg tgttggatgt attatcagtc    1800
tggtacgatg tctcttgtat aatacctcag cttgtacatt tgagatatgt tggtgcagta    1860
attttggaag ctctttcact acccaaattg agaaatctac agaccataat gcttacaagt    1920
gttgaaacca cagagttgaa gcactcacta gatatctgga gaatgtcaga gataagacat    1980
ttggatattg taccgccact atatatatca aatcctcttg aagcagaaca acctttgttt    2040
ctcaataact tgcacacgct ttttctccgt tgctctcctt ttgttgcgaa aatcataaga    2100
agaactccga atctaaaaaa gctaaagatt ttagataaat ctaagcatcc tgactggcct    2160
gatattcttg attctctcaa tcttctagag gagctggaga cactacaaat atcaacagaa    2220
gaaaacattg accggatgat tttctctggg gatattttcc ctcgtaatct caagcaactg    2280
aaattatcat atacttgtat accatgggaa gatatgaaat tgctggctaa tttacccaat    2340
cttgaggtgt tcaagggtca ttatgcattc gatggaacag attggaaact agatgaagat    2400
gttgtgtttt gcaaattaaa atgtctacga ctgtatgagc gcggagatct gcaaggtgg    2460 gaagcagcag gtagtgataa ttttcctatg cttgagcaac tagtactgta tgggttcgaa    2520
aaactggaag agattccgga gagtattgga gaaataatga cactaaaatt cattaaaaca    2580
```

```
gaattttgcg gctctggtgt agagactagt gcaaagaaaa ttcaagaaga gcaagaaagc    2640
ttgggaaatt atgagcttca acttcaaatt actcctaagt taagattttt gatcgaaaat    2700
ttagacgaaa caagcatgtt gccatcgaat gaagtaatcg aaaaaatcaa agaattttgc    2760
agctctggtg tagagactag tgcaaagaaa attcaagaag agcaagaaag cttgggaaat    2820
tatgagcttc aagttcaaat tactcctagg aagcgtttgc tgaggaagca ggacggcact    2880
gtg                                                                 2883

<210> SEQ ID NO 50
<211> LENGTH: 2934
<212> TYPE: DNA
<213> ORGANISM: Solanum nigrescens

<400> SEQUENCE: 50
atggcttatg ctgctctttc ttcacttatg tatacattgc aacaactctt gaaacctaat      60
caatctttcg tttgtcgata ctctacacaa caacttgttc aatctctcta tcaaaatctt     120
actgctctgc aacttttcct tgaccatact acgacaaagg atattgaaac acttaaggtt     180
atagaaaaga ggatcagaga gtagtatac aaagcagaag ataaagttga ttcaagccta      240
agaaacatca ttctagcaga ttgcacagag aatagagaag gggcttgtaa attctttgag     300
gaagaattgc taaagtggaa aaagatgtt gattctctca gcaaagaggt gatgcagatc      360
gagtttaaca agcatggatg cagatctgca gaattagcaa caactgatcc ctcctcatca     420
ggaaaaagta caattgagga acatactatt gttgggatgg aggatgagta caacaccata     480
cttgatcgcc tcactgccca acagacgag ttgactgtca taccaatttt tggtatgggc      540
ggtataggta agacaactct tgccagaaag gtttatgatg attcatctat tcgttctcga     600
tttgatagac atgcatgggt cactacctct gaagaattca tgagagacg aatgcttctc      660 gaagttgttt cttcaattac tactggaagc aatcaaggaa agagcgatga tcaactaatg     720
gagattgtgt atagaagtct gaagggtagg agatttctaa ttgtcataga tgatatttgg     780
agtactcagg cttgggacca aatgcaaaga atatttccaa atgatgacag taaaagccga     840
attctactaa ctacacggct caagtatgtt gctgattatg tcagcagtcc tgattttcca     900
cctcatagta agtcttttct aagtcttgat gatagttgga atctattcac cgaaaaagta     960
ttcaacgaag ataccctgtcc tcctcaccta aagaaacag ggaagcatat tgtacaacaa     1020
tgtcaaggat tacctctctc ggttgttgtc gttgctggac ttgttggaaa aatggaccca    1080
acgcatgaca attgggagaa tgttgaggaa aatctgaact cattctttgg tactgtatcc    1140
gaacggtgcc actcaattct ttcctttgagc tacaattact tgccccaata tttgagggct    1200
tgttttctct atgttggagg ttttcctgaa gataaagaga ttgatgtttc caagttgatt    1260
aggctatgga ttgctgagca attcgtaaag gcgagaagca ataaaaggct agaagtggtg    1320
gcagaggagt atctggaaga gttaattgat agaagtctaa ttttgagtgg tagacaaagg    1380
gctaatggaa ggatgaaaac ttgcaaaatt catgatcttc ttcgccaact atgcctaagt    1440
gaagctcata ctgaaaatat tagtcatatc atgaatagaa atgtccccgt gtcctcagaa    1500
gccatagatg atcaacggcg agtgattgtt ccattggaac tcaagagaa acaagtttat     1560 cctacaaggc atagcagtgg tattacaagt acaacccgca cctttatttc aatggaaata    1620
tgcctaagag aagctcaaac cgaagccata tatgatcaac ggcgagtgat ccttctgtct    1680
aaacgacata ggattgatac aatccgcacc attattccat tcggagatac ttttccaaaa    1740
```

```
gagatttgtt ccatttttc agagttcaag ttgcttaagg tgttggatgt attatcagtc    1800
tggtacgatg tctcttgtat aatacctcag cttgtacatt tgagatatgt tggtgcagta    1860
attttggaag ctctttcact acccaaattg agaaatctac agaccataat gcttacaagt    1920
gttgaaacca cagagttgaa gcactcacta gatatctgga gaatgtcaga gataagacat    1980
ttggatattg taccgccact atatatatca atcctcttg aagcagaaca accttttgttt    2040 ctcaataact tgcacacgct ttttctccgt tgctctcctt ttgttgcgaa atcataaga    2100 agaactccga atctaaaaaa gctaaagatt ttagataaat ctaagcatcc tgactggcct    2160
gatattcttg attctctcaa tcttctagag gagctggaga cactacaaat atcaacagaa    2220
gaaaacattg accggatgat tttctctggg gatattttcc ctcgtaatct caagcaactg    2280
aaattatcat atacttgtat accatgggaa gatatgaaat tgctggctaa tttacccaat    2340
cttgaggtgt tcaagggtca ttatgcattc gatggaacag attggaaact agatgaagat    2400
gttgtgtttt gcaaattaaa atgtctacga ctgtatgagc gcggagatct gcaaaggtgg    2460
gaagcagcag gtagtgataa ttttcctatg cttgagcaac tagtactgta tgggttcgaa    2520
aaactggaag agattccgga gagtattgga gaaataatga cactaaaatt cattaaaaca    2580
gaattttgcg gctctggtgt agagactagt gcaaagaaaa ttcaagaaga gcaagaaagc    2640
ttgggaaatt atgagcttca acttcaaatt actcctaagt taagattttt gatcgaaaat    2700
ttagacgaaa caagcatgtt gccatcgaat gaagtaatcg aaaaaatcaa agagattccg    2760
gagagtactg gacaaataat gacacgaaaa atcatcaaaa cagaattttg cagctctggt    2820
gtagagacta gtgcaaagaa aattcaagaa gagcaagaaa gcttgggaaa ttatgagctt    2880
caagttcaaa ttactcctag gaagcgtttg ctgaggaagc aggacggcac tgtg         2934
```

<210> SEQ ID NO 51
<211> LENGTH: 7842
<212> TYPE: DNA
<213> ORGANISM: Solanum americanum
<400> SEQUENCE: 51

```
gaagaagaaa gtatttagtg aggttttgt agtgagaaat tcttggtgta aattctctat     60
aattctattc ttgtgaaata gagttgtttt tcctcccaaa tattttcat agtgatcaga    120 gaataacaac aaatgtgtct acggactgtt aaaaaataat ggcataagtg ggccctcttt    180
gtaaacgata atggcatggg tgagctcaat atttagcgga tgatataaat gaaatctttt    240
tcaaagtttg attacttatt taagttttt tcttttattt taatttttaa ttcgatgtcc    300
aatatgcaca accaaatttc cactacaacc aaaaaaaaaa aaaagaacg ctgtgtaaca    360 tcatctccaa ccaacctggg tcatatgagt cccaaatgca tttacagcaa caaagagcaa    420
agcaaagcac gactttgaaa tttgaaaaat gatgcaagac aaatatcatt cacaattccc    480
cttaaaataa atgataaatt aaagaagact aaacaataga aaaccttaca atctcaaagg    540
cagtatggat cggagtcgta tttggaagaa attttgatac aacttgaaga agattgaaga    600
ttgttgttca taagtatac tgtgggcggg ttaatctaca acctgtgtgt ttttatcat    660 acaaaattcc acacagtatt attaatttca tgcaatttgg acttttatg ttgtatgttt    720 tcttataaac ataagttgta aaattattaa agttgtccca ttttttatt caatttacc    780 aaataaacaa aaatttacaa aatcacataa tatgctaaca caaactatt ctttaaaaaa    840 tacaatattt attgatcaaa ctttaattca acaaaaaata aaattcaaca taagttgtag    900
tagttgtagt gtactagtct ttaatataat tctcccacat aatacggaca atctcctcac    960
```

```
gttgaacttg catttctcga tcatatgatt gagtagacaa accaacattg ctactttgag    1020
ctataaatgg tttaaaaagt aatgatatga attataaatt ttatttacat atgaaacaaa    1080
tgataagtaa atataaatgt ggggttgttt ttataaaata taaacttatg ggtcaatttt    1140
tgtatttgaa aaatcccaaa ttatgatttg aaattttcaa atcatgattt ttgaagaatt    1200
cagtctgaaa tcgcatgtcc aaatgctgat ttcatctcat gatttcatat cgtgatatga    1260
aatcgcatgt ccaaacgcct actaagtaac ttagacacgt cttgaccttt tataattatc    1320
cctccatcct aatttacttg tcaaatattt tctaatttga ttccctttttt acttgtcatt    1380
ttttacaaat caagaaacga caatttttttt ttcttcctat tataccctca atttattaac    1440
attgaattaa tgtccttgaa aaatatagta agtaaatatg tttaaaactc tatcaaatta    1500
atagggggtaa aataataaac tcattatatt aattattatt ttcttaatag atgcgtcaaa    1560
tcaaaaatcg acaaagtaat ataaatttca aagaaaattt gtatcgaaag ttaattgtat    1620
tcgtcaagtt tgaatccaat gtatatgaat gtttgaaaag tcttgacgaa aactacaaga    1680
gtgtctttat tagaaatcag gacaacttga ctctttatttt ttcatttctt ttttctcact    1740
ttgacttggt caatccatag ttttgcatcc ataaaccaca agttctgttt agatattaaa    1800
tagaaaattg tccaaattta tttagaaaaa tgtggacata aatcatttag acaaaacctc    1860
ttatagccta agcagagaca tttctcttcc agcaaacaaa agagaaatgg cttatgctgc    1920
tctttcttca cttatgtata cattgcaaca actcttgaaa cctaatcaat ctttcgtttg    1980
tcgatactct acacaacaac ttgttcaatc tctctatcaa aatcttactg ctctgcaact    2040
tttccttgac catactacga caaaggatat tgaaacactt aaggtatgta attatctaat    2100
ctcttactca tcttatattt attcaataat aattaattta tcgagtttca attttaaggt    2160
tatagaaaag aggatcagag atgtagtata caaagcagaa gataaagttg attcaagcct    2220
aagaaacatc attctagcag attgcacaga gaatagagaa ggggcttgta aattctttga    2280
ggaagaattg ctaaaagtgg aaaaagatgt tgattctctc agcaaagagg tgatgcagat    2340
cgagtttaac aagcatggat gcagatctgc agaattagca acaactgatc cctcctcatc    2400
aggaaaaagt acaattgagg aacatactat tgttgggatg gaggatgagt acaacaccat    2460
acttgatcgc ctcactgccc aaacagacga gttgactgtc ataccaattt ttggtatggg    2520
cggtataggt aagacaactc ttgccagaaa ggtttatgat gattcatcta ttcgttctcg    2580
atttgataga catgcatggg tcactacctc tgaagaattc aatgagagac gaatgcttct    2640
cgaagttgtt tcttcaatta ctactggaag caatcaagga aagagcgatg atcaactaat    2700
ggagattgtg tatagaagtc tgaagggtag gagatttcta attgtcatag atgatatttg    2760
gagtactcag gcttgggacc aaatgcaaag aatatttcca aatgatgaca gtaaaagccg    2820
aattctacta actacacggc tcaagtatgt tgctgattat gtcagcagtc ctgattttcc    2880
acctcatagt aagtcttttc taagtcttga tgatagttgg aatctattca ccgaaaaagt    2940
attcaacgaa gatacctgtc ctcctcacct agaagaaaca gggaagcata ttgtacaaca    3000
atgtcaagga ttacctctct cggttgttgt cgttgctgga cttgtggaa aaatggaccc    3060
aacgcatgac aattggggaga atgttgagga aaatctgaac tcattctttg gtactgtatc    3120
cgaacggtgc cactcaattc tttctttgag ctacaattac ttgccccaat atttgagggc    3180
ttgttttctc tatgttggag gttttcctga agataaagag attgatgttt ccaagttgat    3240
taggctatgg attgctgagc aattcgtaaa ggcgagaagc aataaaaggc tagaagtggt    3300
```

```
ggcagaggag tatctggaag agttaattga tagaagtcta attttgagtg gtagacaaag    3360
ggctaatgga aggatgaaaa cttgcaaaat tcatgatctt cttcgccaac tatgcctaag    3420
tgaagctcat actgaaaata ttagtcatat catgaataga aatgtccccg tgtcctcaga    3480
agccatagat gatcaacggc gagtgattgt tccattggaa ctcgaagaga aacaattta    3540
tcctacaagg catagcagtg gtattacaag tacaacccgc acctttattt caatggaaat    3600
atgcctaaga gaagctcaaa ccgaagccat atatgatcaa cggcgagtga tccttctgtc    3660
taaacgacat aggattgata caatccgcac cattattcca ttcggagata cttttccaaa    3720
agagatttgt tccatttttt cagagttcaa gttgcttaag gtgttggatg tattatcagt    3780
ctggtacgat gtctcttgta taatacctca gcttgtacat ttgagatatg ttggtgcagt    3840
aattttggaa gctcttttcac tacccaaatt gagaaatcta cagaccataa tgcttacaag    3900
tgttgaaacc acagagttga agcactcact agatatctgg agaatgtcag agataagaca    3960
tttggatatt gtaccgccac tatatatatc aaatcctctt gaagcagaac aacctttgtt    4020
tctcaataac ttgcacacgc ttttctccg ttgctctcct tttgttgcga aaatcataag    4080
aagaactccg aatctaaaaa agctaaagat tttagataaa tctaagcatc ctgactggcc    4140
tgatattctt gattctctca atcttctaga ggagctggac acactacaaa tatcaacaga    4200
agaaaacatt gaccggatga ttttctctgg ggatatttc cctcgtaatc tcaagcaact    4260
gaaattatca tatacttgta taccatggga agatatgaaa ttgctggcta atttacccaa    4320
tcttgaggtg ttcaagggtc attatgcatt cgatggaaca gattggaaac tagatgaaga    4380
tgttgtgttt tgcaaattaa aatgtctacg actgtatgag cgcggagatc tgcaaaggtg    4440
ggaagcagca ggtagtgata attttcctat gcttgagcaa ctagtactgt atgggttcga    4500
aaaactggaa gagattccgg agagtattgg agaaataatg acactaaaat tcattaaaac    4560
agaattttgc ggctctggtg tagagactag tgcaagaaaa attcaagaag agcaagaaag    4620
cttgggaaat tatgagcttc aacttcaaat tactcctaag gtatgttgaa actcaatctt    4680
tgattaatac tctccccag ctagacttt caaagtaata tttcacacgt acaatctcca    4740
ctcggtaaga tttaggattg aaattgtctt cttacattta tgatcatcac ccttcggttt    4800
ttttttatttt tttttagtaa atagtttcat atactctaca aaagttacac ataattaaca    4860
attgacaatt gattctctct tattgataat ttgtcatttt ctctttcagt taagattttt    4920
gatcgaaaat ttagacgaaa caagcatgtt gccatcgaat gaagtaatcg aaaaaatcaa    4980
aggtttgtct atttaattcc ttttattact tcattgaaag aggttcagat atttttaaaca    5040
actttttaac ctttctattt gaatttttta tcgctcagat agatacaaca tttatttga    5100
cgtcaaattg ttattttgat ttaatctctat tcttttttgta tatagtttcc actcggttct    5160
tcatttttt ttcaattata gtttaatttt ttttaattgc acatggttga ttgatttaat    5220
ttgtgagatt cacttttctt tcgattttag gagttcttcg ggattaatgt tattcagatt    5280
taggagtatt atatttcaac tttcggttag atttaggatt caaattgtct tcttacattt    5340
atgatcatca tccttttgat gttatttatt tcttttagta aatagcttca aaaactctat    5400
agaaattaca tataattaac aattgacaat tgattctctc ttattgataa tttctcatgt    5460
ttctctttca attaaaattt ttgatcgaaa actaaaagag attccggaga gtactggaca    5520
aataatgaca cgaaaaatca tcaaaacaga attttgcagc tctggtgtag agactagtgc    5580
aaagaaaatt caagaagagc aagaaagctt gggaaattat gagcttcaag ttcaaattac    5640
tcctagggta tgttaaactc cttctttgat tattagccaa ttctttaatt tcataatatt    5700
```

```
tctagactaa gagcctgtct ggatggactt aaaaaaataa cttataagtt gaaaactgtt    5760
tataagtcaa aaaaaataag taggtctacc ctaacttatt ttttttgact tataagttgt    5820
tttcaacttt taagctgttt taaataagct aagtcaaata gatccaatta ttttttgggc    5880
ttattttaag cacaaaatga ctttaagttg gccagccaaa tactaaaaaa agctaaaaac    5940
aacttataag ttacttttaa gccaatccaa acgaactcta aattaaaata ttaaagata     6000
taaagaattt aattaattta attattcctt tgaaatccaa acatgatgaa tttgagtaaa    6060
ttaaatgaaa tatagttcag attcatttaa ctaataggtc atttactttt aatccggcaa    6120
cgttttaggc ttttagcatt ctctttgaat gtaggtataa tgcattaagt gcagaaattt    6180
aattttatt  taaaaaatga aaacatctca taataacttt ggtcttttta ctccaaacat    6240
cttataataa agtgagtctc ttctacttct cctaacatct cataataaat ttctactatt    6300
cctaacatct cataataaat aagtcttttc tactatttaa ttttgttaaa atattcacaa    6360
tttttgtgtc ttattctcca cccccatctt ttttttttta ctttcttaat attcatatgc    6420
ttgaatcaaa acaaggttct atgaattcta acgcgcttgg attgatcatg atgcaattca    6480
atatatgcat caatttaatt tttatttttc atgcataata gttagtttca caagataaat    6540
attttatttt caatatgtat ttatccttta attaaagtac tatatatgtc actaaagtag    6600
catcaaattt gcaagaattt ctaatctcaa tttatgagtt tgttatattt ttttattgt     6660
attgctttga ttttttatttt ataaccaaag agaaagtcta ataatatacg tgtcattatt    6720
tattttttaa gtattttggg ataaacacga acacacgtac aagttacatt aaaagcggaa    6780
agaatcaagt caaaagtttg tttaccattt ttaacgttga aaaaagcaag ccttcattta    6840
aatagttatt atattgctta cattagaaaa tatattaaaa ttcattagct ccttaaaatt    6900
caatgaatcc aaataattaa acgtttattg ccataatttt atttttatct ctttaacttg    6960
ctaaatggct ccttcactac atgctttgag gaacagaagc gtttgctgag gaagcaggac    7020
ggcactgtgt aacaataatt tgtatggctt cagtgatgag aatattttgt gtgccacgca    7080
gcatagcagt gttcatctaa ctataaattt tataagaaaa gaaaaatcgt tcttaatcgt    7140
tatttcactc attaaattgt ttttctttc  attttccatg gtaatttgaa tttcgaagtg    7200
tggacatgga ctgtgtttgg agcataggtt catatttgtg tagtttaaaa ttgtatgatt    7260
attattttag ttctcttgtc aacgtcctta tcacctttgc agatagttac tattgagaat    7320
gtatttatac tattagttag ttagttacta gtcatgatga ttgtgtgatg atcagcttag    7380
ttagttagat tagtgaattg gttacagctg ttagttacag ttagttaggc taagtcgctt    7440
agtttgttag tgttataaat acacttgtac agattcataa agttcaattc aatgaaacag    7500
ttactctcat cttcctcttc tctcaatatt cacttctcct tctttgcaag tttccgccat    7560
tgaagctcca aagcttggga gctgatttca agttcttgtt cttgacatgg taattcacca    7620
caattacgcc tctggcaaag atgcgacgat atggttgttt gcaacaaatt ttaaataaat    7680
ggaaaataga tcaaccataa ataaaatatg aagaaacaat aatattttac tgataaatat    7740
gcgggtacaa gatctgttcc tcccttgatt cttctctcct aaattttctc cgtgattcga    7800
gggccgttaa tggcgtattt ctcgaattag gatgatttaa ac                       7842
```

<210> SEQ ID NO 52
<211> LENGTH: 961
<212> TYPE: PRT
<213> ORGANISM: Solanum americanum

<400> SEQUENCE: 52

```
Met Ala Tyr Ala Ala Leu Ser Ser Leu Met Tyr Thr Leu Gln Gln Leu
1               5                   10                  15

Leu Lys Pro Asn Gln Ser Phe Val Cys Arg Tyr Ser Thr Gln Gln Leu
            20                  25                  30

Val Gln Ser Leu Tyr Gln Asn Leu Thr Ala Leu Gln Leu Phe Leu Asp
        35                  40                  45

His Thr Thr Thr Lys Asp Ile Glu Thr Leu Lys Val Ile Glu Lys Arg
    50                  55                  60

Ile Arg Asp Val Val Tyr Lys Ala Glu Asp Lys Val Asp Ser Ser Leu
65                  70                  75                  80

Arg Asn Ile Ile Leu Ala Asp Cys Thr Glu Asn Arg Glu Gly Ala Cys
                85                  90                  95

Lys Phe Phe Glu Glu Glu Leu Leu Lys Val Lys Asp Val Asp Ser
            100                 105                 110

Leu Ser Lys Glu Val Met Gln Ile Glu Phe Asn Lys His Gly Cys Arg
            115                 120                 125

Ser Ala Glu Leu Ala Thr Thr Asp Pro Ser Ser Gly Lys Ser Thr
    130                 135                 140

Ile Glu Glu His Thr Ile Val Gly Met Glu Asp Glu Tyr Asn Thr Ile
145                 150                 155                 160

Leu Asp Arg Leu Thr Ala Gln Thr Asp Glu Leu Thr Val Ile Pro Ile
                165                 170                 175

Phe Gly Met Gly Gly Ile Gly Lys Thr Thr Leu Ala Arg Lys Val Tyr
            180                 185                 190

Asp Asp Ser Ser Ile Arg Ser Arg Phe Asp Arg His Ala Trp Val Thr
            195                 200                 205

Thr Ser Glu Glu Phe Asn Glu Arg Met Leu Leu Glu Val Val Ser
    210                 215                 220

Ser Ile Thr Thr Gly Ser Asn Gln Gly Lys Ser Asp Asp Gln Leu Met
225                 230                 235                 240

Glu Ile Val Tyr Arg Ser Leu Lys Gly Arg Arg Phe Leu Ile Val Ile
                245                 250                 255

Asp Asp Ile Trp Ser Thr Gln Ala Trp Asp Gln Met Gln Arg Ile Phe
            260                 265                 270

Pro Asn Asp Asp Ser Lys Ser Arg Ile Leu Leu Thr Thr Arg Leu Lys
            275                 280                 285

Tyr Val Ala Asp Tyr Val Ser Ser Pro Asp Phe Pro Pro His Ser Lys
            290                 295                 300

Ser Phe Leu Ser Leu Asp Asp Ser Trp Asn Leu Phe Thr Glu Lys Val
305                 310                 315                 320

Phe Asn Glu Asp Thr Cys Pro Pro His Leu Glu Glu Thr Gly Lys His
                325                 330                 335

Ile Val Gln Gln Cys Gln Gly Leu Pro Leu Ser Val Val Val Ala
            340                 345                 350

Gly Leu Val Gly Lys Met Asp Pro Thr His Asp Asn Trp Glu Asn Val
            355                 360                 365

Glu Glu Asn Leu Asn Ser Phe Phe Gly Thr Val Ser Glu Arg Cys His
    370                 375                 380

Ser Ile Leu Ser Leu Ser Tyr Asn Tyr Leu Pro Gln Tyr Leu Arg Ala
385                 390                 395                 400

Cys Phe Leu Tyr Val Gly Gly Phe Pro Glu Asp Lys Glu Ile Asp Val
                405                 410                 415
```

```
Ser Lys Leu Ile Arg Leu Trp Ile Ala Glu Gln Phe Val Lys Ala Arg
            420                 425                 430

Ser Asn Lys Arg Leu Glu Val Val Ala Glu Glu Tyr Leu Glu Glu Leu
            435                 440                 445

Ile Asp Arg Ser Leu Ile Leu Ser Gly Arg Gln Arg Ala Asn Gly Arg
        450                 455                 460

Met Lys Thr Cys Lys Ile His Asp Leu Leu Arg Gln Leu Cys Leu Ser
465                 470                 475                 480

Glu Ala His Thr Glu Asn Ile Ser His Ile Met Asn Arg Asn Val Pro
                485                 490                 495

Val Ser Ser Glu Ala Ile Asp Asp Gln Arg Arg Val Ile Val Pro Leu
            500                 505                 510

Glu Leu Glu Glu Lys Gln Phe Tyr Pro Thr Arg His Ser Ser Gly Ile
            515                 520                 525

Thr Ser Thr Thr Arg Thr Phe Ile Ser Met Glu Ile Cys Leu Arg Glu
        530                 535                 540

Ala Gln Thr Glu Ala Ile Tyr Asp Gln Arg Arg Val Ile Leu Leu Ser
545                 550                 555                 560

Lys Arg His Arg Ile Asp Thr Ile Arg Thr Ile Ile Pro Phe Gly Asp
                565                 570                 575

Thr Phe Pro Lys Glu Ile Cys Ser Ile Phe Ser Glu Phe Lys Leu Leu
            580                 585                 590

Lys Val Leu Asp Val Leu Ser Val Trp Tyr Asp Val Ser Cys Ile Ile
            595                 600                 605

Pro Gln Leu Val His Leu Arg Tyr Val Gly Ala Val Ile Leu Glu Ala
        610                 615                 620

Leu Ser Leu Pro Lys Leu Arg Asn Leu Gln Thr Ile Met Leu Thr Ser
625                 630                 635                 640

Val Glu Thr Thr Glu Leu Lys His Ser Leu Asp Ile Trp Arg Met Ser
                645                 650                 655

Glu Ile Arg His Leu Asp Ile Val Pro Pro Leu Tyr Ile Ser Asn Pro
            660                 665                 670

Leu Glu Ala Glu Gln Pro Leu Phe Leu Asn Asn Leu His Thr Leu Phe
            675                 680                 685

Leu Arg Cys Ser Pro Phe Val Ala Lys Ile Ile Arg Arg Thr Pro Asn
        690                 695                 700

Leu Lys Lys Leu Lys Ile Leu Asp Lys Ser Lys His Pro Asp Trp Pro
705                 710                 715                 720

Asp Ile Leu Asp Ser Leu Asn Leu Leu Glu Leu Glu Thr Leu Gln
                725                 730                 735

Ile Ser Thr Glu Glu Asn Ile Asp Arg Met Ile Phe Ser Gly Asp Ile
                740                 745                 750

Phe Pro Arg Asn Leu Lys Gln Leu Lys Leu Ser Tyr Thr Cys Ile Pro
        755                 760                 765

Trp Glu Asp Met Lys Leu Leu Ala Asn Leu Pro Asn Leu Glu Val Phe
        770                 775                 780

Lys Gly His Tyr Ala Phe Asp Gly Thr Asp Trp Lys Leu Asp Glu Asp
785                 790                 795                 800

Val Val Phe Cys Lys Leu Lys Cys Leu Arg Leu Tyr Glu Arg Gly Asp
                805                 810                 815

Leu Gln Arg Trp Glu Ala Ala Gly Ser Asp Asn Phe Pro Met Leu Glu
            820                 825                 830
```

```
Gln Leu Val Leu Tyr Gly Phe Glu Lys Leu Glu Ile Pro Glu Ser
            835                 840                 845

Ile Gly Glu Ile Met Thr Leu Lys Phe Ile Lys Thr Glu Phe Cys Gly
850                 855                 860

Ser Gly Val Glu Thr Ser Ala Lys Lys Ile Gln Glu Glu Gln Glu Ser
865                 870                 875                 880

Leu Gly Asn Tyr Glu Leu Gln Leu Gln Ile Thr Pro Lys Leu Arg Phe
                885                 890                 895

Leu Ile Glu Asn Leu Asp Glu Thr Ser Met Leu Pro Ser Asn Glu Val
            900                 905                 910

Ile Glu Lys Ile Lys Glu Phe Cys Ser Ser Gly Val Glu Thr Ser Ala
            915                 920                 925

Lys Lys Ile Gln Glu Glu Gln Glu Ser Leu Gly Asn Tyr Glu Leu Gln
            930                 935                 940

Val Gln Ile Thr Pro Arg Lys Arg Leu Leu Arg Lys Gln Asp Gly Thr
945                 950                 955                 960

Val

<210> SEQ ID NO 53
<211> LENGTH: 978
<212> TYPE: PRT
<213> ORGANISM: Solanum americanum

<400> SEQUENCE: 53

Met Ala Tyr Ala Ala Leu Ser Ser Leu Met Tyr Thr Leu Gln Gln Leu
1               5                   10                  15

Leu Lys Pro Asn Gln Ser Phe Val Cys Arg Tyr Ser Thr Gln Gln Leu
            20                  25                  30

Val Gln Ser Leu Tyr Gln Asn Leu Thr Ala Leu Gln Leu Phe Leu Asp
        35                  40                  45

His Thr Thr Thr Lys Asp Ile Glu Thr Leu Lys Val Ile Glu Lys Arg
    50                  55                  60

Ile Arg Asp Val Val Tyr Lys Ala Glu Asp Lys Val Asp Ser Ser Leu
65                  70                  75                  80

Arg Asn Ile Ile Leu Ala Asp Cys Thr Glu Asn Arg Glu Gly Ala Cys
                85                  90                  95

Lys Phe Phe Glu Glu Glu Leu Leu Lys Val Glu Lys Asp Val Asp Ser
            100                 105                 110

Leu Ser Lys Glu Val Met Gln Ile Glu Phe Asn Lys His Gly Cys Arg
        115                 120                 125

Ser Ala Glu Leu Ala Thr Thr Asp Pro Ser Ser Ser Gly Lys Ser Thr
    130                 135                 140

Ile Glu Glu His Thr Ile Val Gly Met Glu Asp Glu Tyr Asn Thr Ile
145                 150                 155                 160

Leu Asp Arg Leu Thr Ala Gln Thr Asp Glu Leu Thr Val Ile Pro Ile
                165                 170                 175

Phe Gly Met Gly Gly Ile Gly Lys Thr Thr Leu Ala Arg Lys Val Tyr
            180                 185                 190

Asp Asp Ser Ser Ile Arg Ser Arg Phe Asp Arg His Ala Trp Val Thr
        195                 200                 205

Thr Ser Glu Glu Phe Asn Glu Arg Arg Met Leu Leu Glu Val Val Ser
    210                 215                 220

Ser Ile Thr Thr Gly Ser Asn Gln Gly Lys Ser Asp Asp Gln Leu Met
225                 230                 235                 240
```

```
Glu Ile Val Tyr Arg Ser Leu Lys Gly Arg Phe Leu Ile Val Ile
                245                 250                 255

Asp Asp Ile Trp Ser Thr Gln Ala Trp Asp Gln Met Gln Arg Ile Phe
            260                 265                 270

Pro Asn Asp Asp Ser Lys Ser Arg Ile Leu Leu Thr Thr Arg Leu Lys
        275                 280                 285

Tyr Val Ala Asp Tyr Val Ser Ser Pro Asp Phe Pro Pro His Ser Lys
    290                 295                 300

Ser Phe Leu Ser Leu Asp Ser Trp Asn Leu Phe Thr Glu Lys Val
305                 310                 315                 320

Phe Asn Glu Asp Thr Cys Pro Pro His Leu Glu Glu Thr Gly Lys His
                325                 330                 335

Ile Val Gln Gln Cys Gln Gly Leu Pro Leu Ser Val Val Val Ala
            340                 345                 350

Gly Leu Val Gly Lys Met Asp Pro Thr His Asp Asn Trp Glu Asn Val
        355                 360                 365

Glu Glu Asn Leu Asn Ser Phe Phe Gly Thr Val Ser Glu Arg Cys His
    370                 375                 380

Ser Ile Leu Ser Leu Ser Tyr Asn Tyr Leu Pro Gln Tyr Leu Arg Ala
385                 390                 395                 400

Cys Phe Leu Tyr Val Gly Gly Phe Pro Glu Asp Lys Glu Ile Asp Val
                405                 410                 415

Ser Lys Leu Ile Arg Leu Trp Ile Ala Glu Gln Phe Val Lys Ala Arg
            420                 425                 430

Ser Asn Lys Arg Leu Glu Val Val Ala Glu Glu Tyr Leu Glu Glu Leu
        435                 440                 445

Ile Asp Arg Ser Leu Ile Leu Ser Gly Arg Gln Arg Ala Asn Gly Arg
    450                 455                 460

Met Lys Thr Cys Lys Ile His Asp Leu Leu Arg Gln Leu Cys Leu Ser
465                 470                 475                 480

Glu Ala His Thr Glu Asn Ile Ser His Ile Met Asn Arg Asn Val Pro
                485                 490                 495

Val Ser Ser Glu Ala Ile Asp Asp Gln Arg Arg Val Ile Val Pro Leu
            500                 505                 510

Glu Leu Glu Glu Lys Gln Phe Tyr Pro Thr Arg His Ser Ser Gly Ile
        515                 520                 525

Thr Ser Thr Thr Arg Thr Phe Ile Ser Met Glu Ile Cys Leu Arg Glu
    530                 535                 540

Ala Gln Thr Glu Ala Ile Tyr Asp Gln Arg Arg Val Ile Leu Leu Ser
545                 550                 555                 560

Lys Arg His Arg Ile Asp Thr Ile Arg Thr Ile Ile Pro Phe Gly Asp
                565                 570                 575

Thr Phe Pro Lys Glu Ile Cys Ser Ile Phe Ser Glu Phe Lys Leu Leu
            580                 585                 590

Lys Val Leu Asp Val Leu Ser Val Trp Tyr Asp Val Ser Cys Ile Ile
        595                 600                 605

Pro Gln Leu Val His Leu Arg Tyr Val Gly Ala Val Ile Leu Glu Ala
    610                 615                 620

Leu Ser Leu Pro Lys Leu Arg Asn Leu Gln Thr Ile Met Leu Thr Ser
625                 630                 635                 640

Val Glu Thr Thr Glu Leu Lys His Ser Leu Asp Ile Trp Arg Met Ser
                645                 650                 655

Glu Ile Arg His Leu Asp Ile Val Pro Pro Leu Tyr Ile Ser Asn Pro
```

```
            660                 665                 670
Leu Glu Ala Glu Gln Pro Leu Phe Leu Asn Asn Leu His Thr Leu Phe
        675                 680                 685
Leu Arg Cys Ser Pro Phe Val Ala Lys Ile Ile Arg Arg Thr Pro Asn
    690                 695                 700
Leu Lys Lys Leu Lys Ile Leu Asp Lys Ser Lys His Pro Asp Trp Pro
705                 710                 715                 720
Asp Ile Leu Asp Ser Leu Asn Leu Leu Glu Glu Leu Glu Thr Leu Gln
                725                 730                 735
Ile Ser Thr Glu Glu Asn Ile Asp Arg Met Ile Phe Ser Gly Asp Ile
            740                 745                 750
Phe Pro Arg Asn Leu Lys Gln Leu Lys Leu Ser Tyr Thr Cys Ile Pro
        755                 760                 765
Trp Glu Asp Met Lys Leu Leu Ala Asn Leu Pro Asn Leu Glu Val Phe
    770                 775                 780
Lys Gly His Tyr Ala Phe Asp Gly Thr Asp Trp Lys Leu Asp Glu Asp
785                 790                 795                 800
Val Val Phe Cys Lys Leu Lys Cys Leu Arg Leu Tyr Glu Arg Gly Asp
                805                 810                 815
Leu Gln Arg Trp Glu Ala Ala Gly Ser Asp Asn Phe Pro Met Leu Glu
            820                 825                 830
Gln Leu Val Leu Tyr Gly Phe Glu Lys Leu Glu Glu Ile Pro Glu Ser
        835                 840                 845
Ile Gly Glu Ile Met Thr Leu Lys Phe Ile Lys Thr Glu Phe Cys Gly
    850                 855                 860
Ser Gly Val Glu Thr Ser Ala Lys Lys Ile Gln Glu Glu Gln Glu Ser
865                 870                 875                 880
Leu Gly Asn Tyr Glu Leu Gln Leu Gln Ile Thr Pro Lys Leu Arg Phe
                885                 890                 895
Leu Ile Glu Asn Leu Asp Glu Thr Ser Met Leu Pro Ser Asn Glu Val
            900                 905                 910
Ile Glu Lys Ile Lys Glu Ile Pro Glu Ser Thr Gly Gln Ile Met Thr
        915                 920                 925
Arg Lys Ile Ile Lys Thr Glu Phe Cys Ser Ser Gly Val Glu Thr Ser
    930                 935                 940
Ala Lys Lys Ile Gln Glu Gln Glu Ser Leu Gly Asn Tyr Glu Leu
945                 950                 955                 960
Gln Val Gln Ile Thr Pro Arg Lys Arg Leu Leu Arg Lys Gln Asp Gly
                965                 970                 975
Thr Val

<210> SEQ ID NO 54
<211> LENGTH: 2883
<212> TYPE: DNA
<213> ORGANISM: Solanum americanum

<400> SEQUENCE: 54
atggcttatg ctgctctttc ttcacttatg tatacattgc aacaactctt gaaacctaat      60
caatctttcg tttgtcgata ctctacacaa caacttgttc aatctctcta tcaaaatctt     120
actgctctgc aacttttcct tgaccatact acgacaaagg atattgaaac acttaaggtt     180
atagaaaaga ggatcagaga gtagtatac aaagcagaag ataaagttga ttcaagccta     240
agaaacatca ttctagcaga ttgcacagag aatagagaag gggcttgtaa attctttgag     300
```

```
gaagaattgc taaaagtgga aaaagatgtt gattctctca gcaaagaggt gatgcagatc    360
gagtttaaca agcatggatg cagatctgca gaattagcaa caactgatcc ctcctcatca    420
ggaaaaagta caattgagga acatactatt gttgggatgg aggatgagta caacaccata    480
cttgatcgcc tcactgccca aacagacgag ttgactgtca taccaatttt tggtatgggc    540
ggtataggta agacaactct tgccagaaag gtttatgatg attcatctat tcgttctcga    600
tttgatagac atgcatgggt cactacctct gaagaattca atgagagacg aatgcttctc    660
gaagttgttt cttcaattac tactggaagc aatcaaggaa agagcgatga tcaactaatg    720
gagattgtgt atagaagtct gaagggtagg agatttctaa ttgtcataga tgatatttgg    780
agtactcagg cttgggacca aatgcaaaga atatttccaa atgatgacag taaaagccga    840
attctactaa ctacacggct caagtatgtt gctgattatg tcagcagtcc tgattttcca    900
cctcatagta agtctttct aagtcttgat gatagttgga atctattcac cgaaaaagta    960
ttcaacgaag atacctgtcc tcctcaccta gaagaaacag gaagcatat tgtacaacaa   1020 tgtcaaggat tacctctctc ggttgttgtc gttgctggac ttgttggaaa aatgacccca   1080
acgcatgaca attgggagaa tgttgaggaa aatctgaact cattctttgg tactgtatcc   1140
gaacggtgcc actcaattct ttcttttgagc tacaattact tgccccaata tttgagggct   1200
tgttttctct atgttggagg ttttcctgaa gataaagaga ttgatgtttc caagttgatt   1260
aggctatgga ttgctgagca attcgtaaag gcgagaagca ataaaaggct agaagtggtg   1320
gcagaggagt atctggaaga gttaattgat agaagtctaa ttttgagtgg tagacaaagg   1380
gctaatggaa ggatgaaaac ttgcaaaatt catgatcttc ttcgccaact atgcctaagt   1440
gaagctcata ctgaaaatat tagtcatatc atgaatagaa atgtccccgt gtcctcagaa   1500
gccatagatg atcaacggcg agtgattgtt ccattggaac tcgaagagaa acaattttat   1560
cctacaaggc atagcagtgg tattacaagt acaacccgca cctttatttc aatggaaata   1620
tgcctaagag aagctcaaac cgaagccata tatgatcaac ggcgagtgat ccttctgtct   1680
aaacgacata ggattgatac aatccgcacc attattccat tcggagatac ttttccaaaa   1740
gagatttgtt ccattttttc agagttcaag ttgcttaagg tgttggatgt attatcagtc   1800
tggtacgatg tctcttgtat aataacctcag cttgtacatt tgagatatgt tggtgcagta   1860
attttggaag ctcttttcact acccaaattg agaaatctac agaccataat gcttacaagt   1920
gttgaaacca cagagttgaa gcactcacta gatatctgga gaatgtcaga gataagacat   1980
ttggatattg taccgccact atatatatca aatcctcttg aagcagaaca acctttgttt   2040
ctcaataact tgcacacgct ttttctccgt tgctctcctt tgttgcgaa aatcataaga   2100 agaactccga atctaaaaaa gctaaagatt ttagataaat ctaagcatcc tgactggcct   2160
gatattcttg attctctcaa tcttctagag gagctggaga cactacaaat atcaacagaa   2220
gaaaacattg accggatgat tttctctggg gatattttcc ctcgtaatct caagcaactg   2280
aaattatcat atacttgtat accatgggaa gatatgaaat tgctggctaa tttacccaat   2340
cttgaggtgt tcaagggtca ttatgcattc gatggaacag attggaaact agatgaagat   2400
gttgtgtttt gcaaattaaa atgtctacga ctgtatgagc gcgagatct gcaaaggtgg   2460 gaagcagcag gtagtgataa ttttcctatg cttgagcaac tagtactgta tgggttcgaa   2520
aaactgaaag agattccgga gagtattgga gaaataatga cactaaaatt cattaaaaca   2580
gaattttgcg gctctggtgt agagactagt gcaaagaaaa ttcaagaaga gcaagaaagc   2640
ttgggaaatt atgagcttca acttcaaatt actcctaagt taagattttt gatcgaaaat   2700
```

| | |
|---|---:|
| ttagacgaaa caagcatgtt gccatcgaat gaagtaatcg aaaaaatcaa agaattttgc | 2760 |
| agctctggtg tagagactag tgcaaagaaa attcaagaag agcaagaaag cttgggaaat | 2820 |
| tatgagcttc aagttcaaat tactcctagg aagcgtttgc tgaggaagca ggacggcact | 2880 |
| gtg | 2883 |

<210> SEQ ID NO 55
<211> LENGTH: 2934
<212> TYPE: DNA
<213> ORGANISM: Solanum americanum

<400> SEQUENCE: 55

| | |
|---|---:|
| atggcttatg ctgctctttc ttcacttatg tatacattgc aacaactctt gaaacctaat | 60 |
| caatctttcg tttgtcgata ctctacacaa caacttgttc aatctctcta tcaaaatctt | 120 |
| actgctctgc aacttttcct tgaccatact acgacaaagg atattgaaac acttaaggtt | 180 |
| atagaaaaga ggatcagaga gtagtatac aaagcagaag ataaagttga ttcaagccta | 240 |
| agaaacatca ttctagcaga ttgcacagag aatagagaag gggcttgtaa attctttgag | 300 |
| gaagaattgc taaagtggaa aaagatgtt gattctctca gcaaagaggt gatgcagatc | 360 |
| gagtttaaca agcatggatg cagatctgca gaattagcaa caactgatcc ctcctcatca | 420 |
| ggaaaaagta caattgagga acatactatt gttgggatgg aggatgagta caacaccata | 480 |
| cttgatcgcc tcactgccca aacagacgag ttgactgtca taccaattt tggtatgggc | 540 |
| ggtataggta agacaactct tgccagaaag gtttatgatg attcatctat tcgttctcga | 600 |
| tttgatagac atgcatgggt cactacctct gaagaattca tgagagacg aatgcttctc | 660 |
| gaagttgttt cttcaattac tactggaagc aatcaaggaa agagcgatga tcaactaatg | 720 |
| gagattgtgt atagaagtct gaagggtagg agatttctaa ttgtcataga tgatatttgg | 780 |
| agtactcagg cttgggacca aatgcaaaga atatttccaa atgatgacag taaaagccga | 840 |
| attctactaa ctacacggct caagtatgtt gctgattatg tcagcagtcc tgatttttca | 900 |
| cctcatagta agtcttttct aagtcttgat gatagttgga atctattcac cgaaaaagta | 960 |
| ttcaacgaag ataccctgtcc tcctcaccta gaagaaacag ggaagcatat tgtacaacaa | 1020 |
| tgtcaaggat tacctctctc ggttgttgtc gttgctggac ttgttggaaa aatggaccca | 1080 |
| acgcatgaca attgggagaa tgttgaggaa atctgaact cattctttgg tactgtatcc | 1140 |
| gaacggtgcc actcaattct ttctttgagc tacaattact tgccccaata tttgagggct | 1200 |
| tgttttctct atgttggagg ttttcctgaa gataaagaga ttgatgtttc caagttgatt | 1260 |
| aggctatgga ttgctgagca attcgtaaag gcgagaagca ataaaaggct agaagtggtg | 1320 |
| gcagaggagt atctggaaga gttaattgat agaagtctaa ttttgagtgg tagacaaagg | 1380 |
| gctaatggaa ggatgaaaac ttgcaaaatt catgatcttc ttcgccaact atgcctaagt | 1440 |
| gaagctcata ctgaaaatat tagtcatatc atgaatagaa atgtccccgt gtcctcagaa | 1500 |
| gccatagatg atcaacggcg agtgattgtt ccattggaac tcgaagagaa acaattttat | 1560 |
| cctacaaggc atagcagtgg tattacaagt acaacccgca cctttatttc aatggaaata | 1620 |
| tgcctaagag aagctcaaac cgaagccata tatgatcaac ggcgagtgat ccttctgtct | 1680 |
| aaacgacata ggattgatac aatccgcacc attattccat tcggagatac ttttccaaaa | 1740 |
| gagatttgtt ccattttttc agagttcaag ttgcttaagg tgttggatgt attatcagtc | 1800 |
| tggtacgatg tctcttgtat aatacctcag cttgtacatt tgagatatgt tggtgcagta | 1860 |

```
attttggaag ctctttcact acccaaattg agaaatctac agaccataat gcttacaagt   1920
gttgaaacca cagagttgaa gcactcacta gatatctgga gaatgtcaga gataagacat   1980
ttggatattg taccgccact atatatatca atcctcttg aagcagaaca accttttgttt    2040 ctcaataact tgcacacgct ttttctccgt tgctctcctt ttgttgcgaa atcataaga    2100 agaactccga atctaaaaaa gctaaagatt ttagataaat ctaagcatcc tgactggcct   2160
gatattcttg attctctcaa tcttctagag gagctggaga cactacaaat atcaacagaa   2220
gaaaacattg accggatgat tttctctggg gatattttcc ctcgtaatct caagcaactg   2280
aaattatcat atacttgtat accatgggaa gatatgaaat tgctggctaa tttacccaat   2340
cttgaggtgt tcaagggtca ttatgcattc gatggaacag attggaaact agatgaagat   2400
gttgtgtttt gcaaattaaa atgtctacga ctgtatgagc gcggagatct gcaaaggtgg   2460
gaagcagcag gtagtgataa ttttcctatg cttgagcaac tagtactgta tgggttcgaa   2520
aaactggaag agattccgga gagtattgga gaaataatga cactaaaatt cattaaaaca   2580
gaattttgcg gctctggtgt agagactagt gcaagaaaa ttcaagaaga gcaagaaagc    2640
ttgggaaatt atgagcttca acttcaaatt actcctaagt taagattttt gatcgaaaat   2700
ttagacgaaa caagcatgtt gccatcgaat gaagtaatcg aaaaaatcaa agagattccg   2760
gagagtactg gacaaataat gacacgaaaa atcatcaaaa cagaattttg cagctctggt   2820
gtagagacta gtgcaaagaa aattcaagaa gagcaagaaa gcttgggaaa ttatgagctt   2880
caagttcaaa ttactcctag gaagcgtttg ctgaggaagc aggacggcac tgtg         2934

<210> SEQ ID NO 56
<211> LENGTH: 7456
<212> TYPE: DNA
<213> ORGANISM: Solanum americanum

<400> SEQUENCE: 56
ttatatgggt aaaaatgggt tgggtaaaaa atgaattggg taaaatacta gtttacccat     60
attttcatga gtaataatat tctacttcat aattcaatat ggagaaacat tatagtcttc    120
ttttgaatga aaaagttgt aagggtgata tcatgaatga ataaaagttg gaagcttaac     180
tcatttggct acctcatata gtttacccat atttttaccc atgaatacccc atatttctat   240 gggttgaata tgggtataaa ccaatatttt acccatctaa aaaatcactc acccaaccca    300
ttaaaatatg gacagattgg acgggttacc aaaaatatggg ctcattttgc caccactaac    360
aacaacaaag agcaaagcaa agcataactt tgaaatttga aaaatgatgc aagacaaata    420
tcaaaattag acagtaaaat tcacaattcc ccttaaaata aatgataaat taagaagac     480 taaacaatag aaaaccttac aatcgcaaag gcactatgga tcggagtcgt acctgtgtgt    540
tttttatcgt acaatattcc acacagtatt attaattttt taaggaccat ttggccatgt    600
gatatgaaat catgatatga aattatgaga tgaagttgaa gttttatttg gacatgcaat    660
ttggattttt ttatgttgta tgttttctta taaacataaa aaacccataa gttgtaaaat    720
tattaaactt gtctcatttt tttattcaat tttaccaaat aaataaaaat ttacaaaatc    780
acataatatg ctaacacaaa actattcttt aaaaaataca atatttattg atcaaaattt    840
aattcaacaa aaaataaaat tcaacataag ttgtagtgta ctagtctta atataattct     900 cccacatagt acggacaatc tcctcacgtt gaacttgcat ttctcgatca tatgatcgag    960
tagacaaacc aacattgcta ctttgagcta taatggtttt aaaagtaat gatatgaatt    1020 ataaatttta tttacatatg aaacaaatgg taagtagata taaatgtggg gttgttttta   1080
```

```
taaaatataa acttgggtca attttttgtat ttgaaaaatc tcaaatcatg atttgaaatt    1140
tttaaatcca tgattttga agaatttggg atttcatctc atgatatgaa atcatcagat     1200
gaaatcaatc tgaaatcgca tgtccaaatg ctgatttcat ctcatgattt catatcgtga    1260
tatgaaatcg catgtccaaa cgcctactaa ataacttaga catgtcttga ccttttataa    1320
ttactccctc cgtcctaatt tacttgtcaa atattttcta atttgattcc ccttttactt    1380
gtcattttt acaaatcaag aaacgacaat tttttttct tcctattata ccctcaattt      1440
attaacattg aattaatgtc cttgaaaaat ataggaagta aatatgttta aaactctatc    1500
aaattaataa ggataaaatg gtaaatttat tataccaatt attattttct taatagatgc    1560
gttgacaagt aaaaaaagac ggaagaaaat ttgtatggaa agttaattgt attcgtccac    1620
ttgcacatc atgtctcatg tcttaattat tcaaccagtt tgaatccaat gtatatgaat     1680
cagaaatgtg agacatctct actatcgtgg tggggccaat gtttgaaaag tgttgacgaa    1740
aactacaaga gtgtctttat tagaaatcag gacaacttga ctctttatt ttcatttctt     1800
ttttcttact ttgacttggt caatccatag ttttgcatcc ataaaccaca agttctgttt    1860
agatattaaa tagaaaattg tccaaattca tttagaaaaa tgtggacata atcatttag     1920
acaaacattt ctcttccagc aaacaaaaga gaaatggcat atgctgctct tcttcactt    1980
atctatacat tgcaacaact cttgaaacct aatcaatctt tggtttgtcg aagctctaca    2040
caacagcatg ttcaatctat ctatcacaat cttctgctc tgcaacttt ccttgacgat      2100
actacgacaa aggatattga aactcttaag gtatgtaatt atctaatctc ttactcatct    2160
tatatttatt caataataat taatttatcg agtttcaatt ttaaggttat agaaaagagg    2220
atcagagatg tagtatacaa agcagaagat aaagttgatt caagcctaag aaacatcata    2280
ctagcagatt gcacagagaa tagagaaggg gcttgtaaat tctttgagga agaattgcta    2340
aaagtggaaa aagatgttca ttctctcagc aaagaggtga tgcagatcga gtttaacaag    2400
catggtagca gatctgcaga actaacaaca attcttccct cgccagaaaa aagtacaatt    2460
gaggaacata ctattgttgg gatggaggat gagtacaaca ccatacttga tcgcctcact    2520
gcccaaacag acgagttgac tgtcatacca attttttggta tgggcggtat aggtaagaca    2580
actcttgcca gaaaggttta tgatgattca tctattcgtt ctcgatttga tagacatgta    2640
tgggtcacta cctctgaaga attcaatgag agacgaatgc ttctcgaagt tgtttcttca    2700
attactactg gaagcaatca agaaaagagc gatgatcaac taatggagat tgtgtataga    2760
ggtcttaagg gtaggagatt tctaattgtc atagatgata tttggagtac tgaggcttgg    2820
gaccaaatgc aaagaatatt tccaaatgat gacaataaaa gcagaattct actaactaca    2880
cggctcaagt atgttgctga ttatgtcaac agtcctgatt ttccacctca tagtaagtct    2940
tttctaagtc ttgatgatag ttggaatcta ttcaccgaaa aagtattcaa caaagatacc    3000
tgtcctcctc acctagaaga aacagggaag catattgtac aacaatgtcg aggattacct    3060
ctctcggttg ttgtagttgc tggacttgtt ggaaaaatgg acccaacgca tgacaattgg    3120
gagaacgttg aggaaaatct gaactcattc attggtactg tatctgaacg gtgccaatca    3180
attctttctt taagctacaa ttacttgccc cagtatttga gggcttgttt tctctatgtt    3240
ggatgttttc ctgaagataa agagattgat gtttccaagt tgattaggct atggattgct    3300
gagcaattcg taaaggcgag aagcaataaa aatttagaag tggtggcaga ggagtatctg    3360
gaagagttaa ttgatagaag tctaattttg agtggtagac aaagggctaa tggaaggatg    3420
```

```
aaaacttgta aaattcatga tcttcttcac caactatgcc taagtgaagc tcatactgaa    3480
aatattagtc atatcatgaa tagaaatgtc ctcgtgtcct cagaagccat agatgatcaa    3540
cggcgagtga ttgttccatt ggaactcgaa gagaaacaag tttatccgac aaggcatagc    3600
agtggtatta caagtacaac ccgcaccttt atttcaatgg aaatatgcct aagagaagct    3660
cagaccgaaa ccatatatga tcaacggcga gtgatccttc tctctaaacg acataggatt    3720
gatacaatcc gcaccattat tccattcgga gatacttttc caaagtgat ttgttccatt     3780
ttttcgcagt tgaagttgct taaggtgttg gatgtactat cagtctggta cgatgtctct    3840
tgtataatac ctcagcttgt acatttgaga tatgttggtg cagtaatttt ggaagctgtt    3900
tcactatcca aattgagaaa tctacagacc ataattcttg caagtgttga aaccacagag    3960
ttgaagcacc cagtagatat ctggagaatg tcagagatca gacatttgga tattgtaccg    4020
ccactatata tatcaaatcc tcttgaagca gaacaacctt tgtttctcaa taacttgcac    4080
acgcttttc tccgttgctc tccttttgtt gcgaaaatca aagaagaac tcccaatcta     4140
aaaaagctaa agatttaga taaatctaag catcctgact ggcctgatat tcttgattct    4200
ctcaatcttc tagaggagct ggagacacta caaatatcaa cagaagaaaa cattgaccgg    4260
atgattttct ctggggatat tttccctcgt aatctcaagc aactgaaatt atcatatact    4320
tgtataccat gggaagatat gaaattgctg gctaatttac ccaatcttga ggtgttcaag    4380
ggtcattatg cattcgatgg aacagattgg aaactagatg aagatgttgt gttttgcaaa    4440
ttaaaatgtc tacgactgta tgagcgcgga gatctgcaaa ggtgggaagc tgctggtagt    4500
gataattttc caatgcttga gcaactatta ctgtatggat tcaaaaagct ggaagagatt    4560
ccggagagta ttggagaaat aatgacacta aaattcatta aaacagaatt tgcggctct    4620
ggtgtagaga ctagtgcaaa gaaaattcaa caagagcaag aaagcttggg aaattatgag    4680
cttcaacttc aaattactcc taaggtatgt tgaaactcaa tctttgatta atactctccc    4740
ccagctagac ttttcaaagt aatatttcac acgtacaatc tccactcggt aagatttagg    4800
attgaaattg tcttcttaca tttatgatca tcacccttcg gtttttttt attttttttt    4860
tttagtaaat agcttcatat actctacaaa agttacacat aattaacaat tgacaattga    4920
ttctctctta ttgataattt gtcatttct ctttcagtta agattttga tcgaaaattt     4980
agacgaaaca agcatgttgc catcgaatga agtaatcgaa aaaatcaaag gtttgtctat    5040
ttaattcctt ttattacttc attgaaagag gttcagatat tttaaacaac ttttttaacct  5100
ttctatttga attttttatc gctcagatag atacaacatt tattttgacg tcaaattgtt    5160
attttgattt aatcttattc ttttttgtata tagtttccac tcggttcttc attttttttt   5220
caattatagt ttaattttttt ttaattgcac atggttgatt gatttaattt gtgagattca   5280
cttttctttc gattttagga gttcttcggg attaatgtta ttcagattta ggagtattat    5340
atttcaactt tcggttagat ttaggattca aattgtcttc ttacatttat gatcatcatc    5400
cttttgatgt tatttatttc ttttagtaaa tagcttcaaa aactctatag aaattacata    5460
taattaacaa ttgacaattg attctctctt attgataatt tctcatgttt ctctttcagt    5520
taaaatttt gatcgaaaac taaaagagat tccggagagt actggacaaa taatgacacg    5580
aaaaatcatc aaaacagaat tttgcagctc tagtgtagag actagtgcaa agaaaattca    5640
agaagagcaa gaaagcttgg gaaattatga gcttcaagtt caaattactc ctagggtatg    5700
ttaaactcct ttgattatta tccaattctt taatttcata atatttctag actaagagcc    5760
tgtctggatg aacttaaaaa aagtaactta taagttgaaa actgtttata agtcaaaaaa    5820
```

```
aataagtagg tctaccctaa cttattttt tttgacttat aagttgtttt caactttaa    5880
gctgttttaa ataagctaag tcaaatagac ccaattattt tttgggctta ttttaagcac  5940
aaaatgactt taagttggcc agccaaatac taaaaaaagc taaaacaac  ttataagtta   6000
cttttaagcc aatccaaacg ggctctaaat taaaatatta aaagatataa agaatttaat  6060
taatttaatt attcctttga aatccaaaca tgatgaattt gagtaaatta aatgaaatat  6120
agttcagatt catttaacta ataggtcatt tacttttaat ccggcaacgt tttaggcttt  6180
tagcattctc tttgaatgta ggtataatgc attaagtgca gaaatttaat ttttatttaa  6240
aaaatgaaaa catctcataa taactttggt ctttttactc caaacatctt ataataaagt  6300
gagtctcttc tacttctcct aacatctcat aataaatttc tactattcct aacatctcat  6360
aataaataag tcttttctac tatttaattt tgttaaaata ttcacaattt ttgtgtctta  6420
ttctccaccc ccatctttt  ttttacttt  cttaatattc atatgcttga atcaaaacaa   6480
ggttctatga attctaacgc gcttggattg atcatgatgc aattcaatat atgcatcaat  6540
ttaattttta tttttcatgc ataatagtta gttccacaag ataaatattt ttatttcaat  6600
atgtatttat cctttaatta aagtactata tatgtcacta aagtagcatc aaatttgcaa  6660
gaatttctaa tctcaattta tgagtttgtt atattttttt tattgtattg ctttgatttt  6720
tatttttataa ccaaagagaa agtctaataa tatacgtgtc attatttatt ttttaagtat  6780
tttgggataa gcacgaacac acgtacaagt tacattaaaa gtggaaagaa tcaagtcaaa  6840
agtttgttta ccattttaa  cgttgaaaaa agcaagcctt catttaaata gttattatat   6900
tgcttacatt agaaaatata ttaaaattca ttagctcctt aaaattcaat gaatccaaat  6960
aattaaacgt ttattgccat aattttattt ttatctcttt aacttgctaa atggctcctt  7020
cactacatgc tttgaggaac agaagcgttt gctgaggaag caggacggca ctgtgtaaca  7080
ataatttgta tggcttcagt gatgagaata ttttgtgtgc cacgcagcat agcagtgttc  7140
atctaactat aaattttata agaaaagaaa aatcgtcctt aatcgttatt tcactcatta  7200
aattgttttt tctttcattt tccatggtaa tttgaatttc gaagtgtgga catggactgt  7260
gtttggagca taggttcata tttgtgtagt ttaaaattgt atgattatta ttttagttct  7320
cttgtcaacg tccttatcac ctttgcagat agttactatt gagaatgtat ttatactatt  7380
agttagttag ttactagtca tgatgattgt gtgatgatca gcttagttag ttagattagt  7440
gaattggtta cagctg                                                  7456
```

<210> SEQ ID NO 57
<211> LENGTH: 986
<212> TYPE: PRT
<213> ORGANISM: Solanum americanum

<400> SEQUENCE: 57

Met Ala Tyr Ala Ala Leu Ser Ser Leu Ile Tyr Thr Leu Gln Gln Leu
1               5                   10                  15

Leu Lys Pro Asn Gln Ser Leu Val Cys Arg Ser Ser Thr Gln Gln His
                20                  25                  30

Val Gln Ser Ile Tyr His Asn Leu Ser Ala Leu Gln Leu Phe Leu Asp
            35                  40                  45

Asp Thr Thr Lys Asp Ile Glu Thr Leu Lys Val Ile Glu Lys Arg
        50                  55                  60

Ile Arg Asp Val Val Tyr Lys Ala Glu Asp Lys Val Asp Ser Ser Leu
65                  70                  75                  80

```
Arg Asn Ile Ile Leu Ala Asp Cys Thr Glu Asn Arg Glu Gly Ala Cys
                85                  90                  95

Lys Phe Phe Glu Glu Leu Leu Lys Val Glu Lys Asp Val His Ser
            100                 105                 110

Leu Ser Lys Glu Val Met Gln Ile Glu Phe Asn Lys His Gly Ser Arg
        115                 120                 125

Ser Ala Glu Leu Thr Thr Ile Leu Pro Ser Pro Glu Lys Ser Thr Ile
    130                 135                 140

Glu Glu His Thr Ile Val Gly Met Glu Asp Glu Tyr Asn Thr Ile Leu
145                 150                 155                 160

Asp Arg Leu Thr Ala Gln Thr Asp Glu Leu Thr Val Ile Pro Ile Phe
                165                 170                 175

Gly Met Gly Gly Ile Gly Lys Thr Thr Leu Ala Arg Lys Val Tyr Asp
                180                 185                 190

Asp Ser Ser Ile Arg Ser Arg Phe Asp Arg His Val Trp Val Thr Thr
                195                 200                 205

Ser Glu Glu Phe Asn Glu Arg Arg Met Leu Leu Glu Val Val Ser Ser
    210                 215                 220

Ile Thr Thr Gly Ser Asn Gln Glu Lys Ser Asp Asp Gln Leu Met Glu
225                 230                 235                 240

Ile Val Tyr Arg Gly Leu Lys Gly Arg Arg Phe Leu Ile Val Ile Asp
                245                 250                 255

Asp Ile Trp Ser Thr Glu Ala Trp Asp Gln Met Gln Arg Ile Phe Pro
                260                 265                 270

Asn Asp Asp Asn Lys Ser Arg Ile Leu Leu Thr Thr Arg Leu Lys Tyr
                275                 280                 285

Val Ala Asp Tyr Val Asn Ser Pro Asp Phe Pro Pro His Ser Lys Ser
    290                 295                 300

Phe Leu Ser Leu Asp Asp Ser Trp Asn Leu Phe Thr Glu Lys Val Phe
305                 310                 315                 320

Asn Lys Asp Thr Cys Pro Pro His Leu Glu Glu Thr Gly Lys His Ile
                325                 330                 335

Val Gln Gln Cys Arg Gly Leu Pro Leu Ser Val Val Val Ala Gly
                340                 345                 350

Leu Val Gly Lys Met Asp Pro Thr His Asp Asn Trp Glu Asn Val Glu
        355                 360                 365

Glu Asn Leu Asn Ser Phe Ile Gly Thr Val Ser Glu Arg Cys Gln Ser
    370                 375                 380

Ile Leu Ser Leu Ser Tyr Asn Tyr Leu Pro Gln Tyr Leu Arg Ala Cys
385                 390                 395                 400

Phe Leu Tyr Val Gly Cys Phe Pro Glu Asp Lys Glu Ile Asp Val Ser
                405                 410                 415

Lys Leu Ile Arg Leu Trp Ile Ala Glu Gln Phe Val Lys Ala Arg Ser
                420                 425                 430

Asn Lys Asn Leu Glu Val Val Ala Glu Glu Tyr Leu Glu Glu Leu Ile
        435                 440                 445

Asp Arg Ser Leu Ile Leu Ser Gly Arg Gln Arg Ala Asn Gly Arg Met
    450                 455                 460

Lys Thr Cys Lys Ile His Asp Leu Leu His Gln Leu Cys Leu Ser Glu
465                 470                 475                 480

Ala His Thr Glu Asn Ile Ser His Ile Met Asn Arg Asn Val Leu Val
                485                 490                 495
```

```
Ser Ser Glu Ala Ile Asp Asp Gln Arg Arg Val Ile Val Pro Leu Glu
            500                 505                 510

Leu Glu Glu Lys Gln Val Tyr Pro Thr Arg His Ser Ser Gly Ile Thr
        515                 520                 525

Ser Thr Thr Arg Thr Phe Ile Ser Met Glu Ile Cys Leu Arg Glu Ala
    530                 535                 540

Gln Thr Glu Thr Ile Tyr Asp Gln Arg Val Ile Leu Leu Ser Lys
545                 550                 555                 560

Arg His Arg Ile Asp Thr Ile Arg Thr Ile Ile Pro Phe Gly Asp Thr
                565                 570                 575

Phe Pro Lys Val Ile Cys Ser Ile Phe Ser Gln Leu Lys Leu Leu Lys
            580                 585                 590

Val Leu Asp Val Leu Ser Val Trp Tyr Asp Val Ser Cys Ile Ile Pro
            595                 600                 605

Gln Leu Val His Leu Arg Tyr Val Gly Ala Val Ile Leu Glu Ala Val
    610                 615                 620

Ser Leu Ser Lys Leu Arg Asn Leu Gln Thr Ile Ile Leu Ala Ser Val
625                 630                 635                 640

Glu Thr Thr Glu Leu Lys His Pro Val Asp Ile Trp Arg Met Ser Glu
                645                 650                 655

Ile Arg His Leu Asp Ile Val Pro Pro Leu Tyr Ile Ser Asn Pro Leu
                660                 665                 670

Glu Ala Glu Gln Pro Leu Phe Leu Asn Asn Leu His Thr Leu Phe Leu
        675                 680                 685

Arg Cys Ser Pro Phe Val Ala Lys Ile Ile Arg Arg Thr Pro Asn Leu
690                 695                 700

Lys Lys Leu Lys Ile Leu Asp Lys Ser Lys His Pro Asp Trp Pro Asp
705                 710                 715                 720

Ile Leu Asp Ser Leu Asn Leu Glu Glu Leu Thr Leu Gln Ile
                725                 730                 735

Ser Thr Glu Glu Asn Ile Asp Arg Met Ile Phe Ser Gly Asp Ile Phe
            740                 745                 750

Pro Arg Asn Leu Lys Gln Leu Lys Leu Ser Tyr Thr Cys Ile Pro Trp
            755                 760                 765

Glu Asp Met Lys Leu Leu Ala Asn Leu Pro Asn Leu Glu Val Phe Lys
    770                 775                 780

Gly His Tyr Ala Phe Asp Gly Thr Asp Trp Lys Leu Asp Glu Asp Val
785                 790                 795                 800

Val Phe Cys Lys Leu Lys Cys Leu Arg Leu Tyr Glu Arg Gly Asp Leu
                805                 810                 815

Gln Arg Trp Glu Ala Ala Gly Ser Asp Asn Phe Pro Met Leu Glu Gln
                820                 825                 830

Leu Leu Leu Tyr Gly Phe Lys Lys Leu Glu Glu Ile Pro Glu Ser Ile
        835                 840                 845

Gly Glu Ile Met Thr Leu Lys Phe Ile Lys Thr Glu Phe Cys Gly Ser
    850                 855                 860

Gly Val Glu Thr Ser Ala Lys Lys Ile Gln Gln Glu Gln Glu Ser Leu
865                 870                 875                 880

Gly Asn Tyr Glu Leu Gln Leu Gln Ile Thr Pro Lys Leu Arg Phe Leu
                885                 890                 895

Ile Glu Asn Leu Asp Glu Thr Ser Met Leu Pro Ser Asn Glu Val Ile
            900                 905                 910

Glu Lys Ile Lys Val Lys Ile Phe Asp Arg Lys Leu Lys Glu Ile Pro
```

```
            915                 920                 925
Glu Ser Thr Gly Gln Ile Met Thr Arg Lys Ile Ile Lys Thr Glu Phe
930                 935                 940

Cys Ser Ser Ser Val Glu Thr Ser Ala Lys Lys Ile Gln Glu Glu Gln
945                 950                 955                 960

Glu Ser Leu Gly Asn Tyr Glu Leu Gln Val Gln Ile Thr Pro Arg Lys
                965                 970                 975

Arg Leu Leu Arg Lys Gln Asp Gly Thr Val
            980                 985

<210> SEQ ID NO 58
<211> LENGTH: 960
<212> TYPE: PRT
<213> ORGANISM: Solanum americanum

<400> SEQUENCE: 58

Met Ala Tyr Ala Ala Leu Ser Ser Leu Ile Tyr Thr Leu Gln Gln Leu
1               5                   10                  15

Leu Lys Pro Asn Gln Ser Leu Val Cys Arg Ser Ser Thr Gln Gln His
            20                  25                  30

Val Gln Ser Ile Tyr His Asn Leu Ser Ala Leu Gln Leu Phe Leu Asp
        35                  40                  45

Asp Thr Thr Thr Lys Asp Ile Glu Thr Leu Lys Val Ile Glu Lys Arg
50                  55                  60

Ile Arg Asp Val Val Tyr Lys Ala Glu Asp Lys Val Asp Ser Ser Leu
65                  70                  75                  80

Arg Asn Ile Ile Leu Ala Asp Cys Thr Glu Asn Arg Glu Gly Ala Cys
                85                  90                  95

Lys Phe Phe Glu Glu Glu Leu Leu Lys Val Glu Lys Asp Val His Ser
            100                 105                 110

Leu Ser Lys Glu Val Met Gln Ile Glu Phe Asn Lys His Gly Ser Arg
        115                 120                 125

Ser Ala Glu Leu Thr Thr Ile Leu Pro Ser Pro Glu Lys Ser Thr Ile
130                 135                 140

Glu Glu His Thr Ile Val Gly Met Glu Asp Glu Tyr Asn Thr Ile Leu
145                 150                 155                 160

Asp Arg Leu Thr Ala Gln Thr Asp Glu Leu Thr Val Ile Pro Ile Phe
                165                 170                 175

Gly Met Gly Gly Ile Gly Lys Thr Thr Leu Ala Arg Lys Val Tyr Asp
            180                 185                 190

Asp Ser Ser Ile Arg Ser Arg Phe Asp Arg His Val Trp Val Thr Thr
        195                 200                 205

Ser Glu Glu Phe Asn Glu Arg Arg Met Leu Leu Glu Val Val Ser Ser
210                 215                 220

Ile Thr Thr Gly Ser Asn Gln Glu Lys Ser Asp Asp Gln Leu Met Glu
225                 230                 235                 240

Ile Val Tyr Arg Gly Leu Lys Gly Arg Arg Phe Leu Ile Val Ile Asp
                245                 250                 255

Asp Ile Trp Ser Thr Glu Ala Trp Asp Gln Met Gln Arg Ile Phe Pro
            260                 265                 270

Asn Asp Asp Asn Lys Ser Arg Ile Leu Leu Thr Thr Arg Leu Lys Tyr
        275                 280                 285

Val Ala Asp Tyr Val Asn Ser Pro Asp Phe Pro Pro His Ser Lys Ser
290                 295                 300
```

-continued

Phe Leu Ser Leu Asp Asp Ser Trp Asn Leu Phe Thr Glu Lys Val Phe
305                 310                 315                 320

Asn Lys Asp Thr Cys Pro Pro His Leu Glu Glu Thr Gly Lys His Ile
            325                 330                 335

Val Gln Gln Cys Arg Gly Leu Pro Leu Ser Val Val Val Ala Gly
            340                 345                 350

Leu Val Gly Lys Met Asp Pro Thr His Asp Asn Trp Glu Asn Val Glu
        355                 360                 365

Glu Asn Leu Asn Ser Phe Ile Gly Thr Val Ser Glu Arg Cys Gln Ser
    370                 375                 380

Ile Leu Ser Leu Ser Tyr Asn Tyr Leu Pro Gln Tyr Leu Arg Ala Cys
385                 390                 395                 400

Phe Leu Tyr Val Gly Cys Phe Pro Glu Asp Lys Glu Ile Asp Val Ser
            405                 410                 415

Lys Leu Ile Arg Leu Trp Ile Ala Glu Gln Phe Val Lys Ala Arg Ser
            420                 425                 430

Asn Lys Asn Leu Glu Val Val Ala Glu Glu Tyr Leu Glu Glu Leu Ile
            435                 440                 445

Asp Arg Ser Leu Ile Leu Ser Gly Arg Gln Arg Ala Asn Gly Arg Met
450                 455                 460

Lys Thr Cys Lys Ile His Asp Leu Leu His Gln Leu Cys Leu Ser Glu
465                 470                 475                 480

Ala His Thr Glu Asn Ile Ser His Ile Met Asn Arg Asn Val Leu Val
            485                 490                 495

Ser Ser Glu Ala Ile Asp Asp Gln Arg Arg Val Ile Val Pro Leu Glu
        500                 505                 510

Leu Glu Glu Lys Gln Val Tyr Pro Thr Arg His Ser Ser Gly Ile Thr
    515                 520                 525

Ser Thr Thr Arg Thr Phe Ile Ser Met Glu Ile Cys Leu Arg Glu Ala
530                 535                 540

Gln Thr Glu Thr Ile Tyr Asp Gln Arg Val Ile Leu Leu Ser Lys
545                 550                 555                 560

Arg His Arg Ile Asp Thr Ile Arg Thr Ile Pro Phe Gly Asp Thr
            565                 570                 575

Phe Pro Lys Val Ile Cys Ser Ile Phe Ser Gln Leu Lys Leu Leu Lys
            580                 585                 590

Val Leu Asp Val Leu Ser Val Trp Tyr Asp Val Ser Cys Ile Ile Pro
        595                 600                 605

Gln Leu Val His Leu Arg Tyr Val Gly Ala Val Ile Leu Glu Ala Val
    610                 615                 620

Ser Leu Ser Lys Leu Arg Asn Leu Gln Thr Ile Ile Leu Ala Ser Val
625                 630                 635                 640

Glu Thr Thr Glu Leu Lys His Pro Val Asp Ile Trp Arg Met Ser Glu
            645                 650                 655

Ile Arg His Leu Asp Ile Val Pro Pro Leu Tyr Ile Ser Asn Pro Leu
            660                 665                 670

Glu Ala Glu Gln Pro Leu Phe Leu Asn Asn Leu His Thr Leu Phe Leu
            675                 680                 685

Arg Cys Ser Pro Phe Val Ala Lys Ile Ile Arg Arg Thr Pro Asn Leu
            690                 695                 700

Lys Lys Leu Lys Ile Leu Asp Lys Ser Lys His Pro Asp Trp Pro Asp
705                 710                 715                 720

Ile Leu Asp Ser Leu Asn Leu Leu Glu Glu Leu Glu Thr Leu Gln Ile

| | | | | | 725 | | | 730 | | | 735 | |
|---|---|---|---|---|---|---|---|---|---|---|---|---|

Ser Thr Glu Glu Asn Ile Asp Arg Met Ile Phe Ser Gly Asp Ile Phe
        740                 745                 750

Pro Arg Asn Leu Lys Gln Leu Lys Leu Ser Tyr Thr Cys Ile Pro Trp
        755                 760                 765

Glu Asp Met Lys Leu Leu Ala Asn Leu Pro Asn Leu Glu Val Phe Lys
        770                 775                 780

Gly His Tyr Ala Phe Asp Gly Thr Asp Trp Lys Leu Asp Glu Asp Val
785                 790                 795                 800

Val Phe Cys Lys Leu Lys Cys Leu Arg Leu Tyr Glu Arg Gly Asp Leu
                805                 810                 815

Gln Arg Trp Glu Ala Ala Gly Ser Asp Asn Phe Pro Met Leu Glu Gln
                820                 825                 830

Leu Leu Leu Tyr Gly Phe Lys Lys Leu Glu Glu Ile Pro Glu Ser Ile
                835                 840                 845

Gly Glu Ile Met Thr Leu Lys Phe Ile Lys Thr Glu Phe Cys Gly Ser
850                 855                 860

Gly Val Glu Thr Ser Ala Lys Lys Ile Gln Gln Glu Gln Glu Ser Leu
865                 870                 875                 880

Gly Asn Tyr Glu Leu Gln Leu Gln Ile Thr Pro Lys Leu Arg Phe Leu
                885                 890                 895

Ile Glu Asn Leu Asp Glu Thr Ser Met Leu Pro Ser Asn Glu Val Ile
                900                 905                 910

Glu Lys Ile Lys Glu Phe Cys Ser Ser Ser Val Glu Thr Ser Ala Lys
                915                 920                 925

Lys Ile Gln Glu Glu Gln Ser Leu Gly Asn Tyr Glu Leu Gln Val
        930                 935                 940

Gln Ile Thr Pro Arg Lys Arg Leu Leu Arg Lys Gln Asp Gly Thr Val
945                 950                 955                 960

<210> SEQ ID NO 59
<211> LENGTH: 2880
<212> TYPE: DNA
<213> ORGANISM: Solanum americanum

<400> SEQUENCE: 59

| | | | |
|---|---|---|---|
| atggcatatg ctgctctttc ttcacttatc tatacattgc aacaactctt gaaacctaat | 60 |
| caatctttgg tttgtcgaag ctctacacaa cagcatgttc aatctatcta tcacaatctt | 120 |
| tctgctctgc aacttttcct tgacgatact acgacaaagg atattgaaac tcttaaggtt | 180 |
| atagaaaaga ggatcagaga tgtagtatac aaagcagaag ataaagttga ttcaagccta | 240 |
| agaaacatca tactagcaga ttgcacagag aatagaaag gggcttgtaa attctttgag | 300 |
| gaagaattgc taaaagtgga aaagatgtt cattctctca gcaaagaggt gatgcagatc | 360 |
| gagtttaaca agcatggtag cagatctgca gaactaacaa caattcttcc ctcgccagaa | 420 |
| aaaagtacaa ttgaggaaca tactattgtt gggatggagg atgagtacaa caccatactt | 480 |
| gatcgcctca ctgcccaaac agacgagttg actgtcatac caattttggg tatgggcggt | 540 |
| ataggtaaga caactcttgc cagaaaggtt tatgatgatt catctattcg ttctcgattt | 600 |
| gatagacatg tatgggtcac tacctctgaa gaattcaatg agagacgaat gcttctcgaa | 660 |
| gttgtttctt caattactac tggaagcaat caagaaaaga gcgatgatca actaatggag | 720 |
| attgtgtata gaggtcttaa gggtaggaga tttctaattg tcatagatga tatttggagt | 780 |
| actgaggctt gggaccaaat gcaaagaata tttccaaatg atgacaataa aagcagaatt | 840 |

```
ctactaacta cacggctcaa gtatgttgct gattatgtca acagtcctga ttttccacct      900
catagtaagt cttttctaag tcttgatgat agttggaatc tattcaccga aaaagtattc      960
aacaaagata cctgtcctcc tcacctagaa gaaacaggga agcatattgt acaacaatgt     1020
cgaggattac ctctctcggt tgttgtagtt gctggacttg ttggaaaaat ggacccaacg     1080
catgacaatt gggagaacgt tgaggaaaat ctgaactcat tcattggtac tgtatctgaa     1140
cggtgccaat caattctttc tttaagctac aattacttgc cccagtattt gagggcttgt     1200
tttctctatg ttggatgttt tcctgaagat aaagagattg atgtttccaa gttgattagg     1260
ctatggattc tgagcaatt cgtaaaggcg agaagcaata aaaatttaga agtggtggca      1320
gaggagtatc tggaagagtt aattgataga agtctaattt tgagtggtag acaaagggct     1380
aatggaagga tgaaaacttg taaaattcat gatcttcttc accaactatg cctaagtgaa     1440
gctcatactg aaaatattag tcatatcatg aatagaaatg tcctcgtgtc ctcagaagcc     1500
atagatgatc aacggcgagt gattgttcca ttggaactcg aagagaaaca agtttatccg     1560
acaaggcata gcagtggtat tacaagtaca acccgcacct ttatttcaat ggaaatatgc     1620
ctaagagaag ctcagaccga aaccatatat gatcaacggc gagtgatcct tctctctaaa     1680
cgacatagga ttgatacaat ccgcaccatt attccattcg gagatacttt tccaaaagtg     1740
atttgttcca ttttttcgca gttgaagttg cttaaggtgt tggatgtact atcagtctgg     1800
tacgatgtct cttgtataat acctcagctt gtacatttga gatatgttgg tgcagtaatt     1860
ttggaagctg tttcactatc caaattgaga aatctacaga ccataattct tgcaagtgtt     1920
gaaaccacag agttgaagca cccagtagat atctggagaa tgtcagagat cagacatttg     1980
gatattgtac cgccactata tatatcaaat cctcttgaag cagaacaacc tttgtttctc     2040
aataacttgc acacgctttt tctccgttgc tctccttttg ttgcgaaaat cataagaaga     2100
actcccaatc taaaaaagct aaagatttta gataaatcta agcatcctga ctggcctgat     2160
attcttgatt ctctcaatct tctagaggag ctggagacac tacaaatatc aacagaagaa     2220
aacattgacc ggatgatttt ctctggggat attttccctc gtaatctcaa gcaactgaaa     2280
ttatcatata cttgtatacc atgggaagat atgaaattgc tggctaattt acccaatctt     2340
gaggtgttca aggtcatta tgcattcgat ggaacagatt ggaaactaga tgaagatgtt     2400
gtgttttgca aattaaaatg tctacgactg tatgagcgcg gagatctgca aaggtgggaa     2460
gctgctggta gtgataattt tccaatgctt gagcaactat tactgtatgg attcaaaaag     2520
ctggaagaga ttccggagag tattggagaa ataatgacac taaaattcat taaaacagaa     2580
ttttgcggct ctggtgtaga gactagtgca aagaaaattc aacaagagca agaaagcttg     2640
ggaaattatg agcttcaact tcaaattact cctaagttaa gattttttgat cgaaaattta     2700
gacgaaacaa gcatgttgcc atcgaatgaa gtaatcgaaa aaatcaaaga attttgcagc     2760
tctagtgtag agactagtgc aaagaaaatt caagaagagc aagaaagctt gggaaattat     2820
gagcttcaag ttcaaattac tcctaggaag cgtttgctga ggaagcagga cggcactgtg     2880
```

<210> SEQ ID NO 60
<211> LENGTH: 2958
<212> TYPE: DNA
<213> ORGANISM: Solanum americanum

<400> SEQUENCE: 60

```
atggcatatg ctgctctttc ttcacttatc tatacattgc aacaactctt gaaacctaat       60
```

```
caatctttgg tttgtcgaag ctctacacaa cagcatgttc aatctatcta tcacaatctt    120
tctgctctgc aacttttcct tgacgatact acgacaaagg atattgaaac tcttaaggtt    180
atagaaaaga ggatcagaga tgtagtatac aaagcagaag ataaagttga ttcaagccta    240
agaaacatca tactagcaga ttgcacagag aatagagaag gggcttgtaa attctttgag    300
gaagaattgc taaaagtgga aaaagatgtt cattctctca gcaaagaggt gatgcagatc    360
gagtttaaca agcatggtag cagatctgca gaactaacaa caattcttcc ctcgccagaa    420
aaaagtacaa ttgaggaaca tactattgtt gggatggagg atgagtacaa caccatactt    480
gatcgcctca ctgcccaaac agacgagttg actgtcatac caattttttgg tatgggcggt    540 ataggtaaga caactcttgc cagaaaggtt tatgatgatt catctattcg ttctcgattt    600
gatagacatg tatgggtcac tacctctgaa gaattcaatg agagacgaat gcttctcgaa    660
gttgtttctt caattactac tggaagcaat caagaaaaga gcgatgatca actaatggag    720
attgtgtata gaggtcttaa gggtaggaga tttctaattg tcatagatga tatttggagt    780
actgaggctt gggaccaaat gcaaagaata tttccaaatg atgacaataa aagcagaatt    840
ctactaacta cacggctcaa gtatgttgct gattatgtca acagtcctga tttttccacct    900 catagtaagt cttttctaag tcttgatgat agttggaatc tattcaccga aaaagtattc    960
aacaaagata cctgtcctcc tcacctagaa gaaacaggga agcatattgt acaacaatgt   1020
cgaggattac ctctctcggt tgttgtagtt gctggacttg ttggaaaaat ggacccaacg   1080
catgacaatt gggagaacgt tgaggaaaat ctgaactcat tcattggtac tgtatctgaa   1140
cggtgccaat caattctttc tttaagctac aattacttgc cccagtattt gagggcttgt   1200
tttctctatg ttggatgttt tcctgaagat aaagagattg atgtttccaa gttgattagg   1260
ctatggattg ctgagcaatt cgtaaaggcg agaagcaata aaaatttaga agtggtggca   1320
gaggagtatc tggaagagtt aattgataga agtctaattt tgagtggtag acaaagggct   1380
aatgaaagga tgaaaacttg taaaattcat gatcttcttc accaactatg cctaagtgaa   1440
gctcatactg aaaatattag tcatatcatg aatagaaatg tcctcgtgtc ctcagaagcc   1500
atagatgatc aacggcgagt gattgttcca ttggaactcg aagagaaaca agtttatccg   1560
acaaggcata gcagtggtat tacaagtaca acccgcacct ttatttcaat ggaaatatgc   1620
ctaagagaag ctcagaccga aaccatatat gatcaacggc gagtgatcct tctctctaaa   1680
cgacatagga ttgatacaat ccgcaccatt attccattcg gagatacttt tccaaaagtg   1740
atttgttcca tttttttcgca gttgaagttg cttaaggtgt tggatgtact atcagtctgg   1800
tacgatgtct cttgtataat acctcagctt gtacatttga gatatgttgg tgcagtaatt   1860
ttggaagctg tttcactatc caaattgaga aatctacaga ccataattct tgcaagtgtt   1920
gaaaccacag agttgaagca cccagtagat atctggagaa tgtcagagat cagacatttg   1980
gatattgtac cgccactata tatatcaaat cctcttgaag cagaacaacc tttgtttctc   2040
aataacttgc acacgctttt tctccgttgc tctccttttg ttgcgaaaat cataagaaga   2100
actcccaatc taaaaaagct aaagatttta gataaatcta agcatcctga ctggcctgat   2160
attcttgatt ctctcaatct tctagaggag ctggagacac tacaaatatc aacgaagaa    2220 aacattgacc ggatgatttt ctctggggat atttttccctc gtaatctcaa gcaactgaaa   2280
ttatcatata cttgtatacc atgggaagat atgaaattgc tggctaattt acccaatctt   2340
gaggtgttca agggtcatta tgcattcgat ggaacagatt ggaaactaga tgaagatgtt   2400
gtgttttgca aattaaaatg tctacgactg tatgagcgcg gagatctgca aaggtgggaa   2460
```

```
gctgctggta gtgataattt tccaatgctt gagcaactat tactgtatgg attcaaaaag    2520
ctggaagaga ttccggagag tattggagaa ataatgacac taaaattcat taaaacagaa    2580
ttttgcggct ctggtgtaga gactagtgca agaaaattc aacaagagca agaaagcttg     2640
ggaaattatg agcttcaact tcaaattact cctaagttaa gattttgat cgaaaattta     2700 gacgaaacaa gcatgttgcc atcgaatgaa gtaatcgaaa aaatcaaagt taaaattttt    2760
gatcgaaaac taaagagat tccggagagt actggacaaa taatgacacg aaaaatcatc     2820
aaaacagaat tttgcagctc tagtgtagag actagtgcaa agaaaattca agaagagcaa    2880
gaaagcttgg gaaattatga gcttcaagtt caaattactc ctaggaagcg tttgctgagg    2940
aagcaggacg gcactgtg                                                  2958

<210> SEQ ID NO 61
<211> LENGTH: 9596
<212> TYPE: DNA
<213> ORGANISM: Solanum americanum

<400> SEQUENCE: 61
ttatatgggt aaaaatgggt tgggtaaaaa atggattggg taaaatacta gtttacccat      60
atttacccat attttcatga gtaataatac tctacttcat aattcaatat ggagaaacat     120
tatagtcttt tttgaatgaa aaagttgta agggtgatat catgaatgaa taaaagttgg      180
aagcttaact catttggcta cctcatatag tttacccata tttttaccca tgaatactca     240
tatttctatg ggttgaatat gggtataaac ccatatttta cccatctaaa aaatcactca     300
ccaacccatt aaaatatgaa cagattgggc gggttaccaa aatatgggct cttttttgcca    360 ccactaacaa caacaaagag caaagcaaag cacaactttg aaatttgaaa aatgatgcaa     420
gacaaatatc aaaattagac agtaaaattc acaattcccc ttaaaataaa tgataaatta    480
aagaagacta acaatagaa aaccttacaa tctcaaaggc actatggatc ggagtcgtac     540
ctgtgtgttt tttatcgtac aatattccac acagtattat taatttttta aggaccatt     600 ggccatgtga tatgaaatta tgagatgaag ttgaagtttt atttggacat gcaatttgaa    660
ttttttatgt tgtatgtttt cttataaaca taaaaaaccc ataagttgta aaattattaa    720
acttgtctca tttttttatt caattttacc aaataaataa aaattacaa aatcacataa     780 tatgctaaca caaaactatt cttaaaaaaa tacaatattt attgatcaaa ctttaattca    840 acaaaaata aaattcaaca taagttgtag tgtactagtc tttaatataa ttctcccaca     900
tagtacggac aatctcctca cattgaactt gcatttctcg atcatatgat cgagtagaca    960
aaccaacatt gctactttga gctataaatg gtttaaaaag taatgatatg aattataaat    1020
tttatttaca tatgaaacaa atggtaagta gatataaatg tggggttgtt tttataaaat    1080
ataaacttat gggtcaattt ttgtatttga aaaatctcaa atcatgattt gaaatttta     1140 aatcatgatt tttgaagaat ttgggatttc atctcatgat atgaaatcat gagatgaaat    1200
cagtctgaaa ttgcatgtcc aaatgctgat ttcatctcat gatttcatat cgtgatatga    1260
aataaatcgt gatatgaaat cgcatgtcca aacgtctact aaataactta gacatgtctt    1320
gaccttttat aattactccc tccgtcctaa tttacttgtc aaatattttc taatttgatt    1380
ccccttttac ttgtcatttt ttacaaatca agaaacgaca atttttttt cttcctatta    1440 tacccctcaat ttattaacat tgaattaatg tccttgaaaa atatagaaag taaatatgtt    1500
taaaactcta tcaaattaat agggataaaa tggtaaattt attataccaa ttattatttt    1560
```

```
cttaatagat gcgtcaaatc aaaaattgac aaataaaaaa agacgaaaga aaatttgtat    1620
tgaaagttaa ttgtattcgt ccacttgaca catcatgtct taattattca acaagtttga    1680
atccaatgta tatgaatcat aaatgtgaga catctctact atcgtggtgg ggccaatgtt    1740
tgaaaagtgt tgacgaaaac tacaagagtg tctttattag aaatcaggac aacttgactc    1800 tttattttc atttcttttt tcttactttg acttggtcaa tccatagttt tgcatccata    1860
aaccacaagt tctgtttaga tattaaatag aaaattgtcc aaattcattt agaaaaatgt    1920
ggacataaat catttagaca aaacctctta gcctaagcag agacatttct cttccagcaa    1980
acaaaagaga aatggcatat gctgctcttt cttcacttat ctatacattg caacaactct    2040
tgaaacctaa tcaatctttg gtttgtcgaa gctgtacaca acaacatctt caatctatct    2100
atcacaatct ttctgctctg caacttttcc ttgacgatac tacgacaaag gatattgaaa    2160
ctcttaaggt atgtaattat ctaatctctt actcatctta tatttattca ataataatta    2220
atttatcgag tttcaatttt aaggttatag aaaagaggat cagagatgta gtatacaaag    2280
cagaagatac agttgattca agcctaagaa acatcattct agcagattgc acagagaata    2340
gagaaggggc ttgtaaattc tttgaggaag aattgctaaa agtggaaaaa gatgttgatt    2400
ctctcagcaa agaggtgatg cagatcgact taacaagca tggaagcaga tctgcagaat    2460
tagcaacaac tgatccctcc tcatcaggaa aaagtacaat tgaggaacat actattgttg    2520
ggatggagga tgagtacaac accatacttg atcgcctcac tgcccaaaca gacgagttga    2580
ctgtcatacc aattttggt atgggcggta taggtaagac aactcttgcc agaaaggttt    2640
atgatgattc atctattcgt tctcgatttg atagacatgc atgggtcact acctctgaag    2700
aattcaatga gagacgaatg cttctcgaag ttgtttcttc aattactact ggaagcaatc    2760
aaggaaagag cgatgatcaa ctaatggaga ttgtgtatag aagtctgaag ggtaggagat    2820
ttctaattgt catagatgat atttggagta ctcaggcttg ggaccaaatg caaagaatat    2880
ttccaaatga tgcaataaaa agccgaattc tactaactac acggctcaag tatgttgctg    2940
attatgtcag cagtcctgat tttccacctc atagtaagtc tttttctaagt cttgatgata    3000 gttggaatct attcaccgaa aaagtattca acgaagatac ctgtcctcct cacctagaag    3060
aaacagggaa gcatattgta caacaatgtc aaggattacc tctctcggtt gttgtcgttg    3120
ctggacttgt tggaaaaatg gacccaacgc atgacaattg ggagaatgtt gaggaaaatc    3180
tgaactcatt ctttggtact gtatccgaac ggtgccactc aattctttct ttgagctaca    3240
attacttgcc ccaatatttg agggcttgtt ttctctatgt tggaggtttt cctgaagata    3300
aagagattga tgtttccaag ttgattaggc tatggattgc tgagcaattc gtaaaggcga    3360
gaagcaataa aaggctagaa gtggtggcag aggagtatct ggaagagtta attgatagaa    3420 gtctaattt gagtggtaga caaagggcta atggaaggat gaaaacttgc aaaattcatg    3480
atcttcttcg ccaactatgc ctaagtgaag ctcatactga aaatattagt catatcatga    3540
atagaaatgt ccccgtgtcc tcagaagcca tagatgatca acggcgagtg attgttccat    3600
tggaactcga agagaaacaa gtttatccta caaggcatag cagtggtatt acaagtacaa    3660
cccgcacctt tatttcaatg gaaatatgcc taagagaagc tcaaaccgaa gccatatatg    3720
atcaacggcg agtgatcctt ctgtctaaac gacataggat tgatacaatc cgcaccatta    3780
ttccattcgg agatactttt ccaaaagaga tttgttccat ttttcagag ttcaagttgc    3840 ttaaggtgtt ggatgtatta tcagtctggt acgatgtctc ttgtataata cctcagcttg    3900
tacatttgag atatgttggt gcagtaattt tggaagctct ttcactaccc aaattgagaa    3960
```

```
atctacagac cataatgctt acaagtgttg aaaccacaga gttgaagcac tcactagata    4020
tctggagaat gtcagagata agacatttgg atattgtacc gccactatat atatcaaatc    4080
ctcttgaagc agaacaacct ttgtttctca ataacttgca cacgctttt ctccgttgct     4140 ctccttttgt tgcgaaaatc ataagaagaa ctccgaatct aaaaaagcta aagatttag     4200 ataaatctaa gcatcctgac tggcctgata ttcttgattc tctcaatctt ctagaggagc    4260
tggagacact acaaatatca acagaagaaa acattgaccg gatgattttc tctggggata    4320
atttccctcg taatctcaag caactgaaat tatcaggtac taaaatacca tgggaagata    4380
tgaaattgct ggctaattta cccaatcttg aggtgttcaa gggtcattat gcattcgatg    4440
gaacagattg gaaactagat gaagatgttg tgttttgcaa attaaaatgt ctacgactgt    4500
atgagcgcgg agatctgcaa aggtgggaag cagcaggtag tgataatttt cctatgcttg    4560
agcaactagt actgtatggg ttcgaaaaac tggaagagat tccggagagt attggagaaa    4620
taatgacact aaaattcatc aaaacagaat tttgcggctc tggtgtagag acaagtgcaa    4680
agaaaattca agaagagcaa gaaagctggg gaaattatga gcttcaactt ctaattactc    4740
ctatggtatg ttaaaactcc atctttgata attagactca actatcaact tttttcacag    4800
agagtcaatt ctttcacaag aagtcactca actatcaatt tttttcacaa aaagtcactc    4860
aactttgatt ctttcataga aagttactca actatgggct ttttgcatag aaaaccactc    4920
aacctattta attatatttt tcatatgaaa tttttatttc taatcaaaat tttaaaatcc    4980
aaatatatat ccatttaaac catttaatga atcacccaca ctaaatccga tccgctaaaa    5040
atataatatt taccttttgt tttatcctta ttccctaaa tattctctcc tgtttcctaa     5100
atattctctc ctgttcctg attctttctc ttctgcgttt tcccctcaa tttcagtctc      5160 ttcttttacg tatatatcaa cctctctttc tccataagca tcatattatt gttttctcaa    5220
cttcaaaaac aatataaatt acaacaatct cttgatttac aatttcaata aaaaattcta    5280
tgcacaccat gcttttatca attattatga aaactgataa aattaacaaa caaggctctc    5340
aatctgcata actacgaatc tacgcctata gttgctcttt aattgcaatt attcattcaa    5400
taaaatcaag tgatcaggat agtcctaaat ctagatatag tttgagaaat cgatggaaaa    5460
ttcctagtta atagagattt taaaattgag aaattaaaaa aatgcagtg aatcaggaga     5520 cgggagagaa tatttaggga gataaggata aaacaaaagt caatattata ttttttagcgg   5580 atcgaattta gtggggtgat tcattaaatg gtttaaatgg aaatatattt agattttaaa    5640
attttgatta aaaataaaaa tttcatatga aaaatataat taaataggtt gagtgacttt    5700
ctatgcaaaa gccccatagt tgagtgactt tctgtgaaaa aaattgatag ttgagtgact    5760
ttctgtgaaa gtatcaaagt tgagtgactt tctgtgaaag aatttgatag ttgagtgacc    5820
atcaaagata ttaactcggt gaattgctag attgttttgg acaaattttg tgtcgctata    5880
ttactaattt catatttgtt ttcacatgct agattcctaa catctcatta taaataaatc    5940
ttttctacta tttaatttgg ttaaaatatt cacaattctt gggtcttctt ctccacccca    6000
tctttttttt ttgtttactt tcttaatatt catatgtttg aatcaaaaca aggttctatg    6060
acttctaacg tgtttggatt gatcatgatg cgattcaata tatgcatcaa tttaattttt    6120
atttttccta cataatagtt aattatattt cacaagataa atattcttat ttcaatattt    6180
atttatctgt aaattaaagt attatatatg tcaccaaaat agcatcaaat ttgcaagaat    6240
ttctagtctc aatttatgag ttttttttat ttttttttatt gtattgcttt gattttattt   6300
```

```
ttaataacac tgagaaagtc ttataatata cgtgtcattt aaaatttatc atttgtaata   6360
taaaatttat tttaagtatt ttgtgataaa catgcaacac acgtactggt ctatatctat   6420
ctatattata tttaaagtgt tgtttgaatt ttttattctt cattaaaagg cttttcttta   6480
gacaatacca tcatttacta ttttcttaaa tacttgtctt ttaattatta tcctaatatt   6540
taagacttta aattgattaa agttgtaact attaaaactt tacttattta taataggtaa   6600
gaactaatat ttagtaattt aaattttttt acttcttaca tctttcctta ttttcttatt   6660
tgaacttatg aaaaagaaag tattttttt tgtcataagt catacctgtc gtgtgtgttt    6720
ttttgtagtt aaatactact tttgttttg aacttaggat tcactttagg tttttatac     6780
cattaatact ctcccccagc tagactttcc aaagtaatat ttcacacgta caatctccac   6840
tcggttcttc aattcttttt tctattatag tttaattttt tttaattgca catggttgat   6900
cgatttaatt tgtgggattc acttttcttt cggttttaga agttcttcgc gatgaatgtt   6960
attcagatat aggagtgtta tatttcaact ttcgattaga tttaggattc aaattatctt   7020
cttacattta tgatcgtcac cctttcggta ttctttattt tttttttagt aaatagcttc   7080
aaaaactcta caaaaattac acataattaa caattgacaa ttgattctct cttattgata   7140
atttgtaatt ttctctttca gttaagattt ttgatcgaaa atttagacga aataagcatg   7200
ttgccaccgg atgaagtagc cgaaaaaatc aaaggtttgt ctatttaatt cctttttat    7260
ttcattgaaa gaggttcaga tattttaaac aactttttaa cctttctatt tgaattttt    7320
atcgctaaga tagatacaac atttatttta acatcaaatg ttattttgat ttaattttgt   7380
tcttttttata tatatagttt ccactcggtt cttcaattct ttttcaatta tagttttttt  7440
ttttaattgc acatatggtt gatcgattta atttgtgaga ttcacttttc ttttggtttt   7500
aggagttctt cgcgattaat gttattcaga tttaggagta ttatatttca actttcggtt   7560
agatttagga ttcaaattgt cttcttacat ttatgatcat catccttttg atgttattta   7620
tttcttttag taaatagctt caaaaactct atagaaatta catataatta acaattgaca   7680
attgattctc tcttattgat aatttctcat gtttctcttt cagttaaaat ttttgatcga   7740
aaactaaaag agattctgga gagtactgga caaataatga cacgaaaaat cattaaaacg   7800
gaattttgca gctctggtgt agagactagt gcaagaaaaa ttcaagagca agaaagcttg   7860
ggaaattatg agcttcaagt tcaaattact cctagggtat gttaaactcc ttctttgatt   7920
attagccaat tctttaattt cataatattt ctagactaag agcctgtctg gatggactta   7980
aaaaagtaa cttataagtt gaaaactgtt tataagtcaa aaaaaaaat aagtaggtct     8040
accctaactt attttttttt gatttataag ttgttttcaa cttttaagct gttttaaata   8100
agctaagtca aatagaccca attattttt gggcttattt taagcataaa atgactttaa    8160
gttggccagc caaatactaa aaaagctaaa aacaacttaa taagttactt ttaagccaat   8220
ccaaacgggc tctaaattaa aatattaaaa tatataaaga atttaattaa tttaattatt   8280
cctttgaaat ccaaacatga tgaatttgag taaattaaat gaaatatagt tcagattcat   8340
ttaactaata ggtcatttac ttttaatctg gcaacgtttt aggcttttag cattctcttt   8400
gaatgtaggt ataatgcatt aagtgtagaa atttaatttt tatttaaaaa atgaaaacat   8460
ctcataataa ctttggtctt tttactccaa acatcttata ataaagtgag tctcttctac   8520
ttctcctaac atctcataat aaatttctac tattcctaac atctcataat aaataagtct   8580
tttctactat ttaattttgt taaaatattc acatttttg tgtcttattc tccaccccca    8640
tctttttttt gtttactttc ttaatattca tatgcttgaa tcgaaacaag gttctatgaa   8700
```

-continued

```
ttctaacgcg cttggattga ttatgatgcg attcaatata tgcatgaatt tagtttttat   8760
ttttcatgca taataattag tttcacaaga taaatatttt tatttcaata tgtatttatc   8820
ctttaattaa agtactatat atgtcactaa agtagcatca aatttgcaag aatttctaat   8880
ctcaatttat gagtttgtta tattttttt tattgtattg ctttgatttt tattttataa    8940
ccaaagagaa agtctaataa tatacgtatt ttgggataaa catgcgacac acgtttaagt   9000
tacattataa gtaagaagaa tcaagtcaaa agtttgttta tcattttta cgttgaaaaa    9060
agcaagcctt catttaaata gttattatat tgcttacatt agaaaatata ttaaaattca   9120
ttagctcctt aaaattcaat gaatccaaat aattaaacgt ttattgccat aatttttattt  9180
ttatctcttt aacttgctaa atggctcctt cactacatgc tttgaggaac agaagcgttt   9240
gctgaggaag caggacggca ctgtgtaaca ataatttgta tggcttcagt gatgagaata   9300
ttttgtgtgc cacgcagcat agcagtgttc atctaactag aaattttata agaaaagaaa   9360
aatcgtcctt aatcgttatt tcactcatta aattgttttt tctttcattt tccatggtaa   9420
tttgaatttc gaagtgtgga catggactgt gtttggagca taggttcata tttgtgtagt   9480
ttgaaattgt atgattatta ttttagttct cttgtcaacg tccttgtcac ctttgcagat   9540
agttactatt gagaatgtat ttatactatt agttagttag ttactagtca tgatga       9596
```

<210> SEQ ID NO 62
<211> LENGTH: 1011
<212> TYPE: PRT
<213> ORGANISM: Solanum americanum

<400> SEQUENCE: 62

```
Met Ala Tyr Ala Ala Leu Ser Ser Leu Ile Tyr Thr Leu Gln Gln Leu
1               5                   10                  15

Leu Lys Pro Asn Gln Ser Leu Val Cys Arg Ser Cys Thr Gln Gln His
            20                  25                  30

Leu Gln Ser Ile Tyr His Asn Leu Ser Ala Leu Gln Leu Phe Leu Asp
        35                  40                  45

Asp Thr Thr Thr Lys Asp Ile Glu Thr Leu Lys Val Cys Asn Tyr Leu
    50                  55                  60

Ile Ser Tyr Ser Ser Tyr Ile Tyr Ser Ile Ile Asn Leu Ser Ser
65                  70                  75                  80

Phe Asn Phe Lys Val Ile Glu Lys Arg Ile Arg Asp Val Val Tyr Lys
                85                  90                  95

Ala Glu Asp Thr Val Asp Ser Ser Leu Arg Asn Ile Ile Leu Ala Asp
            100                 105                 110

Cys Thr Glu Asn Arg Glu Gly Ala Cys Lys Phe Phe Glu Glu Glu Leu
        115                 120                 125

Leu Lys Val Glu Lys Asp Val Asp Ser Leu Ser Lys Glu Val Met Gln
    130                 135                 140

Ile Asp Phe Asn Lys His Gly Ser Arg Ser Ala Glu Leu Ala Thr Thr
145                 150                 155                 160

Asp Pro Ser Ser Gly Lys Ser Thr Ile Glu Glu His Thr Ile Val
                165                 170                 175

Gly Met Glu Asp Glu Tyr Asn Thr Ile Leu Asp Arg Leu Thr Ala Gln
            180                 185                 190

Thr Asp Glu Leu Thr Val Ile Pro Ile Phe Gly Met Gly Gly Ile Gly
        195                 200                 205

Lys Thr Thr Leu Ala Arg Lys Val Tyr Asp Asp Ser Ser Ile Arg Ser
```

```
            210                 215                 220
Arg Phe Asp Arg His Ala Trp Val Thr Thr Ser Glu Phe Asn Glu
225                 230                 235                 240

Arg Arg Met Leu Leu Glu Val Val Ser Ser Ile Thr Thr Gly Ser Asn
                    245                 250                 255

Gln Gly Lys Ser Asp Asp Gln Leu Met Glu Ile Val Tyr Arg Ser Leu
                260                 265                 270

Lys Gly Arg Arg Phe Leu Ile Val Ile Asp Asp Ile Trp Ser Thr Gln
            275                 280                 285

Ala Trp Asp Gln Met Gln Arg Ile Phe Pro Asn Asp Asn Lys Ser
290                 295                 300

Arg Ile Leu Leu Thr Thr Arg Leu Lys Tyr Val Ala Asp Tyr Val Ser
305                 310                 315                 320

Ser Pro Asp Phe Pro Pro His Ser Lys Ser Phe Leu Ser Leu Asp Asp
                325                 330                 335

Ser Trp Asn Leu Phe Thr Glu Lys Val Phe Asn Glu Asp Thr Cys Pro
                340                 345                 350

Pro His Leu Glu Glu Thr Gly Lys His Ile Val Gln Gln Cys Gln Gly
                355                 360                 365

Leu Pro Leu Ser Val Val Val Ala Gly Leu Val Gly Lys Met Asp
370                 375                 380

Pro Thr His Asp Asn Trp Glu Asn Val Glu Glu Asn Leu Asn Ser Phe
385                 390                 395                 400

Phe Gly Thr Val Ser Glu Arg Cys His Ser Ile Leu Ser Leu Ser Tyr
                405                 410                 415

Asn Tyr Leu Pro Gln Tyr Leu Arg Ala Cys Phe Leu Tyr Val Gly Gly
                420                 425                 430

Phe Pro Glu Asp Lys Glu Ile Asp Val Ser Lys Leu Ile Arg Leu Trp
                435                 440                 445

Ile Ala Glu Gln Phe Val Lys Ala Arg Ser Asn Lys Arg Leu Glu Val
450                 455                 460

Val Ala Glu Glu Tyr Leu Glu Glu Leu Ile Asp Arg Ser Leu Ile Leu
465                 470                 475                 480

Ser Gly Arg Gln Arg Ala Asn Gly Arg Met Lys Thr Cys Lys Ile His
                485                 490                 495

Asp Leu Leu Arg Gln Leu Cys Leu Ser Glu Ala His Thr Glu Asn Ile
                500                 505                 510

Ser His Ile Met Asn Arg Asn Val Pro Val Ser Ser Glu Ala Ile Asp
                515                 520                 525

Asp Gln Arg Arg Val Ile Val Pro Leu Glu Leu Glu Glu Lys Gln Val
                530                 535                 540

Tyr Pro Thr Arg His Ser Ser Gly Ile Thr Ser Thr Thr Arg Thr Phe
545                 550                 555                 560

Ile Ser Met Glu Ile Cys Leu Arg Glu Ala Gln Thr Glu Ala Ile Tyr
                565                 570                 575

Asp Gln Arg Arg Val Ile Leu Leu Ser Lys Arg His Arg Ile Asp Thr
                580                 585                 590

Ile Arg Thr Ile Ile Pro Phe Gly Asp Thr Phe Pro Lys Glu Ile Cys
                595                 600                 605

Ser Ile Phe Ser Glu Phe Lys Leu Leu Lys Val Leu Asp Val Leu Ser
                610                 615                 620

Val Trp Tyr Asp Val Ser Cys Ile Ile Pro Gln Leu Val His Leu Arg
625                 630                 635                 640
```

```
Tyr Val Gly Ala Val Ile Leu Glu Ala Leu Ser Leu Pro Lys Leu Arg
                645                 650                 655

Asn Leu Gln Thr Ile Met Leu Thr Ser Val Glu Thr Glu Leu Lys
            660                 665                 670

His Ser Leu Asp Ile Trp Arg Met Ser Glu Ile Arg His Leu Asp Ile
675                 680                 685

Val Pro Pro Leu Tyr Ile Ser Asn Pro Leu Glu Ala Glu Gln Pro Leu
        690                 695                 700

Phe Leu Asn Asn Leu His Thr Leu Phe Leu Arg Cys Ser Pro Phe Val
705                 710                 715                 720

Ala Lys Ile Ile Arg Arg Thr Pro Asn Leu Lys Lys Leu Lys Ile Leu
                725                 730                 735

Asp Lys Ser Lys His Pro Asp Trp Pro Asp Ile Leu Asp Ser Leu Asn
            740                 745                 750

Leu Leu Glu Glu Leu Glu Thr Leu Gln Ile Ser Thr Glu Glu Asn Ile
        755                 760                 765

Asp Arg Met Ile Phe Ser Gly Asp Asn Phe Pro Arg Asn Leu Lys Gln
    770                 775                 780

Leu Lys Leu Ser Gly Thr Lys Ile Pro Trp Glu Asp Met Lys Leu Leu
785                 790                 795                 800

Ala Asn Leu Pro Asn Leu Glu Val Phe Lys Gly His Tyr Ala Phe Asp
                805                 810                 815

Gly Thr Asp Trp Lys Leu Asp Glu Asp Val Val Phe Cys Lys Leu Lys
            820                 825                 830

Cys Leu Arg Leu Tyr Glu Arg Gly Asp Leu Gln Arg Trp Glu Ala Ala
        835                 840                 845

Gly Ser Asp Asn Phe Pro Met Leu Glu Gln Leu Val Leu Tyr Gly Phe
    850                 855                 860

Glu Lys Leu Glu Glu Ile Pro Glu Ser Ile Gly Glu Ile Met Thr Leu
865                 870                 875                 880

Lys Phe Ile Lys Thr Glu Phe Cys Gly Ser Gly Val Glu Thr Ser Ala
                885                 890                 895

Lys Lys Ile Gln Glu Glu Gln Glu Ser Trp Gly Asn Tyr Glu Leu Gln
            900                 905                 910

Leu Leu Ile Thr Pro Met Leu Arg Phe Leu Ile Glu Asn Leu Asp Glu
        915                 920                 925

Ile Ser Met Leu Pro Pro Asp Glu Val Ala Glu Lys Ile Lys Val Lys
    930                 935                 940

Ile Phe Asp Arg Lys Leu Lys Glu Ile Leu Glu Ser Thr Gly Gln Ile
945                 950                 955                 960

Met Thr Arg Lys Ile Ile Lys Thr Glu Phe Cys Ser Ser Gly Val Glu
                965                 970                 975

Thr Ser Ala Lys Lys Ile Gln Glu Gln Glu Ser Leu Gly Asn Tyr Glu
            980                 985                 990

Leu Gln Val Gln Ile Thr Pro Arg Lys Arg Leu Leu Arg Lys Gln Asp
        995                 1000                1005

Gly Thr Val
    1010

<210> SEQ ID NO 63
<211> LENGTH: 986
<212> TYPE: PRT
<213> ORGANISM: Solanum americanum
```

```
<400> SEQUENCE: 63

Met Ala Tyr Ala Ala Leu Ser Ser Leu Ile Tyr Thr Leu Gln Gln Leu
1               5                   10                  15

Leu Lys Pro Asn Gln Ser Leu Val Cys Arg Ser Cys Thr Gln Gln His
            20                  25                  30

Leu Gln Ser Ile Tyr His Asn Leu Ser Ala Leu Gln Leu Phe Leu Asp
        35                  40                  45

Asp Thr Thr Thr Lys Asp Ile Glu Thr Leu Lys Val Ile Glu Lys Arg
    50                  55                  60

Ile Arg Asp Val Val Tyr Lys Ala Glu Asp Thr Val Asp Ser Ser Leu
65                  70                  75                  80

Arg Asn Ile Ile Leu Ala Asp Cys Thr Glu Asn Arg Glu Gly Ala Cys
                85                  90                  95

Lys Phe Phe Glu Glu Glu Leu Leu Lys Val Lys Asp Val Asp Ser
            100                 105                 110

Leu Ser Lys Glu Val Met Gln Ile Asp Phe Asn Lys His Gly Ser Arg
        115                 120                 125

Ser Ala Glu Leu Ala Thr Thr Asp Pro Ser Ser Gly Lys Ser Thr
    130                 135                 140

Ile Glu Glu His Thr Ile Val Gly Met Glu Asp Glu Tyr Asn Thr Ile
145                 150                 155                 160

Leu Asp Arg Leu Thr Ala Gln Thr Asp Glu Leu Thr Val Ile Pro Ile
                165                 170                 175

Phe Gly Met Gly Gly Ile Gly Lys Thr Thr Leu Ala Arg Lys Val Tyr
            180                 185                 190

Asp Asp Ser Ser Ile Arg Ser Arg Phe Asp Arg His Ala Trp Val Thr
        195                 200                 205

Thr Ser Glu Glu Phe Asn Glu Arg Met Leu Leu Glu Val Val Ser
    210                 215                 220

Ser Ile Thr Thr Gly Ser Asn Gln Gly Lys Ser Asp Asp Gln Leu Met
225                 230                 235                 240

Glu Ile Val Tyr Arg Ser Leu Lys Gly Arg Arg Phe Leu Ile Val Ile
                245                 250                 255

Asp Asp Ile Trp Ser Thr Gln Ala Trp Asp Gln Met Gln Arg Ile Phe
            260                 265                 270

Pro Asn Asp Asp Asn Lys Ser Arg Ile Leu Leu Thr Thr Arg Leu Lys
        275                 280                 285

Tyr Val Ala Asp Tyr Val Ser Ser Pro Asp Phe Pro Pro His Ser Lys
    290                 295                 300

Ser Phe Leu Ser Leu Asp Asp Ser Trp Asn Leu Phe Thr Glu Lys Val
305                 310                 315                 320

Phe Asn Glu Asp Thr Cys Pro Pro His Leu Glu Thr Gly Lys His
            325                 330                 335

Ile Val Gln Gln Cys Gln Gly Leu Pro Leu Ser Val Val Val Ala
        340                 345                 350

Gly Leu Val Gly Lys Met Asp Pro Thr His Asp Asn Trp Glu Asn Val
    355                 360                 365

Glu Glu Asn Leu Asn Ser Phe Phe Gly Thr Val Ser Glu Arg Cys His
370                 375                 380

Ser Ile Leu Ser Leu Ser Tyr Asn Tyr Leu Pro Gln Tyr Leu Arg Ala
385                 390                 395                 400

Cys Phe Leu Tyr Val Gly Gly Phe Pro Glu Asp Lys Glu Ile Asp Val
                405                 410                 415
```

```
Ser Lys Leu Ile Arg Leu Trp Ile Ala Glu Gln Phe Val Lys Ala Arg
            420                 425                 430

Ser Asn Lys Arg Leu Glu Val Val Ala Glu Glu Tyr Leu Glu Glu Leu
            435                 440                 445

Ile Asp Arg Ser Leu Ile Leu Ser Gly Arg Gln Arg Ala Asn Gly Arg
        450                 455                 460

Met Lys Thr Cys Lys Ile His Asp Leu Leu Arg Gln Leu Cys Leu Ser
465                 470                 475                 480

Glu Ala His Thr Glu Asn Ile Ser His Ile Met Asn Arg Asn Val Pro
                485                 490                 495

Val Ser Ser Glu Ala Ile Asp Asp Gln Arg Arg Val Ile Val Pro Leu
            500                 505                 510

Glu Leu Glu Glu Lys Gln Val Tyr Pro Thr Arg His Ser Ser Gly Ile
            515                 520                 525

Thr Ser Thr Thr Arg Thr Phe Ile Ser Met Glu Ile Cys Leu Arg Glu
        530                 535                 540

Ala Gln Thr Glu Ala Ile Tyr Asp Gln Arg Arg Val Ile Leu Leu Ser
545                 550                 555                 560

Lys Arg His Arg Ile Asp Thr Ile Arg Thr Ile Pro Phe Gly Asp
                565                 570                 575

Thr Phe Pro Lys Glu Ile Cys Ser Ile Phe Ser Glu Phe Lys Leu Leu
            580                 585                 590

Lys Val Leu Asp Val Leu Ser Val Trp Tyr Asp Val Ser Cys Ile Ile
            595                 600                 605

Pro Gln Leu Val His Leu Arg Tyr Val Gly Ala Val Ile Leu Glu Ala
        610                 615                 620

Leu Ser Leu Pro Lys Leu Arg Asn Leu Gln Thr Ile Met Leu Thr Ser
625                 630                 635                 640

Val Glu Thr Thr Glu Leu Lys His Ser Leu Asp Ile Trp Arg Met Ser
                645                 650                 655

Glu Ile Arg His Leu Asp Ile Val Pro Pro Leu Tyr Ile Ser Asn Pro
            660                 665                 670

Leu Glu Ala Glu Gln Pro Leu Phe Leu Asn Asn Leu His Thr Leu Phe
        675                 680                 685

Leu Arg Cys Ser Pro Phe Val Ala Lys Ile Ile Arg Arg Thr Pro Asn
        690                 695                 700

Leu Lys Lys Leu Lys Ile Leu Asp Lys Ser Lys His Pro Asp Trp Pro
705                 710                 715                 720

Asp Ile Leu Asp Ser Leu Asn Leu Leu Glu Glu Leu Thr Leu Gln
                725                 730                 735

Ile Ser Thr Glu Glu Asn Ile Asp Arg Met Ile Phe Ser Gly Asp Asn
            740                 745                 750

Phe Pro Arg Asn Leu Lys Gln Leu Lys Leu Ser Gly Thr Lys Ile Pro
        755                 760                 765

Trp Glu Asp Met Lys Leu Leu Ala Asn Leu Pro Asn Leu Glu Val Phe
        770                 775                 780

Lys Gly His Tyr Ala Phe Asp Gly Thr Asp Trp Lys Leu Asp Glu Asp
785                 790                 795                 800

Val Val Phe Cys Lys Leu Lys Cys Leu Arg Leu Tyr Glu Arg Gly Asp
                805                 810                 815

Leu Gln Arg Trp Glu Ala Ala Gly Ser Asp Asn Phe Pro Met Leu Glu
            820                 825                 830
```

| | | | | | | | | | | | |
|---|---|---|---|---|---|---|---|---|---|---|---|
|Gln|Leu|Val|Leu|Tyr|Gly|Phe|Glu|Lys|Leu|Glu|Ile|Pro|Glu|Ser|
| | |835| | | |840| | | |845| | | | |
|Ile|Gly|Glu|Ile|Met|Thr|Leu|Lys|Phe|Ile|Lys|Thr|Glu|Phe|Cys|Gly|
| |850| | | | |855| | | | |860| | | | |
|Ser|Gly|Val|Glu|Thr|Ser|Ala|Lys|Lys|Ile|Gln|Glu|Glu|Gln|Glu|Ser|
|865| | | | |870| | | | |875| | | | |880|
|Trp|Gly|Asn|Tyr|Glu|Leu|Gln|Leu|Leu|Ile|Thr|Pro|Met|Leu|Arg|Phe|
| | | |885| | | | |890| | | | |895| | |
|Leu|Ile|Glu|Asn|Leu|Asp|Glu|Ile|Ser|Met|Leu|Pro|Pro|Asp|Glu|Val|
| | | | |900| | | | |905| | | | |910| |
|Ala|Glu|Lys|Ile|Lys|Val|Lys|Ile|Phe|Asp|Arg|Lys|Leu|Lys|Glu|Ile|
| | | |915| | | | |920| | | | |925| | |
|Leu|Glu|Ser|Thr|Gly|Gln|Ile|Met|Thr|Arg|Lys|Ile|Ile|Lys|Thr|Glu|
| | |930| | | | |935| | | | |940| | | |
|Phe|Cys|Ser|Ser|Gly|Val|Glu|Thr|Ser|Ala|Lys|Lys|Ile|Gln|Glu|Gln|
|945| | | | |950| | | | |955| | | | |960|
|Glu|Ser|Leu|Gly|Asn|Tyr|Glu|Leu|Gln|Val|Gln|Ile|Thr|Pro|Arg|Lys|
| | | | |965| | | | |970| | | | |975| | |
|Arg|Leu|Leu|Arg|Lys|Gln|Asp|Gly|Thr|Val|
| | | |980| | | | |985| |

<210> SEQ ID NO 64
<211> LENGTH: 2958
<212> TYPE: DNA
<213> ORGANISM: Solanum americanum

<400> SEQUENCE: 64

```
atggcatatg ctgctctttc ttcacttatc tatacattgc aacaactctt gaaacctaat    60
caatctttgg tttgtcgaag ctgtacacaa caacatcttc aatctatcta tcacaatctt   120
tctgctctgc aacttttcct tgacgatact acgacaaagg atattgaaac tcttaaggtt   180
atagaaaaga ggatcagaga tgtagtatac aaagcagaag atacagttga ttcaagccta   240
agaaacatca ttctagcaga ttgcacagag aatagagaag gggcttgtaa attctttgag   300
gaagaattgc taaagtggaa aaagatgtt gattctctca gcaaagaggt gatgcagatc   360
gactttaaca agcatggaag cagatctgca gaattagcaa caactgatcc ctcctcatca   420
ggaaaaagta caattgagga acatactatt gttgggatgg aggatgagta caacaccata   480
cttgatcgcc tcactgccca acagacgag ttgactgtca taccaatttt tggtatgggc   540
ggtataggta agacaactct tgccagaaag gtttatgatg attcatctat tcgttctcga   600
tttgatagac atgcatgggt cactacctct gaagaattca tgagagacg aatgcttctc   660
gaagttgttt cttcaattac tactggaagc aatcaaggaa agagcgatga tcaactaatg   720
gagattgtgt atagaagtct gaagggtagg agatttctaa ttgtcataga tgatatttgg   780
agtactcagg cttgggacca aatgcaaaga tatttccaa tgatgacaa taaaagccga   840
attctactaa ctacacggct caagtatgtt gctgattatg tcagcagtcc tgattttcca   900
cctcatagta agtctttct aagtcttgat gatagttgga atcattcac cgaaaaagta   960
ttcaacgaag atacctgtcc tcctcaccta aaagaaacag gaagcatat tgtacaacaa  1020
tgtcaaggat tacctctctc ggttgttgtc gttgctggac ttgttggaaa aatgaccca  1080
acgcatgaca attgggagaa tgttgaggaa atctgaact cattctttgg tactgtatcc  1140
gaacggtgcc actcaattct ttctttgagc tacaattact tgccccaata tttgagggct  1200
tgttttctct atgttggagg ttttcctgaa gataaagaga ttgatgtttc caagttgatt  1260
```

```
aggctatgga ttgctgagca attcgtaaag gcgagaagca ataaaaggct agaagtggtg    1320
gcagaggagt atctggaaga gttaattgat agaagtctaa ttttgagtgg tagacaaagg    1380
gctaatggaa ggatgaaaac ttgcaaaatt catgatcttc ttcgccaact atgcctaagt    1440
gaagctcata ctgaaaatat tagtcatatc atgaatagaa atgtccccgt gtcctcagaa    1500
gccatagatg atcaacggcg agtgattgtt ccattggaac tcgaagagaa acaagtttat    1560
cctacaaggc atagcagtgg tattacaagt acaacccgca cctttatttc aatgaaaata    1620
tgcctaagag aagctcaaac cgaagccata tatgatcaac ggcgagtgat ccttctgtct    1680
aaacgacata ggattgatac aatccgcacc attattccat tcggagatac ttttccaaaa    1740
gagatttgtt ccattttttc agagttcaag ttgcttaagg tgttggatgt attatcagtc    1800
tggtacgatg tctcttgtat aatacctcag cttgtacatt tgagatatgt tggtgcagta    1860
attttggaag ctctttcact acccaaattg agaaatctac agaccataat gcttacaagt    1920
gttgaaacca cagagttgaa gcactcacta gatatctgga gaatgtcaga gataagacat    1980
ttggatattg taccgccact atatatatca atcctcttg aagcagaaca acctttgttt     2040
ctcaataact tgcacacgct ttttctccgt tgctctcctt ttgttgcgaa aatcataaga    2100
agaactccga atctaaaaaa gctaaagatt ttagataaat ctaagcatcc tgactggcct    2160
gatattcttg attctctcaa tcttctagag gagctggaga cactacaaat atcaacagaa    2220
gaaaacattg accggatgat tttctctggg gataatttcc ctcgtaatct caagcaactg    2280
aaattatcag gtactaaaat accatgggaa gatatgaaat tgctggctaa tttacccaat    2340
cttgaggtgt tcaagggtca ttatgcattc gatggaacag attggaaact agatgaagat    2400
gttgtgtttt gcaaattaaa atgtctacga ctgtatgagc gcggagatct gcaaaggtgg    2460
gaagcagcag gtagtgataa ttttcctatg cttgagcaac tagtactgta tgggttcgaa    2520
aaactggaag agattccgga gagtattgga gaaataatga cactaaaatt catcaaaaca    2580
gaattttgcg gctctggtgt agagacaagt gcaagaaaa ttcaagaaga gcaagaaagc     2640
tggggaaatt atgagcttca acttctaatt actcctatgt taagattttt gatcgaaaat    2700
ttagacgaaa taagcatgtt gccaccggat gaagtagccg aaaaaatcaa agttaaaatt    2760
tttgatcgaa aactaaaaga gattctggag agtactggac aaataatgac acgaaaaatc    2820
attaaaacgg aattttgcag ctctggtgta gagactagtg caagaaaaat tcaagagcaa    2880
gaaagcttgg gaaattatga gcttcaagtt caaattactc ctaggaagcg tttgctgagg    2940
aagcaggacg gcactgtg                                                  2958
```

<210> SEQ ID NO 65
<211> LENGTH: 3033
<212> TYPE: DNA
<213> ORGANISM: Solanum americanum

<400> SEQUENCE: 65

```
atggcatatg ctgctctttc ttcacttatc tatacattgc aacaactctt gaaacctaat      60
caatctttgg tttgtcgaag ctgtacacaa caacatcttc aatctatcta tcacaatctt     120
tctgctctgc aacttttcct tgacgatact acgacaaagg atattgaaac tcttaaggta     180
tgtaattatc taatctctta ctcatcttat atttattcaa aataattaa tttatcgagt      240 ttcaatttta aggttataga aaagaggatc agagatgtag tatacaaagc agaagataca     300
gttgattcaa gcctaagaaa catcattcta gcagattgca cagagaatag agaagggggct    360
```

| | |
|---|---|
| tgtaaattct ttgaggaaga attgctaaaa gtggaaaaag atgttgattc tctcagcaaa | 420 |
| gaggtgatgc agatcgactt taacaagcat ggaagcagat ctgcagaatt agcaacaact | 480 |
| gatccctcct catcaggaaa agtacaatt gaggaacata ctattgttgg gatggaggat | 540 |
| gagtacaaca ccatacttga tcgcctcact gcccaaacag acgagttgac tgtcatacca | 600 |
| attttttggta tgggcggtat aggtaagaca actcttgcca gaaaggttta tgatgattca | 660 |
| tctattcgtt ctcgatttga tagacatgca tgggtcacta cctctgaaga attcaatgag | 720 |
| agacgaatgc ttctcgaagt tgtttcttca attactactg gaagcaatca aggaaagagc | 780 |
| gatgatcaac taatggagat tgtgtataga agtctgaagg gtaggagatt tctaattgtc | 840 |
| atagatgata tttggagtac tcaggcttgg gaccaaatgc aaagaatatt tccaaatgat | 900 |
| gacaataaaa gccgaattct actaactaca cggctcaagt atgttgctga ttatgtcagc | 960 |
| agtcctgatt ttccacctca tagtaagtct tttctaagtc ttgatgatag ttggaatcta | 1020 |
| ttcaccgaaa aagtattcaa cgaagatacc tgtcctcctc acctagaaga aacagggaag | 1080 |
| catattgtac aacaatgtca aggattacct ctctcggttg ttgtcgttgc tggacttgtt | 1140 |
| ggaaaaatgg acccaacgca tgacaattgg gagaatgttg aggaaaatct gaactcattc | 1200 |
| tttggtactg tatccgaacg gtgccactca attctttctt tgagctacaa ttacttgccc | 1260 |
| caatatttga gggcttgttt tctctatgtt ggaggttttc ctgaagataa agagattgat | 1320 |
| gtttccaagt tgattaggct atggattgct gagcaattcg taaaggcgag aagcaataaa | 1380 |
| aggctagaag tggtggcaga ggagtatctg gaagagttaa ttgatagaag tctaattttg | 1440 |
| agtggtagac aaagggctaa tggaaggatg aaaacttgca aaattcatga tcttcttcgc | 1500 |
| caactatgcc taagtgaagc tcatactgaa atattagtc atatcatgaa tagaaatgtc | 1560 |
| cccgtgtcct cagaagccat agatgatcaa cggcgagtga ttgttccatt ggaactcgaa | 1620 |
| gagaaacaag tttatcctac aaggcatagc agtggtatta caagtacaac ccgcaccttt | 1680 |
| atttcaatgg aaatatgcct aagagaagct caaaccgaag ccatatatga tcaacggcga | 1740 |
| gtgatccttc tgtctaaacg acataggatt gatacaatcc gcaccattat tccattcgga | 1800 |
| gatactttc caaagagat tgttccatt ttttcagagt tcaagttgct taaggtgttg | 1860 |
| gatgtattat cagtctggta cgatgtctct tgtataatac ctcagcttgt acatttgaga | 1920 |
| tatgttggtg cagtaatttt ggaagctctt tcactaccca aattgagaaa tctacagacc | 1980 |
| ataatgctta caagtgttga aaccacagag ttgaagcact cactagatat ctggagaatg | 2040 |
| tcagagataa gacatttgga tattgtaccg ccactatata tatcaaatcc tcttgaagca | 2100 |
| gaacaacctt tgtttctcaa taacttgcac acgcttttc tccgttgctc tcctttttgtt | 2160 |
| gcgaaaatca taagaagaac tccgaatcta aaaaagctaa agattttaga taaatctaag | 2220 |
| catcctgact ggcctgatat tcttgattct ctcaatcttc tagaggagct ggagacacta | 2280 |
| caaatatcaa cagaagaaaa cattgaccgg atgattttct ctggggataa tttccctcgt | 2340 |
| aatctcaagc aactgaaatt atcaggtact aaaataccat gggaagatat gaaattgctg | 2400 |
| gctaatttac ccaatcttga ggtgttcaag ggtcattatg cattcgatgg aacagattgg | 2460 |
| aaactagatg aagatgttgt gttttgcaaa ttaaaatgtc tacgactgta tgagcgcgga | 2520 |
| gatctgcaaa ggtgggaagc agcaggtagt gataattttc ctatgcttga gcaactagta | 2580 |
| ctgtatgggt tcgaaaaact ggaagagatt ccggagagta ttggagaaat aatgacacta | 2640 |
| aaattcatca aaacagaatt ttgcggctct ggtgtagaga caagtgcaaa gaaaattcaa | 2700 |
| gaagagcaag aaagctgggg aaattatgag cttcaacttc taattactcc tatgttaaga | 2760 |

-continued

```
tttttgatcg aaaatttaga cgaaataagc atgttgccac cggatgaagt agccgaaaaa    2820
atcaaagtta aaattttga tcgaaaacta aaagagattc tggagagtac tggacaaata    2880
atgacacgaa aaatcattaa aacggaattt tgcagctctg gtgtagagac tagtgcaaag    2940
aaaattcaag agcaagaaag cttgggaaat tatgagcttc aagttcaaat tactcctagg    3000
aagcgtttgc tgaggaagca ggacggcact gtg                                 3033
```